US007473526B2

(12) United States Patent
Wang

(10) Patent No.: US 7,473,526 B2
(45) Date of Patent: Jan. 6, 2009

(54) BREAST CANCER PROGNOSTIC PORTFOLIO

(75) Inventor: Yixin Wang, San Diego, CA (US)

(73) Assignee: Veridex, LLC, Raritan, NJ (US)

( * ) Notice: Subject to any disclaimer, the term of this patent is extended or adjusted under 35 U.S.C. 154(b) by 322 days.

(21) Appl. No.: 10/393,590

(22) Filed: Mar. 21, 2003

(65) Prior Publication Data

US 2003/0190656 A1 Oct. 9, 2003

Related U.S. Application Data

(60) Provisional application No. 60/368,789, filed on Mar. 29, 2002.

(51) Int. Cl.
*C12Q 1/68* (2006.01)
*C07H 21/04* (2006.01)

(52) U.S. Cl. .......................................... 435/6; 536/23.5

(58) Field of Classification Search ....................... None
See application file for complete search history.

(56) References Cited

U.S. PATENT DOCUMENTS

| | | | |
|---|---|---|---|
| 6,003,018 | A | 12/1999 | Michaud et al. |
| 6,037,129 | A | 3/2000 | Cole et al. |
| 6,175,824 | B1 | 1/2001 | Breizman et al. |
| 6,275,814 | B1 | 8/2001 | Giansante et al. |
| 6,350,576 | B1 | 2/2002 | Wigler et al. |
| 6,353,152 | B1 | 3/2002 | Lee et al. |
| 2005/0054826 | A1 * | 3/2005 | Mao |

FOREIGN PATENT DOCUMENTS

| | | | |
|---|---|---|---|
| WO | WO 96/29430 | A1 | 9/1996 |
| WO | WO 00/55633 | A3 | 9/2000 |
| WO | WO00/58473 | * | 10/2000 |
| WO | WO03/070889 | * | 8/2003 |

OTHER PUBLICATIONS van't Veer, Nature, 2002, vol. 415, pp. 530-536.*
Chambers et al., Nature Reviews, 2002, vol. 2, pp. 563-573.*
Welch et al., Breast Cancer Research, 2000, vol. 2, pp. 408-416.*
GenBank Accession No. AA555029, published Sep. 1997.*
GenBank Accession No. AB033007, published Nov. 1999.*
Parks et al., Journal of Biological Chemistry, 2001, vol. 276, No. 22, pp. 19332-19339.*
Cambell, Biology 3rd Edition, 1993, pp. 376-377.*
Relevent pages of WO 00/58473 have been included. Entire sequence listing and sequence tables have not been provided. WO document is 5500 pages long.*
Jaing, Ming et al., "p21/waf1/cip 1 and mdm-2 Expression in Breast Carcinoma Patients as Related to Prognosis", International Journal of Cancer (Pred. Oncol.), vol. 74, pp. 529-534 (1997).
Strausberg, Robert et al., "National Cancer Institute, Cancer Genome Anatomy Project (CGAP), Tumor", Database EMBL 'Online! ebi, Sep. 11, 1997, Database Accession No. AA555029.
Partial European Search Report, dated Oct. 21, 2003, for European Appln. No. EP 03 25 2026.
Paul D. Kaplan,PhD, CFA, Vice-President and Economist, 225 North Michigan Avenue, SUite 700, Chicago, Il 60601-7676;"Asset Allocation Models Using the Markowitz Approach"; http://www.ibbotson.com/Research/papers/Markowitz__Approach/Markowitz__Approach.pdf http://www.ibbotson.com/Research/papers/Markowitz__Approach/Markowitz__Approach.pdf http://www.elseware.fr/en/LINKS/TECHLINK.HTM, Mar. 2003.
Laura J. Van'tveer et al; "Gene expression profiling predicts clinical outcome of breast cancer"; Nature/vol. 415/Jan. 13, 2002/www.nature.com; 2002 Macmillan Magazines Ltd.,pp. 530-536.

* cited by examiner

*Primary Examiner*—Diana B Johannsen
(74) *Attorney, Agent, or Firm*—Todd Volyn

(57) ABSTRACT

A method of prognosticating metastasis in a breast cancer patient involves identifying differential modulation of each gene (relative to the expression of the same genes in a normal population) in a combination of genes as well as kits for employing the method.

2 Claims, No Drawings

BREAST CANCER PROGNOSTIC PORTFOLIO

This application claims the benefit of U.S. Provisional Application No. 60/368,789 filed on Mar. 29, 2002.

BACKGROUND

The invention relates to the selection of portfolios of diagnostic markers.

A few single gene diagnostic markers such as her-2-neu are currently in use. Usually, however, diseases are not easily diagnosed with molecular diagnostics for one particular gene. Multiple markers are often required and the number of such markers that may be included in a assay based on differential gene modulation can be large, even in the hundreds of genes. It is desirable to group markers into portfolios so that the most reliable results are obtained using the smallest number of markers necessary to obtain such a result. This is particularly true in assays that contain multiple steps such as nucleic acid amplification steps.

SUMMARY OF THE INVENTION

The invention is a method of prognosticating metastasis in a breast cancer patient by identifying differential modulation of each gene (relative to the expression of the same genes in a normal population) in a combination of genes selected from the group consisting of Seq. ID. No. 70-97.

Gene expression portfolios and kits for employing the method are further aspects of the invention.

DETAILED DESCRIPTION

The methods of this invention can be used in conjunction with any method for determining the gene expression patterns of relevant cells as well as protein based methods of determining gene expression. Preferred methods for establishing gene expression profiles include determining the amount of RNA that is produced by a gene that can code for a protein or peptide. This is accomplished by reverse transcriptase PCR (RT-PCR), competitive RT-PCR, real time RT-PCR, differential display RT-PCR, Northern Blot analysis and other related tests. While it is possible to conduct these techniques using individual PCR reactions, it is best to amplify copy DNA (cDNA) or copy RNA (cRNA) produced from mRNA and analyze it via microarray. A number of different array configurations and methods for their production are known to those of skill in the art and are described in U.S. Patents such as: U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are incorporated herein by reference.

Microarray technology allows for the measurement of the steady-state mRNA level of thousands of genes simultaneously thereby presenting a powerful tool for identifying effects such as the onset, arrest, or modulation of uncontrolled cell proliferation. Two microarray technologies are currently in wide use. The first are cDNA arrays and the second are oligonucleotide arrays. Although differences exist in the construction of these chips, essentially all downstream data analysis and output are the same. The product of these analyses are typically measurements of the intensity of the signal received from a labeled probe used to detect a cDNA sequence from the sample that hybridizes to a nucleic acid sequence at a known location on the microarray. Typically, the intensity of the signal is proportional to the quantity of cDNA, and thus mRNA, expressed in the sample cells. A large number of such techniques are available and useful. Preferred methods for determining gene expression can be found in U.S. Pat. Nos. 6,271,002 to Linsley, et al.; 6,218,122 to Friend, et al.; 6,218,114 to Peck, et al.; and 6,004,755 to Wang, et al., the disclosure of each of which is incorporated herein by reference.

Analysis of the expression levels is conducted by comparing such intensities. This is best done by generating a ratio matrix of the expression intensities of genes in a test sample versus those in a control sample. For instance, the gene expression intensities from a diseased tissue can be compared with the expression intensities generated from normal tissue of the same type (e.g., diseased colon tissue sample vs. normal colon tissue sample). A ratio of these expression intensities indicates the fold-change in gene expression between the test and control samples.

Modulated genes are those that are differentially expressed as up regulated or down regulated in non-normal cells. Up regulation and down regulation are relative terms meaning that a detectable difference (beyond the contribution of noise in the system used to measure it) is found in the amount of expression of the genes relative to some baseline. In this case, the baseline is the measured gene expression of a normal cell. The genes of interest in the non-normal cells are then either up regulated or down regulated relative to the baseline level using the same measurement method.

Preferably, levels of up and down regulation are distinguished based on fold changes of the intensity measurements of hybridized microarray probes. For example, in the case in which a 1.5 fold or more difference is used to make such distinctions, the diseased cell is found to yield at least 1.5 times more, or 1.5 times less intensity than the normal cells.

Other methods of making distinctions are available. For example, statistical tests can be used to find the genes most significantly different between diverse groups of samples. The Student's t-test is an example of a robust statistical test that can be used to find significant differences between two groups. The lower the p-value, the more compelling the evidence that the gene is showing a difference between the different groups. Nevertheless, since microarrays measure more than one gene at a time, tens of thousands of statistical tests may be asked at one time. Because of this, there is likelihood to see small p-values just by chance and adjustments for this using a Sidak correction as well as a randomization/permutation experiment can be made.

A p-value less than 0.05 by the t-test is evidence that the gene is significantly different. More compelling evidence is a p-value less then 0.05 after the Sidak correct is factored in. For a large number of samples in each group, a p-value less than 0.05 after the randomization/ permutation test is the most compelling evidence of a significant difference.

Genes can be grouped so that information obtained about the set of genes in the group provides a sound basis for making clinically relevant judgments such as a diagnosis, prognosis, or treatment choice. These sets of genes make up the portfolios of the invention. As with most diagnostic markers, it is often desirable to use the fewest number of markers sufficient to make a correct medical judgment. This prevents a delay in treatment pending further analysis as well as inappropriate use of time and resources. Preferred optimal portfolio is one that employs the fewest number of markers for making such judgments while meeting conditions that maximize the probability that such judgments are indeed correct. These conditions will generally include sensitivity and specificity requirements. In the context of microarray based detection methods, the sensitivity of the portfolio can be reflected in the fold differences exhibited by a gene's expression in the diseased or aberrant state relative to the normal state. The detection of the differential expression of a gene is sensitive if it exhibits a large fold change relative to the expression of the gene in another state. Another aspect of sensitivity is the ability to distinguish signal from noise. For example, while the expression of a set of genes may show adequate sensitivity for defining a given disease state, if the signal that is generated by one (e.g., intensity measurements in microarrays) is below a level that easily distinguished from noise in a given setting (e.g., a clinical laboratory) then that gene should be excluded from the optimal portfolio. A procedure for setting conditions such as these that define the optimal portfolio can be incorporated into the inventive methods.

Specificity can be reflected in statistical measurements of the correlation of the signaling of gene expression with the condition of interest. If the differential expression of a set of genes is observed to produce a large fold change but they do so for a number of conditions other than the condition of interest (e.g. multiple disease states) then the gene expression profile for that set of genes is non-specific. Statistical measurements of correlation of data or the degree of consistency of data such as standard deviation, correlation coefficients, and the like can be a used as such measurements. In considering a group of genes for inclusion in a portfolio, a small standard deviation in expression measurements correlates with greater specificity. Genes that display similar expression patterns may be co-regulated by an identical factor that pushes the genes in the same direction. If this factor is sufficient but not necessary for classifying a sample, then these genes will fail to correctly identify a sample if the markers are all related to this single factor. Diversification then results in selecting as few markers as possible, yet covers as many different optimal expression patterns that are contained in the data set In the method of the invention, a group of genetic markers is selected for use in diagnostic applications. These groups of markers are "portfolios". Diagnostic applications include the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, the method can be used to establish portfolios for detecting the presence or likelihood of a subject contracting colon cancer or the likelihood that such a subject will respond favorably to cytotoxic drugs.

The portfolios selected by the method of the invention contain a number and type of markers that assure accurate and precise results and are economized in terms of the number of genes that comprise the portfolio. The method of the invention can be used to establish optimal gene expression portfolios for any disease, condition, or state that is concomitant with the expression of multiple genes. An optimal portfolio in the context of the instant invention refers to a gene expression profile that provides an assessment of the condition of a subject (based upon the condition for which the analysis was undertaken) according to predetermined standards of at least two of the following parameters: accuracy, precision, and number of genes comprising the portfolio.

Most preferably, the markers employed in the portfolio are nucleic acid sequences that express mRNA ("genes"). Expression of the markers may occur ordinarily in a healthy subject and be more highly expressed or less highly expressed when an event that is the object of the diagnostic application occurs. Alternatively, expression may not occur except when the event that is the object of the diagnostic application occurs.

Marker attributes, features, indicia, or measurements that can be compared to make diagnostic judgments are diagnostic parameters used in the method. Indicators of gene expression levels are the most preferred diagnostic parameters. Such indicators include intensity measurements read from microarrays, as described above. Other diagnostic parameters are also possible such as indicators of the relative degree of methylation of the markers.

Distinctions are made among the diagnostic parameters through the use of mathematical/statistical values that are related to each other. The preferred distinctions are mean signal readings indicative of gene expression and measurements of the variance of such readings. The most preferred distinctions are made by use of the mean of signal ratios between different group readings (e.g., microarray intensity measurements) and the standard deviations of the signal ratio measurements. A great number of such mathematical/statistical values can be used in their place such as return at a given percentile.

A relationship among diagnostic parameter distinctions is used to optimize the selection of markers useful for the diagnostic application. Typically, this is done through the use of linear or quadratic programming algorithms. However, heuristic approaches can also be applied or can be used to supplement input data selection or data output. The most preferred relationship is a mean-variance relationship such as that described in *Mean-Variance Analysis in Portfolio Choice and Capital Markets* by Harry M. Markowitz (Frank J. Fabozzi Associates, New Hope, Pa.: 2000, ISBN: 1-883249-75-9) which is incorporated herein by reference. The relationship is best understood in the context of the selection of stocks for a financial investment portfolio. This is the context for which the relationship was developed and elucidated.

The investor looking to optimize a portfolio of stocks can select from a large number of possible stocks, each having a historical rate of return and a risk factor. The mean variance method uses a critical line algorithm of linear programming or quadratic programming to identify all feasible portfolios that minimize risk (as measured by variance or standard deviation) for a given level of expected return and maximize expected return for a given level of risk. When standard deviation is plotted against expected return an efficient frontier is generated. Selection of stocks along the efficient frontier results in a diversified stock portfolio optimized in terms of return and risk.

When the mean variance relationship is used in the method of the instant invention, diagnostic parameters such as microarray signal intensity and standard deviation replace the return and risk factor values used in the selection of financial portfolios. Most preferably, when the mean variance relationship is applied, a commercial computer software application such as the "Wagner Associates Mean-Variance Optimization Application", referred to as "Wagner Software" throughout this specification. This software uses functions from the "Wagner Associates Mean-Variance Optimization Library" to determine an efficient frontier and optimal portfolios in the Markowitz sense. Since such applications are made for financial applications, it may be necessary to preprocess input data so that it can conform to conventions required by the software. For example, when Wagner Software is employed in conjunction with microarray intensity measurements the following data transformation method is employed.

A relationship between each genes baseline and experimental value must first be established. The preferred process is conducted as follows. A baseline class is selected. Typically, this will comprise genes from a population that does not have the condition of interest. For example, if one were interested in selecting a portfolio of genes that are diagnostic for breast cancer, samples from patients without breast cancer can be used to make the baseline class. Once the baseline class is selected, the arithmetic mean and standard deviation is calculated for the indicator of gene expression of each gene for baseline class samples. This indicator is typically the fluorescent intensity of a microarray reading. The statistical data computed is then used to calculate a baseline value of (X*Standard Deviation+Mean) for each gene. This is the baseline reading for the gene from which all other samples will be compared. X is a stringency variable selected by the person formulating the portfolio. Higher values of X are more stringent than lower. Preferably, X is in the range of 0.5 to 3 with 2 to 3 being more preferred and 3 being most preferred.

Ratios between each experimental sample (those displaying the condition of interest) versus baseline readings are then calculated. The ratios are then transformed to base 10 logarithmic values for ease of data handling by the software. This enables down regulated genes to display negative values necessary for optimization according to the Markman mean-variance algorithm using the Wagner Software.

The preprocessed data comprising these transformed ratios are used as inputs in place of the asset return values that are normally used in the Wagner Software when it is used for financial analysis purposes.

Once an efficient frontier is formulated, an optimized portfolio is selected for a given input level (return) or variance that corresponds to a point on the frontier. These inputs or variances are the predetermined standards set by the person formulating the portfolio. Stated differently, one seeking the optimum portfolio determines an acceptable input level (indicative of sensitivity) or a given level of variance (indicative of specificity) and selects the genes that lie along the efficient frontier that correspond to that input level or variance. The Wagner Software can select such genes when an input level or variance is selected. It can also assign a weight to each gene in the portfolio as it would for a stock in a stock portfolio.

Determining whether a sample has the condition for which the portfolio is diagnostic can be conducted by comparing the expression of the genes in the portfolio for the patient sample with calculated values of differentially expressed genes used to establish the portfolio. Preferably, a portfolio value is first generated by summing the multiples of the intensity value of each gene in the portfolio by the weight assigned to that gene in the portfolio selection process. A boundary value is then calculated by (Y*standard deviation+mean of the portfolio value for baseline groups) where Y is a stringency value having the same meaning as X described above. A sample having a portfolio value greater than the boundary value of the baseline class is then classified as having the condition. If desired, this process can be conducted iteratively in accordance with well known statistical methods for improving confidence levels.

Optionally one can reiterate this process until best prediction accuracy is obtained.

The process of portfolio selection and characterization of an unknown is summarized as follows:

1. Choose baseline class
2. Calculate mean, and standard deviation of each gene for baseline class samples
3. Calculate (X*Standard Deviation+Mean) for each gene. This is the baseline reading from which all other samples will be compared. X is a stringency variable with higher values of X being more stringent than lower.
4. Calculate ratio between each Experimental sample versus baseline reading calculated in step 3.
5. Transform ratios such that ratios less than 1 are negative (eg.using Log base 10). (Down regulated genes now correctly have negative values necessary for MV optimization).
6. These transformed ratios are used as inputs in place of the asset returns that are normally used in the software application.
7. The software will plot the efficient frontier and return an optimized portfolio at any point along the efficient frontier.
8. Choose a desired return or variance on the efficient frontier.
9. Calculate the Portfolio's Value for each sample by summing the multiples of each gene's intensity value by the weight generated by the portfolio selection algorithm.
10. Calculate a boundary value by adding the mean Portfolio Value for Baseline groups to the multiple of Y and the Standard Deviation of the Baseline's Portfolio Values. Values greater than this boundary value shall be classified as the Experimental Class.
11. Optionally one can reiterate this process until best prediction accuracy is obtained.

A second portfolio can optionally be created by reversing the baseline and experimental calculation. This creates a new portfolio of genes which are up-regulated in the original baseline class. This second portfolio's value can be subtracted from the first to create a new classification value based on multiple portfolios.

Another useful method of pre-selecting genes from gene expression data so that it can be used as input for a process for selecting a portfolio is based on a threshold given by $$1 \le \left|\frac{(\mu_t - \mu_n)}{(\sigma_t + \sigma_n)}\right|,$$

where $\mu_t$ is the mean of the subset known to possess the disease or condition, $\mu_n$ is the mean of the subset of normal samples, and $\sigma_t + \sigma_n$ represent the combined standard deviations. A signal to noise cutoff can also be used by pre-selecting the data according to a relationship such as $$0.5 \le \left|\frac{(\mu_t - \mathrm{MAX}_n)}{(\sigma_t + \sigma_n)}\right|.$$

This ensures that genes that are pre-selected based on their differential modulation are differentiated in a clinically significant way. That is, above the noise level of instrumentation appropriate to the task of measuring the diagnostic parameters. For each marker pre-selected according to these criteria, a matrix is established in which columns represents samples, rows represent markers and each element is a normalized intensity measurement for the expression of that marker according to the relationship:

$$\left|\frac{(\mu_t - I)}{\mu_t}\right|$$

where I is the intensity measurement.

Using this process of creating input for financial portfolio software make also allows one to set additional boundary conditions to define the optimal portfolios. For example, portfolio size can be limited to a fixed range or number of markers. This can be done either by making data pre-selection criteria more stringent $$\left(\text{e.g, } .8 \le \left|\frac{(\mu_t - \text{MAX}_n)}{(\sigma_t + \sigma_n)}\right| \text{ instead of } 0.5 \le \left|\frac{(\mu_t - \text{MAX}_n)}{(\sigma_t + \sigma_n)}\right|\right)$$

or by using programming features such as restricting portfolio size. One could, for example, set the boundary condition that the efficient frontier is to be selected from among only the optimal 10 genes. One could also use all of the genes preselected for determining the efficient frontier and then limit the number of genes selected (e.g., no more than 10).

The process of selecting a portfolio can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in subjects with breast cancer. Output from the method would be an optimized set of genes that could include some genes that are expressed in peripheral blood as well as in diseased breast tissue. If sample used in the testing method are obtained from peripheral blood and certain genes differentially expressed in instances of breast cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply the rule that only a given percentage of the portfolio can be represented by a particular gene or genes. Commercially available software such as the Wagner Software readily accommodates these types of heuristics. This can be useful, for example, when factors other than accuracy and precision (e.g., anticipated licensing fees) have an impact on the desirability of including one or more genes.

Other relationships aside from the mean-variance relationship can be used in the method of the invention provided that they optimize the portfolio according to predetermined attributes such as assay accuracy and precision. Two examples are the Martin simultaneous equation approach (Elton, Edwin J. and Martin J. Gruber (1987), *Modern Portfolio Theory Investment Analysis*, Third Edition, John Wiley, New York, 1987) and Genetic Algorithms (Davis, L., (1989), *Adapting Operator Probabilities in Genetic Algorithms*, in *Proceedings of the Third International Conference on Genetic Algorithms*, Morgan Kaufmann: San Mateo, pp. 61-69). There are also many ways to adapt the mean-variance relationship to handle skewed data such as where a marker detection technology exhibits a known bias. These include, for example, the Semi-Deviation method in which the square root of the average squared (negative) deviation from a reference signal and includes only those signal values that fall below the reference signal.

Articles of this invention include representations of the gene expression profiles that make up the portfolios useful for treating, diagnosing, prognosticating, and otherwise assessing diseases. These representations are reduced to a medium that can be automatically read by a machine such as computer readable media (magnetic, optical, and the like). The articles can also include instructions for assessing the gene expression profiles in such media. For example, the articles may comprise a CD ROM having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format.

Different types of articles of manufacture according to the invention are media or formatted assays used to reveal gene expression profiles. These can comprise, for example, microarrays in which sequence complements or probes are affixed to a matrix to which the sequences indicative of the genes of interest combine creating a readable determinant of their presence. When such a microarray contains an optimized portfolio great savings in time, process steps, and resources are attained by minimizing the number of cDNA or oligonucleotides that must be applied to the substrate, reacted with the sample, read by an analyzer, processed for results, and (sometimes) verified.

Other articles according to the invention can be fashioned into reagent kits for conducting hybridization, amplification, and signal generation indicative of the level of expression of the genes in the portfolios established through the method of the invention. Kits made according to the invention include formatted assays for determining the gene expression profiles. These can include all or some of the materials needed to conduct the assays such as reagents and instructions.

EXAMPLES

Example 1

Producing an Optimized Portfolio

Gene expression data was recently produced from tissue samples representative of eleven different typees of cancers. The data was published in Cancer Research 61:7388-7393, 2001 and on the worldwide web of the Internet at carrier.gnf.org/welsh/epican. See Andrew 1., Su et al., "Molecular Classification of Human Carcinomas by Use of Gene Expression Signatures. " The data included intensity measurements obtained with the use of an "U95" a ogligonucleotide microarray (commercially available from Affymetrix, Inc.)

Measurements of the expression of genes from the published data (fluorescent intensity measurements) was used to select optimum gene expression portfolios for a panel of markers to determine whether a circulating cell is indicative of the presence of breast cancer, prostate cancer, ovarian cancer, colorectal cancer, or lung cancer. Such circulating cells would preferably be epithelial cells.

The data in the study was collected from the following samples: 24 adenocarcinomas, 12 infilitrating ductal breast adenocarcenomas, 21 colorectal adenocarcinomas, 23 ovarian adenocarcinomas, 25 lung carcinomas, and data from the following additional samples: 19 prostate adenocarcinomas, 12 breast carcinomas, 13 colon carcinomas, 13 ovarian carcinomas, 13 ovarian carcinomas, and 89 lung carcenomas.

Using intensity readings from a collection of normal samples as the baseline class, the arithmetic mean, and standard deviation of each gene were calculated followed by a calculation of the value (X*Standard Deviation+Mean) for each gene. The stringency variable, X, was assigned a value of 3 in this case. Ratios were then calculated between each Experimental sample described in the study versus the baseline value calculations. The ratios were transformed into common logarithms. These values were then used as the input values for the Wagner Software.

This procedure selected an efficient frontier along which a minimum set of markers for each tumor type that have the lowest amount of variation for a selected level of differential (chosen at the best signal to noise ratio point). Optimization by the software resulted in the selection of a portfolio of 24 genes including 2 for prostate cancer, 5 for breast cancer, 6 for colon cancer, 2 for ovarian cancer, and 9 for lung cancer markers (Table 1).

TABLE 1

| Cancer Type | Accession | Name | Description | Seq, ID No. |
|---|---|---|---|---|
| PR | NM_001648 | KLK3 | kallikrein 3, (prostate specific antigen) | Seq. ID No. 1 |
| PR | NM_005551 | KLK2 | kallikrein 2, prostatic | Seq. ID No. 2 |
| BR | NM_004064 | CDKN1B | cyclin-dependent kinase inhibitor 1B(p27, Kip1) | Seq. ID No. 31 |
| BR | NM_002411 | MGB1 | mammaglobin 1 | Seq. ID No. 3 |
| BR | NM_005264 | GFRA1 | GDNF family receptor alpha 1 | Seq. ID No. 4 |
| BR | none | C18ORF1 | chromosome 18 open reading frame 1 | Seq. ID No. 98 |
| BR | NM_000095 | COMP | cartilage oligomeric matrix protein | Seq. ID No. 6 |
| CO | NM_001804 | CDX1 | caudal type homeo box transcription factor 1 | Seq. ID No. 8 |
| CO | NM_001046 | SLC12 A2 | solute carrier family 12 (sodium/potassium/chloride transporters), member 2 | Seq. ID No. 9 |
| CO | NM_001285 | CLCA1 | chloride channel, calcium activated, family member 1 | Seq. ID No. 11 |
| CO | NM_007052 | NOX1 | NADPH oxidase 1 | Seq. ID No. 13 |
| CO | NM_002457 | MUC2 | mucin 2, intestinal/tracheal | Seq. ID No. 14 |
| CO | NM_004063 | CDH17 | cadherin 17, LI cadherin | Seq. ID No. 15 |
| LU_A | NM_021950 | MS4A2 | membrane-spanning 4-domains, subfamily A, member 2 | Seq. ID No. 17 |
| LU_A | NM_000964 | ASAHL | N-acylsphingosine amidohydrolase (acid ceramidase)-like | Seq. ID No. 18 |
| LU_A | NM_006495 | EVI2B | ecotropic viral integration site 2B | Seq. ID No. 20 |
| LU_A | NM_006864 | LILRB3 | leukocyte immunoglobulin-like receptor, subfamily B | Seq. ID No. 21 |
| LU_A | X67301 | None | H.sapiens mRNA for IgM heavy chain constant region(AB63) | Seq. ID No. 22 |
| LU_A | NM_002123 | HLA-DQB1 | major histocompatibility complex, class II, DQ beta 1 | Seq. ID No. 23 |
| LU_S | NM_000673 | ADH7 | alcohol dehydrogenase 7 (class IV), mu or sigma polypeptide | Seq. ID No. 24 |
| LU_S | NM_003722 | TP63 | tumor protein 63 kDa with strong homology to p53 | Seq. ID No. 26 |
| LU_S | none | SOX2 | SRY (sex determining region Y)-box 2 | Seq. ID No. 32 |
| OV | NM_000906 | NPR1 | natriuretic peptide receptor A/guanylate cyclase A | Seq. ID No. 28 |
| OV | NM_000378 | WT1 | Wilms tumor 1 | Seq. ID No. 30 |

Example 2

Heuristic Step

A heuristic rule was further applied to the portfolio obtained in Example 1. That is, the rule stated that if the gene/marker identified would likely be expressed in peripheral blood or were well-characterized tissue markers (e.g. PSA, mammaglobin, etc.), then such genes/marker would be removed from the portfolio. Application of the rule enabled the establishment of a portfolio of genes/markers that are optimized for use in a screening application in which the patient sample is obtained by assaying components found in the peripheral blood such as epithelial cells. The result of the selected portfolio contains 31 genes as shown in Table 2.

| Cancer Type | Accession | Name | Description | Seq. ID No. |
|---|---|---|---|---|
| PR | Hs.12784 | KIAA0293 | KIAA0293 protein | Seq. ID No. 67 |
| PR | NM_006562 | LBX1 | transcription factor similar to D. melanogaster homeodomain protein lady bird late | Seq. ID No. 33 |
| PR | NM_016026 | LOC51109 | CGI-82 protein | Seq. ID No. 34 |
| PR | HG2261-HT2352 | None | Antigen | Seq. ID No. 99 |
| PR | NM_012449 | STEAP | six transmembrane epithelial antigen of the prostate | Seq. ID No.35 |
| PR | NM_001634 | AMD1 | S-adenosylmethionine decarboxylase 1 | Seq. ID No. 36 |

-continued

| Cancer Type | Accession | Name | Description | Seq. ID No. |
|---|---|---|---|---|
| PR | HG2261-HT2351 | None | Antigen \| | Seq. ID No. 100 |
| PR | NM_006457 | LIM | LIM protein (similar to rat protein kinase C-binding enigma) | Seq. ID No. 37 |
| BR | NM_005853 | IRX5 | iroquois homeobox protein 5 | Seq. ID No. 38 |
| BR | NM_005264 | GFRA1 | GDNF family receptor alpha 1 | Seq. ID No. 39 |
| BR | none | C18ORF1 | chromosome 18 open reading frame 1 | Seq. ID No. 98 |
| BR | NM_000095 | COMP | cartilage oligomeric matrix protein (pseudoachondroplasia, epiphyseal dysplasia 1, multiple) | Seq. ID No. 41 |
| CO | NM_001265 | CDX2 | caudal type homeo box transcription factor 2 | Seq. ID No. 43 |
| CO | NM_001046 | SLC12A2 | solute carrier family 12 (sodium/potassium/chloride transporters), member 2 | Seq. ID No. 44 |
| CO | NM_001285 | CLCA1 | chloride channel, calcium activated, family member 1 | Seq. ID No. 46 |
| CO | NM_004063 | CDH17 | cadherin 17, LI cadherin (liver-intestine) | Seq. ID No. 48 |
| OV | NM_000906 | NPR1 | natriuretic peptide receptor A/guanylate cyclase A (atrionatriuretic peptide receptor A) | Seq. ID No. 50 |
| OV | NM_005504 | BCAT1 | branched chain aminotransferase 1, cytosolic | Seq. ID No. 52 |
| OV | NM_002398 | MEIS1 | Meis1 (mouse) homolog | Seq. ID No. 53 |
| OV | none | SPON1 | spondin 1, (f-spondin) extracellular matrix protein | Seq. ID No. 69 |
| OV | NM_001692 | None | M25809:Human endomembrane proton pump subunit mRNA \|GenBank==M25809 | Seq. ID No. 54 |
| OV | NM_002774 | KLK6 | kallikrein 6 (neurosin, zyme) | Seq. ID No. 55 |
| LU_A | NM_000964 | ASAHL | N-acylsphingosine amidohydrolase (acid ceramidase)-like | Seq. ID No. 56 |
| LU_A | NM_002838 | PTPRC | protein tyrosine phosphatase, receptor type, C | Seq. ID No. 58 |
| LU_A | NM_015364 | MD-2 | MD-2 protein | Seq. ID No. 59 |
| LU_A | NM_006875 | PIM2 | pim-2 oncogene | Seq. ID No. 60 |
| LU_S | NM_005554 | KRT6A | keratin 6A | Seq. ID No. 61 |
| LU_S | NM_000673 | ADH7 | alcohol dehydrogenase 7 (class IV), mu or sigma polypeptide | Seq. ID No. 62 |
| LU_S | NM_003722 | TP63 | tumor protein 63 kDa with strong homology to p53 | Seq. ID No. 64 |
| LU_S | none | SOX2 | SRY (sex determining region Y)-box 2 | Seq. ID No. 32 |
| LU_S | NM_005688 | ABCC5 | ATP-binding cassette, sub-family C (CFTR/MRP), member 5 | Seq. ID No. 66 |

Example 3

Prognostic Portfolios

A patient sample set with known clinical outcomes was used to test the portfolio selection method of the invention. The sample set is described in van't Veer, L. J et al. Gene Expression Profiling Predicts Clinical Outcome of Breast Cancer, *Nature,* 415, 530-536, (2002), incorporated herein by reference. In that study, breast tissue samples were obtained from 78 patients exhibiting sporadic breast tumors. The patients were all less than 55 years of age and presented with a tumor less than 5cm. All were lymph node negative. Thirty four of the patients presented with distant metastases in less than 5 years while 44 showed no distant metastases in the same period.

Sample preparation and expression profiling are described in the reference. A prognostic marker portfolio of 70 genes was selected from consideration of about 5,000 genes differentially expressed in patients with different prognoses (metastasis v. no metastasis). The selection was made based on unsupervised clustering followed by a correlation coefficient analysis. This was done by calculating the correlation coefficient of the expression of each gene with disease outcome. Those significantly associated with disease by this analysis were then rank ordered with successive groups of five compared using the "leave-one-out" method until an "optimized" panel of 70 genes was selected.

The data from the study were then processed according to the method of the invention. Sample number 54 was removed from further analysis due to a high percentage of missing values. The mean and standard deviation of the intensity measurements for each gene were calculated using the non-metastatic samples as the baseline. A discriminating value of X*(Standard Deviation+Mean) was then calculated for each baseline gene ( X was assigned a value of 3). This value was used to ensure the resulting portfolio would be stringent. A ratio of the discriminating value to the baseline value was then calculated for each metastatic sample. This ratio was then converted to a common logarithm. This data was then imported into Wagner Software which produced an efficient frontier from which a portfolio of 16 genes was selected. The baseline and experimental values were then reversed and a second portfolio of 12 markers representing genes up-regulated in the non-metastatic cases was produced. The second portfolio's value is subtracted from the first portfolios value to create a combined portfolio value from all 28 genes. This final portfolio is comprised of genes from Seq. ID No.70 -97. 17 of the genes of this portfolio were also present in the 70 gene portfolio described in the reference. The genes of the portfolio are identified below. (Seq. ID No. 70, Seq. ID No. 72, Seq. ID No. 73-77, Seq. ID No. 79, Seq. ID No. 80, Seq. ID No.85, Seq. ID No.87, Seq. ID No.91-93, Seq. ID No.95 and Seq. ID. No.97.)

28 Gene list (2 Portfolios)

Up in Metastatic Patients (Portfolio 1)

| | |
|---|---|
| Contig53226_RC | Seq. ID No. 89 |
| NM_012214 | Seq. ID No. 82 |

-continued

| | |
|---|---|
| NM_020386 | Seq. ID No. 86 |
| NM_004504 | Seq. ID No. 81 |
| AA555029_RC | Seq. ID No. 70 |
| AL080059 | Seq. ID No. 74 |
| AF055033 | Seq. ID No. 73 |
| NM_016448 | Seq. ID No. 85 |
| Contig40831_RC | Seq. ID No. 95 |
| Contig63649_RC | Seq. ID No. 91 |
| Contig24252_RC | Seq. ID No. 93 |
| NM_000436 | Seq. ID No. 75 |
| NM_002019 | Seq. ID No. 77 |
| Contig55313_RC | Seq. ID No. 90 |
| Contig25991 | Seq. ID No. 97 |
| NM_000788 | Seq. ID No. 76 |
| Up in Non-Metastatic Patients (Portfolio 2) AB033007 | Seq. ID No. 71 |
| Contig42421_RC | Seq. ID No. 96 |
| NM_003748 | Seq. ID No. 78 |
| NM_013262 | Seq. ID No. 83 |
| NM_003862 | Seq. ID No. 79 |
| NM_003882 | Seq. ID No. 80 |
| Contig48328_RC | Seq. ID No. 87 |
| NM_015416 | Seq. ID No. 84 |
| AB037863 | Seq. ID No. 72 |
| Contig27312_RC | Seq. ID No. 88 |
| Contig32125_RC | Seq. ID No. 92 |
| Contig49670_RC | Seq. ID No. 94 |

17 Overlap

| Systematic name | |
|---|---|
| NM_003862 | Seq. ID No. 79 |
| NM_003882 | Seq. ID No. 80 |
| Contig48328_RC | Seq. ID No. 87 |
| AA555029_RC | Seq. ID No. 70 |
| AL080059 | Seq. ID No. 74 |
| AF055033 | Seq. ID No. 73 |
| AF055033 | Seq. ID No. 73 |
| NM_016448 | Seq. ID No. 85 |
| AB037863 | Seq. ID No. 72 |
| Contig40831_RO | Seq. ID No. 95 |

-continued

| Systematic name | |
|---|---|
| Contig63649_RC | Seq. ID No. 91 |
| Contig24252_RC | Seq. ID No. 93 |
| NM_000436 | Seq. ID No. 75 |
| NM_002019 | Seq. ID No. 77 |
| Contig32125_RC | Seq. ID No. 92 |
| Contig25991 | Seq. ID No. 97 |
| NM_000788 | Seq. ID No. 76 |

The two portfolios were then used to determine the prognosis of the 78 original samples by comparing gene expression signatures from the microarray data according to the method for testing the classification accuracy described in the reference. In the case of the 70 gene portfolio, 81% of the samples were properly characterized according to an optimized threshold biased to include ambiguous signatures as indicative of poor prognosis (85% for an absolute threshold). This portfolio misclassified 3 patients with a poor prognosis as having a good prognosis using the optimized threshold (5 for the absolute threshold). Twelve patients with a good prognosis were misclassified as having a good prognosis when they had a bad prognosis using the optimized threshold (8 for absolute).

In the case of the 28 gene portfolio, 94% of the samples were properly characterized according to an optimized threshold biased to include ambiguous signatures as indicative of poor prognosis (93% for an absolute threshold). This portfolio misclassified 3 patients with a poor prognosis as having a good prognosis using the optimized threshold (5 for the absolute threshold). Three patients with a good prognosis were misclassified as having a good prognosis when they had a bad prognosis using the optimized threshold (2 for absolute).

Comparing the two profiles, it is apparent that the profiles selected according to the method of the invention are much more economical and produce results that are more accurate and reliable than those of the comparative portfolio.

I claim:

1. A method of prognosticating metastasis in a human breast cancer patient comprising obtaining a breast tissue sample from said patient; determining the expression in said sample of Seq. ID Nos. 70-97; and providing a prognosis that the patient will likely have metastasis if the expression of Seq. ID Nos. 70, 73, 74, 75, 76, 77, 81, 82, 85, 86, 89, 90, 91, 93, 95, and 97 is up-regulated and providing a prognosis that the patient will not likely have metastasis if the expression of Seq. ID Nos. 71, 72, 78, 79, 80, 83, 84, 87, 88, 92, 94, and 96 is up-regulated; wherein up-regulation is relative to a baseline of the measured expression of a normal cell and wherein expression in both the breast tissue sample and normal cell are determined using the same measurement method.

2. The method of claim 1 wherein there is at least a 2-fold difference in the expression of up-regulated Seq. ID Nos. in the breast tissue sample relative to the normal cell.

* * * * *

SEQUENCE LISTING

```
<160> NUMBER OF SEQ ID NOS: 100

<210> SEQ ID NO 1
<211> LENGTH: 1466
<212> TYPE: DNA
<213> ORGANISM: human

<400> SEQUENCE: 1

agccccaagc ttaccacctg cacccggaga gctgtgtgtc accatgtggg tcccggttgt     60

cttcctcacc ctgtccgtga cgtggattgg tgctgcaccc ctcatcctgt ctcggattgt    120

gggaggctgg gagtgcgaga agcattccca accctggcag gtgcttgtgg cctctcgtgg    180

cagggcagtc tgcggcggtg ttctggtgca cccccagtgg gtcctcacag ctgcccactg    240

catcaggaac aaaagcgtga tcttgctggg tcggcacagc ctgtttcatc ctgaagacac    300

aggccaggta tttcaggtca gccacagctt cccacacccg ctctacgata tgagcctcct    360

gaagaatcga ttcctcaggc caggtgatga ctccagccac gacctcatgc tgctccgcct    420

gtcagagcct gccgagctca cggatgctgt gaaggtcatg gacctgccca cccaggagcc    480
```

-continued

```
agcactgggg accacctgct acgcctcagg ctggggcagc attgaaccag aggagttctt    540
gaccccaaag aaacttcagt gtgtggacct ccatgttatt tccaatgacg tgtgtgcgca    600
agttcaccct cagaaggtga ccaagttcat gctgtgtgct ggacgctgga caggggcaa    660
aagcacctgc tcgggtgatt ctgggggccc acttgtctgt aatggtgtgc ttcaaggtat    720
cacgtcatgg ggcagtgaac catgtgccct gcccgaaagg ccttccctgt acaccaaggt    780
ggtgcattac cggaagtgga tcaaggacac catcgtggcc aacccctgag cacccctatc    840
aacccctat tgtagtaaac ttggaacctt ggaaatgacc aggccaagac tcaagcctcc    900
ccagttctac tgacctttgt ccttaggtgt gaggtccagg gttgctagga aaagaaatca    960
gcagacacag gtgtagacca gagtgtttct taaatggtgt aattttgtcc tctctgtgtc   1020
ctggggaata ctggccatgc ctggagacat atcactcaat ttctctgagg acacagatag   1080
gatggggtgt ctgtgttatt tgtggggtac agagatgaaa gaggggtggg atccacactg   1140
agagagtgga gagtgacatg tgctggacac tgtccatgaa gcactgagca gaagctggag   1200
gcacaacgca ccagacactc acagcaagga tggagctgaa aacataaccc actctgtcct   1260
ggaggcactg ggaagcctag agaaggctgt gagccaagga gggagggtct tcctttggca   1320
tgggatgggg atgaagtaag gagagggact ggaccccctg gaagctgatt cactatgggg   1380
ggaggtgtat tgaagtcctc cagacaaccc tcagatttga tgatttccta gtagaactca   1440
cagaaataaa gagctgttat actgtg                                        1466

<210> SEQ ID NO 2
<211> LENGTH: 786
<212> TYPE: DNA
<213> ORGANISM: human

<400> SEQUENCE: 2

atgtgggacc tggttctctc catcgccttg tctgtggggt gcactggtgc cgtgcccctc      60
atccagtctc ggattgtggg aggctgggag tgtgagaagc attcccaacc ctggcaggtg    120
gctgtgtaca gtcatggatg ggcacactgt gggggtgtcc tggtgcaccc ccagtgggtg    180
ctcacagctg cccattgcct aaagaagaat agccaggtct ggctgggtcg gcacaacctg    240
tttgagcctg aagacacagg ccagagggtc cctgtcagcc acagcttccc acacccgctc    300
tacaatatga gccttctgaa gcatcaaagc cttagaccag atgaagactc cagccatgac    360
ctcatgctgc tccgcctgtc agagcctgcc aagatcacag atgttgtgaa ggtcctgggc    420
ctgcccaccc aggagccagc actggggacc acctgctacg cctcaggctg gggcagcatc    480
gaaccagagg agttcttgcg ccccaggagt cttcagtgtg tgagcctcca tctcctgtcc    540
aatgacatgt gtgctagagc ttactctgag aaggtgacag agttcatgtt gtgtgctggg    600
ctctggacag gtggtaaaga cacttgtggg ggtgattctg gggggtccact tgtctgtaat    660
ggggtgcttc aaggtatcac atcatggggc cctgagccat gtgccctgcc tgaaaagcct    720
gctgtgtaca ccaaggtggt gcattaccgg aagtggatca aggacaccat cgcagccaac    780
ccctga                                                               786

<210> SEQ ID NO 3
<211> LENGTH: 503
<212> TYPE: DNA
<213> ORGANISM: human

<400> SEQUENCE: 3
```

-continued

```
gacagcggct tccttgatcc ttgccacccg cgactgaaca ccgacagcag cagcctcacc     60

atgaagttgc tgatggtcct catgctggcg gccctctccc agcactgcta cgcaggctct    120

ggctgcccct tattggagaa tgtgatttcc aagacaatca atccacaagt gtctaagact    180

gaatacaaag aacttcttca agagttcata gacgacaatg ccactacaaa tgccatagat    240

gaattgaagg aatgttttct taaccaaacg gatgaaactc tgagcaatgt tgaggtgttt    300

atgcaattaa tatatgacag cagtctttgt gatttatttt aactttctgc aagacctttg    360

gctcacagaa ctgcagggta tggtgagaaa ccaactacgg attgctgcaa accacacctt    420

ctctttctta tgtcttttta ctacaaacta caagacaatt gttgaaacct gctatacatg    480

tttattttaa taaattgatg gca                                            503
```

```
<210> SEQ ID NO 4
<211> LENGTH: 2560
<212> TYPE: DNA
<213> ORGANISM: human

<400> SEQUENCE: 4

gaattccggc cagaagaaat ctggcctcgg aacacgccat tctccgcgcc gcttccaata     60

accactaaca tccctaacga gcatccgagc cgagggctct gctcggaaat cgtcctggcc    120

caactcggcc cttcgagctc tcgaagatta ccgcatctat tttttttttc tttttttttct   180

tttcctagcg cagataaagt gagcccggaa agggaaggag ggggcgggga caccattgcc    240

ctgaaagaat aaataagtaa ataaacaaac tggctcctcg ccgcagctgg acgcggtcgg    300

ttgagtccag gttgggtcgg acctgaaccc ctaaaagcgg aaccgcctcc cgccctcgcc    360

atcccggagc tgagtcgccg gcggcggtgg ctgctgccag acccggagtt tcctctttca    420

ctggatggag ctgaactttg ggcggccaga gcagcacagc tgtccgggga tcgctgcacg    480

ctgagctccc tcggcaagac ccagcggcgg ctcgggattt ttttgggggg gcggggacca    540

gccccgcgcc ggcaccatgt tcctggcgac cctgtacttc gcgctgccgc tcttggactt    600

gctcctgtcg gccgaagtga gcggcggaga ccgcctggat tgcgtgaaag ccagtgatca    660

gtgcctgaag gagcagagct gcagcaccaa gtaccgcacg ctaaggcagt gcgtggcggg    720

caaggagacc aacttcagcc tggcatccgg cctggaggcc aaggatgagt gccgcagcgc    780

catggaggcc ctgaagcaga agtcgctcta caactgccgc tgcaagcggg gtatgaagaa    840

ggagaagaac tgcctgcgca tttactggag catgtaccag agcctgcagg gaaatgatct    900

gctggaggat tccccatatg aaccagttaa cagcagattg tcagatatat tccgggtggt    960

cccattcata tcagatgttt ttcagcaagt ggagcacatt cccaaaggga acaactgcct   1020

ggatgcagcg aaggcctgca acctcgacga catttgcaag aagtacaggt cggcgtacat   1080

caccccgtgc accaccagcg tgtccaacga tgtctgcaac cgccgcaagt gccacaaggc   1140

cctccggcag ttctttgaca aggtcccggc caagcacagc tacggaatgc tcttctgctc   1200

ctgccgggac atcgcctgca cagagcggag gcgacagacc atcgtgcctg tgtgctccta   1260

tgaagagagg gagaagccca actgtttgaa tttgcaggac tcctgcaaga cgaattacat   1320

ctgcagatct cgccttgcgg attttttttac caactgccag ccagagtcaa ggtctgtcag  1380

cagctgtcta aaggaaaact acgctgactg cctcctcgcc tactcggggc ttattggcac   1440

agtcatgacc cccaactaca tagactccag tagcctcagt gtggccccat ggtgtgactg   1500

cagcaacagt gggaacgacc tagaagagtg cttgaaattt ttgaatttct tcaaggacaa   1560

tacatgtctt aaaaatgcaa ttcaagcctt tggcaatggc tccgatgtga ccgtgtggca   1620
```

```
gccagccttc ccagtacaga ccaccactgc cactaccacc actgccctcc gggttaagaa   1680

caagcccctg gggccagcag ggtctgagaa tgaaattccc actcatgttt tgccaccgtg   1740

tgcaaattta caggcacaga agctgaaatc caatgtgtcg ggcaatacac acctctgtat   1800

ttccaatggt aattatgaaa aagaaggtct cggtgcttcc agccacataa ccacaaaatc   1860

aatggctgct cctccaagct gtggtctgag cccactgctg gtcctggtgg taaccgctct   1920

gtccacccta ttatctttaa cagaaacatc atagctgcat taaaaaaata caatatggac   1980

atgtaaaaag acaaaaacca agttatctgt ttcctgttct cttgtatagc tgaaattcca   2040

gtttaggagc tcagttgaga aacagttcca ttcaactgga acattttttt ttttcctttt   2100

aagaaagctt cttgtgatcc ttcggggctt ctgtgaaaaa cctgatgcag tgctccatcc   2160

aaactcagaa ggctttggga tatgctgtat tttaaaggga cagtttgtaa cttgggctgt   2220

aaagcaaact ggggctgtgt tttcgatgat gatgatcatc atgatcatga tgattttaac   2280

agttttactt ctggcctttc ctagctagag aaggagttaa tatttctaag gtaactccca   2340

tatctccttt aatgacattg atttctaatg atataaattt cagcctacat tgatgccaag   2400

ctttttttgcc acaaagaaga ttcttaccaa gagtgggctt tgtggaaaca gctggtactg   2460

atgttcacct ttatatatgt actagcattt tccacgctga tgtttatgta ctgtaaacag   2520

ttctgcactc ttgtacaaaa gaaaaaacca cccggaattc                         2560


<210> SEQ ID NO 5
<211> LENGTH: 2560
<212> TYPE: DNA
<213> ORGANISM: human

<400> SEQUENCE: 5

gaattccggc cagaagaaat ctggcctcgg aacacgccat tctccgcgcc gcttccaata     60

accactaaca tccctaacga gcatccgagc cgagggctct gctcggaaat cgtcctggcc    120

caactcggcc cttcgagctc tcgaagatta ccgcatctat ttttttttc tttttttct      180

tttcctagcg cagataaagt gagcccggaa agggaaggag ggggcgggga caccattgcc    240

ctgaaagaat aaataagtaa ataaacaaac tggctcctcg ccgcagctgg acgcggtcgg    300

ttgagtccag gttgggtcgg acctgaaccc ctaaaagcgg aaccgcctcc cgccctcgcc    360

atcccggagc tgagtcgccg gcggcggtgg ctgctgccag acccggagtt tcctctttca    420

ctggatggag ctgaactttg ggcggccaga gcagcacagc tgtccgggga tcgctgcacg    480

ctgagctccc tcggcaagac ccagcggcgg ctcgggattt ttttgggggg gcggggacca    540

gccccgcgcc ggcaccatgt tcctggcgac cctgtacttc gcgctgccgc tcttggactt    600

gctcctgtcg gccgaagtga gcggcggaga ccgcctggat tgcgtgaaag ccagtgatca    660

gtgcctgaag gagcagagct gcagcaccaa gtaccgcacg ctaaggcagt gcgtggcggg    720

caaggagacc aacttcagcc tggcatccgg cctggaggcc aaggatgagt gccgcagcgc    780

catggaggcc ctgaagcaga agtcgctcta caactgccgc tgcaagcggg gtatgaagaa    840

ggagaagaac tgcctgcgca tttactggag catgtaccag agcctgcagg gaaatgatct    900

gctggaggat tccccatatg aaccagttaa cagcagattg tcagatatat tccgggtggt    960

cccattcata tcagatgttt ttcagcaagt ggagcacatt cccaaaggga acaactgcct   1020

ggatgcagcg aaggcctgca acctcgacga catttgcaag aagtacaggt cggcgtacat   1080

caccccgtgc accaccagcg tgtccaacga tgtctgcaac cgccgcaagt gccacaaggc   1140
```

-continued

```
cctccggcag ttctttgaca aggtcccggc caagcacagc tacggaatgc tcttctgctc   1200

ctgccgggac atcgcctgca cagagcggag gcgacagacc atcgtgcctg tgtgctccta   1260

tgaagagagg gagaagccca actgtttgaa tttgcaggac tcctgcaaga cgaattacat   1320

ctgcagatct cgccttgcgg attttttac caactgccag ccagagtcaa ggtctgtcag   1380

cagctgtcta aaggaaaact acgctgactg cctcctcgcc tactcggggc ttattggcac   1440

agtcatgacc cccaactaca tagactccag tagcctcagt gtggccccat ggtgtgactg   1500

cagcaacagt gggaacgacc tagaagagtg cttgaaattt ttgaatttct tcaaggacaa   1560

tacatgtctt aaaaatgcaa ttcaagcctt tggcaatggc tccgatgtga ccgtgtggca   1620

gccagccttc ccagtacaga ccaccactgc cactaccacc actgccctcc gggttaagaa   1680

caagcccctg ggccagcag ggtctgagaa tgaaattccc actcatgttt tgccaccgtg   1740

tgcaaattta caggcacaga agctgaaatc caatgtgtcg ggcaatacac acctctgtat   1800

ttccaatggt aattatgaaa aagaaggtct cggtgcttcc agccacataa ccacaaaatc   1860

aatggctgct cctccaagct gtggtctgag cccactgctg gtcctggtgg taaccgctct   1920

gtccacccta ttatctttaa cagaaacatc atagctgcat taaaaaaata caatatggac   1980

atgtaaaaag acaaaaacca agttatctgt ttcctgttct cttgtatagc tgaaattcca   2040

gtttaggagc tcagttgaga aacagttcca ttcaactgga acattttttt ttttcctttt   2100

aagaaagctt cttgtgatcc ttcggggctt ctgtgaaaaa cctgatgcag tgctccatcc   2160

aaactcagaa ggctttggga tatgctgtat tttaaaggga cagtttgtaa cttgggctgt   2220

aaagcaaact ggggctgtgt tttcgatgat gatgatcatc atgatcatga tgattttaac   2280

agttttactt ctggcctttc ctagctagag aaggagttaa tatttctaag gtaactccca   2340

tatctccttt aatgacattg atttctaatg atataaattt cagcctacat tgatgccaag   2400

ctttttttgcc acaaagaaga ttcttaccaa gagtgggctt tgtggaaaca gctggtactg   2460

atgttcacct ttatatatgt actagcattt tccacgctga tgtttatgta ctgtaaacag   2520

ttctgcactc ttgtacaaaa gaaaaaacca cccggaattc                         2560
```

<210> SEQ ID NO 6
<211> LENGTH: 2439
<212> TYPE: DNA
<213> ORGANISM: human

<400> SEQUENCE: 6

```
cagcacccag ctccccgcca ccgccatggt ccccgacacc gcctgcgttc ttctgctcac     60

cctggctgcc ctcggcgcgt ccggacaggg ccagagcccg ttgggctcag acctgggccc    120

gcagatgctt cgggaactgc aggaaaccaa cgcggcgctg caggacgtgc gggactggct    180

gcggcagcag gtcagggaga tcacgttcct gaaaaacacg gtgatggagt gtgacgcgtg    240

cgggatgcag cagtcagtac gcaccggcct acccagcgtg cggcccctgc tccactgcgc    300

gcccggcttc tgcttccccg gcgtggcctg catccagacg gagagcggcg gccgctgcgg    360

cccctgcccc gcgggcttca cgggcaacgg ctcgcactgc accgacgtca acgagtgcaa    420

cgcccacccc tgcttccccc gagtccgctg tatcaacacc agcccggggt tccgctgcga    480

ggcttgcccg ccggggtaca gcggccccac ccaccagggc gtggggctgg ctttcgccaa    540

ggccaacaag caggtttgca cggacatcaa cgagtgtgag accgggcaac ataactgcgt    600

ccccaactcc gtgtgcatca acacccgggg ctccttccag tgcggcccgt gccagcccgg    660

cttcgtgggc gaccaggcgt ccggctgcca gcgcggcgca cagcgcttct gccccgacgg    720
```

-continued

```
ctcgcccagc gagtgccacg agcatgcaga ctgcgtccta gagcgcgatg gctcgcggtc    780

gtgcgtgtgt cgcgttggct gggccggcaa cgggatcctc tgtggtcgcg acactgacct    840

agacggcttc ccggacgaga agctgcgctg cccggagccg cagtgccgta aggacaactg    900

cgtgactgtg cccaactcag ggcaggagga tgtggaccgc gatggcatcg gagacgcctg    960

cgatccggat gccgacgggg acggggtccc caatgaaaag gacaactgcc cgctggtgcg   1020

gaacccagac cagcgcaaca cggacgagga caagtggggc gatgcgtgcg acaactgccg   1080

gtcccagaag aacgacgacc aaaaggacac agaccaggac ggccggggcg atgcgtgcga   1140

cgacgacatc gacggcgacc ggatccgcaa ccaggccgac aactgcccta gggtacccaa   1200

ctcagaccag aaggacagtg atggcgatgg tatagggat gcctgtgaca actgtcccca   1260

gaagagcaac ccggatcagg cggatgtgga ccacgacttt gtgggagatg cttgtgacag   1320

cgatcaagac caggatggag acggacatca ggactctcgg gacaactgtc ccacggtgcc   1380

taacagtgcc caggaggact cagaccacga tggccagggt gatgcctgcg acgacgacga   1440

cgacaatgac ggagtccctg acagtcggga caactgccgc ctggtgccta accccggcca   1500

ggaggacgcg gacagggacg gcgtgggcga cgtgtgccag gacgactttg atgcagacaa   1560

ggtggtagac aagatcgacg tgtgtccgga gaacgctgaa gtcacgctca ccgacttcag   1620

ggccttccag acagtcgtgc tggacccgga gggtgacgcg cagattgacc ccaactgggt   1680

ggtgctcaac cagggaaggg agatcgtgca gacaatgaac agcgacccag gcctggctgt   1740

gggttacact gccttcaatg gcgtggactt cgagggcacg ttccatgtga acacggtcac   1800

ggatgacgac tatgcgggct tcatctttgg ctaccaggac agctccagct tctacgtggt   1860

catgtggaag cagatggagc aaacgtattg gcaggcgaac cccttccgtg ctgtggccga   1920

gcctggcatc caactcaagg ctgtgaagtc ttccacaggc cccggggaac agctgcggaa   1980

cgctctgtgg catacaggag acacagagtc ccaggtgcgg ctgctgtgga aggacccgcg   2040

aaacgtgggt tggaaggaca agaagtccta tcgttggttc ctgcagcacc ggccccaagt   2100

gggctacatc agggtgcgat tctatgaggg ccctgagctg gtggccgaca gcaacgtggt   2160

cttggacaca accatgcggg gtggccgcct gggggtcttc tgcttctccc aggagaacat   2220

catctgggcc aacctgcgtt accgctgcaa tgacaccatc ccagaggact atgagaccca   2280

tcagctgcgg caagcctagg gaccagggtg aggacccgcc ggatgacagc caccctcacc   2340

gcggctggat gggggctctg cacccagccc aaggggtggc cgtcctgagg gggaagtgag   2400

aagggctcag agaggacaaa ataaagtgtg tgtgcaggg                          2439
```

```
<210> SEQ ID NO 7
<211> LENGTH: 2439
<212> TYPE: DNA
<213> ORGANISM: human

<400> SEQUENCE: 7

cagcacccag ctccccgcca ccgccatggt ccccgacacc gcctgcgttc ttctgctcac     60

cctggctgcc ctcggcgcgt ccggacaggg ccagagcccg ttgggctcag acctgggccc    120

gcagatgctt cgggaactgc aggaaaccaa cgcggcgctg caggacgtgc gggactggct    180

gcggcagcag gtcagggaga tcacgttcct gaaaaacacg gtgatggagt gtgacgcgtg    240

cgggatgcag cagtcagtac gcaccggcct acccagcgtg cggcccctgc tccactgcgc    300

gcccggcttc tgcttccccg gcgtggcctg catccagacg gagagcggcg gccgctgcgg    360
```

-continued

```
cccctgcccc gcgggcttca cgggcaacgg ctcgcactgc accgacgtca acgagtgcaa    420
cgcccacccc tgcttccccc gagtccgctg tatcaacacc agcccggggt tccgctgcga    480
ggcttgcccg ccggggtaca gcggccccac ccaccagggc gtggggctgg ctttcgccaa    540
ggccaacaag caggtttgca cggacatcaa cgagtgtgag accgggcaac ataactgcgt    600
ccccaactcc gtgtgcatca acacccgggg ctccttccag tgcggcccgt gccagcccgg    660
cttcgtgggc gaccaggcgt ccggctgcca gcgcggcgca cagcgcttct gccccgacgg    720
ctcgcccagc gagtgccacg agcatgcaga ctgcgtccta gagcgcgatg gctcgcggtc    780
gtgcgtgtgt cgcgttggct gggccggcaa cgggatcctc tgtggtcgcg acactgacct    840
agacggcttc ccggacgaga agctgcgctg cccggagccg cagtgccgta aggacaactg    900
cgtgactgtg cccaactcag ggcaggagga tgtggaccgc gatggcatcg gagacgcctg    960
cgatccggat gccgacgggg acggggtccc caatgaaaag gacaactgcc cgctggtgcg   1020
gaacccagac cagcgcaaca cggacgagga caagtggggc gatgcgtgcg acaactgccg   1080
gtcccagaag aacgacgacc aaaaggacac agaccaggac ggccggggcg atgcgtgcga   1140
cgacgacatc gacggcgacc ggatccgcaa ccaggccgac aactgcccta gggtacccaa   1200
ctcagaccag aaggacagtg atggcgatgg tatagggggat gcctgtgaca actgtcccca   1260
gaagagcaac ccggatcagg cggatgtgga ccacgacttt gtgggagatg cttgtgacag   1320
cgatcaagac caggatggag acggacatca ggactctcgg gacaactgtc ccacggtgcc   1380
taacagtgcc caggaggact cagaccacga tggccagggt gatgcctgcg acgacgacga   1440
cgacaatgac ggagtccctg acagtcggga caactgccgc ctggtgccta accccggcca   1500
ggaggacgcg gacagggacg gcgtgggcga cgtgtgccag gacgactttg atgcagacaa   1560
ggtggtagac aagatcgacg tgtgtccgga gaacgctgaa gtcacgctca ccgacttcag   1620
ggccttccag acagtcgtgc tggacccgga gggtgacgcg cagattgacc ccaactgggt   1680
ggtgctcaac cagggaaggg agatcgtgca gacaatgaac agcgacccag gcctggctgt   1740
gggttacact gccttcaatg gcgtggactt cgagggcacg ttccatgtga acacggtcac   1800
ggatgacgac tatgcgggct tcatctttgg ctaccaggac agctccagct tctacgtggt   1860
catgtggaag cagatggagc aaacgtattg gcaggcgaac cccttccgtg ctgtggccga   1920
gcctggcatc caactcaagg ctgtgaagtc ttccacaggc cccggggaac agctgcggaa   1980
cgctctgtgg catacaggag acacagagtc ccaggtgcgg ctgctgtgga aggacccgcg   2040
aaacgtgggt tggaaggaca agaagtccta tcgttggttc ctgcagcacc ggccccaagt   2100
gggctacatc agggtgcgat tctatgaggg ccctgagctg gtggccgaca gcaacgtggt   2160
cttggacaca accatgcggg gtggccgcct gggggtcttc tgcttctccc aggagaacat   2220
catctgggcc aacctgcgtt accgctgcaa tgacaccatc ccagaggact atgagaccca   2280
tcagctgcgg caagcctagg gaccagggtg aggacccgcc ggatgacagc caccctcacc   2340
gcggctggat gggggctctg cacccagccc aaggggtggc cgtcctgagg gggaagtgag   2400
aagggctcag agaggacaaa ataaagtgtg tgtgcaggg                          2439
```

<210> SEQ ID NO 8
<211> LENGTH: 1699
<212> TYPE: DNA
<213> ORGANISM: human

<400> SEQUENCE: 8

```
aggtgagcgg ttgctcgtcg tcggggcggc cggcagcggc ggctccaggg cccagcatgc     60
```

```
gcgggggacc ccgcggccac catgtatgtg ggctatgtgc tggacaagga ttcgcccgtg    120
taccccggcc cagccaggcc agccagcctc ggcctgggcc cggcaaacta cggccccccg    180
gccccgcccc cggcgccccc gcagtacccc gacttctcca gctactctca cgtggagccg    240
gcccccgcgc ccccgacggc ctggggggcg cccttccctg cgcccaagga cgactgggcc    300
gccgcctacg gcccgggccc cgcggcccct gccgccagcc cagcttcgct ggcattcggg    360
ccccctccag actttagccc ggtgccggcg ccccctgggc ccggcccggg cctcctggcg    420
cagcccctcg gggcccgggg cacaccgtcc tcgcccggag cgcagaggcc gacgccctac    480
gagtggatgc ggcgcagcgt ggcggccgga ggcggcggtg gcagcggtaa gactcggacc    540
aaggacaagt accgcgtggt ctacaccgac caccaacgcc tggagctgga gaaggagttt    600
cattacagcc gttacatcac aatccggcgg aaatcagagc tggctgccaa tctggggctc    660
actgaacggc aggtgaagat ctggttccaa aaccggcggg caaaggagcg caaagtgaac    720
aagaagaaac agcagcagca acagccccca cagccgccga tggcccacga catcacggcc    780
accccagccg ggccatccct gggggggcctg tgtcccagca acaccagcct cctggccacc    840
tcctctccaa tgcctgtgaa agaggagttt ctgccatagc cccatgccca gcctgtgcgc    900
cgggggacct ggggactcgg gtgctgggag tgtggctcct gtgggcccag gaggtctggt    960
ccgagtctca gccctgacct tctgggacat ggtggacagt cacctatcca ccctctgcat   1020
ccccttggcc cattgtgtgc agtaagcctg ttggataaag accttccagc tcctgtgttc   1080
tagacctctg gggataaggg gagtccaggg tggatgatct caatctcccg tgggcatctc   1140
aagccccaaa tggttggggg aggggcctag acaaggctcc aggccccacc tcctcctcca   1200
tacgttcaga ggtgcagctg gaggcctgtg tggggaccac actgatcctg gagaaaaggg   1260
atggagctga aaaagatgga atgcttgcag agcatgacct gaggagggag gaacgtggtc   1320
aactcacacc tgcctcttct gcagcctcac ctctacctgc ccccatcata agggcactga   1380
gcccttccca ggctggatac taagcacaaa gcccatagca ctgggctctg atggctgctc   1440
cactgggtta cagaatcaca gccctcatga tcattctcag tgagggctct ggattgagag   1500
ggaggccctg ggaggagaga agggggcaga gtcttcccta ccaggtttct acacccccgc   1560
caggctgccc atcagggccc agggagcccc cagaggactt tattcggacc aagcagagct   1620
cacagctgga caggtgttgt atatagagtg gaatctcttg gatgcagctt caagaataaa   1680
tttttcttct cttttcaaa                                                1699
```

<210> SEQ ID NO 9
<211> LENGTH: 4098
<212> TYPE: DNA
<213> ORGANISM: human

<400> SEQUENCE: 9

```
ggtggcctct gtggccgtcc aggctagcgg cggcccgcag gcggcgggga gaaagactct     60
ctcacctggt cttgcggctg tggccaccgc cggccagggg tgtggagggc gtgctgccgg    120
agacgtccgc cgggctctgc agttccgccg ggggtcgggc agctatggag ccgcggccca    180
cggcgccctc ctccggcgcc ccgggactgg ccggggtcgg ggagacgccg tcagccgctg    240
cgctggccgc agccagggtg gaactgcccg gcacggctgt gccctcggtg ccggaggatg    300
ctgcgcccgc gagccgggac ggcggcgggg tccgcgatga gggccccgcg gcggccgggg    360
acgggctggg cagacccttg ggcccaccc  cgagccagag ccgtttccag gtggacctgg    420
```

-continued

```
tttccgagaa cgccgggcgg gccgctgctg cggcggcggc ggcggcggcg gcagcggcgg    480
cggctggtgc tggggcgggg gccaagcaga cccccgcgga cggggaagcc agcggcgaga    540
gcgagccagc taaaggcagc gaggaagcca agggccgctt ccgcgtgaac ttcgtggacc    600
cagctgcctc ctcgtcggct gaagacagcc tgtcagatgc tgccggggtc ggagtcgacg    660
ggcccaacgt gagcttccag aacggcgggg acacggtgct gagcgagggc agcagcctgc    720
actccggcgg cggcggcggc agtgggcacc accagcacta ctattatgat acccacacca    780
acacctacta cctgcgcacc ttcggccaca acaccatgga cgctgtgccc aggatcgatc    840
actaccggca cacagccgcg cagctgggcg agaagctgct ccggcctagc ctggcggagc    900
tccacgacga gctggaaaag gaaccttttg aggatggctt tgcaaatggg gaagaaagta    960
ctccaaccag agatgctgtg gtcacgtata ctgcagaaag taaaggagtc gtgaagtttg   1020
gctggatcaa gggtgtatta gtacgttgta tgttaaacat ttggggtgtg atgcttttca   1080
ttagattgtc atggattgtg ggtcaagctg gaataggtct atcagtcctt gtaataatga   1140
tggccactgt tgtgacaact atcacaggat tgtctacttc agcaatagca actaatggat   1200
ttgtaagagg aggaggagca tattatttaa tatctagaag tctagggcca gaatttggtg   1260
gtgcaattgg tctaatcttc gcctttgcca acgctgttgc agttgctatg tatgtggttg   1320
gatttgcaga aaccgtggtg gagttgctta aggaacattc catacttatg atagatgaaa   1380
tcaatgatat ccgaattatt ggagccatta cagtcgtgat tcttttaggt atctcagtag   1440
ctggaatgga gtgggaagca aaagctcaga ttgttctttt ggtgatccta cttcttgcta   1500
ttggtgattt cgtcatagga acatttatcc cactggagag caagaagcca aaagggtttt   1560
ttggttataa atctgaaata tttaatgaga actttgggcc cgattttcga gaggaagaga   1620
ctttcttttc tgtatttgcc atctttttttc ctgctgcaac tggtattctg gctggagcaa   1680
atatctcagg tgatcttgca gatcctcagt cagccatacc caaaggaaca ctcctagcca   1740
ttttaattac tacattggtt tacgtaggaa ttgcagtatc tgtaggttct tgtgttgttc   1800
gagatgccac tggaaacgtt aatgacacta tcgtaacaga gctaacaaac tgtacttctg   1860
cagcctgcaa attaaacttt gatttttcat cttgtgaaag cagtccttgt tcctatggcc   1920
taatgaacaa cttccaggta atgagtatgg tgtcaggatt tacaccacta atttctgcag   1980
gtatattttc agccactctt tcttcagcat tagcatccct agtgagtgct cccaaaatat   2040
ttcaggctct atgtaaggac aacatctacc cagctttcca gatgtttgct aaaggttatg   2100
ggaaaaataa tgaacctctt cgtggctaca tcttaacatt cttaattgca cttggattca   2160
tcttaattgc tgaactgaat gttattgcac caattatctc aaacttcttc cttgcatcat   2220
atgcattgat caatttttca gtattccatg catcacttgc aaaatctcca ggatggcgtc   2280
ctgcattcaa atactacaac atgtggatat cacttcttgg agcaattctt tgttgcatag   2340
taatgttcgt cattaactgg tgggctgcat tgctaacata tgtgatagtc cttgggctgt   2400
atatttatgt tacctacaaa aaaccagatg tgaattgggg atcctctaca caagccctga   2460
cttacctgaa tgcactgcag cattcaattc gtctttctgg agtggaagac cacgtgaaaa   2520
actttaggcc acagtgtctt gttatgacag gtgctccaaa ctcacgtcca gctttacttc   2580
atcttgttca tgatttcaca aaaaatgttg gtttgatgat ctgtggccat gtacatatgg   2640
gtcctcgaag acaagccatg aaagagatgt ccatcgatca agccaaatat cagcgatggc   2700
ttattaagaa caaaatgaag gcattttatg ctccagtaca tgcagatgac ttgagagaag   2760
gtgcacagta tttgatgcag gctgctggtc ttggtcgtat gaagccaaac acacttgtcc   2820
```

-continued

```
ttggatttaa gaaagattgg ttgcaagcag atatgaggga tgtggatatg tatataaact   2880

tatttcatga tgcttttgac atacaatatg gagtagtggt tattcgccta aaagaaggtc   2940

tggatatatc tcatcttcaa ggacaagaag aattattgtc atcacaagag aaatctcctg   3000

gcaccaagga tgtggtagta agtgtggaat atagtaaaaa gtccgattta gatacttcca   3060

aaccactcag tgaaaaacca attacacaca aagttgagga agaggatggc aagactgcaa   3120

ctcaaccact gttgaaaaaa gaatccaaag gccctattgt gcctttaaat gtagctgacc   3180

aaaagcttct tgaagctagt acacagtttc agaaaaaaca aggaaagaat actattgatg   3240

tctggtggct tttgatgat ggaggtttga ccttattgat accttacctt ctgacgacca   3300

agaaaaaatg gaaagactgt aagatcagag tattcattgg tggaaagata aacagaatag   3360

accatgaccg gagagcgatg gctactttgc ttagcaagtt ccggatagac ttttctgata   3420

tcatggttct aggagatatc aataccaaac caaagaaaga aaatattata gcttttgagg   3480

aaatcattga gccatacaga cttcatgaag atgataaaga gcaagatatt gcagataaaa   3540

tgaaagaaga tgaaccatgg cgaataacag ataatgagct tgaactttat aagaccaaga   3600

cataccggca gatcaggtta aatgagttat taaaggaaca ttcaagcaca gctaatatta   3660

ttgtcatgag tctcccagtt gcacgaaaag gtgctgtgtc tagtgctctc tacatggcat   3720

ggttagaagc tctatctaag gacctaccac caatcctcct agttcgtggg aatcatcaga   3780

gtgtccttac cttctattca taaatgttct atacagtgga cagccctcca gaatggtact   3840

tcagtgccta gtgtagtaac ctgaaatctt caatgacaca ttaacatcac aatggcgaat   3900

ggtgactttt ctttcacgat ttcattaatt tgaaagcaca caggaaagct tgctccattg   3960

ataacgtgta tggagacttc ggttttagtc aattccatat ctcaatctta atggtgattc   4020

ttctctgttg aactgaagtt tgtgagagta gttttccttt gctacttgaa tagcaataaa   4080

agcgtgttaa ctttttgg                                                 4098
```

```
<210> SEQ ID NO 10
<211> LENGTH: 4098
<212> TYPE: DNA
<213> ORGANISM: human

<400> SEQUENCE: 10

ggtggcctct gtggccgtcc aggctagcgg cggcccgcag gcggcgggga gaaagactct     60

ctcacctggt cttgcggctg tggccaccgc cggccagggg tgtggagggc gtgctgccgg    120

agacgtccgc cgggctctgc agttccgccg ggggtcgggc agctatggag ccgcggccca    180

cggcgccctc ctccggcgcc ccgggactgg ccggggtcgg ggagacgccg tcagccgctg    240

cgctggccgc agccagggtg gaactgcccg gcacggctgt gccctcggtg ccggaggatg    300

ctgcgcccgc gagccgggac ggcggcgggg tccgcgatga gggcccccgcg gcggccgggg    360

acgggctggg cagacccttg ggcccaccc cgagccagag ccgtttccag gtggacctgg    420

tttccgagaa cgccgggcgg gccgctgctg cggcggcggc ggcggcggcg gcagcggcgg    480

cggctggtgc tggggcgggg gccaagcaga cccccgcgga cggggaagcc agcggcgaga    540

gcgagccagc taaaggcagc gaggaagcca agggccgctt ccgcgtgaac ttcgtggacc    600

cagctgcctc ctcgtcggct gaagacagcc tgtcagatgc tgccggggtc ggagtcgacg    660

ggcccaacgt gagcttccag aacggcgggg acacggtgct gagcgagggc agcagcctgc    720

actccggcgg cggcggcggc agtgggcacc accagcacta ctattatgat acccacacca    780
```

-continued

```
acacctacta cctgcgcacc ttcggccaca acaccatgga cgctgtgccc aggatcgatc    840
actaccggca cacagccgcg cagctgggcg agaagctgct ccggcctagc ctggcggagc    900
tccacgacga gctggaaaag gaaccttttg aggatggctt tgcaaatggg gaagaaagta    960
ctccaaccag agatgctgtg gtcacgtata ctgcagaaag taaaggagtc gtgaagtttg   1020
gctggatcaa gggtgtatta gtacgttgta tgttaaacat ttggggtgtg atgcttttca   1080
ttagattgtc atggattgtg ggtcaagctg gaataggtct atcagtcctt gtaataatga   1140
tggccactgt tgtgacaact atcacaggat tgtctacttc agcaatagca actaatggat   1200
ttgtaagagg aggaggagca tattatttaa tatctagaag tctagggcca gaatttggtg   1260
gtgcaattgg tctaatcttc gcctttgcca acgctgttgc agttgctatg tatgtggttg   1320
gatttgcaga aaccgtggtg gagttgctta aggaacattc catacttatg atagatgaaa   1380
tcaatgatat ccgaattatt ggagccatta cagtcgtgat tcttttaggt atctcagtag   1440
ctggaatgga gtgggaagca aaagctcaga ttgttctttt ggtgatccta cttcttgcta   1500
ttggtgattt cgtcatagga acatttatcc cactggagag caagaagcca aaagggtttt   1560
ttggttataa atctgaaata tttaatgaga actttgggcc cgattttcga gaggaagaga   1620
ctttcttttc tgtatttgcc atctttttttc ctgctgcaac tggtattctg gctggagcaa   1680
atatctcagg tgatcttgca gatcctcagt cagccatacc caaaggaaca ctcctagcca   1740
ttttaattac tacattggtt tacgtaggaa ttgcagtatc tgtaggttct tgtgttgttc   1800
gagatgccac tggaaacgtt aatgacacta tcgtaacaga gctaacaaac tgtacttctg   1860
cagcctgcaa attaaacttt gatttttcat cttgtgaaag cagtccttgt tcctatggcc   1920
taatgaacaa cttccaggta atgagtatgg tgtcaggatt tacaccacta atttctgcag   1980
gtatattttc agccactctt tcttcagcat tagcatccct agtgagtgct cccaaaatat   2040
ttcaggctct atgtaaggac aacatctacc cagctttcca gatgtttgct aaaggttatg   2100
ggaaaaataa tgaacctctt cgtggctaca tcttaacatt cttaattgca cttggattca   2160
tcttaattgc tgaactgaat gttattgcac caattatctc aaacttcttc cttgcatcat   2220
atgcattgat caatttttca gtattccatg catcacttgc aaaatctcca ggatggcgtc   2280
ctgcattcaa atactacaac atgtggatat cacttcttgg agcaattctt tgttgcatag   2340
taatgttcgt cattaactgg tgggctgcat tgctaacata tgtgatagtc cttgggctgt   2400
atatttatgt tacctacaaa aaaccagatg tgaattgggg atcctctaca caagccctga   2460
cttacctgaa tgcactgcag cattcaattc gtctttctgg agtggaagac cacgtgaaaa   2520
actttaggcc acagtgtctt gttatgacag gtgctccaaa ctcacgtcca gctttacttc   2580
atcttgttca tgatttcaca aaaaatgttg gtttgatgat ctgtggccat gtacatatgg   2640
gtcctcgaag acaagccatg aaagagatgt ccatcgatca agccaaatat cagcgatggc   2700
ttattaagaa caaaatgaag gcattttatg ctccagtaca tgcagatgac ttgagagaag   2760
gtgcacagta tttgatgcag gctgctggtc ttggtcgtat gaagccaaac acacttgtcc   2820
ttggatttaa gaaagattgg ttgcaagcag atatgaggga tgtggatatg tatataaact   2880
tatttcatga tgcttttgac atacaatatg gagtagtggt tattcgccta aaagaaggtc   2940
tggatatatc tcatcttcaa ggacaagaag aattattgtc atcacaagag aaatctcctg   3000
gcaccaagga tgtggtagta agtgtggaat atagtaaaaa gtccgattta gatacttcca   3060
aaccactcag tgaaaaacca attacacaca aagttgagga agaggatggc aagactgcaa   3120
ctcaaccact gttgaaaaaa gaatccaaag gccctattgt gcctttaaat gtagctgacc   3180
```

-continued

```
aaaagcttct tgaagctagt acacagtttc agaaaaaaca aggaaagaat actattgatg   3240
tctggtggct tttgatgat ggaggtttga ccttattgat accttacctt ctgacgacca   3300
agaaaaaatg gaaagactgt aagatcagag tattcattgg tggaaagata aacagaatag   3360
accatgaccg gagagcgatg gctactttgc ttagcaagtt ccggatagac ttttctgata   3420
tcatggttct aggagatatc aataccaaac caaagaaaga aaatattata gcttttgagg   3480
aaatcattga gccatacaga cttcatgaag atgataaaga gcaagatatt gcagataaaa   3540
tgaaagaaga tgaaccatgg cgaataacag ataatgagct tgaactttat aagaccaaga   3600
cataccggca gatcaggtta aatgagttat taaaggaaca ttcaagcaca gctaatatta   3660
ttgtcatgag tctcccagtt gcacgaaaag gtgctgtgtc tagtgctctc tacatggcat   3720
ggttagaagc tctatctaag gacctaccac caatcctcct agttcgtggg aatcatcaga   3780
gtgtccttac cttctattca taaatgttct atacagtgga cagccctcca gaatggtact   3840
tcagtgccta gtgtagtaac ctgaaatctt caatgacaca ttaacatcac aatggcgaat   3900
ggtgactttt ctttcacgat ttcattaatt tgaaagcaca caggaaagct tgctccattg   3960
ataacgtgta tggagacttc ggttttagtc aattccatat ctcaatctta atggtgattc   4020
ttctctgttg aactgaagtt tgtgagagta gttttccttt gctacttgaa tagcaataaa   4080
agcgtgttaa ctttttgg                                                 4098
```

```
<210> SEQ ID NO 11
<211> LENGTH: 3311
<212> TYPE: DNA
<213> ORGANISM: human

<400> SEQUENCE: 11

tgctaatgct tttggtacaa atggatgtgg aatataattg aatattttct tgtttaaggg     60
gagcatgaag aggtgttgag gttatgtcaa gcatctggca cagctgaagg cagatggaaa    120
tatttacaag tacgcaattt gagactaaga tattgttatc attctcctat tgaagacaag    180
agcaatagta aaacacatca ggtcaggggg ttaaagacct gtgataaacc acttccgata    240
agttggaaac gtgtgtctat attttcatat ctgtatatat ataatggtaa agaaagacac    300
cttcgtaacc cgcattttcc aaagagagga atcacaggga gatgtacagc aatggggcca    360
tttaagagtt ctgtgttcat cttgattctt caccttctag aaggggccct gagtaattca    420
ctcattcagc tgaacaacaa tggctatgaa ggcattgtcg ttgcaatcga ccccaatgtg    480
ccagaagatg aaacactcat tcaacaaata aaggacatgg tgacccaggc atctctgtat    540
ctgtttgaag ctacaggaaa gcgattttat ttcaaaaatg ttgccatttt gattcctgaa    600
acatggaaga caaaggctga ctatgtgaga ccaaaacttg agacctacaa aaatgctgat    660
gttctggttg ctgagtctac tcctccaggt aatgatgaac cctacactga gcagatgggc    720
aactgtggag agaagggtga aaggatccac ctcactcctg atttcattgc aggaaaaaag    780
ttagctgaat atggaccaca aggtaaggca tttgtccatg agtgggctca tctacgatgg    840
ggagtatttg acgagtacaa taatgatgag aaattctact tatccaatgg aagaatacaa    900
gcagtaagat gttcagcagg tattactggt acaaatgtag taaagaagtg tcagggaggc    960
agctgttaca ccaaaagatg cacattcaat aaagttacag gactctatga aaaaggatgt   1020
gagtttgttc tccaatcccg ccagacggag aaggcttcta taatgtttgc acaacatgtt   1080
gattctatag ttgaattctg tacagaacaa aaccacaaca aagaagctcc aaacaagcaa   1140
```

-continued

```
aatcaaaaat gcaatctccg aagcacatgg gaagtgatcc gtgattctga ggactttaag   1200

aaaaccactc ctatgacaac acagccacca aatcccacct tctcattgct gcagattgga   1260

caaagaattg tgtgtttagt ccttgacaaa tctggaagca tggcgactgg taaccgcctc   1320

aatcgactga atcaagcagg ccagcttttc ctgctgcaga cagttgagct ggggtcctgg   1380

gttgggatgg tgacatttga cagtgctgcc catgtacaaa gtgaactcat acagataaac   1440

agtggcagtg acagggacac actcgccaaa agattacctg cagcagcttc aggagggacg   1500

tccatctgca gcgggcttcg atcggcattt actgtgatta ggaagaaata tccaactgat   1560

ggatctgaaa ttgtgctgct gacggatggg gaagacaaca ctataagtgg gtgctttaac   1620

gaggtcaaac aaagtggtgc catcatccac acagtcgctt tggggccctc tgcagctcaa   1680

gaactagagg agctgtccaa aatgacagga ggtttacaga catatgcttc agatcaagtt   1740

cagaacaatg gcctcattga tgcttttggg gccctttcat caggaaatgg agctgtctct   1800

cagcgctcca tccagcttga gagtaaggga ttaaccctcc agaacagcca gtggatgaat   1860

ggcacagtga tcgtggacag caccgtggga aaggacactt tgtttcttat cacctggaca   1920

acgcagcctc cccaaatcct tctctgggat cccagtggac agaagcaagg tggctttgta   1980

gtggacaaaa acaccaaaat ggcctacctc caaatcccag gcattgctaa ggttggcact   2040

tggaaataca gtctgcaagc aagctcacaa accttgaccc tgactgtcac gtcccgtgcg   2100

tccaatgcta ccctgcctcc aattacagtg acttccaaaa cgaacaagga caccagcaaa   2160

ttccccagcc ctctggtagt ttatgcaaat attcgccaag gagcctcccc aattctcagg   2220

gccagtgtca cagccctgat tgaatcagtg aatggaaaaa cagttacctt ggaactactg   2280

gataatggag caggtgctga tgctactaag gatgacggtg tctactcaag gtatttcaca   2340

acttatgaca cgaatggtag atacagtgta aaagtgcggg ctctgggagg agttaacgca   2400

gccagacgga gagtgatacc ccagcagagt ggagcactgt acatacctgg ctggattgag   2460

aatgatgaaa tacaatggaa tccaccaaga cctgaaatta ataaggatga tgttcaacac   2520

aagcaagtgt gtttcagcag aacatcctcg ggaggctcat ttgtggcttc tgatgtccca   2580

aatgctccca tacctgatct cttcccacct ggccaaatca ccgacctgaa ggcggaaatt   2640

cacgggggca gtctcattaa tctgacttgg acagctcctg gggatgatta tgaccatgga   2700

acagctcaca agtatatcat tcgaataagt acaagtattc ttgatctcag agacaagttc   2760

aatgaatctc ttcaagtgaa tactactgct ctcatcccaa aggaagccaa ctctgaggaa   2820

gtctttttgt ttaaaccaga aaacattact tttgaaaatg gcacagatct tttcattgct   2880

attcaggctg ttgataaggt cgatctgaaa tcagaaatat ccaacattgc acgagtatct   2940

ttgtttattc ctccacagac tccgccagag acacctagtc ctgatgaaac gtctgctcct   3000

tgtcctaata ttcatatcaa cagcaccatt cctggcattc acattttaaa aattatgtgg   3060

aagtggatag gagaactgca gctgtcaata gcctagggct gaatttttgt cagataaata   3120

aaataaatca ttcatccttt ttttgattat aaaattttct aaaatgtatt ttagacttcc   3180

tgtagggggc gatatactaa atgtatatag tacatttata ctaaatgtat tcctgtaggg   3240

ggcgatatac taaatgtatt ttagacttcc tgtagggggc gataaaataa aatgctaaac   3300

aactgggtaa a                                                        3311
```

<210> SEQ ID NO 12
<211> LENGTH: 3311
<212> TYPE: DNA
<213> ORGANISM: human

-continued

<400> SEQUENCE: 12

```
tgctaatgct tttggtacaa atggatgtgg aatataattg aatattttct tgtttaaggg     60
gagcatgaag aggtgttgag gttatgtcaa gcatctggca cagctgaagg cagatggaaa    120
tatttacaag tacgcaattt gagactaaga tattgttatc attctcctat tgaagacaag    180
agcaatagta aaacacatca ggtcaggggg ttaaagacct gtgataaacc acttccgata    240
agttggaaac gtgtgtctat attttcatat ctgtatatat ataatggtaa agaaagacac    300
cttcgtaacc cgcattttcc aaagagagga atcacaggga gatgtacagc aatggggcca    360
tttaagagtt ctgtgttcat cttgattctt caccttctag aaggggccct gagtaattca    420
ctcattcagc tgaacaacaa tggctatgaa ggcattgtcg ttgcaatcga ccccaatgtg    480
ccagaagatg aaacactcat tcaacaaata aaggacatgg tgacccaggc atctctgtat    540
ctgtttgaag ctacaggaaa gcgattttat ttcaaaaatg ttgccatttt gattcctgaa    600
acatggaaga caaaggctga ctatgtgaga ccaaaacttg agacctacaa aaatgctgat    660
gttctggttg ctgagtctac tcctccaggt aatgatgaac cctacactga gcagatgggc    720
aactgtggag agaagggtga aaggatccac ctcactcctg atttcattgc aggaaaaaag    780
ttagctgaat atggaccaca aggtaaggca tttgtccatg agtgggctca tctacgatgg    840
ggagtatttg acgagtacaa taatgatgag aaattctact tatccaatgg aagaatacaa    900
gcagtaagat gttcagcagg tattactggt acaaatgtag taaagaagtg tcagggaggc    960
agctgttaca ccaaaagatg cacattcaat aaagttacag gactctatga aaaaggatgt   1020
gagtttgttc tccaatcccg ccagacggag aaggcttcta taatgtttgc acaacatgtt   1080
gattctatag ttgaattctg tacagaacaa aaccacaaca aagaagctcc aaacaagcaa   1140
aatcaaaaat gcaatctccg aagcacatgg gaagtgatcc gtgattctga ggactttaag   1200
aaaaccactc ctatgacaac acagccacca aatcccacct tctcattgct gcagattgga   1260
caaagaattg tgtgtttagt ccttgacaaa tctggaagca tggcgactgg taaccgcctc   1320
aatcgactga atcaagcagg ccagcttttc ctgctgcaga cagttgagct ggggtcctgg   1380
gttgggatgg tgacatttga cagtgctgcc catgtacaaa gtgaactcat acagataaac   1440
agtggcagtg acagggacac actcgccaaa agattacctg cagcagcttc aggagggacg   1500
tccatctgca gcgggcttcg atcggcattt actgtgatta ggaagaaata tccaactgat   1560
ggatctgaaa ttgtgctgct gacggatggg gaagacaaca ctataagtgg gtgctttaac   1620
gaggtcaaac aaagtggtgc catcatccac acagtcgctt tggggccctc tgcagctcaa   1680
gaactagagg agctgtccaa aatgacagga ggtttacaga catatgcttc agatcaagtt   1740
cagaacaatg gcctcattga tgcttttggg gccctttcat caggaaatgg agctgtctct   1800
cagcgctcca tccagcttga gagtaaggga ttaaccctcc agaacagcca gtggatgaat   1860
ggcacagtga tcgtggacag caccgtggga aaggacactt tgtttcttat cacctggaca   1920
acgcagcctc cccaaatcct tctctgggat cccagtggac agaagcaagg tggctttgta   1980
gtggacaaaa acaccaaaat ggcctacctc caaatcccag gcattgctaa ggttggcact   2040
tggaaataca gtctgcaagc aagctcacaa accttgaccc tgactgtcac gtcccgtgcg   2100
tccaatgcta ccctgcctcc aattacagtg acttccaaaa cgaacaagga caccagcaaa   2160
ttccccagcc ctctggtagt ttatgcaaat attcgccaag gagcctcccc aattctcagg   2220
gccagtgtca cagccctgat tgaatcagtg aatggaaaaa cagttacctt ggaactactg   2280
```

-continued

```
gataatggag caggtgctga tgctactaag gatgacggtg tctactcaag gtatttcaca   2340

acttatgaca cgaatggtag atacagtgta aaagtgcggg ctctgggagg agttaacgca   2400

gccagacgga gagtgatacc ccagcagagt ggagcactgt acatacctgg ctggattgag   2460

aatgatgaaa tacaatggaa tccaccaaga cctgaaatta ataaggatga tgttcaacac   2520

aagcaagtgt gtttcagcag aacatcctcg ggaggctcat ttgtggcttc tgatgtccca   2580

aatgctccca tacctgatct cttcccacct ggccaaatca ccgacctgaa ggcggaaatt   2640

cacgggggca gtctcattaa tctgacttgg acagctcctg gggatgatta tgaccatgga   2700

acagctcaca agtatatcat tcgaataagt acaagtattc ttgatctcag agacaagttc   2760

aatgaatctc ttcaagtgaa tactactgct ctcatcccaa aggaagccaa ctctgaggaa   2820

gtctttttgt ttaaaccaga aaacattact tttgaaaatg gcacagatct tttcattgct   2880

attcaggctg ttgataaggt cgatctgaaa tcagaaatat ccaacattgc acgagtatct   2940

ttgtttattc ctccacagac tccgccagag acacctagtc ctgatgaaac gtctgctcct   3000

tgtcctaata ttcatatcaa cagcaccatt cctggcattc acattttaaa aattatgtgg   3060

aagtggatag gagaactgca gctgtcaata gcctagggct gaatttttgt cagataaata   3120

aaataaatca ttcatccttt ttttgattat aaaattttct aaaatgtatt ttagacttcc   3180

tgtagggggc gatatactaa atgtatatag tacatttata ctaaatgtat tcctgtaggg   3240

ggcgatatac taaatgtatt ttagacttcc tgtagggggc gataaaataa aatgctaaac   3300

aactgggtaa a                                                        3311
```

<210> SEQ ID NO 13
<211> LENGTH: 2609
<212> TYPE: DNA
<213> ORGANISM: human
<220> FEATURE:
<221> NAME/KEY: misc_feature
<222> LOCATION: (2025)..(2025)
<223> OTHER INFORMATION: any kind of base
<220> FEATURE:
<221> NAME/KEY: misc_feature
<222> LOCATION: (2036)..(2036)
<223> OTHER INFORMATION: any kind of base
<220> FEATURE:
<221> NAME/KEY: misc_feature
<222> LOCATION: (2164)..(2164)
<223> OTHER INFORMATION: any kind of base
<220> FEATURE:
<221> NAME/KEY: misc_feature
<222> LOCATION: (2264)..(2264)
<223> OTHER INFORMATION: any kind of base

<400> SEQUENCE: 13

```
gctgatagca cagttctgtc cagagaagga aggcggaata aacttattca ttcccaggaa     60

ctcttggggt aggtgtgtgt ttttcacatc ttaaaggctc acagaccctg cgctggacaa    120

atgttccatt cctgaaggac ctctccagaa tccggattgc tgaatcttcc ctgttgccta    180

gaagggctcc aaaccacctc ttgacaatgg gaaactgggt ggttaaccac tggttttcag    240

ttttgtttct ggttgtttgg ttagggctga atgttttcct gtttgtggat gccttcctga    300

aatatgagaa ggccgacaaa tactactaca caagaaaaat ccttgggtca acattggcct    360

gtgcccgagc gtctgctctc tgcttgaatt ttaacagcac gctgatcctg cttcctgtgt    420

gtcgcaatct gctgtccttc ctgaggggca cctgctcatt ttgcagccgc acactgagaa    480

agcaattgga tcacaacctc accttccaca agctggtggc ctatatgatc tgcctacata    540

cagctattca catcattgca cacctgttta actttgactg ctatagcaga agccgacagg    600
```

-continued

```
ccacagatgg ctcccttgcc tccattctct ccagcctatc tcatgatgag aaaaaggggg    660
gttcttggct aaatcccatc cagtcccgaa acacgacagt ggagtatgtg acattcacca    720
gcgttgctgg tctcactgga gtgatcatga caatagcctt gattctcatg gtaacttcag    780
ctactgagtt catccggagg agttattttg aagtcttctg gtatactcac cacctttttta    840
tcttctatat ccttggctta gggattcacg gcattggtgg aattgtccgg ggtcaaacag    900
aggagagcat gaatgagagt catcctcgca agtgtgcaga gtcttttgag atgtgggatg    960
atcgtgactc ccactgtagg cgccctaagt ttgaagggca tccccctgag tcttggaagt   1020
ggatccttgc accggtcatt ctttatatct gtgaaaggat cctccggttt taccgctccc   1080
agcagaaggt tgtgattacc aaggttgtta tgcacccatc caaagttttg gaattgcaga   1140
tgaacaagcg tggcttcagc atggaagtgg ggcagtatat ctttgttaat tgcccctcaa   1200
tctctctcct ggaatggcat ccttttactt tgacctctgc tccagaggaa gatttcttct   1260
ccattcatat ccgagcagca ggggactgga cagaaaatct cataagggct ttcgaacaac   1320
aatattcacc aattcccagg attgaagtgg atggtccctt tggcacagcc agtgaggatg   1380
ttttccagta tgaagtggct gtgctggttg gagcaggaat tggggtcacc ccctttgctt   1440
ctatcttgaa atccatctgg tacaaattcc agtgtgcaga ccacaacctc aaaacaaaaa   1500
agatctattt ctactggatc tgcagggaga caggtgcctt ttcctggttc aacaacctgt   1560
tgacttccct ggaacaggag atggaggaat taggcaaagt gggttttcta aactaccgtc   1620
tcttcctcac cggatgggac agcaatattg ttggtcatgc agcattaaac tttgacaagg   1680
ccactgacat cgtgacaggt ctgaaacaga aaacctcctt tgggagacca atgtgggaca   1740
atgagttttc tacaatagct acctcccacc ccaagtctgt agtgggagtt ttcttatgtg   1800
gccctcggac tttggcaaag agcctgcgca aatgctgtca ccgatattcc agtctggatc   1860
ctagaaaggt tcaattctac ttcaacaaag aaaatttttg agttatagga ataaggacgg   1920
taatctgcat tttgtctctt tgtatcttca gtaattgagt tataggaata aggacggtaa   1980
tctgcatttt gtctctttgt atcttcagta atttacttgg tctcntcagg tttgancagt   2040
cactttagga taagaatgtg cctctcaagc cttgactccc tggtattctt tttttgattg   2100
cattcaactt cgttacttga gcttcagcaa cttaagaact tctgaagttc ttaaagttct   2160
gaanttctta aagcccatgg atcctttctc agaaaaataa ctgtaaatct ttctggacag   2220
ccatgactgt agcaaggctt gatagcagaa gtttggtggt tcanaattat acaactaatc   2280
ccaggtgatt ttatcaattc cagtgttacc atctcctgag ttttggtttg taatcttttg   2340
tccctcccac ccccacagaa gattttaagt agggtgactt tttaaataaa aatttattga   2400
ataattaatg ataaaacata ataataaaca taaataataa acaaaattac cgagaacccc   2460
atccccatat aacaccaaca gtgtacatgt ttactgtcac ttttgatatg gtttatccag   2520
tgtgaacagc aatttattat ttttgctcat caaaaaataa aggatttttt ttcacttgaa   2580
aaaaaaaaaa aaaaaaaaaa aaaaaaaaa                                     2609
```

<210> SEQ ID NO 14
<211> LENGTH: 15720
<212> TYPE: DNA
<213> ORGANISM: human

<400> SEQUENCE: 14

```
caacccacac cgcccctgcc agccaccatg gggctgccac tagcccgcct ggcggctgtg     60
```

-continued

```
tgcctggccc tgtctttggc agggggctcg gagctccaga cagagggcag aacccgatac    120
cacggccgca acgtctgcag cacctggggc aacttccact acaagacctt cgacggggac    180
gtcttccgct tccccggcct ctgcgactac aacttcgcct ccgactgccg aggctcctac    240
aaggaatttg ctgtgcacct gaagcggggt ccgggccagg ctgaggcccc cgccggggtg    300
gagtccatcc tgctgaccat caaggatgac accatctacc tcacccgcca cctggctgtg    360
cttaacgggg ccgtggtcag caccccgcac tacagccccg ggctgctcat tgagaagagc    420
gatgcctaca ccaaagtcta ctcccgcgcc ggcctcaccc tcatgtggaa ccgggaggat    480
gcactcatgc tggagctgga cactaagttc cggaaccaca cctgtggcct ctgcggggac    540
tacaacggcc tgcagagcta ttcagaattc ctctctgacg gcgtgctctt cagtcccctg    600
gagtttggga acatgcagaa gatcaaccag cccgatgtgg tgtgtgagga tcccgaggag    660
gaggtggccc ccgcatcctg ctccgagcac cgcgccgagt gtgagaggct gctgaccgcc    720
gaggccttcg cggactgtca ggacctggtg ccgctggagc cgtatctgcg cgcctgccag    780
caggaccgct gccggtgccc gggcggtgac acctgcgtct gcagcaccgt ggccgagttc    840
tcccgccagt gctcccacgc cggcggccgg cccgggaact ggaggaccgc cacgctctgc    900
cccaagacct gccccgggaa cctggtgtac ctggagagcg gctcgccctg catggacacc    960
tgctcacacc tggaggtgag cagcctgtgc gaggagcacc gcatggacgg ctgtttctgc   1020
ccagaaggca ccgtatatga cgacatcggg gacagtggct gcgttcctgt gagccagtgc   1080
cactgcaggc tgcacggaca cctgtacaca ccgggccagg agatcaccaa tgactgcgag   1140
cagtgtgtct gtaacgctgg ccgctgggtg tgcaaagacc tgccctgccc cggcacctgt   1200
gccctggaag gcggctccca catcaccacc ttcgatggga agacgtacac cttccacggg   1260
gactgctact atgtcctggc caagggtgac cacaacgatt cctacgctct cctgggcgag   1320
ctggcccccct gtggctccac agacaagcag acctgcctga agacggtggt gctgctggct   1380
gacaagaaga agaatgcggt ggtcttcaag tccgatggca gtgtactgct caaccagctg   1440
caggtgaacc tgccccacgt gaccgcgagc ttctctgtct tccgcccgtc ttcctaccac   1500
atcatggtga gcatggccat tggcgtccgg ctgcaggtgc agctggcccc agtcatgcaa   1560
ctctttgtga cactggacca ggcctcccag gggcaggtgc agggcctctg cgggaacttc   1620
aacggcctgg aaggtgacga cttcaagacg gccagcgggc tggtggaggc cacgggggcc   1680
ggctttgcca acacctggaa ggcacagtca acctgccatg acaagctgga ctggttggac   1740
gatccctgct ccctgaacat cgagagcgcc aactacgccg agcactggtg ctccctcctg   1800
aagaagacag agaccccctt tggcaggtgc cactcggctg tggaccctgc tgagtattac   1860
aagaggtgca aatatgacac gtgtaactgt cagaacaatg aggactgcct gtgcgccgcc   1920
ctgtcctcct acgcgcgcgc ctgcaccgcc aagggcgtca tgctgtgggg ctggcgggag   1980
catgtctgca acaaggatgt gggctcctgc cccaactcgc aggtcttcct gtacaacctg   2040
accacctgcc agcagacctg ccgctccctc tccgaggccg acagccactg tctcgagggc   2100
tttgcgcctg tggacggctg cggctgccct gaccacacct tcctggacga gaagggccgc   2160
tgcgtacccc tggccaagtg ctcctgttac caccgcggtc tctacctgga ggcgggggat   2220
gtggtcgtca ggcaggaaga acgatgtgtg tgccgggatg ggcggctgca ctgtaggcag   2280
atccggctga tcggccagag ctgcacggcc ccaaagatcc acatggactg cagcaacctg   2340
actgcactgg ccacctcgaa gccccgagcc ctcagctgcc agacgctggc cgccggctat   2400
taccacacag agtgtgtcag tggctgtgtg tgccccgacg ggctgatgga tgacggccgg   2460
```

-continued

```
ggtggctgcg tggtggagaa ggaatgccct tgcgtccata acaacgacct gtattcttcc   2520
ggcgccaaga tcaaggtgga ctgcaatacc tgcacctgca agagaggacg ctgggtgtgc   2580
acccaggctg tgtgccatgg cacctgctcc atttacggga gtggccacta catcaccttt   2640
gatgggaagt actacgactt tgacggacac tgctcctacg tggctgttca ggactactgc   2700
ggccagaact cctcactggg ctcattcagc atcatcaccg agaacgtccc ctgtggcact   2760
acgggcgtca cctgctccaa ggccatcaag atcttcatgg ggaggacgga gctgaagttg   2820
gaagacaagc accgtgtggt gatccagcgt gatgagggtc accacgtggc ctacaccacg   2880
cgggaggtgg gccagtacct ggtggtggag tccagcacgg gcatcatcgt catctgggac   2940
aagaggacca ccgtgttcat caagctggct ccctcctaca agggcaccgt gtgtggcctg   3000
tgtgggaact ttgaccaccg ctccaacaac gacttcacca cgcgggacca catggtggtg   3060
agcagcgagc tggacttcgg gaacagctgg aaggaggccc ccacctgccc agatgtgagc   3120
accaaccccg agccctgcag cctgaacccg caccgccgct cctgggccga gaagcagtgc   3180
agcatcctca aaagcagcgt gttcagcatc tgccacagca aggtggaccc caagcccttc   3240
tacgaggcct gtgtgcacga ctcgtgctcc tgtgacacgg gtggggactg tgagtgcttc   3300
tgctctgccg tggcctccta cgcccaggag tgtaccaaag agggggcctg cgtgttctgg   3360
aggacgccgg acctgtgccc catattctgc gactactaca accctccgca tgagtgtgag   3420
tggcactatg agccatgtgg gaaccggagc ttcgagacct gcaggaccat caacggcatc   3480
cactccaaca tctccgtgtc ctacctggag ggctgctacc cccggtgccc caaggacagg   3540
cccatctatg aggaggatct gaagaagtgt gtcactgcag acaagtgtgg ctgctatgtc   3600
gaggacaccc actacccacc tggagcatcg gttcccaccg aggagacctg caagtcctgc   3660
gtgtgtacca actcctccca agtcgtctgc aggccggagg aaggaaagat tcttaaccag   3720
acccaggatg gcgccttctg ctactgggag atctgtggcc ccaacgggac ggtggagaag   3780
cacttcaaca tctgttccat tacgacacgc ccgtccaccc tgaccacctt caccaccatc   3840
accctcccca ccaccccccac ctccttcacc actaccacca ccaccaccac cccgacctcc   3900
agcacagttt tatcaacaac tccgaagctg tgctgcctct ggtctgactg gatcaatgag   3960
gaccacccca gcagtggcag cgacgacggt gaccgagaac catttgatgg ggtctgcggg   4020
gcccctgagg acatcgagtg caggtcggtc aaggatcccc acctcagctt ggagcagcat   4080
ggccagaagg tgcagtgtga tgtctctgtt gggttcattt gcaagaatga agaccagttt   4140
ggaaatggac catttggact gtgttacgac tacaagatac gtgtcaattg ttgctggccc   4200
atggataagt gtatcaccac tcccagccct ccaactacca ctcccagccc tccaccaacc   4260
acgacgacca cccttccacc aaccaccacc cccagccctc caaccaccac cacaaccacc   4320
cctccaccaa ccaccacccc cagccctcca ataaccacca cgaccacccc tctaccaacc   4380
accactccca gccctccaat aagcaccaca accacccctc caccaaccac cactcccagc   4440
cctccaacca ccactcccag ccctccaacc accactccca gccctccaac aaccaccaca   4500
accacccctc caccaaccac cactcccagc cctccaatga ctacgcccat cactccacca   4560
gccagcacta ccacccttcc accaaccacc actcccagcc ctccaacaac caccacaacc   4620
acccctccac caaccaccac tcccagtcct ccaacgacta cgcccatcac tccaccaacc   4680
agcactacta cccttccacc aaccaccact cccagccctc caccaaccac cacaaccacc   4740
cctccaccaa ccaccactcc cagccctcca acaaccacca ctcccagtcc tccaacaatc   4800
```

-continued

```
accacaacca cccctccacc aaccaccact cccagccctc caacaacgac cacaaccacc   4860
cctccaccaa ccaccactcc cagccctcca acgactacac ccatcactcc accaaccagc   4920
actaccaccc ttccaccaac caccactccc agccctccac caaccaccac aaccacccct   4980
ccaccaacca ccactcccag ccctccaaca accaccactc ccagccctcc aataaccacc   5040
acaaccaccc ctccaccaac caccactccc agctctccaa taaccaccac tcccagccct   5100
ccaacaacca ccatgaccac cccttcacca accaccaccc ccagctctcc aataaccacc   5160
acaaccaccc cttcctcaac taccactccc agccctccac caaccaccat gaccacccct   5220
tcaccaacca ccactcccag ccctccaaca accaccatga ccacccttcc accaaccacc   5280
acttccagcc ctctaacaac tactcctcta cctccatcaa taactcctcc tacattttca   5340
ccattctcaa cgacaacccc tactacccca tgcgtgcctc tctgcaattg gactggctgg   5400
ctggattctg gaaaacccaa ctttcacaaa ccaggtggag acacagaatt gattggagac   5460
gtctgtggac caggctgggc agctaacatc tcttgcagag ccaccatgta tcctgatgtt   5520
cccattggac agcttggaca aacagtggtg tgtgatgtct ctgtggggct gatatgcaaa   5580
aatgaagacc aaaagccagg tggggtcatc cctatggcct tctgcctcaa ctacgagatc   5640
aacgttcagt gctgtgagtg tgtcacccaa cccaccacca tgacaaccac caccacagag   5700
aacccaactc cgccaaccac gacacccatc accaccacca ctacggtgac ccccaacccca   5760
acacccaccg gcacacagac cccaaccacg acacccatca ccaccaccac tacggtgacc   5820
ccaaccccaa cacccaccgg cacacagacc ccaaccacga cacccatcac caccaccact   5880
acggtgaccc caaccccaac acccaccggc acacagaccc caaccacgac acccatcacc   5940
accaccacta cggtgacccc aaccccaaca cccaccggca cacagacccc aaccacgaca   6000
cccatcacca ccaccactac ggtgacccca accccaacac ccaccggcac acagacccca   6060
accacgacac ccatcaccac caccactacg gtgaccccaa ccccaacacc caccggcaca   6120
cagaccccaa ccacgacacc catcaccacc accactacgg tgaccccaac cccaacaccc   6180
accggcacac agaccccaac cacgacaccc atcaccacca ccactacggt gaccccaacc   6240
ccaacaccca ccggcacaca gaccccaacc acgacaccca tcaccaccac cactacggtg   6300
accccaaccc caacacccac cggcacacag accccaacca cgacacccat caccaccacc   6360
actacggtga ccccaacccc aacacccacc ggcacacaga ccccaaccac gacacccatc   6420
accaccacca ctacggtgac cccaacccca acacccaccg gcacacagac cccaaccacg   6480
acacccatca ccaccaccac tacggtgacc ccaaccccaa cacccaccgg cacacagacc   6540
ccaaccacga cacccatcac caccaccact acggtgaccc caaccccaac acccaccggc   6600
acacagaccc caaccacgac acccatcacc accaccacta cggtgacccc aaccccaaca   6660
cccaccggca cacagacccc aaccacgaca cccatcacca ccaccactac ggtgacccca   6720
accccaacac ccaccggcac acagacccca accacgacac ccatcaccac caccactacg   6780
gtgaccccaa ccccaacacc caccggcaca cagaccccaa ccacgacacc catcaccacc   6840
accactacgg tgaccccaac cccaacaccc accggcacac agaccccaac cacgacaccc   6900
atcaccacca ccactacggt gaccccaacc ccaacaccca ccggcacaca gaccccaacc   6960
acgacaccca tcaccaccac cactacggtg accccaaccc caacacccac cggcacacag   7020
accccaacca cgacacccat caccaccacc actacggtga ccccaacccc aacacccacc   7080
ggcacacaga ccccaaccac gacacccatc accaccacca ctacggtgac cccaacccca   7140
acacccaccg gcacacagac cccaaccacg acacccatca ccaccaccac tacggtgacc   7200
```

-continued

```
ccaaccccaa cacccaccgg cacacagacc ccaaccacga cacccatcac caccaccact   7260
acggtgaccc caaccccaac acccaccggc acacagaccc caaccacgac acccatcacc   7320
accaccacta cggtgacccc aaccccaaca cccaccggca cacagacccc aaccacgaca   7380
cccatcacca ccaccactac ggtgacccca accccaacac ccaccggcac acagacccca   7440
accacgacac ccatcaccac caccactacg gtgaccccaa ccccaacacc caccggcaca   7500
cagaccccaa ccacgacacc catcaccacc accactacgg tgaccccaac cccaacaccc   7560
accggcacac agaccccaac cacgacaccc atcaccacca ccactacggt gaccccaacc   7620
ccaacaccca ccggcacaca gaccccaacc acgacaccca tcaccaccac cactacggtg   7680
accccaaccc caacacccac cggcacacag accccaacca cgacacccat caccaccacc   7740
actacggtga ccccaacccc aacacccacc ggcacacaga ccccaaccac gacacccatc   7800
accaccacca ctacggtgac cccaacccca acacccaccg gcacacagac cccaaccacg   7860
acacccatca ccaccaccac tacggtgacc ccaaccccaa cacccaccgg cacacagacc   7920
ccaaccacga cacccatcac caccaccact acggtgaccc caaccccaac acccaccggc   7980
acacagaccc caaccacgac acccatcacc accaccacta cggtgacccc aaccccaaca   8040
cccaccggca cacagacccc aaccacgaca cccatcacca ccaccactac ggtgacccca   8100
accccaacac ccaccggcac acagacccca accacgacac ccatcaccac caccactacg   8160
gtgaccccaa ccccaacacc caccggcaca cagaccccaa ccacgacacc catcaccacc   8220
accactacgg tgaccccaac cccaacaccc accggcacac agaccccaac cacgacaccc   8280
atcaccacca ccactacggt gaccccaacc ccaacaccca ccggcacaca gaccccaacc   8340
acgacaccca tcaccaccac cactacggtg accccaaccc caacacccac cggcacacag   8400
accccaacca cgacacccat caccaccacc actacggtga ccccaacccc aacacccacc   8460
ggcacacaga ccccaaccac gacacccatc accaccacca ctacggtgac cccaacccca   8520
acacccaccg gcacacagac cccaaccacg acacccatca ccaccaccac tacggtgacc   8580
ccaaccccaa cacccaccgg cacacagacc ccaaccacga cacccatcac caccaccact   8640
acggtgaccc caaccccaac acccaccggc acacagaccc caaccacgac acccatcacc   8700
accaccacta cggtgacccc aaccccaaca cccaccggca cacagacccc aaccacgaca   8760
cccatcacca ccaccactac ggtgacccca accccaacac ccaccggcac acagacccca   8820
accacgacac ccatcaccac caccactacg gtgaccccaa ccccaacacc caccggcaca   8880
cagaccccaa ccacgacacc catcaccacc accactacgg tgaccccaac cccaacaccc   8940
accggcacac agaccccaac cacgacaccc atcaccacca ccactacggt gaccccaacc   9000
ccaacaccca ccggcacaca gaccccaacc acgacaccca tcaccaccac cactacggtg   9060
accccaaccc caacacccac cggcacacag accccaacca cgacacccat caccaccacc   9120
actacggtga ccccaacccc aacacccacc ggcacacaga ccccaaccac gacacccatc   9180
accaccacca ctacggtgac cccaacccca acacccaccg gcacacagac cccaaccacg   9240
acacccatca ccaccaccac tacggtgacc ccaaccccaa cacccaccgg cacacagacc   9300
ccaaccacga cacccatcac caccaccact acggtgaccc caaccccaac acccaccggc   9360
acacagaccc caaccacgac acccatcacc accaccacta cggtgacccc aaccccaaca   9420
cccaccggca cacagacccc aaccacgaca cccatcacca ccaccactac ggtgacccca   9480
accccaacac ccaccggcac acagacccca accacgacac ccatcaccac caccactacg   9540
```

-continued

```
gtgaccccaa ccccaacacc caccggcaca cagaccccaa ccacgacacc catcaccacc   9600
accactacgg tgaccccaac cccaacaccc accggcacac agaccccaac cacgacaccc   9660
atcaccacca ccactacggt gaccccaacc ccaacaccca ccggcacaca gaccccaacc   9720
acgacaccca tcaccaccac cactacggtg accccaaccc caacacccac cggcacacag   9780
accccaacca cgacacccat caccaccacc actacggtga ccccaacccc aacacccacc   9840
ggcacacaga ccccaaccac gacacccatc accaccacca ctacggtgac cccaacccca   9900
acacccaccg gcacacagac cccaaccacg acacccatca ccaccaccac tacggtgacc   9960
ccaaccccaa cacccaccgg cacacagacc ccaaccacga cacccatcac caccaccact  10020
acggtgaccc caaccccaac acccaccggc acacagaccc caaccacgac acccatcacc  10080
accaccacta cggtgacccc aaccccaaca cccaccggca cacagacccc aaccacgaca  10140
cccatcacca ccaccactac ggtgacccca accccaacac ccaccggcac acagacccca  10200
accacgacac ccatcaccac caccactacg gtgaccccaa ccccaacacc caccggcaca  10260
cagaccccaa ccacgacacc catcaccacc accactacgg tgaccccaac cccaacaccc  10320
accggcacac agaccccaac cacgacaccc atcaccacca ccactacggt gaccccaacc  10380
ccaacaccca ccggcacaca gaccccaacc acgacaccca tcaccaccac cactacggtg  10440
accccaaccc caacacccac cggcacacag accccaacca cgacacccat caccaccacc  10500
actacggtga ccccaacccc aacacccacc ggcacacaga ccccaaccac gacacccatc  10560
accaccacca ctacggtgac cccaacccca acacccaccg gcacacagac cccaaccacg  10620
acacccatca ccaccaccac tacggtgacc ccaaccccaa cacccaccgg cacacagacc  10680
ccaaccacga cacccatcac caccaccact acggtgaccc caaccccaac acccaccggc  10740
acacagaccc caaccacgac acccatcacc accaccacta cggtgacccc aaccccaaca  10800
cccaccggca cacagacccc aaccacgaca cccatcacca ccaccactac ggtgacccca  10860
accccaacac ccaccggcac acagacccca accacgacac ccatcaccac caccactacg  10920
gtgaccccaa ccccaacacc caccggcaca cagaccccaa ccacgacacc catcaccacc  10980
accactacgg tgaccccaac cccaacaccc accggcacac agaccccaac cacgacaccc  11040
atcaccacca ccactacggt gaccccaacc ccaacaccca ccggcacaca gaccccaacc  11100
acgacaccca tcaccaccac cactacggtg accccaaccc caacacccac cggcacacag  11160
accccaacca cgacacccat caccaccacc actacggtga ccccaacccc aacacccacc  11220
ggcacacaga ccccaaccac gacacccatc accaccacca ctacggtgac cccaacccca  11280
acacccaccg gcacacagac cccaaccacg acacccatca ccaccaccac tacggtgacc  11340
ccaaccccaa cacccaccgg cacacagacc ccaaccacga cacccatcac caccaccact  11400
acggtgaccc caaccccaac acccaccggc acacagaccc caaccacgac acccatcacc  11460
accaccacta cggtgacccc aaccccaaca cccaccggca cacagacccc aaccacgaca  11520
cccatcacca ccaccactac ggtgacccca accccaacac ccaccggcac acagacccca  11580
accacgacac ccatcaccac caccactacg gtgaccccaa ccccaacacc caccggcaca  11640
cagaccccaa ccacgacacc catcaccacc accactacgg tgaccccaac cccaacaccc  11700
accggcacac agaccccaac cacgacaccc atcaccacca ccactacggt gaccccaacc  11760
ccaacaccca ccggcacaca gaccccaacc acgacaccca tcaccaccac cactacggtg  11820
accccaaccc caacacccac cggcacacag accccaacca cgacacccat caccaccacc  11880
actacggtga ccccaacccc aacacccacc ggcacacaga ccccaaccac gacacccatc  11940
```

-continued

```
accaccacca ctacggtgac cccaacccca acacccaccg gcacacagac cccaaccacg  12000
acacccatca ccaccaccac tacggtgacc ccaaccccaa cacccaccgg cacacagacc  12060
ccaaccacga cacccatcac caccaccact acggtgaccc caaccccaac acccaccggc  12120
acacagaccc caaccacgac acccatcacc accaccacta cggtgacccc aaccccaaca  12180
cccaccggca cacagacccc aaccacgaca cccatcacca ccaccactac ggtgacccca  12240
accccaacac ccaccggcac acagacccca accacgacac ccatcaccac caccactacg  12300
gtgaccccaa ccccaacacc caccggcaca cagaccccaa ccacgacacc catcaccacc  12360
accactacgg tgaccccaac cccaacaccc accggcacac agaccccaac cacgacaccc  12420
atcaccacca ccactacggt gaccccaacc ccaacaccca ccggcacaca gaccccaacc  12480
acgacaccca tcaccaccac cactacggtg accccaaccc caacacccac cggcacacag  12540
accccaacca cgacacccat caccaccacc actacggtga ccccaacccc aacacccacc  12600
ggcacacaga ccgggccccc cacccacaca agcacagcac cgattgctga gttgaccaca  12660
tccaatcctc cgcctgagtc ctcaacccct cagacctctc ggtccacctc ttcccctctc  12720
acggagtcaa ccacccttct gagtacccta ccacctgcca ttgagatgac cagcacggcc  12780
ccaccctcca cacccacggc acccacgacc acgagcggag gccacacact gtctccaccg  12840
cccagcacca ccacgtcccc tccaggcacc cccactcgcg gtaccacgac cgggtcatct  12900
tcagccccca cccccagcac tgtgcagacg accaccacca gtgcctggac cccaacgccg  12960
accccactct ccacacccag catcatcagg accacaggcc tgaggcccta cccttcctct  13020
gtgcttatct gctgtgtcct gaacgacacc tactacgcac caggtgagga ggtgtacaac  13080
ggcacatacg gagacacctg ttatttcgtc aactgctcac tgagctgtac gttggagttc  13140
tataactggt cctgcccatc cacgccctcc ccaacaccca cgccctccaa gtcgacgccc  13200
acgccttcca agccatcgtc cacgccctcc aagccgacgc ccggcaccaa gccccccgag  13260
tgcccagact ttgatcctcc cagacaggag aacgagactt ggtggctgtg cgactgcttc  13320
atggccacgt gcaagtacaa caacacggtg gagatcgtga aggtggagtg tgagccgccg  13380
cccatgccca cctgctccaa cggcctccaa cccgtgcgcg tcgaggaccc cgacggctgc  13440
tgctggcact gggagtgcga ctgctactgc acgggctggg gcgacccgca ctatgtcacc  13500
ttcgacggac tctactacag ctaccagggc aactgcacct acgtgctggt ggaggagatc  13560
agcccctccg tggacaactt cggagtttac atcgacaact accactgcga tcccaacgac  13620
aaggtgtcct gtccccgcac cctcatcgtg cgccacgaga cccaggaggt gctgatcaag  13680
accgtgcata tgatgcccat gcaggtgcag gtgcaggtga acaggcaggc ggtggcactg  13740
ccctacaaga agtacgggct ggaggtgtac cagtctggca tcaactacgt ggtggacatc  13800
cccgagctgg gtgtcctcgt ctcctacaat ggcctgtcct tctccgtcag gctgccctac  13860
caccggtttg gcaacaacac caagggccag tgtggcacct gcaccaacac cacctccgac  13920
gactgcattc tgcccagcgg ggagatcgtc tccaactgtg aggctgcggc tgaccagtgg  13980
ctggtgaacg acccctccaa gccacactgc ccccacagca gctccacgac caagcgcccg  14040
gccgtcactg tgcccggggg cggtaaaacg accccacaca aggactgcac cccatctccc  14100
ctctgccagc tcatcaagga cagcctgttt gcccagtgcc acgcactggt gcccccgcag  14160
cactactacg atgcctgcgt gttcgacagc tgcttcatgc cgggctcgag cctggagtgc  14220
gccagtctgc aggcctacgc agccctctgt gcccagcaga acatctgcct cgactggcgg  14280
```

-continued

```
aaccacacgc atggggcctg cttggtggag tgcccatctc acagggagta ccaggcctgt  14340

ggccctgcag aagagcccac gtgcaaatcc agctcctccc agcagaacaa cacagtcctg  14400

gtggaaggct gcttctgtcc tgagggcacc atgaactacg ctcctggctt tgatgtctgc  14460

gtgaagacct gcggctgtgt gggacctgac aatgtgccca gagagtttgg ggagcacttc  14520

gagttcgact gcaagaactg tgtctgcctg gagggtggaa gtggcatcat ctgccaaccc  14580

aagaggtgca gccagaagcc cgttacccac tgcgtggaag acggcaccta cctcgccacg  14640

gaggtcaacc ctgccgacac ctgctgcaac attaccgtct gcaagtgcaa caccagcctg  14700

tgcaaagaga agccctccgt gtgcccgctg ggattcgaag tgaagagcaa gatggtgcct  14760

ggaaggtgct gtcccttcta ctggtgtgag tccaaggggg tgtgtgttca cgggaatgct  14820

gagtaccagc ccggttctcc agtttattcc tccaagtgcc aggactgcgt gtgcacggac  14880

aaggtggaca acaacaccct gctcaacgtc atcgcctgca cccacgtgcc ctgcaacacc  14940

tcctgcagcc ctggcttcga actcatggag gcccccgggg agtgctgtaa gaagtgtgaa  15000

cagacgcact gtatcatcaa acggcccgac aaccagcacg tcatcctgaa gcccggggac  15060

ttcaagagcg acccgaagaa caactgcaca ttcttcagct gcgtgaagat ccacaaccag  15120

ctcatctcgt ccgtctccaa catcacctgc cccaactttg atgccagcat ttgcatcccg  15180

ggctccatca cattcatgcc caatggatgc tgcaagacct gcacccctcg caatgagacc  15240

agggtgccct gctccaccgt ccccgtcacc acggaggttt cgtacgccgg ctgcaccaag  15300

accgtcctca tgaatcattg ctccgggtcc tgcgggacat ttgtcatgta ctcggccaag  15360

gcccaggccc tggaccacag ctgctcctgc tgcaaagagg agaaaaccag ccagcgtgag  15420

gtggtcctga gctgccccaa tggcggctcg ctgacacaca cctacaccca catcgagagc  15480

tgccagtgcc aggacaccgt ctgcgggctc cccaccggca cctcccgccg ggcccggcgc  15540

tcccctaggc atctggggag cgggtgagcg gggtgggcac agccccccttc actgccctcg  15600

acagctttac ctcccccgga ccctctgagc ctcctaagct cggcttcctc tcttcagata  15660

tttattgtct gagtctttgt tcagtccttg ctttccaata ataaactcag gggacatgc  15720
```

<210> SEQ ID NO 15
<211> LENGTH: 3697
<212> TYPE: DNA
<213> ORGANISM: human

<400> SEQUENCE: 15

```
agggagtgtt cccgggggag atactccagt cgtagcaaga gtctcgacca ctgaatggaa     60

gaaaaggact tttaaccacc attttgtgac ttacagaaag gaatttgaat aaagaaaact    120

atgatacttc aggcccatct tcactccctg tgtcttctta tgctttattt ggcaactgga    180

tatggccaag aggggaagtt tagtggaccc ctgaaaccca tgacattttc tatttatgaa    240

ggccaagaac cgagtcaaat tatattccag tttaaggcca atcctcctgc tgtgactttt    300

gaactaactg gggagacaga caacatattt gtgatagaac gggagggact tctgtattac    360

aacagagcct tggacaggga aacaagatct actcacaatc tccaggttgc agccctggac    420

gctaatggaa ttatagtgga gggtccagtc cctatcacca tagaagtgaa ggacatcaac    480

gacaatcgac ccacgtttct ccagtcaaag tacgaaggct cagtaaggca gaactctcgc    540

ccaggaaagc ccttcttgta tgtcaatgcc acagacctgg atgatccggc cactcccaat    600

ggccagcttt attaccagat tgtcatccag cttcccatga tcaacaatgt catgtacttt    660

cagatcaaca acaaaacggg agccatctct cttacccgag agggatctca ggaattgaat    720
```

-continued

```
cctgctaaga atccttccta taatctggtg atctcagtga aggacatggg aggccagagt    780
gagaattcct tcagtgatac cacatctgtg gatatcatag tgacagagaa tatttggaaa    840
gcaccaaaac ctgtggagat ggtggaaaac tcaactgatc ctcaccccat caaaatcact    900
caggtgcggt ggaatgatcc cggtgcacaa tattccttag ttgacaaaga gaagctgcca    960
agattcccat tttcaattga ccaggaagga gatatttacg tgactcagcc cttggaccga   1020
gaagaaaagg atgcatatgt tttttatgca gttgcaaagg atgagtacgg aaaaccactt   1080
tcatatccgc tggaaattca tgtaaaagtt aaagatatta atgataatcc acctacatgt   1140
ccgtcaccag taaccgtatt tgaggtccag gagaatgaac gactgggtaa cagtatcggg   1200
acccttactg cacatgacag ggatgaagaa aatactgcca acagttttct aaactacagg   1260
attgtggagc aaactcccaa acttcccatg gatggactct tcctaatcca aacctatgct   1320
ggaatgttac agttagctaa acagtccttg aagaagcaag atactcctca gtacaactta   1380
acgatagagg tgtctgacaa agatttcaag accctttgtt ttgtgcaaat caacgttatt   1440
gatatcaatg atcagatccc catctttgaa aaatcagatt atggaaacct gactcttgct   1500
gaagacacaa acattgggtc caccatctta accatccagg ccactgatgc tgatgagcca   1560
tttactggga gttctaaaat tctgtatcat atcataaagg gagacagtga gggacgcctg   1620
ggggttgaca cagatcccca taccaacacc ggatatgtca taattaaaaa gcctcttgat   1680
tttgaaacag cagctgtttc caacattgtg ttcaaagcag aaaatcctga gcctctagtg   1740
tttggtgtga agtacaatgc aagttctttt gccaagttca cgcttattgt gacagatgtg   1800
aatgaagcac ctcaattttc ccaacacgta ttccaagcga aagtcagtga ggatgtagct   1860
ataggcacta aagtgggcaa tgtgactgcc aaggatccag aaggtctgga cataagctat   1920
tcactgaggg gagacacaag aggttggctt aaaattgacc acgtgactgg tgagatcttt   1980
agtgtggctc cattggacag agaagccgga agtccatatc gggtacaagt ggtggccaca   2040
gaagtagggg ggtcttcctt gagctctgtg tcagagttcc acctgatcct tatggatgtg   2100
aatgacaacc ctcccaggct agccaaggac tacacgggct tgttcttctg ccatcccctc   2160
agtgcacctg gaagtctcat tttcgaggct actgatgatg atcagcactt atttcggggt   2220
ccccatttta cattttccct cggcagtgga agcttacaaa acgactggga agtttccaaa   2280
atcaatggta ctcatgcccg actgtctacc aggcacacag agtttgagga gagggagtat   2340
gtcgtcttga tccgcatcaa tgatgggggt cggccaccct tggaaggcat tgtttcttta   2400
ccagttacat tctgcagttg tgtggaagga agttgtttcc ggccagcagg tcaccagact   2460
gggataccca ctgtgggcat ggcagttggt atactgctga ccacccttct ggtgattggt   2520
ataattttag cagttgtgtt tatccgcata aagaaggata aaggcaaaga taatgttgaa   2580
agtgctcaag catctgaagt caaacctctg agaagctgaa tttgaaaagg aatgtttgaa   2640
tttatatagc aagtgctatt tcagcaacaa ccatctcatc ctattacttt tcatctaacg   2700
tgcattataa ttttttaaac agatattccc tcttgtcctt taatatttgc taaatatttc   2760
tttttgaggg tggagtcttg ctctgtcgcc caggctggag tacagtggtg tgatcccagc   2820
tcactgcaac ctccgcctcc tgggttcaca tgattctcct gcctcagctt cctaagtagc   2880
tgggtttaca ggcacccacc accatgccca gctaattttt gtatttttaa tagagacggg   2940
gtttcgccat ttggccaggc tggtcttgaa ctcctgacgt caagtgatct gcctgccttg   3000
gtctcccaat acaggcatga accactgcac ccacctactt agatatttca tgtgctatag   3060
```

-continued

```
acattagaga gatttttcat ttttccatga catttttcct ctctgcaaat ggcttagcta   3120
cttgtgtttt tccctttgg ggcaagacag actcattaaa tattctgtac attttttctt   3180
tatcaaggag atatatcagt gttgtctcat agaactgcct ggattccatt tatgtttttt   3240
ctgattccat cctgtgtccc cttcatcctt gactcctttg gtatttcact gaatttcaaa   3300
catttgtcag agaagaaaaa cgtgaggact caggaaaaat aaataaataa aagaacagcc   3360
ttttccctta gtattaacag aaatgtttct gtgtcattaa ccatctttaa tcaatgtgac   3420
atgttgctct ttggctgaaa ttcttcaact tggaaatgac acagacccac agaaggtgtt   3480
caaacacaac ctactctgca aaccttggta aaggaaccag tcagctggcc agatttcctc   3540
actacctgcc atgcatacat gctgcgcatg ttttcttcat tcgtatgtta gtaaagtttt   3600
ggttattata tatttaacat gtggaagaaa acaagacatg aaaagagtgg tgacaaatca   3660
agaataaaca ctggttgtag tcagttttgt ttgttaa                             3697
```

<210> SEQ ID NO 16
<211> LENGTH: 3697
<212> TYPE: DNA
<213> ORGANISM: human

<400> SEQUENCE: 16

```
agggagtgtt cccgggggag atactccagt cgtagcaaga gtctcgacca ctgaatggaa     60
gaaaaggact tttaaccacc attttgtgac ttacagaaag gaatttgaat aaagaaaact    120
atgatacttc aggcccatct tcactccctg tgtcttctta tgctttattt ggcaactgga    180
tatggccaag aggggaagtt tagtggaccc ctgaaaccca tgacattttc tatttatgaa    240
ggccaagaac cgagtcaaat tatattccag tttaaggcca atcctcctgc tgtgactttt    300
gaactaactg gggagacaga caacatattt gtgatagaac gggagggact tctgtattac    360
aacagagcct tggacaggga aacaagatct actcacaatc tccaggttgc agccctggac    420
gctaatggaa ttatagtgga gggtccagtc cctatcacca tagaagtgaa ggacatcaac    480
gacaatcgac ccacgtttct ccagtcaaag tacgaaggct cagtaaggca gaactctcgc    540
ccaggaaagc ccttcttgta tgtcaatgcc acagacctgg atgatccggc cactcccaat    600
ggccagcttt attaccagat tgtcatccag cttcccatga tcaacaatgt catgtacttt    660
cagatcaaca acaaaaacggg agccatctct cttacccgag agggatctca ggaattgaat    720
cctgctaaga atccttccta taatctggtg atctcagtga aggacatggg aggccagagt    780
gagaattcct tcagtgatac cacatctgtg gatatcatag tgacagagaa tatttggaaa    840
gcaccaaaac ctgtggagat ggtggaaaac tcaactgatc ctcaccccat caaaatcact    900
caggtgcggt ggaatgatcc cggtgcacaa tattccttag ttgacaaaga gaagctgcca    960
agattcccat tttcaattga ccaggaagga gatatttacg tgactcagcc cttggaccga   1020
gaagaaaagg atgcatatgt tttttatgca gttgcaaagg atgagtacgg aaaaccactt   1080
tcatatccgc tggaaattca tgtaaaagtt aaagatatta atgataatcc acctacatgt   1140
ccgtcaccag taaccgtatt tgaggtccag gagaatgaac gactgggtaa cagtatcggg   1200
acccttactg cacatgacag ggatgaagaa aatactgcca acagttttct aaactacagg   1260
attgtggagc aaactcccaa acttcccatg gatggactct tcctaatcca aacctatgct   1320
ggaatgttac agttagctaa acagtccttg aagaagcaag atactcctca gtacaactta   1380
acgatagagg tgtctgacaa agatttcaag accctttgtt ttgtgcaaat caacgttatt   1440
gatatcaatg atcagatccc catctttgaa aaatcagatt atggaaacct gactcttgct   1500
```

-continued

```
gaagacacaa acattgggtc caccatctta accatccagg ccactgatgc tgatgagcca   1560

tttactggga gttctaaaat tctgtatcat atcataaagg gagacagtga gggacgcctg   1620

ggggttgaca cagatcccca taccaacacc ggatatgtca taattaaaaa gcctcttgat   1680

tttgaaacag cagctgtttc caacattgtg ttcaaagcag aaaatcctga gcctctagtg   1740

tttggtgtga agtacaatgc aagttctttt gccaagttca cgcttattgt gacagatgtg   1800

aatgaagcac ctcaattttc ccaacacgta ttccaagcga aagtcagtga ggatgtagct   1860

ataggcacta aagtgggcaa tgtgactgcc aaggatccag aaggtctgga cataagctat   1920

tcactgaggg gagacacaag aggttggctt aaaattgacc acgtgactgg tgagatcttt   1980

agtgtggctc cattggacag agaagccgga agtccatatc gggtacaagt ggtggccaca   2040

gaagtagggg ggtcttcctt gagctctgtg tcagagttcc acctgatcct tatggatgtg   2100

aatgacaacc ctcccaggct agccaaggac tacacgggct tgttcttctg ccatcccctc   2160

agtgcacctg gaagtctcat tttcgaggct actgatgatg atcagcactt atttcggggt   2220

ccccatttta cattttccct cggcagtgga agcttacaaa acgactggga agtttccaaa   2280

atcaatggta ctcatgcccg actgtctacc aggcacacag agtttgagga gagggagtat   2340

gtcgtcttga tccgcatcaa tgatgggggt cggccaccct tggaaggcat tgtttcttta   2400

ccagttacat tctgcagttg tgtggaagga agttgtttcc ggccagcagg tcaccagact   2460

gggataccca ctgtgggcat ggcagttggt atactgctga ccacccttct ggtgattggt   2520

ataattttag cagttgtgtt tatccgcata aagaaggata aaggcaaaga taatgttgaa   2580

agtgctcaag catctgaagt caaacctctg agaagctgaa tttgaaaagg aatgtttgaa   2640

tttatatagc aagtgctatt tcagcaacaa ccatctcatc ctattacttt tcatctaacg   2700

tgcattataa tttttttaaac agatattccc tcttgtcctt taatatttgc taaatatttc   2760

ttttttgagg tggagtcttg ctctgtcgcc caggctggag tacagtggtg tgatcccagc   2820

tcactgcaac ctccgcctcc tgggttcaca tgattctcct gcctcagctt cctaagtagc   2880

tgggtttaca ggcacccacc accatgccca gctaattttt gtatttttaa tagagacggg   2940

gtttcgccat ttggccaggc tggtcttgaa ctcctgacgt caagtgatct gcctgccttg   3000

gtctcccaat acaggcatga accactgcac ccacctactt agatatttca tgtgctatag   3060

acattagaga gatttttcat ttttccatga catttttcct ctctgcaaat ggcttagcta   3120

cttgtgtttt tccctttttgg ggcaagacag actcattaaa tattctgtac atttttttctt   3180

tatcaaggag atatatcagt gttgtctcat agaactgcct ggattccatt tatgtttttt   3240

ctgattccat cctgtgtccc cttcatcctt gactcctttg gtatttcact gaatttcaaa   3300

catttgtcag agaagaaaaa cgtgaggact caggaaaaat aaataaataa aagaacagcc   3360

ttttccctta gtattaacag aaatgtttct gtgtcattaa ccatctttaa tcaatgtgac   3420

atgttgctct ttggctgaaa ttcttcaact tggaaatgac acagacccac agaaggtgtt   3480

caaacacaac ctactctgca aaccttggta aaggaaccag tcagctggcc agatttcctc   3540

actacctgcc atgcatacat gctgcgcatg ttttcttcat tcgtatgtta gtaaagtttt   3600

ggttattata tatttaacat gtggaagaaa acaagacatg aaaagagtgg tgacaaatca   3660

agaataaaca ctggttgtag tcagttttgt ttgttaa                            3697
```

<210> SEQ ID NO 17
<211> LENGTH: 1597
<212> TYPE: DNA

<213> ORGANISM: human

<400> SEQUENCE: 17

```
aacaaactgc acccactgaa ctccgcagct agcatccaaa tcagcccttg agatttgagg     60
ccttggagac tcaggagttt tgagagcaaa atgacaacac ccagaaattc agtaaatggg    120
actttcctgg cagagccaat gaaaggccct attgctatgc aatctggtcc aaaaccactc    180
ttcaggagga tgtcttcact ggtgggcccc acgcaaagct tcttcatgag ggaatctaag    240
actttggggg ctgtccagat tatgaatggg ctcttccaca ttgccctggg gggtcttctg    300
atgatcccag cagggatcta tgcacccatc tgtgtgactg tgtggtaccc tctctgggga    360
ggcattatgt atattatttc cggatcactc ctggcagcaa cggagaaaaa ctccaggaag    420
tgtttggtca aaggaaaaat gataatgaat tcattgagcc tctttgctgc catttctgga    480
atgattcttt caatcatgga catacttaat attaaaattt cccatttttt aaaaatggag    540
agtctgaatt ttattagagc tcacacacca tatattaaca tatacaactg tgaaccagct    600
aatccctctg agaaaaactc cccatctacc caatactgtt acagcataca atctctgttc    660
ttgggcattt tgtcagtgat gctgatcttt gccttcttcc aggaacttgt aatagctggc    720
atcgttgaga atgaatggaa aagaacgtgc tccagaccca aatctaacat agttctcctg    780
tcagcagaag aaaaaaaaga acagactatt gaaataaaag aagaagtggt tgggctaact    840
gaaacatctt cccaaccaaa gaatgaagaa gacattgaaa ttattccaat ccaagaagag    900
gaagaagaag aaacagagac gaactttcca gaacctcccc aagatcagga atcctcacca    960
atagaaaatg acagctctcc ttaagtgatt tcttctgttt tctgtttcct tttttaaaca   1020
ttagtgttca tagcttccaa gagacatgct gactttcatt tcttgaggta ctctgcacat   1080
acgcaccaca tctctatctg gcctttgcat ggagtgacca tagctccttc tctcttacat   1140
tgaatgtaga gaatgtagcc attgtagcag cttgtgttgt cacgcttctt cttttgagca   1200
actttcttac actgaagaaa ggcagaatga gtgcttcaga atgtgatttc ctactaacct   1260
gttccttgga taggcttttt agtatagtat tttttttgt cattttctcc atcagcaacc    1320
agggagactg cacctgatgg aaaagatata tgactgcttc atgacattcc taaactatct   1380
ttttttatt ccacatctac gtttttggtg gagtcccttt tgcatcattg ttttaaggat    1440
gataaaaaaa aaataacaac tagggacaat acagaaccca ttccatttat ctttctacag   1500
ggctgacatt gtggcacatt cttagagtta ccacacccca tgagggaagc tctaaatagc   1560
caacacccat ctgtttttg taaaaacagc atagctt                             1597
```

<210> SEQ ID NO 18
<211> LENGTH: 2907
<212> TYPE: DNA
<213> ORGANISM: human

<400> SEQUENCE: 18

```
gccatctggg cccaggcccc atgccccgag gaggggtggt ctgaagccca ccagagcccc     60
ctgccagact gtctgcctcc cttctgactg tggccgcttg gcatggccag caacagcagc    120
tcctgcccga cacctggggg cgggcacctc aatgggtacc cggtgcctcc ctacgccttc    180
ttcttccccc ctatgctggg tggactctcc ccgccaggcg ctctgaccac tctccagcac    240
cagcttccag ttagtggata tagcacacca tccccagcca ccattgagac ccagagcagc    300
agttctgaag agatagtgcc cagccctccc tcgccacccc ctctaccccg catctacaag    360
ccttgctttg tctgtcagga caagtcctca ggctaccact atggggtcag cgcctgtgag    420
```

-continued

```
ggctgcaagg gcttcttccg ccgcagcatc cagaagaaca tggtgtacac gtgtcaccgg    480
gacaagaact gcatcatcaa caaggtgacc cggaaccgct gccagtactg ccgactgcag    540
aagtgctttg aagtgggcat gtccaaggag tctgtgagaa acgaccgaaa caagaagaag    600
aaggaggtgc ccaagcccga gtgctctgag agctacacgc tgacgccgga ggtgggggag    660
ctcattgaga aggtgcgcaa agcgcaccag gaaaccttcc ctgccctctg ccagctgggc    720
aaatacacta cgaacaacag ctcagaacaa cgtgtctctc tggacattga cctctgggac    780
aagttcagtg aactctccac caagtgcatc attaagactg tggagttcgc caagcagctg    840
cccggcttca ccaccctcac catcgccgac cagatcaccc tcctcaaggc tgcctgcctg    900
gacatcctga tcctgcggat ctgcacgcgg tacacgcccg agcaggacac catgaccttc    960
tcggacgggc tgaccctgaa ccggacccag atgcacaacg ctggcttcgg cccccctcacc   1020
gacctggtct ttgccttcgc caaccagctg ctgcccctgg agatggatga tgcggagacg   1080
gggctgctca gcgccatctg cctcatctgc ggagaccgcc aggacctgga gcagccggac   1140
cgggtggaca tgctgcagga gccgctgctg gaggcgctaa aggtctacgt gcggaagcgg   1200
aggcccagcc gcccccacat gttccccaag atgctaatga agattactga cctgcgaagc   1260
atcagcgcca agggggctga gcgggtgatc acgctgaaga tggagatccc gggctccatg   1320
ccgcctctca tccaggaaat gttggagaac tcagagggcc tggacactct gagcggacag   1380
ccgggggggtg gggggcggga cgggggtggc ctggcccccc cgccaggcag ctgtagcccc   1440
agcctcagcc ccagctccaa cagaagcagc ccggccaccc actccccgtg accgcccacg   1500
ccacatggac acagccctcg ccctccgccc cggcttttct ctgcctttct accgaccatg   1560
tgaccccgca ccagccctgc ccccacctgc cctcccgggc agtactgggg accttccctg   1620
ggggacgggg agggaggagg cagcgactcc ttggacagag gcctgggccc tcagtggact   1680
gcctgctccc acagcctggg ctgacgtcag aggccgaggc caggaactga gtgaggcccc   1740
tggtcctggg tctcaggatg ggtcctgggg gcctcgtgtt catcaagaca cccctctgcc   1800
cagctcacca catcttcatc accagcaaac gccaggactt ggctccccca tcctcagaac   1860
tcacaagcca ttgctcccca gctggggaac ctcaacctcc cccctgcctc ggttggtgac   1920
agagggggtg ggacaggggc ggggggttcc ccctgtacat accctgccat accaacccca   1980
ggtattaatt ctcgctggtt ttgtttttat tttaattttt ttgttttgat ttttttaata   2040
agaattttca ttttaagcac atttatactg aaggaatttg tgctgtgtat tggggggagc   2100
tggatccaga gctggagggg gtgggtccgg gggagggagt ggctcggaag ggcccccac    2160
tctcctttca tgtccctgtg ccccccagtt ctcctcctca gccttttcct cctcagtttt   2220
ctctttaaaa ctgtgaagta ctaactttcc aaggcctgcc ttcccctccc tcccactgga   2280
gaagccgcca gcccctttct ccctctgcct gaccactggg tgtggacggt gtggggcagc   2340
cctgaaagga caggctcctg gccttggcac ttgcctgcac ccaccatgag gcatggagca   2400
gggcagagca agggccccgg gacagagttt tcccagacct ggctcctcgg cagagctgcc   2460
tcccgtcagg gcccacatca tctaggctcc ccagccccca ctgtgaaggg gctggccagg   2520
ggcccgagct gcccccaccc ccggcctcag ccaccagcac ccccataggg cccccagaca   2580
ccacacacat gcgcgtgcgc acacacacaa acacacacac actggacagt agatgggccg   2640
acacacactt ggcccgagtt cctccatttc cctggcctgc cccccacccc caacctgtcc   2700
cacccccgtg ccccctcctt accccgcagg acgggcctac agggggggtct cccctcaccc   2760
```

-continued

```
ctgcaccccc agctggggga gctggctctg ccccgacctc cttcaccagg ggttggggcc   2820

ccttcccctg gagcccgtgg gtgcacctgt tactgttggg ctttccactg agatctactg   2880

gataaagaat aaagttctat ttattct                                       2907
```

<210> SEQ ID NO 19
<211> LENGTH: 2907
<212> TYPE: DNA
<213> ORGANISM: human

<400> SEQUENCE: 19

```
gccatctggg cccaggcccc atgccccgag gaggggtggt ctgaagccca ccagagcccc     60

ctgccagact gtctgcctcc cttctgactg tggccgcttg gcatggccag caacagcagc    120

tcctgcccga cacctggggg cgggcacctc aatgggtacc cggtgcctcc ctacgccttc    180

ttcttccccc ctatgctggg tggactctcc ccgccaggcg ctctgaccac tctccagcac    240

cagcttccag ttagtggata tagcacacca tccccagcca ccattgagac ccagagcagc    300

agttctgaag agatagtgcc cagccctccc tcgccacccc ctctaccccg catctacaag    360

ccttgctttg tctgtcagga caagtcctca ggctaccact atggggtcag cgcctgtgag    420

ggctgcaagg gcttcttccg ccgcagcatc cagaagaaca tggtgtacac gtgtcaccgg    480

gacaagaact gcatcatcaa caaggtgacc cggaaccgct gccagtactg ccgactgcag    540

aagtgctttg aagtgggcat gtccaaggag tctgtgagaa acgaccgaaa caagaagaag    600

aaggaggtgc ccaagcccga gtgctctgag agctacacgc tgacgccgga ggtgggggag    660

ctcattgaga aggtgcgcaa agcgcaccag gaaaccttcc ctgccctctg ccagctgggc    720

aaatacacta cgaacaacag ctcagaacaa cgtgtctctc tggacattga cctctgggac    780

aagttcagtg aactctccac caagtgcatc attaagactg tggagttcgc caagcagctg    840

cccggcttca ccaccctcac catcgccgac cagatcaccc tcctcaaggc tgcctgcctg    900

gacatcctga tcctgcggat ctgcacgcgg tacacgcccg agcaggacac catgaccttc    960

tcggacgggc tgaccctgaa ccggacccag atgcacaacg ctggcttcgg cccccctcacc   1020

gacctggtct ttgccttcgc caaccagctg ctgcccctgg agatggatga tgcggagacg   1080

gggctgctca gcgccatctg cctcatctgc ggagaccgcc aggacctgga gcagccggac   1140

cgggtggaca tgctgcagga gccgctgctg gaggcgctaa aggtctacgt gcggaagcgg   1200

aggcccagcc gcccccacat gttccccaag atgctaatga agattactga cctgcgaagc   1260

atcagcgcca agggggctga gcgggtgatc acgctgaaga tggagatccc gggctccatg   1320

ccgcctctca tccaggaaat gttggagaac tcagagggcc tggacactct gagcggacag   1380

ccgggggggtg gggggcggga cgggggtggc ctggcccccc cgccaggcag ctgtagcccc   1440

agcctcagcc ccagctccaa cagaagcagc ccggccaccc actccccgtg accgcccacg   1500

ccacatggac acagccctcg ccctccgccc cggcttttct ctgcctttct accgaccatg   1560

tgaccccgca ccagccctgc cccacctgc cctcccgggc agtactgggg accttccctg   1620

ggggacgggg agggaggagg cagcgactcc ttggacagag gcctgggccc tcagtggact   1680

gcctgctccc acagcctggg ctgacgtcag aggccgaggc caggaactga gtgaggcccc   1740

tggtcctggg tctcaggatg ggtcctgggg gcctcgtgtt catcaagaca cccctctgcc   1800

cagctcacca catcttcatc accagcaaac gccaggactt ggctcccccca tcctcagaac   1860

tcacaagcca ttgctcccca gctggggaac ctcaacctcc cccctgcctc ggttggtgac   1920

agagggggtg ggacaggggc gggggggttcc ccctgtacat accctgccat accaacccca   1980
```

-continued ggtattaatt ctcgctggtt ttgtttttat tttaattttt ttgttttgat ttttttaata 2040
agaattttca ttttaagcac atttatactg aaggaatttg tgctgtgtat tggggggagc 2100
tggatccaga gctggagggg gtgggtccgg gggagggagt ggctcggaag gggcccccac 2160
tctcctttca tgtccctgtg ccccccagtt ctcctcctca gccttttcct cctcagtttt 2220
ctctttaaaa ctgtgaagta ctaactttcc aaggcctgcc ttcccctccc tcccactgga 2280
gaagccgcca gccccttttct ccctctgcct gaccactggg tgtggacggt gtggggcagc 2340
cctgaaagga caggctcctg gccttggcac ttgcctgcac ccaccatgag gcatggagca 2400
gggcagagca agggccccgg gacagagttt tcccagacct ggctcctcgg cagagctgcc 2460
tcccgtcagg gcccacatca tctaggctcc ccagccccca ctgtgaaggg gctggccagg 2520
ggcccgagct gcccccaccc ccggcctcag ccaccagcac ccccataggg cccccagaca 2580
ccacacacat gcgcgtgcgc acacacacaa acacacacac actggacagt agatgggccg 2640
acacacactt ggcccgagtt cctccatttc cctggcctgc cccccacccc caacctgtcc 2700
cacccccgtg ccccctcctt accccgcagg acgggcctac agggggggtct cccctcaccc 2760 ctgcaccccc agctggggga gctggctctg ccccgacctc cttcaccagg ggttggggcc 2820
ccttcccctg gagcccgtgg gtgcacctgt tactgttggg ctttccactg agatctactg 2880
gataaagaat aaagttctat ttattct 2907

<210> SEQ ID NO 20
<211> LENGTH: 1347
<212> TYPE: DNA
<213> ORGANISM: human

<400> SEQUENCE: 20
atggatccca aatatttcat cttaattttg ttttgtggac acctgaacaa tacatttttt 60
tcaaagacag agacaattac aacagagaag cagtcacagc ctaccttata cacatcatca 120
atgtcacagg tattggctaa ttctcaaaac acaacaggga atcctttggg tcaaccaaca 180
caattcagcg acactttttc tggacaatca atatcacctg ccaaagtcac tgctggacaa 240
ccaacaccag ctgtctatac ctcttctgaa aaaccagaag cacatacttc tgctggacaa 300
ccacttgcct acaacaccaa acaaccaaca ccaatagcca acacctcctc ccagcaagcc 360
gtgttcacct ctgccagaca actaccatct gcccgtactt ctaccacaca accaccaaag 420
tcatttgtct atacttttac tcaacaatca tcatctgtcc agatcccttc tagaaaacaa 480
ataactgttc ataatccatc cacacaacca acatcaactg tcaaaaattc acctaggagt 540
acaccaggat ttatcttaga tactaccagt aacaaacaaa ccccacaaaa aaacaattat 600
aattcaatag ctgccatact aattggtgta cttctgactt ctatgttggt agctataatc 660
atcattgtac tttggaaatg cttaaggaaa ccagttttaa atgatcaaaa ttgggcaggt 720
agatctccat ttgctgatgg agaaacccct gacatttgta tggataacat cagagaaaat 780
gaaatatcca caaaacgtac atcaatcatt tcacttacac cctggaaacc aagcaaaagc 840
acacttttag cagatgactt agaaattaag ttgtttgaat caagtgaaaa cattgaagac 900
tccaacaacc ccaaaacaga gaaaataaaa gatcaagtaa atggtacatc agaagatagt 960
gctgatggtt caacagttgg aactgctgtt tcttcttcag atgatgcaga tctgcctcca 1020
ccacctcccc ttctggattt ggaaggacag gaaagtaacc aatctgacaa acccacaatg 1080
acaattgtat ctcctcttcc aaatgattct actagtctcc ctccatctct ggactgtctc 1140

-continued

```
aatcaagact gtggagatca taaatctgag ataatacaat catttccacc gcttgactca   1200

cttaacttgc ccctgccacc agtagatttt atgaaaaacc aagaagattc caaccttgag   1260

atccagtgtc aggagttctc tattcctccc aactctgatc aagatcttaa tgaatccctg   1320

ccacctccac ctgcagaact gttataa                                        1347
```

<210> SEQ ID NO 21
<211> LENGTH: 2170
<212> TYPE: DNA
<213> ORGANISM: human

<400> SEQUENCE: 21

```
ctgagggctc atccctctgc agagcgcggg gtcaccggga ggagacgcca tgacgcccgc     60

cctcacagcc ctgctctgcc ttgggctgag tctgggcccc aggacccgcg tgcaggcagg    120

gcccttcccc aaacccaccc tctgggctga gccaggctct gtgatcagct gggggagccc    180

cgtgaccatc tggtgtcagg ggagcctgga ggcccaggag taccgactgg ataaagaggg    240

aagcccagag cccttggaca gaaataaccc actggaaccc aagaacaagg ccagattctc    300

catcccatcc atgacagagc accatgcggg gagataccgc tgccactatt acagctctgc    360

aggctggtca gagcccagcg accccctgga gctggtgatg acaggattct acaacaaacc    420

caccctctca gccctgccca gccctgtggt ggcctcaggg gggaatatga ccctccgatg    480

tggctcacag aagggatatc accattttgt tctgatgaag gaaggagaac accagctccc    540

ccggaccctg gactcacagc agctccacag tggggggttc caggccctgt tccctgtggg    600

ccccgtgaac cccagccaca ggtggaggtt cacatgctat tactattata tgaacacccc    660

ccaggtgtgg tcccacccca gtgacccccct ggagattctg ccctcaggcg tgtctaggaa    720

gccctccctc ctgaccctgc agggccctgt cctggcccct gggcagagcc tgaccctcca    780

gtgtggctct gatgtcggct acgacagatt tgttctgtat aaggaggggg aacgtgactt    840

cctccagcgc cctggccagc agccccaggc tgggctctcc caggccaact tcaccctggg    900

ccctgtgagc cctcccacgg ggggccagta caggtgctat ggtgcacaca acctctcctc    960

cgagtggtcg gcccccagcg acccccctgaa catcctgatg gcaggacaga tctatgacac   1020

cgtctccctg tcagcacagc cgggccccac agtggcctca ggagagaacg tgaccctgct   1080

gtgtcagtca tggtggcagt ttgacacttt ccttctgacc aaagaagggg cagcccatcc   1140

cccactgcgt ctgagatcaa tgtacggagc tcataagtac caggctgaat tccccatgag   1200

tcctgtgacc tcagcccacg cggggaccta caggtgctac ggctcataca gctccaaccc   1260

ccacctgctg tctttcccca gtgagcccct ggaactcatg gtctcaggac actctggagg   1320

ctccagcctc ccacccacag ggccgccctc cacacctggt ctgggaagat acctggaggt   1380

tttgattggg gtctcggtgg ccttcgtcct gctgctcttc ctcctcctct tcctcctcct   1440

ccgacgtcag cgtcacagca aacacaggac atctgaccag agaaagactg atttccagcg   1500

tcctgcaggg gctgcggaga cagagcccaa ggacaggggc ctgctgagga ggtccagccc   1560

agctgctgac gtccaggaag aaaacctcta tgctgccgtg aaggacacac agtctgagga   1620

cagggtggag ctggacagtc agagcccaca cgatgaagac ccccaggcag tgacgtatgc   1680

cccggtgaaa cactccagtc ctaggagaga aatggcctct cctccctcct cactgtctgg   1740

ggaattcctg gacacaaagg acagacaggt ggaagaggac aggcagatgg acactgaggc   1800

tgctgcatct gaagcctccc aggatgtgac ctacgcccag ctgcacagct tgacccttag   1860

acggaaggca actgagcctc ctccatccca ggaaggggaa cctccagctg agcccagcat   1920
```

-continued

```
ctacgccact ctggccatcc actagcccgg ggggtacgca gaccccacac tcagcagaag   1980

gagactcagg actgctgaag gcacgggagc tgcccccagt ggacaccagt gaaccccagt   2040

cagcctggac ccctaacaca gaccatgagg agacgctggg aacttgtggg actcacctga   2100

ctcaaagatg actaatatcg tcccattttg gaaataaagc aacagacttc tcaacaatca   2160

atgagttaat                                                          2170
```

<210> SEQ ID NO 22
<211> LENGTH: 1453
<212> TYPE: DNA
<213> ORGANISM: human

<400> SEQUENCE: 22

```
gggagtgcat ccgccccaac ccttttcccc ctcgtctcct gtgagaattc cccgtcggat     60

acgagcagcg tggccgttgg ctgcctcgca caggacttcc ttcccgactc catcactttc    120

tcctggaaat acaagaacaa ctctgacatc agcagcaccc ggggcttccc atcagtcctg    180

agagggggca agtacgcagc cacctcacag gtgctgctgc cttccaagga cgtcatgcag    240

ggcacagacg aacacgtggt gtgcaaagtc cagcacccca acggcaacaa agaaaagaac    300

gtgcctcttc cagtgattgc cgagctgcct cccaaagtga gcgtcttcgt cccaccccgc    360

gacggcttct tcggcaaccc ccgcaagtcc aagctcatct gccaggccac gggtttcagt    420

ccccggcaga ttcaggtgtc ctggctgcgc gaggggaagc aggtggggtc tggcgtcacc    480

acggaccagg tgcaggctga ggccaaagag tctgggccca cgacctacaa ggtgaccagc    540

acactgacca tcaaagagag cgactggctc agccagagca tgttcacctg ccgcgtggat    600

cacaggggcc tgaccttcca gcagaatgcg tcctccatgt gtgtccccga tcaagacaca    660

gccatccggg tcttcgccat ccccccatcc tttgccagca tcttcctcac caagtccacc    720

aagttgacct gcctggtcac agacctgacc acctatgaca gcgtgaccat ctcctggacc    780

cgccagaatg gcgaagctgt gaaaacccac accaacatct ccgagagcca ccccaatgcc    840

actttcagcg ccgtgggtga ggccagcatc tgcgaggatg actggaattc cggggagagg    900

ttcacgtgca ccgtgaccca cacagacctg ccctcgccac tgaagcagac catctcccgg    960

cccaaggggg tggccctgca caggcccgat gtctacttgc tgccaccagc ccgggagcag   1020

ctgaacctgc gggagtcggc caccatcacg tgcctggtga cgggcttctc tcccgcggac   1080

gtcttcgtgc agtggatgca gagggggcag cccttgtccc cggagaagta tgtgaccagc   1140

gccccaatgc ctgagcccca ggccccaggc cggtacttcg cccacagcat cctgaccgtg   1200

tccgaagagg aatggaacac gggggagacc tacacctgcg tggtggccca tgaggccctg   1260

cccaacaggg tcaccgagag gaccgtggac aagtccaccg gtaaacccac cctgtacaac   1320

gtgtccctgg tcatgtccga cacagctggc acctgctact gaccctgctg gcctgcccac   1380

aggctcgggg cggctggccg ctctgtgtgt gcatgcaaac taacccgtgt caacggggtg   1440

agatgttgca tct                                                      1453
```

<210> SEQ ID NO 23
<211> LENGTH: 1192
<212> TYPE: DNA
<213> ORGANISM: human

<400> SEQUENCE: 23

```
cagatccatc aggtccaagc tgtgttgact accactgctt ttcccttcgt ctcaattatg     60
```

-continued

```
tcttggaaga aggctttgcg gatccctgga ggccttcggg tagcaactgt gaccttgatg    120

ctggcgatgc tgagcacccc ggtggctgag ggcagagact ctcccgagga tttcgtgtac    180

cagtttaagg gcatgtgcta cttcaccaac gggacggagc gcgtgcgtct tgtgaccaga    240

tacatctata accgagagga gtacgcacgc ttcgacagcg acgtgggggt gtatcgggcg    300

gtgacgccgc tggggccgcc tgacgccgag tactggaaca gccagaagga agtcctggag    360

aggacccggg cggagttgga cacggtgtgc agacacaact accagttgga gctccgcacg    420

accttgcagc ggcgagtgga gcccacagtg accatctccc catccaggac agaggccctc    480

aaccaccaca acctgctggt ctgctcagtg acagatttct atccagccca gatcaaagtc    540

cggtggtttc ggaatgacca ggaggagaca actggcgttg tgtccacccc ccttattagg    600

aacggtgact ggaccttcca gatcctggtg atgctggaaa tgactcccca gcgtggagac    660

gtctacacct gccacgtgga gcaccccagc ctccagaacc ccatcatcgt ggagtggcgg    720

gctcagtctg aatctgccca gagcaagatg ctgagtggca ttggaggctt cgtgctgggg    780

ctgatcttcc tcgggctggg ccttattatc catcacagga gtcagaaagg gctcctgcac    840

tgactcctga gactatttta actgggattg gttatcactt ttctgtaacg cctgcttgtc    900

cctgcccaga attcccagct gcctgtgtca gcctgtcccc cgagatcaga gtcctaccgt    960

ggctgtcacg cagccaccag gtcatctcct ttcatcccca cctcaaggct gatggctgtg   1020

accctgcttc ctgcactgac ccagagcctc tgcctgtgca cggccagctg cgtctactga   1080

ggccccaagg ggtttctgtt tctattctct cctcagactg ctcaagagaa gcacatgaaa   1140

accattacct gactttagag ctttttttaca taattaaaca tgatcctgag tt          1192
```

<210> SEQ ID NO 24
<211> LENGTH: 2048
<212> TYPE: DNA
<213> ORGANISM: human

<400> SEQUENCE: 24

```
atgtgaaggc acaagctgct gttatataca acagagtgaa ctgagcatca gtcagaaaaa     60

gtctatgttt gcagaaatac agatccaaga caaagacagg atgggcactg ctggaaaagt    120

tattaaatgc aaagcagctg tgctttggga gcagaagcaa cccttctcca ttgaggaaat    180

agaagttgcc ccaccaaaga ctaaagaagt tcgcattaag attttggcca caggaatctg    240

tcgcacagat gaccatgtga taaaaggaac aatggtgtcc aagtttccag tgattgtggg    300

acatgaggca actgggattg tagagagcat tggagaagga gtgactacag tgaaaccagg    360

tgacaaagtc atccctctct ttctgccaca atgtagagaa tgcaatgctt gtcgcaaccc    420

agatggcaac ctttgcatta ggagcgatat tactggtcgt ggagtactgg ctgatggcac    480

caccagattt acatgcaagg gcaaaccagt acaccacttc atgaacacca gtacatttac    540

cgagtacaca gtggtggatg aatcttctgt tgctaagatt gatgatgcag ctcctcctga    600

gaaagtctgt ttaattggct gtgggttttc cactggatat ggcgctgctg ttaaaactgg    660

caaggtcaaa cctggttcca cttgcgtcgt ctttggcctg ggaggagttg gcctgtcagt    720

catcatgggc tgtaagtcag ctggtgcatc taggatcatt gggattgacc tcaacaaaga    780

caaatttgag aaggccatgg ctgtaggtgc cactgagtgt atcagtccca aggactctac    840

caaacccatc agtgaggtgc tgtcagaaat gacaggcaac aacgtgggat acacctttga    900

agttattggg catcttgaaa ccatgattga tgccctggca tcctgccaca tgaactatgg    960

gaccagcgtg gttgtaggag ttcctccatc agccaagatg ctcacctatg acccgatgtt   1020
```

```
gctcttcact ggacgcacat ggaagggatg tgtctttgga ggtttgaaaa gcagagatga   1080

tgtcccaaaa ctagtgactg agttcctggc aaagaaattt gacctggacc agttgataac   1140

tcatgtttta ccatttaaaa aaatcagtga aggatttgag ctgctcaatt caggacaaag   1200

cattcgaacg gtcctgacgt tttgagatcc aaagtggcag gaggtctgtg ttgtcatggt   1260

gaactggagt ttctcttgtg agagttccct catctgaaat catgtatctg tctcacaaat   1320

acaagcataa gtagaagatt tgttgaagac atagaaccct tataaagaat tattaacctt   1380

tataaacatt taaagtcttg tgagcacctg ggaattagta taataacaat gttaatattt   1440

ttgatttaca ttttgtaagg ctataattgt atcttttaag aaaacataca cttggatttc   1500

tatgttgaaa tggagatttt taagagtttt aaccagctgc tgcagatata taactcaaaa   1560

cagatatagc gtataaagat atagtaaatg catctcccag agtaatattc acttaacaca   1620

ttgaaactat tattttttag atttgaatat aaatgtattt tttaaacact tgttatgagt   1680

taacttggat tacattttga aatcagttca ttccatgatg catattactg gattagatta   1740

agaaagacag aaaagattaa gggacgggca catttttcaa cgattaagaa tcatcattac   1800

ataacttggt gaaactgaaa aagtatatca tatgggtaca caaggctatt tgccagcata   1860

tattaatatt ttagaaaata ttccttttgt aatactgaat ataaacatag agctagagtc   1920

atattatcat acttatcata atgttcaatt tgatacagta gaattgcaag tccctaagtc   1980

cctattcact gtgcttagta gtgactccat ttaataaaaa gtgtttttag tttttaacaa   2040

ctaaaccg                                                             2048
```

<210> SEQ ID NO 25
<211> LENGTH: 2048
<212> TYPE: DNA
<213> ORGANISM: human

<400> SEQUENCE: 25

```
atgtgaaggc acaagctgct gttatataca acagagtgaa ctgagcatca gtcagaaaaa     60

gtctatgttt gcagaaatac agatccaaga caaagacagg atgggcactg ctggaaaagt    120

tattaaatgc aaagcagctg tgctttggga gcagaagcaa cccttctcca ttgaggaaat    180

agaagttgcc ccaccaaaga ctaaagaagt tcgcattaag attttggcca caggaatctg    240

tcgcacagat gaccatgtga taaaaggaac aatggtgtcc aagtttccag tgattgtggg    300

acatgaggca actgggattg tagagagcat tggagaagga gtgactacag tgaaaccagg    360

tgacaaagtc atccctctct ttctgccaca atgtagagaa tgcaatgctt gtcgcaaccc    420

agatggcaac ctttgcatta ggagcgatat tactggtcgt ggagtactgg ctgatggcac    480

caccagattt acatgcaagg gcaaaccagt acaccacttc atgaacacca gtacatttac    540

cgagtacaca gtggtggatg aatcttctgt tgctaagatt gatgatgcag ctcctcctga    600

gaaagtctgt ttaattggct gtgggttttc cactggatat ggcgctgctg ttaaaactgg    660

caaggtcaaa cctggttcca cttgcgtcgt ctttggcctg ggaggagttg gcctgtcagt    720

catcatgggc tgtaagtcag ctggtgcatc taggatcatt gggattgacc tcaacaaaga    780

caaatttgag aaggccatgg ctgtaggtgc cactgagtgt atcagtccca aggactctac    840

caaacccatc agtgaggtgc tgtcagaaat gacaggcaac aacgtgggat acacctttga    900

agttattggg catcttgaaa ccatgattga tgccctggca tcctgccaca tgaactatgg    960

gaccagcgtg gttgtaggag ttcctccatc agccaagatg ctcacctatg acccgatgtt   1020
```

-continued

```
gctcttcact ggacgcacat ggaagggatg tgtctttgga ggtttgaaaa gcagagatga   1080

tgtcccaaaa ctagtgactg agttcctggc aaagaaattt gacctggacc agttgataac   1140

tcatgtttta ccatttaaaa aaatcagtga aggatttgag ctgctcaatt caggacaaag   1200

cattcgaacg gtcctgacgt tttgagatcc aaagtggcag gaggtctgtg ttgtcatggt   1260

gaactggagt ttctcttgtg agagttccct catctgaaat catgtatctg tctcacaaat   1320

acaagcataa gtagaagatt tgttgaagac atagaaccct tataaagaat tattaacctt   1380

tataaacatt taaagtcttg tgagcacctg ggaattagta taataacaat gttaatattt   1440

ttgatttaca ttttgtaagg ctataattgt atcttttaag aaaacataca cttggatttc   1500

tatgttgaaa tggagatttt taagagtttt aaccagctgc tgcagatata taactcaaaa   1560

cagatatagc gtataaagat atagtaaatg catctcccag agtaatattc acttaacaca   1620

ttgaaactat tattttttag atttgaatat aaatgtattt tttaaacact tgttatgagt   1680

taacttggat tacattttga aatcagttca ttccatgatg catattactg gattagatta   1740

agaaagacag aaaagattaa gggacgggca catttttcaa cgattaagaa tcatcattac   1800

ataacttggt gaaactgaaa aagtatatca tatgggtaca caaggctatt tgccagcata   1860

tattaatatt ttagaaaata ttccttttgt aatactgaat ataaacatag agctagagtc   1920

atattatcat acttatcata atgttcaatt tgatacagta gaattgcaag tccctaagtc   1980

cctattcact gtgcttagta gtgactccat ttaataaaaa gtgtttttag tttttaacaa   2040

ctaaaccg                                                            2048
```

<210> SEQ ID NO 26
<211> LENGTH: 2816
<212> TYPE: DNA
<213> ORGANISM: human

<400> SEQUENCE: 26

```
tcgttgatat caaagacagt tgaaggaaat gaattttgaa acttcacggt gtgccaccct     60

acagtactgc cctgaccctt acatccagcg tttcgtagaa acccagctca tttctcttgg    120

aaagaaagtt attaccgatc caccatgtcc cagagcacac agacaaatga attcctcagt    180

ccagaggttt tccagcatat ctgggatttt ctggaacagc ctatatgttc agttcagccc    240

attgacttga actttgtgga tgaaccatca gaagatggtg cgacaaacaa gattgagatt    300

agcatggact gtatccgcat gcaggactcg gacctgagtg accccatgtg gccacagtac    360

acgaacctgg ggctcctgaa cagcatggac cagcagattc agaacggctc ctcgtccacc    420

agtccctata acacagacca cgcgcagaac agcgtcacgg cgccctcgcc ctacgcacag    480

cccagctcca ccttcgatgc tctctctcca tcacccgcca tcccctccaa caccgactac    540

ccaggcccgc acagtttcga cgtgtccttc cagcagtcga gcaccgccaa gtcggccacc    600

tggacgtatt ccactgaact gaagaaactc tactgccaaa ttgcaaagac atgccccatc    660

cagatcaagg tgatgacccc acctcctcag ggagctgtta tccgcgccat gcctgtctac    720

aaaaaagctg agcacgtcac ggaggtggtg aagcggtgcc ccaaccatga gctgagccgt    780

gaattcaacg agggacagat tgcccctcct agtcatttga ttcgagtaga ggggaacagc    840

catgcccagt atgtagaaga tcccatcaca ggaagacaga gtgtgctggt accttatgag    900

ccaccccagg ttggcactga attcacgaca gtcttgtaca atttcatgtg taacagcagt    960

tgtgttggag ggatgaaccg ccgtccaatt ttaatcattg ttactctgga aaccagagat   1020

gggcaagtcc tgggccgacg ctgctttgag gcccggatct gtgcttgccc aggaagagac   1080
```

-continued

```
aggaaggcgg atgaagatag catcagaaag cagcaagttt cggacagtac aaagaacggt   1140
gatggtacga agcgcccgtt tcgtcagaac acacatggta tccagatgac atccatcaag   1200
aaacgaagat ccccagatga tgaactgtta tacttaccag tgaggggccg tgagacttat   1260
gaaatgctgt tgaagatcaa agagtccctg gaactcatgc agtaccttcc tcagcacaca   1320
attgaaacgt acaggcaaca gcaacagcag cagcaccagc acttacttca gaaacatctc   1380
ctttcagcct gcttcaggaa tgagcttgtg gagccccgga gagaaactcc aaaacaatct   1440
gacgtcttct ttagacattc caagcccca aaccgatcag tgtacccata gagccctatc   1500
tctatatttt aagtgtgtgt gttgtatttc catgtgtata tgtgagtgtg tgtgtgtgta   1560
tgtgtgtgcg tgtgtatcta gccctcataa acaggacttg aagacacttt ggctcagaga   1620
cccaactgct caaaggcaca aagccactag tgagagaatc ttttgaaggg actcaaacct   1680
ttacaagaaa ggatgttttc tgcagatttt gtatccttag accggccatt ggtgggtgag   1740
gaaccactgt gtttgtctgt gagctttctg ttgtttcctg ggagggaggg gtcaggtggg   1800
gaaaggggca ttaagatgtt tattggaacc cttttctgtc ttcttctgtt gtttttctaa   1860
aattcacagg gaagcttttg agcaggtctc aaacttaaga tgtcttttta agaaaaggag   1920
aaaaaagttg ttattgtctg tgcataagta agttgtaggt gactgagaga ctcagtcaga   1980
cccttttaat gctggtcatg taataatatt gcaagtagta agaaacgaag gtgtcaagtg   2040
tactgctggg cagcgaggtg atcattacca aaagtaatca actttgtggg tggagagttc   2100
tttgtgagaa cttgcattat ttgtgtcctc ccctcatgtg taggtagaac atttcttaat   2160
gctgtgtacc tgcctctgcc actgtatgtt ggcatctgtt atgctaaagt tttcttgta    2220
catgaaaccc tggaagacct actacaaaaa aactgttgtt tggcccccat agcaggtgaa   2280
ctcattttgt gcttttaata gaaagacaaa tccaccccag taatattgcc cttacgtagt   2340
tgtttaccat tattcaaagc tcaaaataga atttgaagcc ctctcacaaa atctgtgatt   2400
aatttgctta attagagctt ctatccctca agcctaccta ccataaaacc agccatatta   2460
ctgatactgt tcagtgcatt tagccaggag acttacgttt tgagtaagtg agatccaagc   2520
agacgtgtta aaatcagcac tcctggactg gaaattaaag attgaaaggg tagactactt   2580
ttcttttttt tactcaaaag tttagagaat ctctgtttct ttccatttta aaaacatatt   2640
ttaagataat agcataaaga ctttaaaaat gttcctcccc tccatcttcc cacacccagt   2700
caccagcact gtattttctg tcaccaagac aatgatttct tgttattgag gctgttgctt   2760
ttgtggatgt gtgattttaa ttttcaataa acttttgcat cttggtttaa aagaaa       2816
```

<210> SEQ ID NO 27
<211> LENGTH: 2816
<212> TYPE: DNA
<213> ORGANISM: human

<400> SEQUENCE: 27

```
tcgttgatat caaagacagt tgaaggaaat gaattttgaa acttcacggt gtgccaccct     60
acagtactgc cctgaccctt acatccagcg tttcgtagaa acccagctca tttctcttgg    120
aaagaaagtt attaccgatc caccatgtcc cagagcacac agacaaatga attcctcagt    180
ccagaggttt tccagcatat ctgggatttt ctggaacagc ctatatgttc agttcagccc    240
attgacttga actttgtgga tgaaccatca gaagatggtg cgacaaacaa gattgagatt    300
agcatggact gtatccgcat gcaggactcg gacctgagtg accccatgtg gccacagtac    360
```

-continued

```
acgaacctgg ggctcctgaa cagcatggac cagcagattc agaacggctc ctcgtccacc    420
agtccctata acacagacca cgcgcagaac agcgtcacgg cgccctcgcc ctacgcacag    480
cccagctcca ccttcgatgc tctctctcca tcacccgcca tcccctccaa caccgactac    540
ccaggcccgc acagtttcga cgtgtccttc cagcagtcga gcaccgccaa gtcggccacc    600
tggacgtatt ccactgaact gaagaaactc tactgccaaa ttgcaaagac atgccccatc    660
cagatcaagg tgatgacccc acctcctcag ggagctgtta tccgcgccat gcctgtctac    720
aaaaaagctg agcacgtcac ggaggtggtg aagcggtgcc ccaaccatga gctgagccgt    780
gaattcaacg agggacagat tgcccctcct agtcatttga ttcgagtaga ggggaacagc    840
catgcccagt atgtagaaga tcccatcaca ggaagacaga gtgtgctggt accttatgag    900
ccaccccagg ttggcactga attcacgaca gtcttgtaca atttcatgtg taacagcagt    960
tgtgttggag ggatgaaccg ccgtccaatt ttaatcattg ttactctgga aaccagagat   1020
gggcaagtcc tgggccgacg ctgctttgag gcccggatct gtgcttgccc aggaagagac   1080
aggaaggcgg atgaagatag catcagaaag cagcaagttt cggacagtac aaagaacggt   1140
gatggtacga agcgcccgtt tcgtcagaac acacatggta tccagatgac atccatcaag   1200
aaacgaagat ccccagatga tgaactgtta tacttaccag tgaggggccg tgagacttat   1260
gaaatgctgt tgaagatcaa agagtccctg gaactcatgc agtaccttcc tcagcacaca   1320
attgaaacgt acaggcaaca gcaacagcag cagcaccagc acttacttca gaaacatctc   1380
ctttcagcct gcttcaggaa tgagcttgtg gagccccgga gagaaactcc aaaacaatct   1440
gacgtcttct ttagacattc caagcccccca aaccgatcag tgtacccata gagccctatc   1500
tctatatttt aagtgtgtgt gttgtatttc catgtgtata tgtgagtgtg tgtgtgtgta   1560
tgtgtgtgcg tgtgtatcta gccctcataa acaggacttg aagacacttt ggctcagaga   1620
cccaactgct caaaggcaca aagccactag tgagagaatc ttttgaaggg actcaaacct   1680
ttacaagaaa ggatgttttc tgcagatttt gtatccttag accggccatt ggtgggtgag   1740
gaaccactgt gtttgtctgt gagctttctg ttgtttcctg ggagggaggg gtcaggtggg   1800
gaaaggggca ttaagatgtt tattggaacc cttttctgtc ttcttctgtt gtttttctaa   1860
aattcacagg gaagcttttg agcaggtctc aaacttaaga tgtcttttta agaaaaggag   1920
aaaaaagttg ttattgtctg tgcataagta agttgtaggt gactgagaga ctcagtcaga   1980
cccttttaat gctggtcatg taataatatt gcaagtagta agaaacgaag gtgtcaagtg   2040
tactgctggg cagcgaggtg atcattacca aaagtaatca actttgtggg tggagagttc   2100
tttgtgagaa cttgcattat ttgtgtcctc ccctcatgtg taggtagaac atttcttaat   2160
gctgtgtacc tgcctctgcc actgtatgtt ggcatctgtt atgctaaagt ttttcttgta   2220
catgaaaccc tggaagacct actacaaaaa aactgttgtt tggcccccat agcaggtgaa   2280
ctcattttgt gcttttaata gaaagacaaa tccaccccag taatattgcc cttacgtagt   2340
tgtttaccat tattcaaagc tcaaaataga atttgaagcc ctctcacaaa atctgtgatt   2400
aatttgctta attagagctt ctatccctca agcctaccta ccataaaacc agccatatta   2460
ctgatactgt tcagtgcatt tagccaggag acttacgttt tgagtaagtg agatccaagc   2520
agacgtgtta aaatcagcac tcctggactg gaaattaaag attgaaaggg tagactactt   2580
ttcttttttt tactcaaaag tttagagaat ctctgtttct ttccatttta aaaacatatt   2640
ttaagataat agcataaaga ctttaaaaat gttcctcccc tccatcttcc cacacccagt   2700
caccagcact gtattttctg tcaccaagac aatgatttct tgttattgag gctgttgctt   2760
```

```
ttgtggatgt gtgattttaa ttttcaataa acttttgcat cttggtttaa aagaaa      2816


<210> SEQ ID NO 28
<211> LENGTH: 3803
<212> TYPE: DNA
<213> ORGANISM: human

<400> SEQUENCE: 28

ccatggtagg agcgctcgcc tcgctgcggt gcccgctgag gccatgccgg ggccccggcg     60

ccccgctggc tcccgcctgc gcctgctcct gctcctgctg ctgccgccgc tgctgctgct    120

gctccggggc agccacgcgg gcaacctgac ggtagccgtg gtactgccgc tggccaatac    180

ctcgtacccc tggtcgtggg cgcgcgtggg acccgccgtg gagctggccc tggcccaggt    240

gaaggcgcgc cccgacttgc tgccgggctg gacggtccgc acggtgctgg gcagcagcga    300

aaacgcgctg ggcgtctgct ccgacaccgc agcgcccctg gccgcggtgg acctcaagtg    360

ggagcacaac cccgctgtgt tcctgggccc cggctgcgtg tacgccgccg ccccagtggg    420

gcgcttcacc gcgcactggc gggtcccgct gctgaccgcc ggcgccccgg cgctgggctt    480

cggtgtcaag gacgagtatg cgctgaccac ccgcgcgggg cccagctacg ccaagctggg    540

ggacttcgtg gcggcgctgc accgacggct gggctgggag cgccaagcgc tcatgctcta    600

cgcctaccgg ccgggtgacg aagagcactg cttcttcctc gtggaggggc tgttcatgcg    660

ggtccgcgac cgcctcaata ttacggtgga ccacctggag ttcgccgagg acgacctcag    720

ccactacacc aggctgctgc ggaccatgcc gcgcaaaggc cgagttatct acatctgcag    780

ctcccctgat gccttcagaa ccctcatgct cctggccctg gaagctggct tgtgtgggga    840

ggactacgtt ttcttccacc tggatatctt tgggcaaagc ctgcaaggtg gacagggccc    900

tgctccccgc aggccctggg agagagggga tgggcaggat gtcagtgccc gccaggcctt    960

tcaggctgcc aaaatcatta catataaaga cccagataat cccgagtact tggaattcct   1020

gaagcagtta aaacacctgg cctatgagca gttcaacttc accatggagg atggcctggt   1080

gaacaccatc ccagcatcct tccacgacgg gctcctgctc tatatccagg cagtgacgga   1140

gactctggca catgggggaa ctgttactga tggggagaac atcactcagc ggatgtggaa   1200

ccgaagcttt caaggtgtga caggatacct gaaaattgat agcagtggcg atcgggaaac   1260

agacttctcc ctctgggata tggatcccga gaatggtgcc ttcagggttg tactgaacta   1320

caatgggact tcccaagagc tggtggctgt gtcggggcgc aaactgaact ggcccctggg   1380

gtaccctcct cctgacatcc ccaaatgtgg ctttgacaac gaagacccag catgcaacca   1440

agatcacctt tccaccctgg aggtgctggc tttggtgggc agcctctcct tgctcggcat   1500

tctgattgtc tccttcttca tatacaggaa gatgcagctg gagaaggaac tggcctcgga   1560

gctgtggcgg gtgcgctggg aggacgttga gcccagtagc cttgagaggc acctgcggag   1620

tgcaggcagc cggctgaccc tgagcgggag aggctccaat tacggctccc tgctaaccac   1680

agagggccag ttccaagtct ttgccaagac agcatattat aagggcaacc tcgtggctgt   1740

gaaacgtgtg aaccgtaaac gcattgagct gacacgaaaa gtcctgtttg aactgaagca   1800

tatgcgggat gtgcagaatg aacacctgac caggtttgtg ggagcctgca ccgacccccc   1860

caatatctgc atcctcacag agtactgtcc ccgtgggagc ctgcaggaca ttctggagaa   1920

tgagagcatc accctggact ggatgttccg gtactcactc accaatgaca tcgtcaaggg   1980

catgctgttt ctacacaatg ggctatctgt ttcccatggg aacctcaagt catccaactg   2040
```

-continued

```
cgtggtagat gggcgctttg tgctcaagat caccgactat gggctggaga gcttcaggga   2100

cctggaccca gagcaaggac acaccgttta tgccaaaaag ctgtggacgg cccctgagct   2160

cctgcgaatg gcttcacccc ctgtgcgggg ctcccaggct ggtgacgtat acagctttgg   2220

gatcatcctt caggagattg ccctgaggag tggggtcttc cacgtggaag gtttggacct   2280

gagccccaaa gagatcatcg agcgggtgac tcggggtgag cagcccccct tccggccctc   2340

cctggccctg cagagtcacc tggaggagtt ggggctgctc atgcagcggt gctgggctga   2400

ggacccacag gagaggccac cattccagca gatccgcctg acgttgcgca aatttaacag   2460

ggagaacagc agcaacatcc tggacaacct gctgtcccgc atggagcagt acgcgaacaa   2520

tctggaggaa ctggtggagg agcggaccca ggcatacctg gaggagaagc gcaaggctga   2580

ggccctgctc taccagatcc tgcctcactc agtggctgag cagctgaagc gtggggagac   2640

ggtgcaggcc gaagcctttg acagtgttac catctacttc agtgacattg tgggtttcac   2700

agcgctgtcg gcggagagca cacccatgca ggtggtgacc ctgctcaatg acctgtacac   2760

ttgctttgat gctgtcatag acaactttga tgtgtacaag gtggagacaa ttggcgatgc   2820

ctacatggtg gtgtcagggc tccctgtgcg gaacgggcgg ctacacgcct gcgaggtagc   2880

ccgcatggcc ctggcactgc tggatgctgt gcgctccttc cgaatccgcc accggcccca   2940

ggagcagctg cgcttgcgca ttggcatcca cacaggacct gtgtgtgctg gagtggtggg   3000

actgaagatg ccccgttact gtctctttgg ggatacagtc aacacagcct caagaatgga   3060

gtctaatggg gaagccctga agatccactt gtcttctgag accaaggctg tcctggagga   3120

gtttggtggt ttcgagctgg agcttcgagg ggatgtagaa atgaagggca aaggcaaggt   3180

tcggacctac tggctccttg ggagaggggg gagtagcacc cgaggctgac ctgcctcctc   3240

tcctatccct ccacacctcc cctaccctgt gccagaagca acagaggtgc caggcctcag   3300

cctcacccac agcagcccca tcgccaaagg atggaagtaa tttgaatagc tcaggtgtgc   3360

tgaccccagt gaagacacca gataggacct ctgagagggg actggcatgg ggggatctca   3420

gagcttacag gctgagccaa gcccacggcc atgcacaggg acactcacac aggcacacgc   3480

acctgctctc cacctggact caggccgggc tgggctgtgg atccttgatc cctcccctc    3540

cccatgctct cctccctcag ccttgctacc ctgtgactta ctgggaggag agtcacctga   3600

aggggaacat gaaaagagac taggtgaaga gagggcaggg gagcccacat ctggggctgg   3660

cccacaatac ctgctccccc gacccctcc acccagcagt agacacagtg cacaggggag    3720

aagaggggtg gcgcagaagg gttgggggcc tgtatgcctt gcttctacca tgagcagaga   3780

caattaaaat ctttattcca gtg                                           3803
```

<210> SEQ ID NO 29
<211> LENGTH: 3803
<212> TYPE: DNA
<213> ORGANISM: human

<400> SEQUENCE: 29

```
ccatggtagg agcgctcgcc tcgctgcggt gcccgctgag gccatgccgg ggccccggcg     60

ccccgctggc tcccgcctgc gcctgctcct gctcctgctg ctgccgccgc tgctgctgct    120

gctccggggc agccacgcgg gcaacctgac ggtagccgtg gtactgccgc tggccaatac    180

ctcgtacccc tggtcgtggg cgcgcgtggg acccgccgtg gagctggccc tggcccaggt    240

gaaggcgcgc cccgacttgc tgccgggctg gacggtccgc acggtgctgg gcagcagcga    300

aaacgcgctg ggcgtctgct ccgacaccgc agcgcccctg gccgcggtgg acctcaagtg    360
```

-continued

```
ggagcacaac cccgctgtgt tcctgggccc cggctgcgtg tacgccgccg ccccagtggg    420
gcgcttcacc gcgcactggc gggtcccgct gctgaccgcc ggcgccccgg cgctgggctt    480
cggtgtcaag gacgagtatg cgctgaccac ccgcgcgggg cccagctacg ccaagctggg    540
ggacttcgtg gcggcgctgc accgacggct gggctgggag cgccaagcgc tcatgctcta    600
cgcctaccgg ccgggtgacg aagagcactg cttcttcctc gtggaggggc tgttcatgcg    660
ggtccgcgac cgcctcaata ttacggtgga ccacctggag ttcgccgagg acgacctcag    720
ccactacacc aggctgctgc ggaccatgcc gcgcaaaggc cgagttatct acatctgcag    780
ctcccctgat gccttcagaa ccctcatgct cctggccctg gaagctggct tgtgtgggga    840
ggactacgtt ttcttccacc tggatatctt tgggcaaagc ctgcaaggtg gacagggccc    900
tgctccccgc aggccctggg agagagggga tgggcaggat gtcagtgccc gccaggcctt    960
tcaggctgcc aaaatcatta catataaaga cccagataat cccgagtact tggaattcct   1020
gaagcagtta aaacacctgg cctatgagca gttcaacttc accatggagg atggcctggt   1080
gaacaccatc ccagcatcct tccacgacgg gctcctgctc tatatccagg cagtgacgga   1140
gactctggca catgggggaa ctgttactga tggggagaac atcactcagc ggatgtggaa   1200
ccgaagcttt caaggtgtga caggatacct gaaaattgat agcagtggcg atcgggaaac   1260
agacttctcc ctctgggata tggatcccga gaatggtgcc ttcagggttg tactgaacta   1320
caatgggact tcccaagagc tggtggctgt gtcggggcgc aaactgaact ggcccctggg   1380
gtaccctcct cctgacatcc ccaaatgtgg ctttgacaac gaagacccag catgcaacca   1440
agatcacctt tccaccctgg aggtgctggc tttggtgggc agcctctcct tgctcggcat   1500
tctgattgtc tccttcttca tatacaggaa gatgcagctg gagaaggaac tggcctcgga   1560
gctgtggcgg gtgcgctggg aggacgttga gcccagtagc cttgagaggc acctgcggag   1620
tgcaggcagc cggctgaccc tgagcgggag aggctccaat tacggctccc tgctaaccac   1680
agagggccag ttccaagtct ttgccaagac agcatattat aagggcaacc tcgtggctgt   1740
gaaacgtgtg aaccgtaaac gcattgagct gacacgaaaa gtcctgtttg aactgaagca   1800
tatgcgggat gtgcagaatg aacacctgac caggtttgtg ggagcctgca ccgacccccc   1860
caatatctgc atcctcacag agtactgtcc ccgtgggagc ctgcaggaca ttctggagaa   1920
tgagagcatc accctggact ggatgttccg gtactcactc accaatgaca tcgtcaaggg   1980
catgctgttt ctacacaatg ggctatctgg ttcccatggg aacctcaagt catccaactg   2040
cgtggtagat gggcgctttg tgctcaagat caccgactat gggctggaga gcttcaggga   2100
cctggaccca gagcaaggac acaccgttta tgccaaaaag ctgtggacgg cccctgagct   2160
cctgcgaatg gcttcacccc ctgtgcgggg ctcccaggct ggtgacgtat acagctttgg   2220
gatcatcctt caggagattg ccctgaggag tggggtcttc cacgtggaag gtttggacct   2280
gagccccaaa gagatcatcg agcgggtgac tcggggtgag cagcccccct tccggccctc   2340
cctggccctg cagagtcacc tggaggagtt ggggctgctc atgcagcggt gctgggctga   2400
ggacccacag gagaggccac cattccagca gatccgcctg acgttgcgca aatttaacag   2460
ggagaacagc agcaacatcc tggacaacct gctgtcccgc atggagcagt acgcgaacaa   2520
tctggaggaa ctggtggagg agcggaccca ggcatacctg gaggagaagc gcaaggctga   2580
ggccctgctc taccagatcc tgcctcactc agtggctgag cagctgaagc gtggggagac   2640
ggtgcaggcc gaagcctttg acagtgttac catctacttc agtgacattg tgggtttcac   2700
```

-continued

```
agcgctgtcg gcggagagca cacccatgca ggtggtgacc ctgctcaatg acctgtacac   2760

ttgctttgat gctgtcatag acaactttga tgtgtacaag gtggagacaa ttggcgatgc   2820

ctacatggtg gtgtcagggc tccctgtgcg gaacgggcgg ctacacgcct gcgaggtagc   2880

ccgcatggcc ctggcactgc tggatgctgt gcgctccttc cgaatccgcc accggcccca   2940

ggagcagctg cgcttgcgca ttggcatcca cacaggacct gtgtgtgctg gagtggtggg   3000

actgaagatg ccccgttact gtctctttgg ggatacagtc aacacagcct caagaatgga   3060

gtctaatggg gaagccctga agatccactt gtcttctgag accaaggctg tcctggagga   3120

gtttggtggt ttcgagctgg agcttcgagg ggatgtagaa atgaagggca aaggcaaggt   3180

tcggacctac tggctccttg ggagaggggg gagtagcacc cgaggctgac ctgcctcctc   3240

tcctatccct ccacacctcc cctaccctgt gccagaagca acagaggtgc caggcctcag   3300

cctcacccac agcagcccca tcgccaaagg atggaagtaa tttgaatagc tcaggtgtgc   3360

tgaccccagt gaagacacca gataggacct ctgagagggg actggcatgg ggggatctca   3420

gagcttacag gctgagccaa gcccacggcc atgcacaggg acactcacac aggcacacgc   3480

acctgctctc cacctggact caggccgggc tgggctgtgg atccttgatc ccctcccctc   3540

cccatgctct cctccctcag ccttgctacc ctgtgactta ctgggaggag agtcacctga   3600

aggggaacat gaaaagagac taggtgaaga gagggcaggg gagcccacat ctggggctgg   3660

cccacaatac ctgctccccc gacccccctcc acccagcagt agacacagtg cacaggggag   3720

aagaggggtg gcgcagaagg gttgggggcc tgtatgcctt gcttctacca tgagcagaga   3780

caattaaaat ctttattcca gtg                                             3803
```

<210> SEQ ID NO 30
<211> LENGTH: 2970
<212> TYPE: DNA
<213> ORGANISM: human

<400> SEQUENCE: 30

```
ggggtaagga gttcaaggca gcgcccacac ccgggggctc tccgcaaccc gaccgcctgt     60

ccgctccccc acttcccgcc ctccctccca cctactcatt cacccaccca cccacccaga    120

gccgggacgg cagcccaggc gcccgggccc cgccgtctcc tcgccgcgat cctggacttc    180

ctcttgctgc aggacccggc ttccacgtgt gtcccggagc cggcgtctca gcacacgctc    240

cgctccgggc ctgggtgcct acagcagcca gagcagcagg gagtccggga cccgggcggc    300

atctgggcca agttaggcgc cgccgaggcc agcgctgaac gtctccaggg ccggaggagc    360

cgcggggcgt ccgggtctga gcctcagcaa atgggctccg acgtgcggga cctgaacgcg    420

ctgctgcccg ccgtcccctc cctgggtggc ggcggcggct gtgccctgcc tgtgagcggc    480

gcggcgcagt gggcgccggt gctggacttt gcgcccccgg gcgcttcggc ttacgggtcg    540

ttgggcggcc ccgcgccgcc accggctccg ccgccacccc cgccgccgcc gcctcactcc    600

ttcatcaaac aggagccgag ctggggcggc gcggagccgc acgaggagca gtgcctgagc    660

gccttcactg tccacttttc cggccagttc actggcacag ccggagcctg tcgctacggg    720

cccttcggtc ctcctccgcc cagccaggcg tcatccggcc aggccaggat gtttcctaac    780

gcgccctacc tgcccagctg cctcgagagc cagcccgcta ttcgcaatca gggttacagc    840

acggtcacct tcgacgggac gcccagctac ggtcacacgc cctcgcacca tgcggcgcag    900

ttccccaacc actcattcaa gcatgaggat cccatgggcc agcagggctc gctgggtgag    960

cagcagtact cggtgccgcc cccggtctat ggctgccaca cccccaccga cagctgcacc   1020
```

ggcagccagg ctttgctgct gaggacgccc tacagcagtg acaatttata ccaaatgaca 1080
tcccagcttg aatgcatgac ctggaatcag atgaacttag gagccacctt aaagggccac 1140
agcacagggt acgagagcga taaccacaca acgcccatcc tctgcggagc ccaatacaga 1200
atacacacgc acggtgtctt cagaggcatt caggatgtgc gacgtgtgcc tggagtagcc 1260
ccgactcttg tacggtcggc atctgagacc agtgagaaac gccccttcat gtgtgcttac 1320
ccaggctgca ataagagata ttttaagctg tcccacttac agatgcacag caggaagcac 1380
actggtgaga aaccatacca gtgtgacttc aaggactgtg aacgaaggtt ttctcgttca 1440
gaccagctca aaagacacca aaggagacat acaggtgtga aaccattcca gtgtaaagct 1500
tgtcagcgaa agttctcccg gtccgaccac ctgaagaccc acaccaggac tcatacaggt 1560
gaaaagccct tcagctgtcg gtggccaagt tgtcagaaaa agtttgcccg gtcagatgaa 1620
ttagtccgcc atcacaacat gcatcagaga aacatgacca aactccagct ggcgctttga 1680
ggggtctccc tcggggaccg ttcagtgtcc caggcagcac agtgtgtgaa ctgctttcaa 1740
gtctgactct ccactcctcc tcactaaaaa ggaaacttca gttgatcttc ttcatccaac 1800
ttccaagaca agataccggt gcttctggaa actaccaggt gtgcctggaa gagttggtct 1860
ctgccctgcc tacttttagt tgactcacag gccctggaga agcagctaac aatgtctggt 1920
tagttaaaag cccattgcca tttggtctgg attttctact gtaagaagag ccatagctga 1980
tcatgtcccc ctgacccttc ccttcttttt ttatgctcgt tttcgctggg gatggaatta 2040
ttgtaccatt ttctatcatg gaatatttat aggccagggc atgtgtatgt gtctgctaat 2100
gtaaactttg tcatggtttc catttactaa cagcaacagc aagaaataaa tcagagagca 2160
aggcatcggg ggtgaatctt gtctaacatt cccgaggtca gccaggctgc taacctggaa 2220
agcaggatgt agttctgcca ggcaactttt aaagctcatg catttcaagc agctgaagaa 2280
agaatcagaa ctaaccagta cctctgtata gaaatctaaa agaattttac cattcagtta 2340
attcaatgtg aacactggca cactgctctt aagaaactat gaagatctga gatttttttg 2400
tgtatgtttt tgactctttt gagtggtaat catatgtgtc tttatagatg tacatacctc 2460
cttgcacaaa tggaggggaa ttcattttca tcactgggag tgtccttagt gtataaaaac 2520
catgctggta tatggcttca agttgtaaaa atgaaagtga ctttaaaaga aaatagggga 2580
tggtccagga tctccactga taagactgtt tttaagtaac ttaaggacct ttgggtctac 2640
aagtatatgt gaaaaaaatg agacttactg ggtgaggaaa tccattgttt aaagatggtc 2700
gtgtgtgtgt gtgtgtgtgt gtgtgtgttg tgttgtgttt tgttttttaa gggagggaat 2760
ttattattta ccgttgcttg aaattactgt gtaaatatat gtctgataat gatttgctct 2820
ttgacaacta aaattaggac tgtataagta ctagatgcat cactgggtgt tgatcttaca 2880
agatattgat gataacactt aaaattgtaa cctgcatttt tcactttgct ctcaattaaa 2940
gtctattcaa aaggaaaaaa aaaaaaaaaa 2970

<210> SEQ ID NO 31
<211> LENGTH: 2422
<212> TYPE: DNA
<213> ORGANISM: human

<400> SEQUENCE: 31
gtcagcctcc cttccaccgc catattgggc cactaaaaaa agggggctcg tcttttcggg 60
gtgtttttct ccccctcccc tgtccccgct tgctcacggc tctgcgactc cgacgccggc 120

-continued

```
aaggtttgga gagcggctgg gttcgcggga cccgcgggct tgcacccgcc cagactcgga    180
cgggctttgc caccctctcc gcttgcctgg tcccctctcc tctccgccct cccgctcgcc    240
agtccatttg atcagcggag actcggcggc cgggccgggg cttccccgca gcccctgcgc    300
gctcctagag ctcgggccgt ggctcgtcgg ggtctgtgtc ttttggctcc gagggcagtc    360
gctgggcttc cgagaggggt tcgggccgcg taggggcgct ttgttttgtt cggttttgtt    420
tttttgagag tgcgagagag gcggtcgtgc agacccggga gaaagatgtc aaacgtgcga    480
gtgtctaacg ggagccctag cctggagcgg atggacgcca ggcaggcgga gcaccccaag    540
ccctcggcct gcaggaacct cttcggcccg gtggaccacg aagagttaac ccgggacttg    600
gagaagcact gcagagacat ggaagaggcg agccagcgca agtggaattt cgattttcag    660
aatcacaaac ccctagaggg caagtacgag tggcaagagg tggagaaggg cagcttgccc    720
gagttctact acagaccccc gcggcccccc aaaggtgcct gcaaggtgcc ggcgcaggag    780
agccaggatg tcagcgggag ccgcccggcg gcgcctttaa ttggggctcc ggctaactct    840
gaggacacgc atttggtgga cccaaagact gatccgtcgg acagccagac ggggttagcg    900
gagcaatgcg caggaataag gaagcgacct gcaaccgacg attcttctac tcaaaacaaa    960
agagccaaca gaacagaaga aaatgtttca gacggttccc caaatgccgg ttctgtggag   1020
cagacgccca agaagcctgg cctcagaaga cgtcaaacgt aaacagctcg aattaagaat   1080
atgtttcctt gtttatcaga tacatcactg cttgatgaag caaggaagat atacatgaaa   1140
attttaaaaa tacatatcgc tgacttcatg gaatggacat cctgtataag cactgaaaaa   1200
caacaacaca ataacactaa aattttaggc actcttaaat gatctgcctc taaaagcgtt   1260
ggatgtagca ttatgcaatt aggtttttcc ttatttgctt cattgtacta cctgtgtata   1320
tagtttttac cttttatgta gcacataaac tttggggaag ggagggcagg gtggggctga   1380
ggaactgacg tggagcgggg tatgaagagc ttgctttgat ttacagcaag tagataaata   1440
tttgacttgc atgaagagaa gcaattttgg ggaagggttt gaattgtttt ctttaaagat   1500
gtaatgtccc tttcagagac agctgatact tcatttaaaa aaatcacaaa aatttgaaca   1560
ctggctaaag ataattgcta tttattttta caagaagttt attctcattt gggagatctg   1620
gtgatctccc aagctatcta aagtttgtta gatagctgca tgtggctttt ttaaaaaagc   1680
aacagaaacc tatcctcact gccctcccca gtctctctta aagttggaat ttaccagtta   1740
attactcagc agaatggtga tcactccagg tagtttgggg caaaaatccg aggtgcttgg   1800
gagttttgaa tgttaagaat tgaccatctg cttttattaa atttgttgac aaaattttct   1860
cattttcttt tcacttcggg ctgtgtaaac acagtcaaaa taattctaaa tccctcgata   1920
tttttaaaga tctgtaagta acttcacatt aaaaaatgaa atattttta atttaaagct   1980
tactctgtcc atttatccac aggaaagtgt tatttttaaa ggaaggttca tgtagagaaa   2040
agcacacttg taggataagt gaaatggata ctacatcttt aaacagtatt tcattgcctg   2100
tgtatggaaa aaccatttga agtgtacctg tgtacataac tctgtaaaaa cactgaaaaa   2160
ttatactaac ttatttatgt taaaagattt tttttaatct agacaatata caagccaaag   2220
tggcatgttt tgtgcatttg taaatgctgt gttgggtaga ataggttttc cctcttttg    2280
ttaaataata tggctatgct taaaaggttg catactgagc caagtataat tttttgtaat   2340
gtgtgaaaaa gatgccaatt attgttacac attaagtaat caataaagaa aacttccata   2400
gctaaaaaaa aaaaaaaaaa aa                                            2422
```

-continued

<210> SEQ ID NO 32
<211> LENGTH: 1181
<212> TYPE: DNA
<213> ORGANISM: human

<400> SEQUENCE: 32

```
ggcacgaggc ccgggccccc caaagtcccg gccgggccga gggtcggcgg ccgccggcgg      60
gccgggcccg cgcacagcgc ccgcatgtac aacatgatgg agacggagct gaagccgccg     120
ggcccgcagc aaacttcggg gggcggcggc ggcaactcca ccgcggcggc ggccggcggc     180
aaccagaaaa acagcccgga ccgcgtcaag cggcccatga atgccttcat ggtgtggtcc     240
cgcgggcagc ggcgcaagat ggcccaggag aaccccaaga tgcacaactc ggagatcagc     300
aagcgcctgg gcgccgagtg gaaacttttg tcggagacgg agaagcggcc gttcatcgac     360
gaggctaagc ggctgcgagc gctgcacatg aaggagcacc cggattataa ataccggccc     420
cggcggaaaa ccaagacgct catgaagaag gataagtaca cgctgcccgg cgggctgctg     480
gcccccggcg gcaatagcat ggcgagcggg gtcggggtgg gcgccggcct gggcgcgggc     540
gtgaaccagc gcatggacag ttacgcgcac atgaacggct ggagcaacgg cagctacagc     600
atgatgcagg accagctggg ctacccgcag cacccgggcc tcaatgcgca cggcgcagcg     660
cagatgcagc ccatgcaccg ctacgacgtg agcgccctgc agtacaactc catgaccagc     720
tcgcagacct acatgaacgg ctcgcccacc tacagcatgt cctactcgca gcagggcacc     780
cctggcatgg ctcttggctc catgggttcg gtggtcaagt ccgaggccag ctccagcccc     840
cctgtggtta cctcttcctc ccactccagg gcgccctgcc aggccgggga cctccgggac     900
atgatcagca tgtatctccc cggcgccgag gtgccggaac ccgccgcccc cagcagactt     960
cacatgtccc agcactacca gagcggcccg gtgcccggca cggccattaa cggcacactg    1020
cccctctcac acatgtgagg gccggacagc gaactggagg ggggagaaat tttcaaagaa    1080
aaacgaggga aatgggaggg gtgcaaaaga ggagagtaag aaacagcatg gagaaaaccc    1140
ggtacgctca aaaaaaaaaa aaaaaaaaaa aaaaaaaaaa a                        1181
```

<210> SEQ ID NO 33
<211> LENGTH: 1305
<212> TYPE: DNA
<213> ORGANISM: human

<400> SEQUENCE: 33

```
ggggccccgc gccggcccgc gccctgccca gtgcggcctc cttccacccg ccgctgcctg      60
gcccgcgccg tccggccgag ctgcccggcg ggctggtccc cgcgcccgag ccgcccggcc     120
gggaccccga acaaggccga gatgacttcc aaggaggacg gcaaggcggc gccgggggag     180
gagcggcgcc gcagcccgct ggaccacctg cctccgcctg ccaactccaa caagccagac     240
gccgttcagc atcgaggaca tcctcaacaa gccgtctgtg cggagaagtt actcgctgcg     300
tggggcggcg cacctgctgg ccgccgcgga caagcacgcg cagggcggct tgccctggcg     360
ggccgcgcgc tgctctcgaa gacctcgccg ctgtgcgcgc tggaggagct cgccagcaag     420
acgtttaagg ggctggaggt cagcgttctg caggcagccg aaggccgcga cggtatgacc     480
atctttgggc agcggcagac ccctaagaag cggcgaaagt cgcgcacggc cttcaccaac     540
caccagatct atgaattgga aaagcgcttt ctataccaga agtacctgtc ccccgccgat     600
cgcgaccaaa tcgcgcagca gctgggcctc accaacgcgc aagtcatcac ctggttccag     660
aatcggcgcg ctaagctcaa gcgggaactg gaggagatga aggccgacgt ggagtccccc     720
```

-continued

```
aagaaactgg gccccagcgg gcagatggac atcgtggcgc tggccgaact cgagcagaac    780

tcggaggcca cagccggcgg tggcggcggc tgcggcaggg ccaagtcgag gcccggctct    840

ccggtcctcc ccccaggcgc cccgaaggcc cccgggcgct gcgccctgca gctctcgcct    900

gcctctccgc tcacggacca gccggccagc agccaggact gctcggagga cgaggaagac    960

gaagagatcg acgtggacga ttgagcggcg ccccgggtct tccgccgccc tgggctccta   1020

gcgctcgaaa gcccaacgcc tcccggaccg gaccgccgag gggagctggg acctcctctg   1080

ccactcccgc ctcctcccct gtccccggac tcggctcctg gcagccgcct cttccctctc   1140

gaagcaataa acccaggctg gccggccggg ccggccgcca ccagcggcct ccgccgcccc   1200

ggaagccctc gccgagcaat tctgtatggc ttctatataa atatttaaac ctatatagcg   1260

ggttctcccc aaaaaaaaaa aaaaaaaaaa aaaaaaaaaa aaaaa                   1305
```

<210> SEQ ID NO 34
<211> LENGTH: 1926
<212> TYPE: DNA
<213> ORGANISM: human

<400> SEQUENCE: 34

```
gctggagcat cccgctctgg tgccgctgca gccggcagag atggttgagc tcatgttccc     60

gctgttgctc ctccttctgc ccttccttct gtatatggct gcgccccaaa tcaggaaaat    120

gctgtccagt ggggtgtgta catcaactgt tcagcttcct gggaaagtag ttgtggtcac    180

aggagctaat acaggtatcg ggaaggagac agccaaagag ctggctcaga gaggagctcg    240

agtatattta gcttgccggg atgtggaaaa gggggaattg gtggccaaag agatccagac    300

cacgacaggg aaccagcagg tgttggtgcg gaaactggac ctgtctgata ctaagtctat    360

tcgagctttt gctaagggct tcttagctga ggaaaagcac ctccacgttt tgatcaacaa    420

tgcaggagtg atgatgtgtc cgtactcgaa gacagcagat ggctttgaga tgcacatagg    480

agtcaaccac ttgggtcact tcctcctaac ccatctgctg ctagagaaac taaaggaatc    540

agccccatca aggatagtaa atgtgtcttc cctcgcacat cacctgggaa ggatccactt    600

ccataacctg cagggcgaga aattctacaa tgcaggcctg gcctactgtc acagcaagct    660

agccaacatc ctcttcaccc aggaactggc ccggagacta aaaggctctg gcgttacgac    720

gtattctgta caccctggca cagtccaatc tgaactggtt cggcactcat ctttcatgag    780

atggatgtgg tggcttttct cctttttcat caagactcct cagcagggag cccagaccag    840

cctgcactgt gccttaacag aaggtcttga gattctaagt gggaatcatt tcagtgactg    900

tcatgtggca tgggtctctg cccaagctcg taatgagact atagcaaggc ggctgtggga    960

cgtcagttgt gacctgctgg gcctcccaat agactaacag gcagtgcagt tggacccaag   1020

agaagactgc agcagactac acagtacttc ttgtcaaaat gattctcctt caaggttttc   1080

aaaaccttta gcacaaagag agcaaaacct tccagccttg cctgcttggt gtccagttaa   1140

aactcagtgt actgccagat tcgtctaaat gtctgtcatg tccagattta ctttgcttct   1200

gttactgcca gagttactag agatatcata ataggataag aagaccctca tatgacctgc   1260

acagctcatt ttccttctga aagaaactac tacctaggag aatctaagct atagcaggga   1320

tgatttatgc aaatttgaac tagcttcttt gttcacaatt cagttcctcc caaccaacca   1380

gtcttcactt caagagggcc acactgcaac ctcagcttaa catgaataac aaagactggc   1440

tcaggagcag ggcttgccca ggcatggtgg atcaccggag tcagtagttc aagaccagcc   1500

tggccaacat ggtgaaaccc cacctctact aaaaattgtg tatatctttg tgtgtcttcc   1560
```

-continued

```
tgtttatgtg tgccaaggga gtattttcac aaagttcaaa acagccacaa taatcagaga   1620
tggagcaaac cagtgccatc cagtctttat gcaaatgaaa tgctgcaaag ggaagcagat   1680
tctgtatatg ttggtaacta cccaccaaga gcacatgggt agcagggaag aagtaaaaaa   1740
agagaaggag aatactggaa gataatgcac aaaatgaagg gactagttaa ggattaacta   1800
gccctttaag gattaactag ttaaggatta atagcaaaag acattaaata tgctaacata   1860
gctatggagg aattgagggc aagcacccag gactgatgag gtcttaacaa aaaccagtgt   1920
ggcaaa                                                              1926
```

<210> SEQ ID NO 35
<211> LENGTH: 1195
<212> TYPE: DNA
<213> ORGANISM: human

<400> SEQUENCE: 35

```
ccgagactca cggtcaagct aaggcgaaga gtgggtggct gaagccatac tattttatag     60
aattaatgga aagcagaaaa gacatcacaa accaagaaga actttggaaa atgaagccta    120
ggagaaattt agaagaagac gattatttgc ataaggacac gggagagacc agcatgctaa    180
aaagacctgt gcttttgcat ttgcaccaaa cagcccatgc tgatgaattt gactgccctt    240
cagaacttca gcacacacag gaactctttc cacagtggca cttgccaatt aaaatagctg    300
ctattatagc atctctgact ttctttaca ctcttctgag ggaagtaatt caccctttag    360
caacttccca tcaacaatat ttttataaaa ttccaatcct ggtcatcaac aaagtcttgc    420
caatggtttc catcactctc ttggcattgg tttacctgcc aggtgtgata gcagcaattg    480
tccaacttca taatggaacc aagtataaga agtttccaca ttggttggat aagtggatgt    540
taacaagaaa gcagtttggg cttctcagtt tctttttgc tgtactgcat gcaatttata    600
gtctgtctta cccaatgagg cgatcctaca gatacaagtt gctaaactgg gcatatcaac    660
aggtccaaca aaataaagaa gatgcctgga ttgagcatga tgtttggaga atggagattt    720
atgtgtctct gggaattgtg ggattggcaa tactggctct gttggctgtg acatctattc    780
catctgtgag tgactctttg acatggagag aatttcacta tattcagagc aagctaggaa    840
ttgtttccct tctactgggc acaatacacg cattgatttt tgcctggaat aagtggatag    900
atataaaaca atttgtatgg tatacacctc caacttttat gatagctgtt ttccttccaa    960
ttgttgtcct gatatttaaa agcatactat tcctgccatg cttgaggaag aagatactga   1020
agattagaca tggttgggaa gacgtcacca aaattaacaa aactgagata tgttcccagt   1080
tgtagaatta ctgtttacac acatttttgt tcaatattga tatattttat caccaacatt   1140
tcaagtttgt atttgttaat aaaatgatta ttcaaggaaa aaaaaaaaaa aaaaa        1195
```

<210> SEQ ID NO 36
<211> LENGTH: 3414
<212> TYPE: DNA
<213> ORGANISM: human

<400> SEQUENCE: 36

```
gcttacacag tatggccggc gacattagct agcgctcgct ctactctctc taacgggaaa     60
gcagcggaat acaagagact gaactgtatc tgcctctatt tccaaaagac tcacgttcaa    120
ctttcgctca cacaaagccg ggaaaatttt attagtcctt tttttaaaaa aagttaatat    180
aaaattatag caaaaaaaaa aaggaacctg aactttagta acacagctgg aacaatcgca    240
```

-continued

```
gcggcggcgg cagcggcggg agaagaggtt taatttagtt gattttctgt ggttgttggt    300
tgttcgctag tctcacggtg atggaagctg cacatttttt cgaagggacc gagaagctgc    360
tggaggtttg gttctcccgg cagcagcccg acgcaaacca aggatctggg gatcttcgca    420
ctatcccaag atctgagtgg gacatacttt tgaaggatgt gcaatgttca atcataagtg    480
tgacaaaaac tgacaagcag gaagcttatg tactcagtga gagtagcatg tttgtctcca    540
agagacgttt cattttgaag acatgtggta ccaccctctt gctgaaagca ctggttcccc    600
tgttgaagct tgctagggat tacagtgggt ttgactcaat tcaaagcttc ttttattctc    660
gtaagaattt catgaagcct tctcaccaag ggtacccaca ccggaatttc caggaagaaa    720
tagagtttct taatgcaatt ttcccaaatg gagcaggata ttgtatggga cgtatgaatt    780
ctgactgttg gtacttatat actctggatt tcccagagag tcgggtaatc agtcagccag    840
atcaaacctt ggaaattctg atgagtgagc ttgacccagc agttatggac cagttctaca    900
tgaaagatgg tgttactgca aaggatgtca ctcgtgagag tggaattcgt gacctgatac    960
caggttctgt cattgatgcc acaatgttca atccttgtgg gtattcgatg aatggaatga   1020
aatcggatgg aacttattgg actattcaca tcactccaga accagaattt tcttatgtta   1080
gctttgaaac aaacttaagt cagacctcct atgatgacct gatcaggaaa gttgtagaag   1140
tcttcaagcc aggaaaattt gtgaccacct tgtttgttaa tcagagttct aaatgtcgca   1200
cagtgcttgc ttcgccccag aagattgaag gttttaagcg tcttgattgc cagagtgcta   1260
tgttcaatga ttacaatttt gtttttacca gttttgctaa gaagcagcaa caacagcaga   1320
gttgattaag aaaaatgaag aaaaaacgca aaaagagaac acatgtagaa ggtggtggat   1380
gctttctaga tgtcgatgct gggggcagtg ctttccataa ccaccactgt gtagttgcag   1440
aaagccctag atgtaatgat agtgtaatca ttttgaattg tatgcattat tatatcaagg   1500
agttagatat cttgcatgaa tgctctcttc tgtgtttagg tattctctgc cactcttgct   1560
gtgaaattga agtggatgta gaaaaaacct tttactatat gaaactttac aacacttgtg   1620
aaagcaactc aatttggttt atgcacagtg taatatttct ccaagtatca tccaaaattc   1680
cccacagaca aggctttcgt cctcattagg tgttggcctc agcctaaccc tctaggactg   1740
ttctattaaa ttgctgccag aattttacat ccagttacct ccactttcta gaacatattc   1800
tttactaatg ttattgaaac caatttctac ttcatactga tgtttttgga aacagcaatt   1860
aaagtttttc ttccatagtt gagtccttag aaaatgattc cagttactca ttttgcatat   1920
tgctatttaa cattattgga ccctgcattt atagtccttt gatttcttcc ctctccctgg   1980
tgtctccccc aagaccccaa ataaagcaat accctgttaa cactgtgggt ttatatacta   2040
attctatacc ccagatgggg aattaggggg gagatggtcc ctgggcttaa tattctttaa   2100
agggcatggg aatttagcct ctcttttatt gtaatgtgct cttttggaaa atagttggtt   2160
agcagggaga ccagagttgt agattgagat tgggtgtact ggctgttctg tggaaaacat   2220
acattctgtg ttcctcgaat aagtgaaatt gagcttctaa tgagatgcac ccctttacta   2280
acttgatgat gatataaaat tcatttttat ttagttaatt accagagaga tttagcataa   2340
ttttgcttct ggattcagta aatcaagtca gcttggatca ttcaccttaa cttttccttt   2400
agcagccctt tccactagtt tcccattaag tagtgttcta taaactttga tccaaagcag   2460
aatcaatgtc ttttccatct cgtgacttaa agttctgtga ctgtgatgca tgtgagtgtt   2520
ccgacttcat ctgttcctct taactacggt gtttccctta ccgatcggca ttcataggat   2580
gaaatgaatg actgtcccag aatgagaatt tgtccagatt attcagataa acatcataaa   2640
```

```
gagaataaca ttataaataa gtagaatatg aataaataga ataataaaat tccaaaatac   2700
tcaatgggaa atgactagta atataggctt tcaagagttg gtacctttac gtatatttgc   2760
agattctctg ggattttaag gaactgagaa aacagaaaag ttgactaaat tttatatttc   2820
ttgtcctcta aatattttga taatttctgg attgatgcag tgatgttttt cgttccttgt   2880
atttataaat gaaaaccttt ttttggtgtt tctaaaccta aaatctactt ggtttgaaat   2940
caagtggttg gaacactgtt tgacttttat ttgaagcatg ttgttgattg aaaatttcat   3000
tgaggaagtt ttcaatcagt gtgatcagtt tgattctgta atgagcacag cacctaatat   3060
tttgaggagc tctgttttga ggaccaatgc ttaaggtgga ccttgttgct aaacaatatc   3120
ccaatagatt tgttgacttg aggtctggtt tggttttgtt tttgttttgt tttggttttg   3180
ttttgtttcc caatagaatt aagaattcta atgttgaaaa actgtataaa tttttatggg   3240
acaaagccta gaaaagagaa atgtagtttg aatcataatc taaatcatcg tatgatagga   3300
aggaaaagtt ttggtgccat aatttctcct ttcactggtg ttggacttaa atcagttgaa   3360
atgtatttct gtaccacaat ttacgcttca ataaaagttt aattgtctag tgag         3414
```

<210> SEQ ID NO 37
<211> LENGTH: 3287
<212> TYPE: DNA
<213> ORGANISM: human

<400> SEQUENCE: 37

```
agactgaggc ggaggcagcc ccgcgccgcg ccggacccga gcatatttca ttttctgtca     60
ttggactttg agccattaga accatgagca actacagtgt gtcactggtt ggcccagctc    120
cttggggttt ccggctgcag ggcggtaagg atttcaacat gcctctgaca atctctagtc    180
taaaagatgg cggcaaggca gcccaggcaa atgtaagaat aggcgatgtg gttctcagca    240
ttgatggaat aaatgcacaa ggaatgactc atcttgaagc ccagaataag attaagggtt    300
gtacaggctc tttgaatatg actctgcaaa gagcatctgc tgcacccaag cctgagccgg    360
ttcctgttca aaagggagaa cctaaagaag tagttaaacc tgtgcccatt acatctcctg    420
ctgtgtccaa agtcacttcc acaaacaaca tggcctacaa taaggcacca cggccttttg    480
gttctgtgtc ttcaccaaaa gtcacatcca tcccatcacc atcgtctgcc ttcaccccag    540
cccatgcgac cacctcatca catgcttccc cttcacccgt ggctgccgtc actcctcccc    600
tgttcgctgc atctggactg catgctaatg ccaatcttag tgctgaccag tctccatctg    660
cactgagcgc tggtaaaact gcagttaatg tcccacggca gcccacagtc accagcgtgt    720
gttccgagac ttctcaggag ctagcagagg gacagagaag aggatcccag ggtgacagta    780
aacagcaaaa tggcccacca agaaaacaca ttgtggagcg ctatacagag ttttatcatg    840
tacccactca cagtgatgcc agcaagaaga gactgattga ggatactgaa gactggcgtc    900
caagaactgg aacaactcag tctcgctctt tccgaatcct tgcccagatc actgggactg    960
aacatttgaa agaatctgaa gccgataata caaagaaggc aaataactct caggagcctt   1020
ctccgcagtt ggcttccttg gtagcttcca cacggagcat gcccgagagc ctggacagcc   1080
caacctctgg cagaccaggg gttaccagcc tcacaactgc agctgccttc aagcctgtag   1140
gatccactgg cgtcatcaag tcaccaagct ggcaacggcc aaaccaagga gtaccttcca   1200
ctggaagaat ctcaaacagc gctacttact caggatcagt ggcaccagcc aactcagctt   1260
tgggacaaac ccagccaagt gaccaggaca ctttagtgca aagagctgag cacattccag   1320
```

-continued

```
cagggaaacg aactccgatg tgcgcccatt gtaaccaggt catcagagga ccattcttag   1380
tggcactggg gaaatcttgg cacccagaag aattcaactg cgctcactgc aaaaatacaa   1440
tggcctacat tggatttgta gaggagaaag gagccctgta ttgtgagctg tgctatgaga   1500
aattctttgc ccctgaatgt ggtcgatgcc aaaggaagat ccttggagaa gtcatcaatg   1560
cgttgaaaca aacttggcat gtttcctgtt ttgtgtgtgt agcctgtgga aagcccattc   1620
ggaacaatgt ttttcacttg gaggatggtg aaccctactg tgagactgat tattatgccc   1680
tctttggtac tatatgccat ggatgtgaat ttcccataga agctggtgac atgttcctgg   1740
aagctctggg ctacacctgg catgacactt gctttgtatg ctcagtgtgt tgtgaaagtt   1800
tggaaggtca gacctttttc tccaagaagg acaagcccct gtgtaagaaa catgctcatt   1860
ctgtgaattt ttgaaagtca acagttcagg agaagagaag gaatttgaag agaaaaagga   1920
aaattaaaat tactaattaa tttttagatt caatatttat atggagtttt gaaaaataat   1980
agtggccctg aaggaataaa ttccagcttt aaaaaccaag tctgaggaaa tatttggctt   2040
cataaagtaa agagacggtt tggcatttat tattactttt tcctgtattt tatgcccata   2100
aaataagctt tataaaaacc aatttcctga tggactatta aattcatctt agaataaatt   2160
agtgaagaat ttaattttag aataaataat ccaatctgaa ataattatac cttctttcct   2220
tgttaggtag ttatgagtaa atctgcaaaa ggcaatgaaa atgccttaaa ttttatcaat   2280
aacagaatta ttgtatttaa aaaaaaacta atacttatct ttaaaatagt aaataggatt   2340
ttaaacagag aattttatca gtaataggtg tcagttttta aaaaattgct tgtaggctga   2400
gcgcggtggc tcacgcctgt aatcccagca ctttgggagg ccaaggtggg tggaccacat   2460
gaggtcagga gtttgagatc agcctggcca acatggtgaa accccatctc tactaaaaat   2520
acaaaaatta gccggacgca gtggcacgcg cctgtaatcc cagctactca agaggctgag   2580
gcacgagaat cacttgaacc cgggagggag aggttgcagt gagccaagat cgtaccactg   2640
cactccagcc tgggtgacag agtgagactc cgtctccaaa aaaaaacttt gcttgtatat   2700
tatttttgcc ttacagtgga tcattctagt aggaaaggac aataagattt tttatcaaaa   2760
tgtgtcatgc cagtaagaga tgttatattc ttttcttatt tcttccccac ccaaaaataa   2820
gctaccatat agcttataag tctcaaattt ttgcctttta ctaaaatgtg attgtttctg   2880
ttcattgtgt atgcttcatc acctatatta ggcaaattcc attttttccc ttgcgctaag   2940
gtaaagattt aattaaataa ttttggcctc tcatagtttt ctctctcttt aaagagaata   3000
aatagagggc caggtgtggt ggctcacgcc tgtgatccca gcactttggg aggccaagac   3060
gggcggatca tgaggtcaag agatcaagat catcctggcc aacatggtga aaccctgtct   3120
ctactaaaaa tacaaaaatg agctgggcat ggtggggcgt gcctgtagtc ccatgtactt   3180
gggaggctga ggcaggaaaa ttcttgaacc caggagacgg aagttgcagt gagctgagat   3240
cacaccactg cactccagcc tggtgacaga gcaagactcc ggctctt                 3287
```

<210> SEQ ID NO 38
<211> LENGTH: 1254
<212> TYPE: DNA
<213> ORGANISM: human

<400> SEQUENCE: 38

```
atggcagtgg agaccacggt ccacactcac ctctctgcgt ctccaccgca gggctctccc     60
tacgaccaca cacccggcat ggcgggctcc ttggggtacc atccttacgc ggcgcccctg    120
ggatcgtacc cttacgggga cccagcgtac cggaagaacg ccacaaggga cgccacggct    180
```

-continued

```
accctcaagg cctggctcaa cgagcaccgc aagaacccct accccaccaa gggcgagaag    240
atcatgctgg ccatcatcac caagatgacc ctcacccagg tgtccacctg gttcgccaac    300
gcgcgccggc gcctcaagaa agagaataaa atgacgtgga cgccgcggaa ccgcagcgag    360
gacgaggaag aggaggagaa cattgacctg gagaagaacg acgaggacga gccccagaag    420
cccgaggaca agggcgaccc cgagggcccc gaagcaggag gagctgagca gaaggcggct    480
tcgggctgcg aacggcttca gggaccaccc acccctgcag gcaaggagac ggagggcagc    540
ctcagcgact cggattttaa ggagccgccc tcggagggcc gcctcgacgc gctgcagggc    600
cccccccgca ccggcgggcc ctccccggct gggccagcgg cggcgcggct ggcggaggac    660
ccggcccctc actaccccgc cggagcgccg gcgcccggcc cgcatccagc cgcgggcgag    720
gtgcctccgg gtcccggcgg gccctcggtt atccattcgc cgcctccgcc gccgcctcct    780
gcggtgctcg ccaagcccaa actgtggtct ttggcagaga tcgccacatt gtcggacaag    840
gtcaaggacg gggggcggcgg gaacgagggc tctccatgcc caccgtgtcc cgggcccata    900
gccgggcaag ccctaggagg cagccgggcg tcgccggccc cggcgccgtc acgctcgccc    960
tcggcgcagt gtccttttcc aggcgggacg gtgctgtccc ggcctctcta ctacaccgcg   1020
cccttctatc ccggctacac gaactatggc tccttcggac accttcatgg ccacccgggg   1080
cccgggccag gccccacaac cggtccgggg tctcatttca atggattaaa ccagaccgtg   1140
ttgaaccgag cggacgcttt ggctaaagac ccgaaaatgt tgcggagcca gtctcagcta   1200
gacctgtgca aagactctcc ctatgaattg aagaaaggta tgtccgacat ttaa         1254
```

<210> SEQ ID NO 39
<211> LENGTH: 2560
<212> TYPE: DNA
<213> ORGANISM: human

<400> SEQUENCE: 39

```
gaattccggc cagaagaaat ctggcctcgg aacacgccat tctccgcgcc gcttccaata     60
accactaaca tccctaacga gcatccgagc cgagggctct gctcggaaat cgtcctggcc    120
caactcggcc cttcgagctc tcgaagatta ccgcatctat tttttttttc tttttttttct   180
tttcctagcg cagataaagt gagcccggaa agggaaggag ggggcgggga caccattgcc    240
ctgaaagaat aaataagtaa ataaacaaac tggctcctcg ccgcagctgg acgcggtcgg    300
ttgagtccag gttgggtcgg acctgaaccc ctaaaagcgg aaccgcctcc cgccctcgcc    360
atcccggagc tgagtcgccg gcggcggtgg ctgctgccag acccggagtt tcctctttca    420
ctggatggag ctgaactttg ggcggccaga gcagcacagc tgtccgggga tcgctgcacg    480
ctgagctccc tcggcaagac ccagcggcgg ctcgggattt ttttgggggg gcggggacca    540
gccccgcgcc ggcaccatgt tcctggcgac cctgtacttc gcgctgccgc tcttggactt    600
gctcctgtcg gccgaagtga gcggcggaga ccgcctggat tgcgtgaaag ccagtgatca    660
gtgcctgaag gagcagagct gcagcaccaa gtaccgcacg ctaaggcagt gcgtggcggg    720
caaggagacc aacttcagcc tggcatccgg cctggaggcc aaggatgagt gccgcagcgc    780
catggaggcc ctgaagcaga agtcgctcta caactgccgc tgcaagcggg gtatgaagaa    840
ggagaagaac tgcctgcgca tttactggag catgtaccag agcctgcagg gaaatgatct    900
gctggaggat tccccatatg aaccagttaa cagcagattg tcagatatat tccgggtggt    960
cccattcata tcagatgttt ttcagcaagt ggagcacatt cccaaaggga acaactgcct   1020
```

-continued

```
ggatgcagcg aaggcctgca acctcgacga catttgcaag aagtacaggt cggcgtacat   1080

caccccgtgc accaccagcg tgtccaacga tgtctgcaac cgccgcaagt gccacaaggc   1140

cctccggcag ttctttgaca aggtcccggc caagcacagc tacggaatgc tcttctgctc   1200

ctgccgggac atcgcctgca cagagcggag gcgacagacc atcgtgcctg tgtgctccta   1260

tgaagagagg gagaagccca actgtttgaa tttgcaggac tcctgcaaga cgaattacat   1320

ctgcagatct cgccttgcgg attttttac caactgccag ccagagtcaa ggtctgtcag   1380

cagctgtcta aaggaaaact acgctgactg cctcctcgcc tactcggggc ttattggcac   1440

agtcatgacc cccaactaca tagactccag tagcctcagt gtggccccat ggtgtgactg   1500

cagcaacagt gggaacgacc tagaagagtg cttgaaattt ttgaatttct tcaaggacaa   1560

tacatgtctt aaaaatgcaa ttcaagcctt tggcaatggc tccgatgtga ccgtgtggca   1620

gccagccttc ccagtacaga ccaccactgc cactaccacc actgccctcc gggttaagaa   1680

caagcccctg gggccagcag ggtctgagaa tgaaattccc actcatgttt tgccaccgtg   1740

tgcaaattta caggcacaga agctgaaatc caatgtgtcg ggcaatacac acctctgtat   1800

ttccaatggt aattatgaaa aagaaggtct cggtgcttcc agccacataa ccacaaaatc   1860

aatggctgct cctccaagct gtggtctgag cccactgctg gtcctggtgg taaccgctct   1920

gtccacccta ttatctttaa cagaaacatc atagctgcat taaaaaaata caatatggac   1980

atgtaaaaag acaaaaacca agttatctgt ttcctgttct cttgtatagc tgaaattcca   2040

gtttaggagc tcagttgaga aacagttcca ttcaactgga acattttttt ttttcctttt   2100

aagaaagctt cttgtgatcc ttcggggctt ctgtgaaaaa cctgatgcag tgctccatcc   2160

aaactcagaa ggctttggga tatgctgtat tttaaaggga cagtttgtaa cttgggctgt   2220

aaagcaaact ggggctgtgt tttcgatgat gatgatcatc atgatcatga tgattttaac   2280

agttttactt ctggcctttc ctagctagag aaggagttaa tatttctaag gtaactccca   2340

tatctccttt aatgacattg atttctaatg atataaattt cagcctacat tgatgccaag   2400

ctttttttgcc acaaagaaga ttcttaccaa gagtgggctt tgtggaaaca gctggtactg   2460

atgttcacct ttatatatgt actagcattt tccacgctga tgtttatgta ctgtaaacag   2520

ttctgcactc ttgtacaaaa gaaaaaacca cccggaattc                         2560

<210> SEQ ID NO 40
<211> LENGTH: 2560
<212> TYPE: DNA
<213> ORGANISM: human

<400> SEQUENCE: 40

gaattccggc cagaagaaat ctggcctcgg aacacgccat tctccgcgcc gcttccaata     60

accactaaca tccctaacga gcatccgagc cgagggctct gctcggaaat cgtcctggcc    120

caactcggcc cttcgagctc tcgaagatta ccgcatctat ttttttttc tttttttct    180

tttcctagcg cagataaagt gagcccggaa agggaaggag ggggcgggga caccattgcc    240

ctgaaagaat aaataagtaa ataaacaaac tggctcctcg ccgcagctgg acgcggtcgg    300

ttgagtccag gttgggtcgg acctgaaccc ctaaaagcgg aaccgcctcc cgccctcgcc    360

atcccggagc tgagtcgccg gcggcggtgg ctgctgccag acccggagtt tcctctttca    420

ctggatggag ctgaactttg ggcggccaga gcagcacagc tgtccgggga tcgctgcacg    480

ctgagctccc tcggcaagac ccagcggcgg ctcgggattt ttttgggggg gcggggacca    540

gccccgcgcc ggcaccatgt tcctggcgac cctgtacttc gcgctgccgc tcttggactt    600
```

-continued

```
gctcctgtcg gccgaagtga gcggcggaga ccgcctggat tgcgtgaaag ccagtgatca    660

gtgcctgaag gagcagagct gcagcaccaa gtaccgcacg ctaaggcagt gcgtggcggg    720

caaggagacc aacttcagcc tggcatccgg cctggaggcc aaggatgagt gccgcagcgc    780

catggaggcc ctgaagcaga agtcgctcta caactgccgc tgcaagcggg gtatgaagaa    840

ggagaagaac tgcctgcgca tttactggag catgtaccag agcctgcagg gaaatgatct    900

gctggaggat tccccatatg aaccagttaa cagcagattg tcagatatat tccgggtggt    960

cccattcata tcagatgttt ttcagcaagt ggagcacatt cccaaaggga acaactgcct   1020

ggatgcagcg aaggcctgca acctcgacga catttgcaag aagtacaggt cggcgtacat   1080

caccccgtgc accaccagcg tgtccaacga tgtctgcaac cgccgcaagt gccacaaggc   1140

cctccggcag ttctttgaca aggtcccggc caagcacagc tacggaatgc tcttctgctc   1200

ctgccgggac atcgcctgca cagagcggag gcgacagacc atcgtgcctg tgtgctccta   1260

tgaagagagg gagaagccca actgtttgaa tttgcaggac tcctgcaaga cgaattacat   1320

ctgcagatct cgccttgcgg atttttttac caactgccag ccagagtcaa ggtctgtcag   1380

cagctgtcta aaggaaaact acgctgactg cctcctcgcc tactcggggc ttattggcac   1440

agtcatgacc cccaactaca tagactccag tagcctcagt gtggccccat ggtgtgactg   1500

cagcaacagt gggaacgacc tagaagagtg cttgaaattt ttgaatttct tcaaggacaa   1560

tacatgtctt aaaaatgcaa ttcaagcctt tggcaatggc tccgatgtga ccgtgtggca   1620

gccagccttc ccagtacaga ccaccactgc cactaccacc actgccctcc gggttaagaa   1680

caagcccctg gggccagcag ggtctgagaa tgaaattccc actcatgttt tgccaccgtg   1740

tgcaaattta caggcacaga agctgaaatc caatgtgtcg ggcaatacac acctctgtat   1800

ttccaatggt aattatgaaa aagaaggtct cggtgcttcc agccacataa ccacaaaatc   1860

aatggctgct cctccaagct gtggtctgag cccactgctg gtcctggtgg taaccgctct   1920

gtccacccta ttatctttaa cagaaacatc atagctgcat taaaaaaata caatatggac   1980

atgtaaaaag acaaaaacca agttatctgt ttcctgttct cttgtatagc tgaaattcca   2040

gtttaggagc tcagttgaga aacagttcca ttcaactgga acattttttt ttttcctttt   2100

aagaaagctt cttgtgatcc ttcggggctt ctgtgaaaaa cctgatgcag tgctccatcc   2160

aaactcagaa ggctttggga tatgctgtat tttaaaggga cagtttgtaa cttgggctgt   2220

aaagcaaact ggggctgtgt tttcgatgat gatgatcatc atgatcatga tgattttaac   2280

agttttactt ctggcctttc ctagctagag aaggagttaa tatttctaag gtaactccca   2340

tatctccttt aatgacattg atttctaatg atataaattt cagcctacat tgatgccaag   2400

ctttttttgcc acaaagaaga ttcttaccaa gagtgggctt tgtggaaaca gctggtactg   2460

atgttcacct ttatatatgt actagcattt tccacgctga tgtttatgta ctgtaaacag   2520

ttctgcactc ttgtacaaaa gaaaaaacca cccggaattc                          2560
```

<210> SEQ ID NO 41
<211> LENGTH: 2439
<212> TYPE: DNA
<213> ORGANISM: human

<400> SEQUENCE: 41

```
cagcacccag ctccccgcca ccgccatggt ccccgacacc gcctgcgttc ttctgctcac     60

cctggctgcc ctcggcgcgt ccggacaggg ccagagcccg ttgggctcag acctgggccc    120
```

-continued

```
gcagatgctt cgggaactgc aggaaaccaa cgcggcgctg caggacgtgc gggactggct    180
gcggcagcag gtcagggaga tcacgttcct gaaaaacacg gtgatggagt gtgacgcgtg    240
cgggatgcag cagtcagtac gcaccggcct acccagcgtg cggcccctgc tccactgcgc    300
gcccggcttc tgcttccccg gcgtggcctg catccagacg gagagcggcg gccgctgcgg    360
cccctgcccc gcgggcttca cgggcaacgg ctcgcactgc accgacgtca acgagtgcaa    420
cgcccacccc tgcttccccc gagtccgctg tatcaacacc agcccggggt tccgctgcga    480
ggcttgcccg ccggggtaca gcggccccac ccaccagggc gtggggctgg ctttcgccaa    540
ggccaacaag caggtttgca cggacatcaa cgagtgtgag accgggcaac ataactgcgt    600
ccccaactcc gtgtgcatca acacccgggg ctccttccag tgcggcccgt gccagcccgg    660
cttcgtgggc gaccaggcgt ccggctgcca gcgcggcgca cagcgcttct gccccgacgg    720
ctcgcccagc gagtgccacg agcatgcaga ctgcgtccta gagcgcgatg gctcgcggtc    780
gtgcgtgtgt cgcgttggct gggccggcaa cgggatcctc tgtggtcgcg acactgacct    840
agacggcttc ccggacgaga agctgcgctg cccggagccg cagtgccgta aggacaactg    900
cgtgactgtg cccaactcag ggcaggagga tgtggaccgc gatggcatcg gagacgcctg    960
cgatccggat gccgacgggg acggggtccc caatgaaaag gacaactgcc cgctggtgcg   1020
gaacccagac cagcgcaaca cggacgagga caagtggggc gatgcgtgcg acaactgccg   1080
gtcccagaag aacgacgacc aaaaggacac agaccaggac ggccggggcg atgcgtgcga   1140
cgacgacatc gacggcgacc ggatccgcaa ccaggccgac aactgcccta gggtacccaa   1200
ctcagaccag aaggacagtg atggcgatgg tatagggggat gcctgtgaca actgtcccca   1260
gaagagcaac ccggatcagg cggatgtgga ccacgacttt gtgggagatg cttgtgacag   1320
cgatcaagac caggatggag acggacatca ggactctcgg gacaactgtc ccacggtgcc   1380
taacagtgcc caggaggact cagaccacga tggccagggt gatgcctgcg acgacgacga   1440
cgacaatgac ggagtccctg acagtcggga caactgccgc ctggtgccta accccggcca   1500
ggaggacgcg gacagggacg gcgtgggcga cgtgtgccag gacgactttg atgcagacaa   1560
ggtggtagac aagatcgacg tgtgtccgga gaacgctgaa gtcacgctca ccgacttcag   1620
ggccttccag acagtcgtgc tggacccgga gggtgacgcg cagattgacc ccaactgggt   1680
ggtgctcaac cagggaaggg agatcgtgca gacaatgaac agcgacccag gcctggctgt   1740
gggttacact gccttcaatg gcgtggactt cgagggcacg ttccatgtga acacggtcac   1800
ggatgacgac tatgcgggct tcatctttgg ctaccaggac agctccagct tctacgtggt   1860
catgtggaag cagatggagc aaacgtattg gcaggcgaac cccttccgtg ctgtggccga   1920
gcctggcatc caactcaagg ctgtgaagtc ttccacaggc cccggggaac agctgcggaa   1980
cgctctgtgg catacaggag acacagagtc ccaggtgcgg ctgctgtgga aggacccgcg   2040
aaacgtgggt tggaaggaca agaagtccta tcgttggttc ctgcagcacc ggccccaagt   2100
gggctacatc agggtgcgat tctatgaggg ccctgagctg gtggccgaca gcaacgtggt   2160
cttggacaca accatgcggg gtggccgcct gggggtcttc tgcttctccc aggagaacat   2220
catctgggcc aacctgcgtt accgctgcaa tgacaccatc ccagaggact atgagaccca   2280
tcagctgcgg caagcctagg gaccagggtg aggacccgcc ggatgacagc caccctcacc   2340
gcggctggat gggggctctg cacccagccc aaggggtggc cgtcctgagg gggaagtgag   2400
aagggctcag agaggacaaa ataaagtgtg tgtgcaggg                          2439
```

<210> SEQ ID NO 42
<211> LENGTH: 2439
<212> TYPE: DNA
<213> ORGANISM: human

<400> SEQUENCE: 42

```
cagcacccag ctccccgcca ccgccatggt ccccgacacc gcctgcgttc ttctgctcac     60
cctggctgcc ctcggcgcgt ccggacaggg ccagagcccg ttgggctcag acctgggccc    120
gcagatgctt cgggaactgc aggaaaccaa cgcggcgctg caggacgtgc gggactggct    180
gcggcagcag gtcagggaga tcacgttcct gaaaaacacg gtgatggagt gtgacgcgtg    240
cgggatgcag cagtcagtac gcaccggcct acccagcgtg cggcccctgc tccactgcgc    300
gcccggcttc tgcttccccg gcgtggcctg catccagacg gagagcggcg gccgctgcgg    360
cccctgcccc gcgggcttca cgggcaacgg ctcgcactgc accgacgtca acgagtgcaa    420
cgcccacccc tgcttccccc gagtccgctg tatcaacacc agcccggggt tccgctgcga    480
ggcttgcccg ccggggtaca gcggccccac ccaccagggc gtggggctgg ctttcgccaa    540
ggccaacaag caggtttgca cggacatcaa cgagtgtgag accgggcaac ataactgcgt    600
ccccaactcc gtgtgcatca acacccgggg ctccttccag tgcggcccgt gccagcccgg    660
cttcgtgggc gaccaggcgt ccggctgcca gcgcggcgca cagcgcttct gccccgacgg    720
ctcgcccagc gagtgccacg agcatgcaga ctgcgtccta gagcgcgatg gctcgcggtc    780
gtgcgtgtgt cgcgttggct gggccggcaa cgggatcctc tgtggtcgcg acactgacct    840
agacggcttc ccggacgaga agctgcgctg cccggagccg cagtgccgta aggacaactg    900
cgtgactgtg cccaactcag ggcaggagga tgtggaccgc gatggcatcg gagacgcctg    960
cgatccggat gccgacgggg acggggtccc caatgaaaag gacaactgcc cgctggtgcg   1020
gaacccagac cagcgcaaca cggacgagga caagtggggc gatgcgtgcg acaactgccg   1080
gtcccagaag aacgacgacc aaaaggacac agaccaggac ggccggggcg atgcgtgcga   1140
cgacgacatc gacggcgacc ggatccgcaa ccaggccgac aactgcccta gggtacccaa   1200
ctcagaccag aaggacagtg atggcgatgg tataggggat gcctgtgaca actgtcccca   1260
gaagagcaac ccggatcagg cggatgtgga ccacgacttt gtgggagatg cttgtgacag   1320
cgatcaagac caggatggag acggacatca ggactctcgg gacaactgtc ccacggtgcc   1380
taacagtgcc caggaggact cagaccacga tggccagggt gatgcctgcg acgacgacga   1440
cgacaatgac ggagtccctg acagtcggga caactgccgc ctggtgccta accccggcca   1500
ggaggacgcg gacagggacg gcgtgggcga cgtgtgccag gacgactttg atgcagacaa   1560
ggtggtagac aagatcgacg tgtgtccgga gaacgctgaa gtcacgctca ccgacttcag   1620
ggccttccag acagtcgtgc tggacccgga gggtgacgcg cagattgacc ccaactgggt   1680
ggtgctcaac cagggaaggg agatcgtgca gacaatgaac agcgacccag gcctggctgt   1740
gggttacact gccttcaatg gcgtggactt cgagggcacg ttccatgtga acacggtcac   1800
ggatgacgac tatgcgggct tcatctttgg ctaccaggac agctccagct tctacgtggt   1860
catgtggaag cagatggagc aaacgtattg gcaggcgaac cccttccgtg ctgtggccga   1920
gcctggcatc caactcaagg ctgtgaagtc ttccacaggc cccggggaac agctgcggaa   1980
cgctctgtgg catacaggag acacagagtc ccaggtgcgg ctgctgtgga aggacccgcg   2040
aaacgtgggt tggaaggaca agaagtccta tcgttggttc ctgcagcacc ggccccaagt   2100
gggctacatc agggtgcgat tctatgaggg ccctgagctg gtggccgaca gcaacgtggt   2160
```

```
cttggacaca accatgcggg gtggccgcct gggggtcttc tgcttctccc aggagaacat   2220

catctgggcc aacctgcgtt accgctgcaa tgacaccatc ccagaggact atgagaccca   2280

tcagctgcgg caagcctagg gaccagggtg aggacccgcc ggatgacagc caccctcacc   2340

gcggctggat gggggctctg cacccagccc aaggggtggc cgtcctgagg gggaagtgag   2400

aagggctcag agaggacaaa ataaagtgtg tgtgcaggg                         2439
```

<210> SEQ ID NO 43
<211> LENGTH: 1385
<212> TYPE: DNA
<213> ORGANISM: human

<400> SEQUENCE: 43

```
ctccagccat tggtgtctgt gtcattacta atagagtctt gtaaacactc gttaatcacg     60

gaagccgccg gcctggggct ccgcacgcca gcctgtgcgg gtcttccccg cctctgcagc    120

ctagtgggaa ggaggtggga ggaaagaagg aagaaaggga gggagggagg aggcaggcca    180

gagggaggga ccgcctcgga ggcagaagag ccgcgaggag ccagcggagc accgcgggct    240

ggggcgcagc cacccgccgc tcctcgagtc ccctcgcccc tttcccttcg tgccccccgg    300

cagcctccag cgtcggtccc caggcagcat ggtgaggtct gctcccggtc cctcgccacc    360

atgtacgtga gctacctcct ggacaaggac gtgagcatgt accctagctc cgtgcgccac    420

tctggcggcc tcaacctggc gccgcagaac ttcgtcagcc ccccgcagta cccggactac    480

ggcggttacc acgtggcggc cgcagctgca gcggcagcga acttggacag cgcgcagtcc    540

ccggggccat cctggccggc agcgtatggc gccccactcc gggaggactg gaatggctac    600

gcgcccggag gcgccgcggc cgccgccaac gccgtggctc acggcctcaa cggtggctcc    660

ccggccgcag ccatgggcta cagcagcccc gcagactacc atccgcacca ccacccgcat    720

caccacccgc accacccggc cgcggcgcct tcctgcgctt ctgggctgct gcaaacgctc    780

aaccccggcc ctcctgggcc cgccgccacc gctgccgccg agcagctgtc tcccggcggc    840

cagcggcgga acctgtgcga gtggatgcgg aagccggcgc agcagtccct cggcagccaa    900

gtgaaaacca ggacgaaaga caaatatcga gtggtgtaca cggaccacca gcggctggag    960

ctggagaagg agtttcacta cagtcgctac atcaccatcc ggaggaaagc cgagctagcc   1020

gccacgctgg ggctctctga gaggcaggtt aaaatctggt ttcagaaccg cagagcaaag   1080

gagaggaaaa tcaacaagaa gaagttgcag cagcaacagc agcagcagcc accacagccg   1140

cctccgccgc caccacagcc tccccagcct cagccaggtc ctctgagaag tgtcccagag   1200

cccttgagtc cggtgtcttc cctgcaagcc tcagtgtctg gctctgtccc tggggttctg   1260

gggccaactg ggggggtgct aaaccccacc gtcacccagt gacccaccgg ggttctgcag   1320

cggcagagca attccaggct gagccatgag gagcgtggac tctgctagac tcctcaggag   1380

agacc                                                              1385
```

<210> SEQ ID NO 44
<211> LENGTH: 4098
<212> TYPE: DNA
<213> ORGANISM: human

<400> SEQUENCE: 44

```
ggtggcctct gtggccgtcc aggctagcgg cggcccgcag gcggcgggga gaaagactct     60

ctcacctggt cttgcggctg tggccaccgc cggccagggg tgtggagggc gtgctgccgg    120

agacgtccgc cgggctctgc agttccgccg gggtcgggc agctatggag ccgcggccca    180
```

```
cggcgccctc ctccggcgcc ccgggactgg ccggggtcgg ggagacgccg tcagccgctg    240
cgctggccgc agccagggtg gaactgcccg gcacggctgt gccctcggtg ccggaggatg    300
ctgcgcccgc gagccgggac ggcggcgggg tccgcgatga gggccccgcg gcggccgggg    360
acgggctggg cagacccttg gggcccaccc cgagccagag ccgtttccag gtggacctgg    420
tttccgagaa cgccgggcgg gccgctgctg cggcggcggc ggcggcggcg gcagcggcgg    480
cggctggtgc tggggcgggg gccaagcaga cccccgcgga cggggaagcc agcggcgaga    540
gcgagccagc taaaggcagc gaggaagcca agggccgctt ccgcgtgaac ttcgtggacc    600
cagctgcctc ctcgtcggct gaagacagcc tgtcagatgc tgccggggtc ggagtcgacg    660
ggcccaacgt gagcttccag aacggcgggg acacggtgct gagcgagggc agcagcctgc    720
actccggcgg cggcggcggc agtgggcacc accagcacta ctattatgat acccacacca    780
acacctacta cctgcgcacc ttcggccaca acaccatgga cgctgtgccc aggatcgatc    840
actaccggca cacagccgcg cagctgggcg agaagctgct ccggcctagc ctggcggagc    900
tccacgacga gctggaaaag gaaccttttg aggatggctt tgcaaatggg gaagaaagta    960
ctccaaccag agatgctgtg gtcacgtata ctgcagaaag taaaggagtc gtgaagtttg   1020
gctggatcaa gggtgtatta gtacgttgta tgttaaacat ttggggtgtg atgcttttca   1080
ttagattgtc atggattgtg ggtcaagctg gaataggtct atcagtcctt gtaataatga   1140
tggccactgt tgtgacaact atcacaggat tgtctacttc agcaatagca actaatggat   1200
ttgtaagagg aggaggagca tattatttaa tatctagaag tctagggcca gaatttggtg   1260
gtgcaattgg tctaatcttc gcctttgcca acgctgttgc agttgctatg tatgtggttg   1320
gatttgcaga aaccgtggtg gagttgctta aggaacattc catacttatg atagatgaaa   1380
tcaatgatat ccgaattatt ggagccatta cagtcgtgat tcttttaggt atctcagtag   1440
ctggaatgga gtgggaagca aaagctcaga ttgttctttt ggtgatccta cttcttgcta   1500
ttggtgattt cgtcatagga acatttatcc cactggagag caagaagcca aaagggtttt   1560
ttggttataa atctgaaata tttaatgaga actttggccc cgattttcga gaggaagaga   1620
ctttcttttc tgtatttgcc atcttttttc ctgctgcaac tggtattctg gctggagcaa   1680
atatctcagg tgatcttgca gatcctcagt cagccatacc caaaggaaca ctcctagcca   1740
ttttaattac tacattggtt tacgtaggaa ttgcagtatc tgtaggttct tgtgttgttc   1800
gagatgccac tggaaacgtt aatgacacta tcgtaacaga gctaacaaac tgtacttctg   1860
cagcctgcaa attaaacttt gatttttcat cttgtgaaag cagtccttgt tcctatggcc   1920
taatgaacaa cttccaggta atgagtatgg tgtcaggatt tacaccacta atttctgcag   1980
gtatattttc agccactctt tcttcagcat tagcatccct agtgagtgct cccaaaatat   2040
ttcaggctct atgtaaggac aacatctacc cagctttcca gatgtttgct aaaggttatg   2100
ggaaaaataa tgaacctctt cgtggctaca tcttaacatt cttaattgca cttggattca   2160
tcttaattgc tgaactgaat gttattgcac caattatctc aaacttcttc cttgcatcat   2220
atgcattgat caatttttca gtattccatg catcacttgc aaaatctcca ggatggcgtc   2280
ctgcattcaa atactacaac atgtggatat cacttcttgg agcaattctt tgttgcatag   2340
taatgttcgt cattaactgg tgggctgcat tgctaacata tgtgatagtc cttgggctgt   2400
atatttatgt tacctacaaa aaaccagatg tgaattgggg atcctctaca caagccctga   2460
cttacctgaa tgcactgcag cattcaattc gtctttctgg agtggaagac cacgtgaaaa   2520
```

-continued

```
actttaggcc acagtgtctt gttatgacag gtgctccaaa ctcacgtcca gctttacttc   2580

atcttgttca tgatttcaca aaaaatgttg gtttgatgat ctgtggccat gtacatatgg   2640

gtcctcgaag acaagccatg aaagagatgt ccatcgatca agccaaatat cagcgatggc   2700

ttattaagaa caaaatgaag gcattttatg ctccagtaca tgcagatgac ttgagagaag   2760

gtgcacagta tttgatgcag gctgctggtc ttggtcgtat gaagccaaac acacttgtcc   2820

ttggatttaa gaaagattgg ttgcaagcag atatgaggga tgtggatatg tatataaact   2880

tatttcatga tgcttttgac atacaatatg gagtagtggt tattcgccta aaagaaggtc   2940

tggatatatc tcatcttcaa ggacaagaag aattattgtc atcacaagag aaatctcctg   3000

gcaccaagga tgtggtagta agtgtggaat atagtaaaaa gtccgattta gatacttcca   3060

aaccactcag tgaaaaacca attacacaca aagttgagga agaggatggc aagactgcaa   3120

ctcaaccact gttgaaaaaa gaatccaaag gccctattgt gcctttaaat gtagctgacc   3180

aaaagcttct tgaagctagt acacagtttc agaaaaaaca aggaaagaat actattgatg   3240

tctggtggct tttgatgat ggaggtttga ccttattgat accttacctt ctgacgacca   3300

agaaaaaatg gaaagactgt aagatcagag tattcattgg tggaaagata aacagaatag   3360

accatgaccg gagagcgatg gctactttgc ttagcaagtt ccggatagac ttttctgata   3420

tcatggttct aggagatatc aataccaaac caaagaaaga aaatattata gcttttgagg   3480

aaatcattga gccatacaga cttcatgaag atgataaaga gcaagatatt gcagataaaa   3540

tgaaagaaga tgaaccatgg cgaataacag ataatgagct tgaactttat aagaccaaga   3600

cataccggca gatcaggtta aatgagttat taaaggaaca ttcaagcaca gctaatatta   3660

ttgtcatgag tctcccagtt gcacgaaaag gtgctgtgtc tagtgctctc tacatggcat   3720

ggttagaagc tctatctaag gacctaccac caatcctcct agttcgtggg aatcatcaga   3780

gtgtccttac cttctattca taaatgttct atacagtgga cagccctcca gaatggtact   3840

tcagtgccta gtgtagtaac ctgaaatctt caatgacaca ttaacatcac aatggcgaat   3900

ggtgactttt ctttcacgat ttcattaatt tgaaagcaca caggaaagct tgctccattg   3960

ataacgtgta tggagacttc ggttttagtc aattccatat ctcaatctta atggtgattc   4020

ttctctgttg aactgaagtt tgtgagagta gttttccttt gctacttgaa tagcaataaa   4080

agcgtgttaa ctttttgg                                                 4098


<210> SEQ ID NO 45
<211> LENGTH: 4098
<212> TYPE: DNA
<213> ORGANISM: human

<400> SEQUENCE: 45

ggtggcctct gtggccgtcc aggctagcgg cggcccgcag gcggcgggga gaaagactct     60

ctcacctggt cttgcggctg tggccaccgc cggccagggg tgtggagggc gtgctgccgg    120

agacgtccgc cgggctctgc agttccgccg gggtcgggc agctatggag ccgcggccca    180

cggcgccctc ctccggcgcc ccgggactgg ccggggtcgg ggagacgccg tcagccgctg    240

cgctggccgc agccagggtg gaactgcccg gcacggctgt gccctcggtg ccggaggatg    300

ctgcgcccgc gagccgggac ggcggcgggg tccgcgatga gggccccgcg gcggccgggg    360

acgggctggg cagacccttg gggcccaccc cgagccagag ccgtttccag gtggacctgg    420

tttccgagaa cgccgggcgg gccgctgctg cggcggcggc ggcggcggcg gcagcggcgg    480

cggctggtgc tggggcgggg gccaagcaga cccccgcgga cggggaagcc agcggcgaga    540
```

-continued

```
gcgagccagc taaaggcagc gaggaagcca agggccgctt ccgcgtgaac ttcgtggacc    600
cagctgcctc ctcgtcggct gaagacagcc tgtcagatgc tgccggggtc ggagtcgacg    660
ggcccaacgt gagcttccag aacggcgggg acacggtgct gagcgagggc agcagcctgc    720
actccggcgg cggcggcggc agtgggcacc accagcacta ctattatgat acccacacca    780
acacctacta cctgcgcacc ttcggccaca acaccatgga cgctgtgccc aggatcgatc    840
actaccggca cacagccgcg cagctgggcg agaagctgct ccggcctagc ctggcggagc    900
tccacgacga gctggaaaag gaacctttttg aggatggctt tgcaaatggg gaagaaagta    960
ctccaaccag agatgctgtg gtcacgtata ctgcagaaag taaaggagtc gtgaagtttg   1020
gctggatcaa gggtgtatta gtacgttgta tgttaaacat ttggggtgtg atgcttttca   1080
ttagattgtc atggattgtg ggtcaagctg gaataggtct atcagtcctt gtaataatga   1140
tggccactgt tgtgacaact atcacaggat tgtctacttc agcaatagca actaatggat   1200
ttgtaagagg aggaggagca tattatttaa tatctagaag tctagggcca gaatttggtg   1260
gtgcaattgg tctaatcttc gcctttgcca acgctgttgc agttgctatg tatgtggttg   1320
gatttgcaga aaccgtggtg gagttgctta aggaacattc catacttatg atagatgaaa   1380
tcaatgatat ccgaattatt ggagccatta cagtcgtgat tcttttaggt atctcagtag   1440
ctggaatgga gtgggaagca aaagctcaga ttgttctttt ggtgatccta cttcttgcta   1500
ttggtgattt cgtcatagga acatttatcc cactggagag caagaagcca aaagggtttt   1560
ttggttataa atctgaaata tttaatgaga actttgggcc cgattttcga gaggaagaga   1620
ctttcttttc tgtatttgcc atcttttttc ctgctgcaac tggtattctg gctggagcaa   1680
atatctcagg tgatcttgca gatcctcagt cagccatacc caaaggaaca ctcctagcca   1740
ttttaattac tacattggtt tacgtaggaa ttgcagtatc tgtaggttct tgtgttgttc   1800
gagatgccac tggaaacgtt aatgacacta tcgtaacaga gctaacaaac tgtacttctg   1860
cagcctgcaa attaaacttt gatttttcat cttgtgaaag cagtccttgt tcctatggcc   1920
taatgaacaa cttccaggta atgagtatgg tgtcaggatt tacaccacta atttctgcag   1980
gtatattttc agccactctt tcttcagcat tagcatccct agtgagtgct cccaaaatat   2040
ttcaggctct atgtaaggac aacatctacc cagctttcca gatgtttgct aaaggttatg   2100
ggaaaaataa tgaacctctt cgtggctaca tcttaacatt cttaattgca cttggattca   2160
tcttaattgc tgaactgaat gttattgcac caattatctc aaacttcttc cttgcatcat   2220
atgcattgat caatttttca gtattccatg catcacttgc aaaatctcca ggatggcgtc   2280
ctgcattcaa atactacaac atgtggatat cacttcttgg agcaattctt tgttgcatag   2340
taatgttcgt cattaactgg tgggctgcat tgctaacata tgtgatagtc cttgggctgt   2400
atatttatgt tacctacaaa aaaccagatg tgaattgggg atcctctaca caagccctga   2460
cttacctgaa tgcactgcag cattcaattc gtctttctgg agtggaagac cacgtgaaaa   2520
actttaggcc acagtgtctt gttatgacag gtgctccaaa ctcacgtcca gctttacttc   2580
atcttgttca tgatttcaca aaaaatgttg gtttgatgat ctgtggccat gtacatatgg   2640
gtcctcgaag acaagccatg aaagagatgt ccatcgatca agccaaatat cagcgatggc   2700
ttattaagaa caaaatgaag gcattttatg ctccagtaca tgcagatgac ttgagagaag   2760
gtgcacagta tttgatgcag gctgctggtc ttggtcgtat gaagccaaac acacttgtcc   2820
ttggatttaa gaaagattgg ttgcaagcag atatgaggga tgtggatatg tatataaact   2880
```

-continued

```
tatttcatga tgcttttgac atacaatatg gagtagtggt tattcgccta aaagaaggtc   2940

tggatatatc tcatcttcaa ggacaagaag aattattgtc atcacaagag aaatctcctg   3000

gcaccaagga tgtggtagta agtgtggaat atagtaaaaa gtccgattta gatacttcca   3060

aaccactcag tgaaaaacca attacacaca aagttgagga agaggatggc aagactgcaa   3120

ctcaaccact gttgaaaaaa gaatccaaag gccctattgt gcctttaaat gtagctgacc   3180

aaaagcttct tgaagctagt acacagtttc agaaaaaaca aggaaagaat actattgatg   3240

tctggtggct tttgatgat ggaggtttga ccttattgat accttacctt ctgacgacca   3300

agaaaaaatg gaaagactgt aagatcagag tattcattgg tggaaagata aacagaatag   3360

accatgaccg gagagcgatg gctactttgc ttagcaagtt ccggatagac ttttctgata   3420

tcatggttct aggagatatc aataccaaac caaagaaaga aaatattata gcttttgagg   3480

aaatcattga gccatacaga cttcatgaag atgataaaga gcaagatatt gcagataaaa   3540

tgaaagaaga tgaaccatgg cgaataacag ataatgagct tgaactttat aagaccaaga   3600

cataccggca gatcaggtta aatgagttat taaaggaaca ttcaagcaca gctaatatta   3660

ttgtcatgag tctcccagtt gcacgaaaag gtgctgtgtc tagtgctctc tacatggcat   3720

ggttagaagc tctatctaag gacctaccac caatcctcct agttcgtggg aatcatcaga   3780

gtgtccttac cttctattca taaatgttct atacagtgga cagccctcca gaatggtact   3840

tcagtgccta gtgtagtaac ctgaaatctt caatgacaca ttaacatcac aatggcgaat   3900

ggtgactttt ctttcacgat ttcattaatt tgaaagcaca caggaaagct tgctccattg   3960

ataacgtgta tggagacttc ggttttagtc aattccatat ctcaatctta atggtgattc   4020

ttctctgttg aactgaagtt tgtgagagta gttttccttt gctacttgaa tagcaataaa   4080

agcgtgttaa ctttttgg                                                 4098
```

<210> SEQ ID NO 46
<211> LENGTH: 3311
<212> TYPE: DNA
<213> ORGANISM: human

<400> SEQUENCE: 46

```
tgctaatgct tttggtacaa atggatgtgg aatataattg aatattttct tgtttaaggg     60

gagcatgaag aggtgttgag gttatgtcaa gcatctggca cagctgaagg cagatggaaa    120

tatttacaag tacgcaattt gagactaaga tattgttatc attctcctat tgaagacaag    180

agcaatagta aaacacatca ggtcaggggg ttaaagacct gtgataaacc acttccgata    240

agttggaaac gtgtgtctat attttcatat ctgtatatat ataatggtaa agaaagacac    300

cttcgtaacc cgcattttcc aaagagagga atcacaggga gatgtacagc aatggggcca    360

tttaagagtt ctgtgttcat cttgattctt caccttctag aaggggccct gagtaattca    420

ctcattcagc tgaacaacaa tggctatgaa ggcattgtcg ttgcaatcga ccccaatgtg    480

ccagaagatg aaacactcat tcaacaaata aaggacatgg tgacccaggc atctctgtat    540

ctgtttgaag ctacaggaaa gcgattttat ttcaaaaatg ttgccatttt gattcctgaa    600

acatggaaga caaaggctga ctatgtgaga ccaaaacttg agacctacaa aaatgctgat    660

gttctggttg ctgagtctac tcctccaggt aatgatgaac cctacactga gcagatgggc    720

aactgtggag agaagggtga aaggatccac ctcactcctg atttcattgc aggaaaaaag    780

ttagctgaat atggaccaca aggtaaggca tttgtccatg agtgggctca tctacgatgg    840

ggagtatttg acgagtacaa taatgatgag aaattctact tatccaatgg aagaatacaa    900
```

-continued

```
gcagtaagat gttcagcagg tattactggt acaaatgtag taaagaagtg tcagggaggc    960
agctgttaca ccaaaagatg cacattcaat aaagttacag gactctatga aaaaggatgt   1020
gagtttgttc tccaatcccg ccagacggag aaggcttcta taatgtttgc acaacatgtt   1080
gattctatag ttgaattctg tacagaacaa aaccacaaca aagaagctcc aaacaagcaa   1140
aatcaaaaat gcaatctccg aagcacatgg gaagtgatcc gtgattctga ggactttaag   1200
aaaaccactc ctatgacaac acagccacca aatcccacct tctcattgct gcagattgga   1260
caaagaattg tgtgtttagt ccttgacaaa tctggaagca tggcgactgg taaccgcctc   1320
aatcgactga atcaagcagg ccagcttttc ctgctgcaga cagttgagct ggggtcctgg   1380
gttgggatgg tgacatttga cagtgctgcc catgtacaaa gtgaactcat acagataaac   1440
agtggcagtg acagggacac actcgccaaa agattacctg cagcagcttc aggagggacg   1500
tccatctgca gcgggcttcg atcggcattt actgtgatta ggaagaaata tccaactgat   1560
ggatctgaaa ttgtgctgct gacggatggg gaagacaaca ctataagtgg gtgctttaac   1620
gaggtcaaac aaagtggtgc catcatccac acagtcgctt tggggccctc tgcagctcaa   1680
gaactagagg agctgtccaa aatgacagga ggtttacaga catatgcttc agatcaagtt   1740
cagaacaatg gcctcattga tgcttttggg gccctttcat caggaaatgg agctgtctct   1800
cagcgctcca tccagcttga gagtaaggga ttaaccctcc agaacagcca gtggatgaat   1860
ggcacagtga tcgtggacag caccgtggga aaggacactt tgtttcttat cacctggaca   1920
acgcagcctc cccaaatcct tctctgggat cccagtggac agaagcaagg tggctttgta   1980
gtggacaaaa acaccaaaat ggcctacctc caaatcccag gcattgctaa ggttggcact   2040
tggaaataca gtctgcaagc aagctcacaa accttgaccc tgactgtcac gtcccgtgcg   2100
tccaatgcta ccctgcctcc aattacagtg acttccaaaa cgaacaagga caccagcaaa   2160
ttccccagcc ctctggtagt ttatgcaaat attcgccaag gagcctcccc aattctcagg   2220
gccagtgtca cagccctgat tgaatcagtg aatggaaaaa cagttacctt ggaactactg   2280
gataatggag caggtgctga tgctactaag gatgacggtg tctactcaag gtatttcaca   2340
acttatgaca cgaatggtag atacagtgta aaagtgcggg ctctgggagg agttaacgca   2400
gccagacgga gagtgatacc ccagcagagt ggagcactgt acatacctgg ctggattgag   2460
aatgatgaaa tacaatggaa tccaccaaga cctgaaatta ataaggatga tgttcaacac   2520
aagcaagtgt gtttcagcag aacatcctcg ggaggctcat ttgtggcttc tgatgtccca   2580
aatgctccca tacctgatct cttcccacct ggccaaatca ccgacctgaa ggcggaaatt   2640
cacgggggca gtctcattaa tctgacttgg acagctcctg gggatgatta tgaccatgga   2700
acagctcaca agtatatcat tcgaataagt acaagtattc ttgatctcag agacaagttc   2760
aatgaatctc ttcaagtgaa tactactgct ctcatcccaa aggaagccaa ctctgaggaa   2820
gtctttttgt ttaaaccaga aaacattact tttgaaaatg gcacagatct tttcattgct   2880
attcaggctg ttgataaggt cgatctgaaa tcagaaatat ccaacattgc acgagtatct   2940
ttgtttattc ctccacagac tccgccagag acacctagtc ctgatgaaac gtctgctcct   3000
tgtcctaata ttcatatcaa cagcaccatt cctggcattc acattttaaa aattatgtgg   3060
aagtggatag gagaactgca gctgtcaata gcctagggct gaatttttgt cagataaata   3120
aaataaatca ttcatccttt ttttgattat aaaattttct aaaatgtatt ttagacttcc   3180
tgtagggggc gatatactaa atgtatatag tacatttata ctaaatgtat tcctgtaggg   3240
```

-continued

```
ggcgatatac taaatgtatt ttagacttcc tgtagggggc gataaaataa aatgctaaac   3300

aactgggtaa a                                                        3311
```

<210> SEQ ID NO 47
<211> LENGTH: 3311
<212> TYPE: DNA
<213> ORGANISM: human

<400> SEQUENCE: 47

```
tgctaatgct tttggtacaa atggatgtgg aatataattg aatattttct tgtttaaggg     60

gagcatgaag aggtgttgag gttatgtcaa gcatctggca cagctgaagg cagatggaaa    120

tatttacaag tacgcaattt gagactaaga tattgttatc attctcctat tgaagacaag    180

agcaatagta aaacacatca ggtcaggggg ttaaagacct gtgataaacc acttccgata    240

agttggaaac gtgtgtctat attttcatat ctgtatatat ataatggtaa agaaagacac    300

cttcgtaacc cgcatttttcc aaagagagga atcacaggga gatgtacagc aatggggcca    360

tttaagagtt ctgtgttcat cttgattctt caccttctag aaggggccct gagtaattca    420

ctcattcagc tgaacaacaa tggctatgaa ggcattgtcg ttgcaatcga ccccaatgtg    480

ccagaagatg aaacactcat tcaacaaata aaggacatgg tgacccaggc atctctgtat    540

ctgtttgaag ctacaggaaa gcgattttat ttcaaaaatg ttgccatttt gattcctgaa    600

acatggaaga caaaggctga ctatgtgaga ccaaaacttg agacctacaa aaatgctgat    660

gttctggttg ctgagtctac tcctccaggt aatgatgaac cctacactga gcagatgggc    720

aactgtggag agaagggtga aaggatccac ctcactcctg atttcattgc aggaaaaaag    780

ttagctgaat atggaccaca aggtaaggca tttgtccatg agtgggctca tctacgatgg    840

ggagtatttg acgagtacaa taatgatgag aaattctact tatccaatgg aagaatacaa    900

gcagtaagat gttcagcagg tattactggt acaaatgtag taaagaagtg tcagggaggc    960

agctgttaca ccaaaagatg cacattcaat aaagttacag gactctatga aaaaggatgt   1020

gagtttgttc tccaatcccg ccagacggag aaggcttcta taatgtttgc acaacatgtt   1080

gattctatag ttgaattctg tacagaacaa aaccacaaca aagaagctcc aaacaagcaa   1140

aatcaaaaat gcaatctccg aagcacatgg gaagtgatcc gtgattctga ggactttaag   1200

aaaaccactc ctatgacaac acagccacca aatcccacct tctcattgct gcagattgga   1260

caaagaattg tgtgtttagt ccttgacaaa tctggaagca tggcgactgg taaccgcctc   1320

aatcgactga atcaagcagg ccagcttttc ctgctgcaga cagttgagct ggggtcctgg   1380

gttgggatgg tgacatttga cagtgctgcc catgtacaaa gtgaactcat acagataaac   1440

agtggcagtg acagggacac actcgccaaa agattacctg cagcagcttc aggagggacg   1500

tccatctgca gcgggcttcg atcggcattt actgtgatta ggaagaaata tccaactgat   1560

ggatctgaaa ttgtgctgct gacggatggg gaagacaaca ctataagtgg gtgctttaac   1620

gaggtcaaac aaagtggtgc catcatccac acagtcgctt tggggccctc tgcagctcaa   1680

gaactagagg agctgtccaa aatgacagga ggtttacaga catatgcttc agatcaagtt   1740

cagaacaatg gcctcattga tgcttttggg gccctttcat caggaaatgg agctgtctct   1800

cagcgctcca tccagcttga gagtaaggga ttaaccctcc agaacagcca gtggatgaat   1860

ggcacagtga tcgtggacag caccgtggga aaggacactt tgtttcttat cacctggaca   1920

acgcagcctc cccaaatcct tctctgggat cccagtggac agaagcaagg tggctttgta   1980

gtggacaaaa acaccaaaat ggcctacctc caaatcccag gcattgctaa ggttggcact   2040
```

-continued

```
tggaaataca gtctgcaagc aagctcacaa accttgaccc tgactgtcac gtcccgtgcg   2100
tccaatgcta ccctgcctcc aattacagtg acttccaaaa cgaacaagga caccagcaaa   2160
ttccccagcc ctctggtagt ttatgcaaat attcgccaag gagcctcccc aattctcagg   2220
gccagtgtca cagccctgat tgaatcagtg aatggaaaaa cagttacctt ggaactactg   2280
gataatggag caggtgctga tgctactaag gatgacggtg tctactcaag gtatttcaca   2340
acttatgaca cgaatggtag atacagtgta aaagtgcggg ctctgggagg agttaacgca   2400
gccagacgga gagtgatacc ccagcagagt ggagcactgt acatacctgg ctggattgag   2460
aatgatgaaa tacaatggaa tccaccaaga cctgaaatta ataaggatga tgttcaacac   2520
aagcaagtgt gtttcagcag aacatcctcg ggaggctcat ttgtggcttc tgatgtccca   2580
aatgctccca tacctgatct cttcccacct ggccaaatca ccgacctgaa ggcggaaatt   2640
cacgggggca gtctcattaa tctgacttgg acagctcctg gggatgatta tgaccatgga   2700
acagctcaca agtatatcat tcgaataagt acaagtattc ttgatctcag agacaagttc   2760
aatgaatctc ttcaagtgaa tactactgct ctcatcccaa aggaagccaa ctctgaggaa   2820
gtcttttgt ttaaaccaga aaacattact tttgaaaatg gcacagatct tttcattgct   2880
attcaggctg ttgataaggt cgatctgaaa tcagaaatat ccaacattgc acgagtatct   2940
ttgtttattc ctccacagac tccgccagag acacctagtc ctgatgaaac gtctgctcct   3000
tgtcctaata ttcatatcaa cagcaccatt cctggcattc acattttaaa aattatgtgg   3060
aagtggatag gagaactgca gctgtcaata gcctagggct gaatttttgt cagataaata   3120
aaataaatca ttcatccttt ttttgattat aaaatttttct aaaatgtatt ttagacttcc   3180
tgtagggggc gatatactaa atgtatatag tacatttata ctaaatgtat tcctgtaggg   3240
ggcgatatac taaatgtatt ttagacttcc tgtagggggc gataaaataa aatgctaaac   3300
aactgggtaa a                                                        3311
```

```
<210> SEQ ID NO 48
<211> LENGTH: 3697
<212> TYPE: DNA
<213> ORGANISM: human

<400> SEQUENCE: 48
```

```
agggagtgtt cccgggggag atactccagt cgtagcaaga gtctcgacca ctgaatggaa     60
gaaaaggact tttaaccacc attttgtgac ttacagaaag gaatttgaat aaagaaaact    120
atgatacttc aggcccatct tcactccctg tgtcttctta tgctttattt ggcaactgga    180
tatggccaag aggggaagtt tagtggaccc ctgaaaccca tgacattttc tatttatgaa    240
ggccaagaac cgagtcaaat tatattccag tttaaggcca atcctcctgc tgtgactttt    300
gaactaactg gggagacaga caacatattt gtgatagaac gggagggact tctgtattac    360
aacagagcct tggacaggga aacaagatct actcacaatc tccaggttgc agccctggac    420
gctaatggaa ttatagtgga gggtccagtc cctatcacca tagaagtgaa ggacatcaac    480
gacaatcgac ccacgtttct ccagtcaaag tacgaaggct cagtaaggca gaactctcgc    540
ccaggaaagc ccttcttgta tgtcaatgcc acagacctgg atgatccggc cactcccaat    600
ggccagcttt attaccagat tgtcatccag cttcccatga tcaacaatgt catgtacttt    660
cagatcaaca acaaaacggg agccatctct cttacccgag agggatctca ggaattgaat    720
cctgctaaga atccttccta taatctggtg atctcagtga aggacatggg aggccagagt    780
```

-continued

```
gagaattcct tcagtgatac cacatctgtg gatatcatag tgacagagaa tatttggaaa    840
gcaccaaaac ctgtggagat ggtggaaaac tcaactgatc ctcaccccat caaaatcact    900
caggtgcggt ggaatgatcc cggtgcacaa tattccttag ttgacaaaga gaagctgcca    960
agattcccat tttcaattga ccaggaagga gatatttacg tgactcagcc cttggaccga   1020
gaagaaaagg atgcatatgt tttttatgca gttgcaaagg atgagtacgg aaaaccactt   1080
tcatatccgc tggaaattca tgtaaaagtt aaagatatta atgataatcc acctacatgt   1140
ccgtcaccag taaccgtatt tgaggtccag gagaatgaac gactgggtaa cagtatcggg   1200
acccttactg cacatgacag ggatgaagaa aatactgcca acagttttct aaactacagg   1260
attgtggagc aaactcccaa acttcccatg gatggactct tcctaatcca aacctatgct   1320
ggaatgttac agttagctaa acagtccttg aagaagcaag atactcctca gtacaactta   1380
acgatagagg tgtctgacaa agatttcaag accctttgtt ttgtgcaaat caacgttatt   1440
gatatcaatg atcagatccc catctttgaa aaatcagatt atggaaacct gactcttgct   1500
gaagacacaa acattgggtc caccatctta accatccagg ccactgatgc tgatgagcca   1560
tttactggga gttctaaaat tctgtatcat atcataaagg gagacagtga gggacgcctg   1620
ggggttgaca cagatcccca taccaacacc ggatatgtca taattaaaaa gcctcttgat   1680
tttgaaacag cagctgtttc caacattgtg ttcaaagcag aaaatcctga gcctctagtg   1740
tttggtgtga agtacaatgc aagttctttt gccaagttca cgcttattgt gacagatgtg   1800
aatgaagcac ctcaattttc ccaacacgta ttccaagcga aagtcagtga ggatgtagct   1860
ataggcacta aagtgggcaa tgtgactgcc aaggatccag aaggtctgga cataagctat   1920
tcactgaggg gagacacaag aggttggctt aaaattgacc acgtgactgg tgagatcttt   1980
agtgtggctc cattggacag agaagccgga agtccatatc gggtacaagt ggtggccaca   2040
gaagtagggg ggtcttcctt gagctctgtg tcagagttcc acctgatcct tatggatgtg   2100
aatgacaacc ctcccaggct agccaaggac tacacgggct tgttcttctg ccatcccctc   2160
agtgcacctg gaagtctcat tttcgaggct actgatgatg atcagcactt atttcggggt   2220
ccccatttta cattttccct cggcagtgga agcttacaaa acgactggga agtttccaaa   2280
atcaatggta ctcatgcccg actgtctacc aggcacacag agtttgagga gagggagtat   2340
gtcgtcttga tccgcatcaa tgatgggggt cggccaccct tggaaggcat tgtttcttta   2400
ccagttacat tctgcagttg tgtggaagga agttgtttcc ggccagcagg tcaccagact   2460
gggataccca ctgtgggcat ggcagttggt atactgctga ccacccttct ggtgattggt   2520
ataattttag cagttgtgtt tatccgcata aagaaggata aaggcaaaga taatgttgaa   2580
agtgctcaag catctgaagt caaacctctg agaagctgaa tttgaaaagg aatgtttgaa   2640
tttatatagc aagtgctatt tcagcaacaa ccatctcatc ctattacttt tcatctaacg   2700
tgcattataa ttttttaaac agatattccc tcttgtcctt taatatttgc taaatatttc   2760
tttttgagg tggagtcttg ctctgtcgcc caggctggag tacagtggtg tgatcccagc   2820
tcactgcaac ctccgcctcc tgggttcaca tgattctcct gcctcagctt cctaagtagc   2880
tgggtttaca ggcacccacc accatgccca gctaattttt gtatttttaa tagagacggg   2940
gtttcgccat ttggccaggc tggtcttgaa ctcctgacgt caagtgatct gcctgccttg   3000
gtctcccaat acaggcatga accactgcac ccacctactt agatatttca tgtgctatag   3060
acattagaga gatttttcat ttttccatga catttttcct ctctgcaaat ggcttagcta   3120
cttgtgtttt tccctttttgg ggcaagacag actcattaaa tattctgtac atttttttctt   3180
```

-continued

```
tatcaaggag atatatcagt gttgtctcat agaactgcct ggattccatt tatgtttttt   3240

ctgattccat cctgtgtccc cttcatcctt gactcctttg gtatttcact gaatttcaaa   3300

catttgtcag agaagaaaaa cgtgaggact caggaaaaat aaataaataa aagaacagcc   3360

ttttccctta gtattaacag aaatgtttct gtgtcattaa ccatctttaa tcaatgtgac   3420

atgttgctct ttggctgaaa ttcttcaact tggaaatgac acagacccac agaaggtgtt   3480

caaacacaac ctactctgca aaccttggta aaggaaccag tcagctggcc agatttcctc   3540

actacctgcc atgcatacat gctgcgcatg ttttcttcat tcgtatgtta gtaaagtttt   3600

ggttattata tatttaacat gtggaagaaa acaagacatg aaaagagtgg tgacaaatca   3660

agaataaaca ctggttgtag tcagttttgt ttgttaa                            3697
```

```
<210> SEQ ID NO 49
<211> LENGTH: 3697
<212> TYPE: DNA
<213> ORGANISM: human

<400> SEQUENCE: 49

agggagtgtt cccgggggag atactccagt cgtagcaaga gtctcgacca ctgaatggaa     60

gaaaaggact tttaaccacc attttgtgac ttacagaaag gaatttgaat aaagaaaact    120

atgatacttc aggcccatct tcactccctg tgtcttctta tgctttattt ggcaactgga    180

tatggccaag aggggaagtt tagtggaccc ctgaaaccca tgacattttc tatttatgaa    240

ggccaagaac cgagtcaaat tatattccag tttaaggcca atcctcctgc tgtgactttt    300

gaactaactg gggagacaga caacatattt gtgatagaac gggagggact tctgtattac    360

aacagagcct tggacaggga aacaagatct actcacaatc tccaggttgc agccctggac    420

gctaatggaa ttatagtgga gggtccagtc cctatcacca tagaagtgaa ggacatcaac    480

gacaatcgac ccacgtttct ccagtcaaag tacgaaggct cagtaaggca gaactctcgc    540

ccaggaaagc ccttcttgta tgtcaatgcc acagacctgg atgatccggc cactcccaat    600

ggccagcttt attaccagat tgtcatccag cttcccatga tcaacaatgt catgtacttt    660

cagatcaaca acaaaacggg agccatctct cttacccgag agggatctca ggaattgaat    720

cctgctaaga atccttccta taatctggtg atctcagtga aggacatggg aggccagagt    780

gagaattcct tcagtgatac cacatctgtg gatatcatag tgacagagaa tatttggaaa    840

gcaccaaaac ctgtggagat ggtggaaaac tcaactgatc ctcaccccat caaaatcact    900

caggtgcggt ggaatgatcc cggtgcacaa tattccttag ttgacaaaga gaagctgcca    960

agattcccat tttcaattga ccaggaagga gatatttacg tgactcagcc cttggaccga   1020

gaagaaaagg atgcatatgt tttttatgca gttgcaaagg atgagtacgg aaaaccactt   1080

tcatatccgc tggaaattca tgtaaaagtt aaagatatta atgataatcc acctacatgt   1140

ccgtcaccag taaccgtatt tgaggtccag gagaatgaac gactgggtaa cagtatcggg   1200

acccttactg cacatgacag ggatgaagaa aatactgcca acagttttct aaactacagg   1260

attgtggagc aaactcccaa acttcccatg gatggactct tcctaatcca aacctatgct   1320

ggaatgttac agttagctaa acagtccttg aagaagcaag atactcctca gtacaactta   1380

acgatagagg tgtctgacaa agatttcaag accctttgtt ttgtgcaaat caacgttatt   1440

gatatcaatg atcagatccc catctttgaa aaatcagatt atggaaacct gactcttgct   1500

gaagacacaa acattgggtc caccatctta accatccagg ccactgatgc tgatgagcca   1560
```

-continued

```
tttactggga gttctaaaat tctgtatcat atcataaagg gagacagtga gggacgcctg   1620
ggggttgaca cagatcccca taccaacacc ggatatgtca taattaaaaa gcctcttgat   1680
tttgaaacag cagctgtttc caacattgtg ttcaaagcag aaaatcctga gcctctagtg   1740
tttggtgtga agtacaatgc aagttctttt gccaagttca cgcttattgt gacagatgtg   1800
aatgaagcac ctcaattttc ccaacacgta ttccaagcga aagtcagtga ggatgtagct   1860
ataggcacta aagtgggcaa tgtgactgcc aaggatccag aaggtctgga cataagctat   1920
tcactgaggg gagacacaag aggttggctt aaaattgacc acgtgactgg tgagatcttt   1980
agtgtggctc cattggacag agaagccgga agtccatatc gggtacaagt ggtggccaca   2040
gaagtagggg ggtcttcctt gagctctgtg tcagagttcc acctgatcct tatggatgtg   2100
aatgacaacc ctcccaggct agccaaggac tacacgggct tgttcttctg ccatcccctc   2160
agtgcacctg gaagtctcat tttcgaggct actgatgatg atcagcactt atttcggggt   2220
ccccatttta cattttccct cggcagtgga agcttacaaa acgactggga agtttccaaa   2280
atcaatggta ctcatgcccg actgtctacc aggcacacag agtttgagga gagggagtat   2340
gtcgtcttga tccgcatcaa tgatgggggt cggccaccct tggaaggcat tgtttcttta   2400
ccagttacat tctgcagttg tgtggaagga agttgtttcc ggccagcagg tcaccagact   2460
gggataccca ctgtgggcat ggcagttggt atactgctga ccacccttct ggtgattggt   2520
ataattttag cagttgtgtt tatccgcata aagaaggata aaggcaaaga taatgttgaa   2580
agtgctcaag catctgaagt caaacctctg agaagctgaa tttgaaaagg aatgtttgaa   2640
tttatatagc aagtgctatt tcagcaacaa ccatctcatc ctattacttt tcatctaacg   2700
tgcattataa ttttttaaac agatattccc tcttgtcctt taatatttgc taaatatttc   2760
tttttgagg tggagtcttg ctctgtcgcc caggctggag tacagtggtg tgatcccagc   2820
tcactgcaac ctccgcctcc tgggttcaca tgattctcct gcctcagctt cctaagtagc   2880
tgggtttaca ggcacccacc accatgccca gctaattttt gtatttttaa tagagacggg   2940
gtttcgccat ttggccaggc tggtcttgaa ctcctgacgt caagtgatct gcctgccttg   3000
gtctcccaat acaggcatga accactgcac ccacctactt agatatttca tgtgctatag   3060
acattagaga gatttttcat ttttccatga catttttcct ctctgcaaat ggcttagcta   3120
cttgtgtttt tccctttgg ggcaagacag actcattaaa tattctgtac atttttttctt   3180
tatcaaggag atatatcagt gttgtctcat agaactgcct ggattccatt tatgtttttt   3240
ctgattccat cctgtgtccc cttcatcctt gactcctttg gtatttcact gaatttcaaa   3300
catttgtcag agaagaaaaa cgtgaggact caggaaaaat aaataaataa aagaacagcc   3360
ttttccctta gtattaacag aaatgtttct gtgtcattaa ccatctttaa tcaatgtgac   3420
atgttgctct ttggctgaaa ttcttcaact tggaaatgac acagacccac agaaggtgtt   3480
caaacacaac ctactctgca aaccttggta aaggaaccag tcagctggcc agatttcctc   3540
actacctgcc atgcatacat gctgcgcatg ttttcttcat tcgtatgtta gtaaagtttt   3600
ggttattata tatttaacat gtggaagaaa acaagacatg aaaagagtgg tgacaaatca   3660
agaataaaca ctggttgtag tcagttttgt ttgttaa                            3697
```

<210> SEQ ID NO 50
<211> LENGTH: 3803
<212> TYPE: DNA
<213> ORGANISM: human

<400> SEQUENCE: 50

-continued

```
ccatggtagg agcgctcgcc tcgctgcggt gcccgctgag gccatgccgg ggccccggcg     60
ccccgctggc tcccgcctgc gcctgctcct gctcctgctg ctgccgccgc tgctgctgct    120
gctccggggc agccacgcgg gcaacctgac ggtagccgtg gtactgccgc tggccaatac    180
ctcgtacccc tggtcgtggg cgcgcgtggg acccgccgtg gagctggccc tggcccaggt    240
gaaggcgcgc cccgacttgc tgccgggctg gacggtccgc acggtgctgg gcagcagcga    300
aaacgcgctg ggcgtctgct ccgacaccgc agcgcccctg gccgcggtgg acctcaagtg    360
ggagcacaac cccgctgtgt tcctgggccc cggctgcgtg tacgccgccg ccccagtggg    420
gcgcttcacc gcgcactggc gggtcccgct gctgaccgcc ggcgccccgg cgctgggctt    480
cggtgtcaag gacgagtatg cgctgaccac ccgcgcgggg cccagctacg ccaagctggg    540
ggacttcgtg gcggcgctgc accgacggct gggctgggag cgccaagcgc tcatgctcta    600
cgcctaccgg ccgggtgacg aagagcactg cttcttcctc gtggaggggc tgttcatgcg    660
ggtccgcgac cgcctcaata ttacggtgga ccacctggag ttcgccgagg acgacctcag    720
ccactacacc aggctgctgc ggaccatgcc gcgcaaaggc cgagttatct acatctgcag    780
ctcccctgat gccttcagaa ccctcatgct cctggccctg gaagctggct tgtgtgggga    840
ggactacgtt ttcttccacc tggatatctt tgggcaaagc ctgcaaggtg gacagggccc    900
tgctccccgc aggccctggg agagagggga tgggcaggat gtcagtgccc gccaggcctt    960
tcaggctgcc aaaatcatta catataaaga cccagataat cccgagtact tggaattcct   1020
gaagcagtta aaacacctgg cctatgagca gttcaacttc accatggagg atggcctggt   1080
gaacaccatc ccagcatcct tccacgacgg gctcctgctc tatatccagg cagtgacgga   1140
gactctggca catgggggaa ctgttactga tggggagaac atcactcagc ggatgtggaa   1200
ccgaagcttt caaggtgtga caggatacct gaaaattgat agcagtggcg atcgggaaac   1260
agacttctcc ctctgggata tggatcccga gaatggtgcc ttcagggttg tactgaacta   1320
caatgggact tcccaagagc tggtggctgt gtcggggcgc aaactgaact ggcccctggg   1380
gtaccctcct cctgacatcc ccaaatgtgg ctttgacaac gaagacccag catgcaacca   1440
agatcacctt tccaccctgg aggtgctggc tttggtgggc agcctctcct tgctcggcat   1500
tctgattgtc tccttcttca tatacaggaa gatgcagctg gagaaggaac tggcctcgga   1560
gctgtggcgg gtgcgctggg aggacgttga gcccagtagc cttgagaggc acctgcggag   1620
tgcaggcagc cggctgaccc tgagcgggag aggctccaat tacggctccc tgctaaccac   1680
agagggccag ttccaagtct ttgccaagac agcatattat aagggcaacc tcgtggctgt   1740
gaaacgtgtg aaccgtaaac gcattgagct gacacgaaaa gtcctgtttg aactgaagca   1800
tatgcgggat gtgcagaatg aacacctgac caggtttgtg ggagcctgca ccgacccccc   1860
caatatctgc atcctcacag agtactgtcc ccgtgggagc ctgcaggaca ttctggagaa   1920
tgagagcatc accctggact ggatgttccg gtactcactc accaatgaca tcgtcaaggg   1980
catgctgttt ctacacaatg gggctatctg ttcccatggg aacctcaagt catccaactg   2040
cgtggtagat gggcgctttg tgctcaagat caccgactat gggctggaga gcttcaggga   2100
cctggaccca gagcaaggac acaccgttta tgccaaaaag ctgtggacgg cccctgagct   2160
cctgcgaatg gcttcacccc ctgtgcgggg ctcccaggct ggtgacgtat acagctttgg   2220
gatcatcctt caggagattg ccctgaggag tggggtcttc cacgtggaag gtttggacct   2280
gagccccaaa gagatcatcg agcgggtgac tcggggtgag cagcccccct tccggccctc   2340
```

-continued

```
cctggccctg cagagtcacc tggaggagtt ggggctgctc atgcagcggt gctgggctga   2400

ggacccacag gagaggccac cattccagca gatccgcctg acgttgcgca aatttaacag   2460

ggagaacagc agcaacatcc tggacaacct gctgtcccgc atggagcagt acgcgaacaa   2520

tctggaggaa ctggtggagg agcggaccca ggcatacctg gaggagaagc gcaaggctga   2580

ggccctgctc taccagatcc tgcctcactc agtggctgag cagctgaagc gtggggagac   2640

ggtgcaggcc gaagcctttg acagtgttac catctacttc agtgacattg tgggtttcac   2700

agcgctgtcg gcggagagca cacccatgca ggtggtgacc ctgctcaatg acctgtacac   2760

ttgctttgat gctgtcatag acaactttga tgtgtacaag gtggagacaa ttggcgatgc   2820

ctacatggtg gtgtcagggc tccctgtgcg gaacgggcgg ctacacgcct gcgaggtagc   2880

ccgcatggcc ctggcactgc tggatgctgt gcgctccttc cgaatccgcc accggcccca   2940

ggagcagctg cgcttgcgca ttggcatcca cacaggacct gtgtgtgctg gagtggtggg   3000

actgaagatg ccccgttact gtctctttgg ggatacagtc aacacagcct caagaatgga   3060

gtctaatggg gaagccctga agatccactt gtcttctgag accaaggctg tcctggagga   3120

gtttggtggt ttcgagctgg agcttcgagg ggatgtagaa atgaagggca aaggcaaggt   3180

tcggacctac tggctccttg gggagagggg gagtagcacc cgaggctgac ctgcctcctc   3240

tcctatccct ccacacctcc cctaccctgt gccagaagca acagaggtgc caggcctcag   3300

cctcacccac agcagcccca tcgccaaagg atggaagtaa tttgaatagc tcaggtgtgc   3360

tgaccccagt gaagacacca gataggacct ctgagagggg actggcatgg ggggatctca   3420

gagcttacag gctgagccaa gcccacggcc atgcacaggg acactcacac aggcacacgc   3480

acctgctctc cacctggact caggccgggc tgggctgtgg atccttgatc ccctcccctc   3540

cccatgctct cctccctcag ccttgctacc ctgtgactta ctgggaggag agtcacctga   3600

aggggaacat gaaaagagac taggtgaaga gagggcaggg gagcccacat ctggggctgg   3660

cccacaatac ctgctccccc gacccctcc acccagcagt agacacagtg cacaggggag    3720

aagaggggtg gcgcagaagg gttgggggcc tgtatgcctt gcttctacca tgagcagaga   3780

caattaaaat ctttattcca gtg                                           3803
```

```
<210> SEQ ID NO 51
<211> LENGTH: 3803
<212> TYPE: DNA
<213> ORGANISM: human

<400> SEQUENCE: 51

ccatggtagg agcgctcgcc tcgctgcggt gcccgctgag gccatgccgg ggccccggcg     60

ccccgctggc tcccgcctgc gcctgctcct gctcctgctg ctgccgccgc tgctgctgct    120

gctccggggc agccacgcgg gcaacctgac ggtagccgtg gtactgccgc tggccaatac    180

ctcgtacccc tggtcgtggg cgcgcgtggg acccgccgtg gagctggccc tggcccaggt    240

gaaggcgcgc cccgacttgc tgccgggctg gacggtccgc acggtgctgg gcagcagcga    300

aaacgcgctg ggcgtctgct ccgacaccgc agcgcccctg gccgcggtgg acctcaagtg    360

ggagcacaac cccgctgtgt tcctgggccc cggctgcgtg tacgccgccg ccccagtggg    420

gcgcttcacc gcgcactggc gggtcccgct gctgaccgcc ggcgccccgg cgctgggctt    480

cggtgtcaag gacgagtatg cgctgaccac ccgcgcgggg cccagctacg ccaagctggg    540

ggacttcgtg gcggcgctgc accgacggct gggctgggag cgccaagcgc tcatgctcta    600

cgcctaccgg ccgggtgacg aagagcactg cttcttcctc gtggaggggc tgttcatgcg    660
```

-continued

```
ggtccgcgac cgcctcaata ttacggtgga ccacctggag ttcgccgagg acgacctcag    720
ccactacacc aggctgctgc ggaccatgcc gcgcaaaggc cgagttatct acatctgcag    780
ctcccctgat gccttcagaa ccctcatgct cctggccctg gaagctggct tgtgtgggga    840
ggactacgtt ttcttccacc tggatatctt tgggcaaagc ctgcaaggtg gacagggccc    900
tgctccccgc aggccctggg agagagggga tgggcaggat gtcagtgccc gccaggcctt    960
tcaggctgcc aaaatcatta catataaaga cccagataat cccgagtact tggaattcct   1020
gaagcagtta aaacacctgg cctatgagca gttcaacttc accatggagg atggcctggt   1080
gaacaccatc ccagcatcct tccacgacgg gctcctgctc tatatccagg cagtgacgga   1140
gactctggca catgggggaa ctgttactga tggggagaac atcactcagc ggatgtggaa   1200
ccgaagcttt caaggtgtga caggatacct gaaaattgat agcagtggcg atcgggaaac   1260
agacttctcc ctctgggata tggatcccga gaatggtgcc ttcagggttg tactgaacta   1320
caatgggact tcccaagagc tggtggctgt gtcggggcgc aaactgaact ggcccctggg   1380
gtaccctcct cctgacatcc ccaaatgtgg ctttgacaac gaagacccag catgcaacca   1440
agatcacctt tccaccctgg aggtgctggc tttggtgggc agcctctcct tgctcggcat   1500
tctgattgtc tccttcttca tatacaggaa gatgcagctg gagaaggaac tggcctcgga   1560
gctgtggcgg gtgcgctggg aggacgttga gcccagtagc cttgagaggc acctgcggag   1620
tgcaggcagc cggctgaccc tgagcgggag aggctccaat tacggctccc tgctaaccac   1680
agagggccag ttccaagtct ttgccaagac agcatattat aagggcaacc tcgtggctgt   1740
gaaacgtgtg aaccgtaaac gcattgagct gacacgaaaa gtcctgtttg aactgaagca   1800
tatgcgggat gtgcagaatg aacacctgac caggtttgtg ggagcctgca ccgacccccc   1860
caatatctgc atcctcacag agtactgtcc ccgtgggagc ctgcaggaca ttctggagaa   1920
tgagagcatc accctggact ggatgttccg gtactcactc accaatgaca tcgtcaaggg   1980
catgctgttt ctacacaatg gggctatctg ttcccatggg aacctcaagt catccaactg   2040
cgtggtagat gggcgctttg tgctcaagat caccgactat gggctggaga gcttcaggga   2100
cctggaccca gagcaaggac acaccgttta tgccaaaaag ctgtggacgg cccctgagct   2160
cctgcgaatg gcttcacccc ctgtgcgggg ctcccaggct ggtgacgtat acagctttgg   2220
gatcatcctt caggagattg ccctgaggag tggggtcttc cacgtggaag gtttggacct   2280
gagccccaaa gagatcatcg agcgggtgac tcggggtgag cagcccccct tccggccctc   2340
cctggccctg cagagtcacc tggaggagtt ggggctgctc atgcagcggt gctgggctga   2400
ggacccacag gagaggccac cattccagca gatccgcctg acgttgcgca aatttaacag   2460
ggagaacagc agcaacatcc tggacaacct gctgtcccgc atggagcagt acgcgaacaa   2520
tctggaggaa ctggtggagg agcggaccca ggcatacctg gaggagaagc gcaaggctga   2580
ggccctgctc taccagatcc tgcctcactc agtggctgag cagctgaagc gtggggagac   2640
ggtgcaggcc gaagcctttg acagtgttac catctacttc agtgacattg tgggtttcac   2700
agcgctgtcg gcggagagca cacccatgca ggtggtgacc ctgctcaatg acctgtacac   2760
ttgctttgat gctgtcatag acaactttga tgtgtacaag gtggagacaa ttggcgatgc   2820
ctacatggtg gtgtcagggc tccctgtgcg gaacgggcgg ctacacgcct gcgaggtagc   2880
ccgcatggcc ctggcactgc tggatgctgt gcgctccttc cgaatccgcc accggcccca   2940
ggagcagctg cgcttgcgca ttggcatcca cacaggacct gtgtgtgctg gagtggtggg   3000
```

-continued

```
actgaagatg ccccgttact gtctctttgg ggatacagtc aacacagcct caagaatgga   3060

gtctaatggg gaagccctga agatccactt gtcttctgag accaaggctg tcctggagga   3120

gtttggtggt ttcgagctgg agcttcgagg ggatgtagaa atgaagggca aaggcaaggt   3180

tcggacctac tggctccttg ggagaggggg gagtagcacc cgaggctgac ctgcctcctc   3240

tcctatccct ccacacctcc cctaccctgt gccagaagca acagaggtgc caggcctcag   3300

cctcacccac agcagcccca tcgccaaagg atggaagtaa tttgaatagc tcaggtgtgc   3360

tgaccccagt gaagacacca gataggacct ctgagagggg actggcatgg ggggatctca   3420

gagcttacag gctgagccaa gcccacggcc atgcacaggg acactcacac aggcacacgc   3480

acctgctctc cacctggact caggccgggc tgggctgtgg atccttgatc cctcccctc    3540

cccatgctct cctccctcag ccttgctacc ctgtgactta ctgggaggag agtcacctga   3600

aggggaacat gaaaagagac taggtgaaga gagggcaggg gagcccacat ctggggctgg   3660

cccacaatac ctgctccccc gaccccctcc acccagcagt agacacagtg cacaggggag   3720

aagaggggtg gcgcagaagg gttgggggcc tgtatgcctt gcttctacca tgagcagaga   3780

caattaaaat ctttattcca gtg                                           3803
```

<210> SEQ ID NO 52
<211> LENGTH: 1155
<212> TYPE: DNA
<213> ORGANISM: human

<400> SEQUENCE: 52

```
atggattgca gtaacggatc ggcagagtgt accggagaag gaggatcaaa agaggtggtg     60

gggactttta aggctaaaga cctaatagtc acaccagcta ccattttaaa ggaaaaacca    120

gaccccaata atctggtttt tggaactgtg ttcacggatc atatgctgac ggtggagtgg    180

tcctcagagt ttggatggga gaaacctcat atcaagcctc ttcagaacct gtcattgcac    240

cctggctcat cagctttgca ctatgcagtg gaattatttg aaggattgaa ggcatttcga    300

ggagtagata ataaaattcg actgtttcag ccaaacctca acatggatag aatgtatcgc    360

tctgctgtga gggcaactct gccggtattt gacaaagaag agctcttaga gtgtattcaa    420

cagcttgtga aattggatca agaatgggtc ccatattcaa catctgctag tctgtatatt    480

cgtcctgcat tcattggaac tgagccttct cttggagtca agaagcctac caaagccctg    540

ctctttgtac tcttgagccc agtgggacct tattttttcaa gtggaacctt taatccagtg   600

tccctgtggg ccaatcccaa gtatgtaaga gcctggaaag gtggaactgg ggactgcaag    660

atgggaggga attacggctc atctcttttt gcccaatgtg aagacgtaga taatgggtgt    720

cagcaggtcc tgtggctcta tggcagagac catcagatca ctgaagtggg aactatgaat    780

ctttttcttt actggataaa tgaagatgga gaagaagaac tggcaactcc tccactagat    840

ggcatcattc ttccaggagt gacaaggcgg tgcattctgg acctggcaca tcagtggggt    900

gaatttaagg tgtcagagag atacctcacc atggatgact tgacaacagc cctggagggg    960

aacagagtga gagagatgtt tagctctggt acagcctgtg ttgtttgccc agtttctgat   1020

atactgtaca aaggcgagac aatacacatt ccaactatgg agaatggtcc taagctggca   1080

agccgcatct tgagcaaatt aactgatatc cagtatggaa gagaagagag cgactggaca   1140

attgtgctat cctga                                                    1155
```

<210> SEQ ID NO 53
<211> LENGTH: 2511

<212> TYPE: DNA
<213> ORGANISM: human

<400> SEQUENCE: 53

```
cttttcacac tggccttaaa gaggatatat tagaagttga agtaggaagg gagccagaga     60
ggccgatggc gcaaaggtac gacgatctac cccattacgg gggcatggat ggagtaggca    120
tcccctccac gatgtatggg gacccgcatg cagccaggtc catgcagccg gtccaccacc    180
tgaaccacgg gcctcctctg cactcgcatc agtacccgca cacagctcat accaacgcca    240
tggcccccag catgggctcc tctgtcaatg acgctttaaa gagagataaa gatgccattt    300
atggacaccc cctcttccct ctcttagcac tgatttttga gaaatgtgaa ttagctactt    360
gtaccccccg cgagccgggg gtggcgggcg gggacgtctg ctcgtcagag tcattcaatg    420
aagatatagc cgtgttcgcc aaacagattc gcgcagaaaa acctctattt tcttctaatc    480
cagaactgga taacttgatg attcaagcca tacaagtatt aaggtttcat ctattggaat    540
tagagaaggt acacgaatta tgtgacaatt tctgccaccg gtatattagc tgtttgaaag    600
ggaaaatgcc tatcgatttg gtgatagacg atagagaagg aggatcaaaa tcagacagtg    660
aagatataac aagatcagca aatctaactg accagccctc ttggaacaga gatcatgatg    720
acacggcatc tactcgttca ggaggaaccc caggcccttc cagcggtggc cacacgtcac    780
acagtgggga caacagcagt gagcaaggtg atggcttgga caacagtgta gcttccccca    840
gcacaggtga cgatgatgac cctgataagg acaaaaagcg tcacaaaaag cgtggcatct    900
ttcccaaagt agccacaaat atcatgaggg cgtggctgtt ccagcatcta acacaccctt    960
acccttctga agaacagaaa aagcagttgg cacaagacac gggactcacc atccttcaag   1020
tgaacaattg gtttattaat gcccggagaa gaatagtgca gcccatgata gaccagtcca   1080
accgagcagt aagtcaagga acaccttata atcctgatgg acagcccatg ggaggtttcg   1140
taatggacgg tcagcaacat atgggaatta gagcaccagg acctatgagt ggaatgggca   1200
tgaatatggg catggagggg cagtggcact acatgtaacc ttcatctagt taaccaatcg   1260
caaagcaagg gggaaggctg caaagtatgc caggggagta tgtagcccgg ggtggtccaa   1320
tgggtgtgag tatgggacag ccaagttata cccaacccca gatgcccccc catcctgctc   1380
agctgcgtca tgggcccccc atgcatacgt acattcctgg acaccctcac cacccaacag   1440
tgatgatgca tggaggaccg ccccaccctg gaatgccaat gtcagcatca agccccacag   1500
ttcttaatac aggagaccca acaatgagtg gacaagtcat ggacattcat gctcagtagc   1560
ttaagggaat atgcattgtc tgcaatggtg actgatttca aatcatgttt tttctgcaat   1620
gactgtggag ttccattctt ggcatctact ctggaccaag gagcatccct aattcttcat   1680
agggaccttt aaaaagcagg aaataccaac tgaagtcaat ttgggggaca tgctaaataa   1740
ctatataaga cattaagaga acaaagagtg aaatattgta aatgctatta tactgttatc   1800
catattacgt tgtttcttat agatttttta aaaaaaatgt gaaatttttc cacactatgt   1860
gtgttgtttc catagctctt cacttcctcc agaagcctcc ttacattaaa aagccttaca   1920
gttatcctgc aagggacagg aaggtctgat ttgcaggatt tttagagcat taaaataact   1980
atcaggcaga agaatctttc ttctcgccta ggatttcagc catgcgcgcg ctctctctct   2040
ttctctctct tttcctctct ctccctcttt ctagcctggg gcttgaattt gcatgtctaa   2100
ttcatttact caccatattt gaattggcct gaacagatgt aaatcgggaa ggatgggaaa   2160
aactgcagtc atcaacaatg attaatcagc tgttgcaggc agtgtcttaa ggagactggt   2220
```

-continued

```
aggaggaggc atggaaacca aaaggccgtg tgtttagaag cctaattgtc acatcaagca   2280

tcattgtccc catgcaacaa ccaccacctt atacatcact tcctgtttta agcagctcta   2340

aaacatagac tgaagattta tttttaatat gttgacttta tttctgagca aagcatcggt   2400

catgtgtgta ttttttcata gtcccacctt ggagcattta tgtagacatt gtaaataaat   2460

tttgtgcaaa aaggactgga aaaatgaact gtattattgc aatttttttt t            2511
```

<210> SEQ ID NO 54
<211> LENGTH: 1887
<212> TYPE: DNA
<213> ORGANISM: human

<400> SEQUENCE: 54

```
tcgcccaatt ccgggctcag acactgggct cccagctggg gactgctcca tggccatgga     60

gatagacagc aggcctgggg ggctccccgg cagtagctgc aacctaggtg cagcccgaga    120

acacatgcag gcggtcaccc gaaactacat cacccacccc cgtgtcacct acaggactgt    180

gtgcagcgtg aacgggcccc tggtggtgct ggaccgggtc aagtttgccc agtatgcgga    240

gatcgtccac ttcaccctcc cagatgggac tcagaggagc gggcaggtgc ttgaggtggc    300

tggcaccaag gcgattgttc aggtgtttga agggacatca gggatcgatg ccaggaagac    360

cacttgcgaa tttacagggg acatcctacg aactccggtg tcagaggaca tgctgggtcg    420

ggttttcaat ggctccggca agcccattga caaggggcca gtggtcatgg cggaggactt    480

tctggatatc aatggccagc ccatcaaccc gcactcccgc atctaccccg aggagatgat    540

tcagacgggc atttctccta ttgacgtcat gaacagcatt gcccgcggcc agaagatccc    600

catcttctca gcagccgggc tcccccacaa tgagattgcc gctcagatct gccgccaggc    660

ggggctggtg aagaagtcca aggctgtgct ggattaccat gacgacaact tcgccatcgt    720

ctttgcagcc atgggggtga acatggagac agccagattc ttcaagtctg actttgagca    780

gaatggaacc atggggaacg tctgcctctt cctgaacttg gccaatgacc ccacgatcga    840

gcggatcatc accccgcgcc tggcgctgac cactgctgaa ttccttgcct accagtgtga    900

gaagcatgtg ctggtcatac tgacggacat gagttcctat gcagaggcct tgcgggaggt    960

ctctgctgct agagaggagg tgcctgggcg ccgagggttt cctggatata tgtacacaga   1020

cctggccacc atctacgagc gggcgggccg tgtggagggt cggggaggat ccatcacaca   1080

gatccccatc ctcaccatgc ccaacgacga tatcacccac cctatcccag acttgacggg   1140

cttcatcaca gagggacaga tctacgtgga cagacagctt cacaacagac agatctaccc   1200

ccccatcaac gtgctccctt ccctgtcgcg gctgatgaag tcagccattg ggaaaggcat   1260

gacaagaaag gaccatggag atgtctccaa ccagctgtac gcctgctatg ccatcgggaa   1320

ggacgtgcag gccatgaagg cagtagttgg ggaggaggcg ctcacctctg aggacctgct   1380

ctacctggaa ttcctgcaga agtttgagaa gaacttcatc aatcagggcc cctacgagaa   1440

ccgctcgatg ttcgagtcgc tggaccttag ctggaagctg ctgcgcatct tccccaagga   1500

gatgctgaag cgcattccgc aggccgtgat cgacgagttc tattcccgcg aggggcggct   1560

gcaggacctc gcgcctgaca ctgcgctcta gccccgcgcg ccgtggcacc ccaacaccgg   1620

caggaaccta ccctcggctc ccgggtctcc ccgtccctcg ccacccctaa ccagcggctt   1680

tcgcgccgcc ctccgccctc cgtggctccg aggtggtggg gggcgccgca gtcatccctt   1740

tcctcgctcg attccttttc ccgcgctcca tgcctccccc tcagctcccg gtgctgcgga   1800

agaactgaag gttcatgcct actctgacgg gagcatctgt attttttatg ttaaaagccc   1860
```

acaaaataaa aataaaaatg aactgag 1887

<210> SEQ ID NO 55
<211> LENGTH: 1506
<212> TYPE: DNA
<213> ORGANISM: human

<400> SEQUENCE: 55
aggcggacaa agcccgattg ttcctgggcc ctttccccat cgcgcctggg cctgctcccc 60
agcccggggc aggggcgggg gccagtgtgg tgacacacgc tgtagctgtc tccccggctg 120
gctggctcgc tctctcctgg ggacacagag gtcggcaggc agcacacaga gggacctacg 180
ggcagctgtt ccttcccccg actcaagaat ccccggaggc ccggaggcct gcagcaggag 240
cggccatgaa gaagctgatg gtggtgctga gtctgattgc tgcagcctgg gcagaggagc 300
agaataagtt ggtgcatggc ggaccctgcg acaagacatc tcacccctac caagctgccc 360
tctacacctc gggccacttg ctctgtggtg gggtccttat ccatccactg tgggtcctca 420
cagctgccca ctgcaaaaaa ccgaatcttc aggtcttcct ggggaagcat aaccttcggc 480
aaagggagag ttcccaggag cagagttctg ttgtccgggc tgtgatccac cctgactatg 540
atgccgccag ccatgaccag gacatcatgc tgttgcgcct ggcacgccca gccaaactct 600
ctgaactcat ccagcccctt cccctggaga gggactgctc agccaacacc accagctgcc 660
acatcctggg ctggggcaag acagcagatg gtgatttccc tgacaccatc cagtgtgcat 720
acatccacct ggtgtcccgt gaggagtgtg agcatgccta ccctggccag atcacccaga 780
acatgttgtg tgctggggat gagaagtacg ggaaggattc ctgccagggt gattctgggg 840
gtccgctggt atgtggagac cacctccgag gccttgtgtc atggggtaac atcccctgtg 900
gatcaaagga gaagccagga gtctacacca acgtctgcag atacacgaac tggatccaaa 960
aaaccattca ggccaagtga ccctgacatg tgacatctac ctcccgacct accaccccac 1020
tggctggttc cagaacgtct ctcacctaga ccttgcctcc cctcctctcc tgcccagctc 1080
tgaccctgat gcttaataaa cgcagcgacg tgagggtcct gattctccct ggttttaccc 1140
cagctccatc cttgcatcac tggggaggac gtgatgagtg aggacttggg tcctcggtct 1200
tacccccacc actaagagaa tacaggaaaa tcccttctag gcatctcctc tccccaaccc 1260
ttccacacgt ttgatttctt cctgcagagg cccagccacg tgtctggaat cccagctccg 1320
ctgcttactg tcggtgtccc cttgggatgt acctttcttc actgcagatt tctcacctgt 1380
aagatgaaga taaggatgat acagtctcca tcaggcagtg gctgttggaa agatttaaga 1440
tttcacacct atgacataca tgggatagca cctgggccgc catgcactca ataaagaatg 1500
tatttt 1506

<210> SEQ ID NO 56
<211> LENGTH: 2907
<212> TYPE: DNA
<213> ORGANISM: human

<400> SEQUENCE: 56
gccatctggg cccaggcccc atgccccgag gaggggtggt ctgaagccca ccagagcccc 60
ctgccagact gtctgcctcc cttctgactg tggccgcttg gcatggccag caacagcagc 120

-continued

```
tcctgcccga cacctggggg cgggcacctc aatgggtacc cggtgcctcc ctacgccttc    180
ttcttccccc ctatgctggg tggactctcc ccgccaggcg ctctgaccac tctccagcac    240
cagcttccag ttagtggata tagcacacca tccccagcca ccattgagac ccagagcagc    300
agttctgaag agatagtgcc cagccctccc tcgccacccc ctctaccccg catctacaag    360
ccttgctttg tctgtcagga caagtcctca ggctaccact atggggtcag cgcctgtgag    420
ggctgcaagg gcttcttccg ccgcagcatc cagaagaaca tggtgtacac gtgtcaccgg    480
gacaagaact gcatcatcaa caaggtgacc cggaaccgct gccagtactg ccgactgcag    540
aagtgctttg aagtgggcat gtccaaggag tctgtgagaa acgaccgaaa caagaagaag    600
aaggaggtgc ccaagcccga gtgctctgag agctacacgc tgacgccgga ggtgggggag    660
ctcattgaga aggtgcgcaa agcgcaccag gaaaccttcc ctgccctctg ccagctgggc    720
aaatacacta cgaacaacag ctcagaacaa cgtgtctctc tggacattga cctctgggac    780
aagttcagtg aactctccac caagtgcatc attaagactg tggagttcgc caagcagctg    840
cccggcttca ccaccctcac catcgccgac cagatcaccc tcctcaaggc tgcctgcctg    900
gacatcctga tcctgcggat ctgcacgcgg tacacgcccg agcaggacac catgaccttc    960
tcggacgggc tgaccctgaa ccggacccag atgcacaacg ctggcttcgg cccccctcacc   1020
gacctggtct ttgccttcgc caaccagctg ctgcccctgg agatggatga tgcggagacg   1080
gggctgctca gcgccatctg cctcatctgc ggagaccgcc aggacctgga gcagccggac   1140
cgggtggaca tgctgcagga gccgctgctg gaggcgctaa aggtctacgt gcggaagcgg   1200
aggcccagcc gcccccacat gttccccaag atgctaatga agattactga cctgcgaagc   1260
atcagcgcca aggggggctga gcgggtgatc acgctgaaga tggagatccc gggctccatg   1320
ccgcctctca tccaggaaat gttggagaac tcagagggcc tggacactct gagcggacag   1380
ccgggggggtg gggggcggga cgggggtggc ctggcccccc cgccaggcag ctgtagcccc   1440
agcctcagcc ccagctccaa cagaagcagc ccggccaccc actccccgtg accgcccacg   1500
ccacatggac acagccctcg ccctccgccc cggcttttct ctgcctttct accgaccatg   1560
tgaccccgca ccagccctgc cccccacctgc cctcccgggc agtactgggg accttccctg   1620
ggggacgggg agggaggagg cagcgactcc ttggacagag gcctgggccc tcagtggact   1680
gcctgctccc acagcctggg ctgacgtcag aggccgaggc caggaactga gtgaggcccc   1740
tggtcctggg tctcaggatg ggtcctgggg gcctcgtgtt catcaagaca cccctctgcc   1800
cagctcacca catcttcatc accagcaaac gccaggactt ggctccccca tcctcagaac   1860
tcacaagcca ttgctcccca gctggggaac ctcaacctcc cccctgcctc ggttggtgac   1920
agaggggggtg ggacaggggc ggggggttcc ccctgtacat accctgccat accaacccca   1980
ggtattaatt ctcgctggtt ttgtttttat tttaattttt ttgttttgat ttttttaata   2040
agaattttca ttttaagcac atttatactg aaggaatttg tgctgtgtat tggggggagc   2100
tggatccaga gctggagggg gtgggtccgg gggagggagt ggctcggaag ggcccccac    2160
tctcctttca tgtccctgtg ccccccagtt ctcctcctca gccttttcct cctcagtttt   2220
ctctttaaaa ctgtgaagta ctaactttcc aaggcctgcc ttcccctccc tcccactgga   2280
gaagccgcca gcccctttct ccctctgcct gaccactggg tgtggacggt gtggggcagc   2340
cctgaaagga caggctcctg gccttggcac ttgcctgcac ccaccatgag gcatggagca   2400
gggcagagca agggccccgg gacagagttt tcccagacct ggctcctcgg cagagctgcc   2460
```

-continued

```
tcccgtcagg gcccacatca tctaggctcc ccagccccca ctgtgaaggg gctggccagg   2520

ggcccgagct gcccccaccc ccggcctcag ccaccagcac ccccataggg cccccagaca   2580

ccacacacat gcgcgtgcgc acacacacaa acacacacac actggacagt agatgggccg   2640

acacacactt ggcccgagtt cctccatttc cctggcctgc cccccacccc caacctgtcc   2700

cacccccgtg ccccctcctt accccgcagg acgggcctac agggggggtct cccctcaccc   2760

ctgcaccccc agctggggga gctggctctg ccccgacctc cttcaccagg ggttggggcc   2820

ccttcccctg gagcccgtgg gtgcacctgt tactgttggg ctttccactg agatctactg   2880

gataaagaat aaagttctat ttattct                                     2907
```

<210> SEQ ID NO 57
<211> LENGTH: 2907
<212> TYPE: DNA
<213> ORGANISM: human

<400> SEQUENCE: 57

```
gccatctggg cccaggcccc atgccccgag gaggggtggt ctgaagccca ccagagcccc     60

ctgccagact gtctgcctcc cttctgactg tggccgcttg gcatggccag caacagcagc    120

tcctgcccga cacctggggg cgggcacctc aatgggtacc cggtgcctcc ctacgccttc    180

ttcttccccc ctatgctggg tggactctcc ccgccaggcg ctctgaccac tctccagcac    240

cagcttccag ttagtggata tagcacacca tccccagcca ccattgagac ccagagcagc    300

agttctgaag agatagtgcc cagccctccc tcgccacccc ctctaccccg catctacaag    360

ccttgctttg tctgtcagga caagtcctca ggctaccact atggggtcag cgcctgtgag    420

ggctgcaagg gcttcttccg ccgcagcatc cagaagaaca tggtgtacac gtgtcaccgg    480

gacaagaact gcatcatcaa caaggtgacc cggaaccgct gccagtactg ccgactgcag    540

aagtgctttg aagtgggcat gtccaaggag tctgtgagaa acgaccgaaa caagaagaag    600

aaggaggtgc ccaagcccga gtgctctgag agctacacgc tgacgccgga ggtgggggag    660

ctcattgaga aggtgcgcaa agcgcaccag gaaaccttcc ctgccctctg ccagctgggc    720

aaatacacta cgaacaacag ctcagaacaa cgtgtctctc tggacattga cctctgggac    780

aagttcagtg aactctccac caagtgcatc attaagactg tggagttcgc caagcagctg    840

cccggcttca ccaccctcac catcgccgac cagatcaccc tcctcaaggc tgcctgcctg    900

gacatcctga tcctgcggat ctgcacgcgg tacacgcccg agcaggacac catgaccttc    960

tcggacgggc tgaccctgaa ccggacccag atgcacaacg ctggcttcgg cccccctcacc  1020

gacctggtct ttgccttcgc caaccagctg ctgcccctgg agatggatga tgcggagacg   1080

gggctgctca gcgccatctg cctcatctgc ggagaccgcc aggacctgga gcagccggac   1140

cgggtggaca tgctgcagga gccgctgctg gaggcgctaa aggtctacgt gcggaagcgg   1200

aggcccagcc gcccccacat gttccccaag atgctaatga agattactga cctgcgaagc   1260

atcagcgcca agggggctga gcgggtgatc acgctgaaga tggagatccc gggctccatg   1320

ccgcctctca tccaggaaat gttggagaac tcagagggcc tggacactct gagcggacag   1380

ccgggggggtg gggggcggga cgggggtggc ctggcccccc cgccaggcag ctgtagcccc   1440

agcctcagcc ccagctccaa cagaagcagc ccggccaccc actccccgtg accgcccacg   1500

ccacatggac acagccctcg ccctccgccc cggcttttct ctgcctttct accgaccatg   1560

tgaccccgca ccagccctgc ccccacctgc cctcccgggc agtactgggg accttccctg   1620

ggggacgggg agggaggagg cagcgactcc ttggacagag gcctgggccc tcagtggact   1680
```

-continued

```
gcctgctccc acagcctggg ctgacgtcag aggccgaggc caggaactga gtgaggcccc   1740
tggtcctggg tctcaggatg ggtcctgggg gcctcgtgtt catcaagaca cccctctgcc   1800
cagctcacca catcttcatc accagcaaac gccaggactt ggctccccca tcctcagaac   1860
tcacaagcca ttgctcccca gctggggaac ctcaacctcc cccctgcctc ggttggtgac   1920
agagggggtg ggacaggggc ggggggttcc ccctgtacat accctgccat accaacccca   1980
ggtattaatt ctcgctggtt ttgtttttat tttaattttt ttgttttgat ttttttaata   2040
agaattttca ttttaagcac atttatactg aaggaatttg tgctgtgtat tggggggagc   2100
tggatccaga gctggagggg gtgggtccgg gggagggagt ggctcggaag ggcccccac   2160
tctcctttca tgtccctgtg ccccccagtt ctcctcctca gccttttcct cctcagtttt   2220
ctctttaaaa ctgtgaagta ctaactttcc aaggcctgcc ttcccctccc tcccactgga   2280
gaagccgcca gccccttcct ccctctgcct gaccactggg tgtggacggt gtggggcagc   2340
cctgaaagga caggctcctg gccttggcac ttgcctgcac ccaccatgag gcatggagca   2400
gggcagagca agggccccgg gacagagttt tcccagacct ggctcctcgg cagagctgcc   2460
tcccgtcagg gcccacatca tctaggctcc ccagccccca ctgtgaaggg gctggccagg   2520
ggcccgagct gcccccaccc ccggcctcag ccaccagcac ccccataggg cccccagaca   2580
ccacacacat gcgcgtgcgc acacacacaa acacacacac actggacagt agatgggccg   2640
acacacactt ggcccgagtt cctccatttc cctggcctgc cccccacccc caacctgtcc   2700
cacccccgtg ccccctcctt accccgcagg acgggcctac aggggggtct cccctcaccc   2760
ctgcaccccc agctggggga gctggctctg ccccgacctc cttcaccagg ggttggggcc   2820
ccttcccctg gagcccgtgg gtgcacctgt tactgttggg ctttccactg agatctactg   2880
gataaagaat aaagttctat ttattct                                       2907
```

<210> SEQ ID NO 58
<211> LENGTH: 5026
<212> TYPE: DNA
<213> ORGANISM: human

<400> SEQUENCE: 58

```
agaggaggaa attgttcctc gtctgataag acaacagtgg agaaaggacg catgctgttt     60
cttagggaca cggctgactt ccagatatga ccatgtattt gtggcttaaa ctcttggcat    120
ttggctttgc ctttctggac acagaagtat ttgtgacagg gcaaagccca acaccttccc    180
ccactggatt gactacagca aagatgccca gtgttccact ttcaagtgac cccttaccta    240
ctcacaccac tgcattctca cccgcaagca cctttgaaag agaaaatgac ttctcagaga    300
ccacaacttc tcttagtcca gacaatactt ccacccaagt atccccggac tctttggata    360
atgctagtgc ttttaatacc acaggtgttt catcagtaca gacgcctcac cttcccacgc    420
acgcagactc gcagacgccc tctgctggaa ctgacacgca gacattcagc ggctccgccg    480
ccaatgcaaa actcaaccct accccaggca gcaatgctat ctcagatgtc ccaggagaga    540
ggagtacagc cagcaccttt cctacagacc cagtttcccc attgacaacc accctcagcc    600
ttgcacacca cagctctgct gccttacctg cacgcacctc caacaccacc atcacagcga    660
acacctcaga tgcctacctt aatgcctctg aaacaaccac tctgagccct tctggaagcg    720
ctgtcatttc aaccacaaca atagctacta ctccatctaa gccaacatgt gatgaaaaat    780
atgcaaacat cactgtggat tacttatata acaaggaaac taaattattt acagcaaagc    840
```

-continued

```
taaatgttaa tgagaatgtg gaatgtggaa acaatacttg cacaaacaat gaggtgcata    900
accttacaga atgtaaaaat gcgtctgttt ccatatctca taattcatgt actgctcctg    960
ataagacatt aatattagat gtgccaccag ggttgaaaa gtttcagtta catgattgta   1020
cacaagttga aaaagcagat actactattt gtttaaaatg gaaaaatatt gaaaccttta   1080
cttgtgatac acagaatatt acctacagat ttcagtgtgg taatatgata tttgataata   1140
aagaaattaa attagaaaac cttgaacccg aacatgagta taagtgtgac tcagaaatac   1200
tctataataa ccacaagttt actaacgcaa gtaaaattat taaaacagat tttgggagtc   1260
caggagagcc tcagattatt ttttgtagaa gtgaagctgc acatcaagga gtaattacct   1320
ggaatccccc tcaaagatca tttcataatt ttaccctctg ttatataaaa gagacagaaa   1380
aagattgcct caatctggat aaaaacctga tcaaatatga tttgcaaaat ttaaaacctt   1440
atacgaaata tgttttatca ttacatgcct acatcattgc aaaagtgcaa cgtaatggaa   1500
gtgctgcaat gtgtcatttc acaactaaaa gtgctcctcc aagccaggtc tggaacatga   1560
ctgtctccat gacatcagat aatagtatgc atgtcaagtg taggcctccc agggaccgta   1620
atggccccca tgaacgttac catttggaag ttgaagctgg aaatactctg gttagaaatg   1680
agtcgcataa gaattgcgat ttccgtgtaa aagatcttca atattcaaca gactacactt   1740
ttaaggccta ttttcacaat ggagactatc ctggagaacc ctttatttta catcattcaa   1800
catcttataa ttctaaggca ctgatagcat ttctggcatt tctgattatt gtgacatcaa   1860
tagccctgct tgttgttctc tacaaaatct atgatctaca taagaaaaga tcctgcaatt   1920
tagatgaaca gcaggagctt gttgaaaggg atgatgaaaa acaactgatg aatgtggagc   1980
caatccatgc agatattttg ttggaaactt ataagaggaa gattgctgat gaaggaagac   2040
tttttctggc tgaatttcag agcatcccgc gggtgttcag caagtttcct ataaaggaag   2100
ctcgaaagcc ctttaaccag aataaaaacc gttatgttga cattcttcct tatgattata   2160
accgtgttga actctctgag ataaacggag atgcagggtc aaactacata aatgccagct   2220
atattgatgg tttcaaagaa cccaggaaat acattgctgc acaaggtccc agggatgaaa   2280
ctgttgatga tttctggagg atgatttggg aacagaaagc cacagttatt gtcatggtca   2340
ctcgatgtga agaaggaaac aggaacaagt gtgcagaata ctggccgtca atggaagagg   2400
gcactcgggc ttttggagat gttgttgtaa agatcaacca gcacaaaaga tgtccagatt   2460
acatcattca gaaattgaac attgtaaata aaaaagaaaa agcaactgga agagaggtga   2520
ctcacattca gttcaccagc tggccagacc acggggtgcc tgaggatcct cacttgctcc   2580
tcaaactgag aaggagagtg aatgccttca gcaatttctt cagtggtccc attgtggtgc   2640
actgcagtgc tggtgttggg cgcacaggaa cctatatcgg aattgatgcc atgctagaag   2700
gcctggaagc cgagaacaaa gtggatgttt atggttatgt tgtcaagcta aggcgacaga   2760
gatgcctgat ggttcaagta gaggcccagt acatcttgat ccatcaggct ttggtggaat   2820
acaatcagtt tggagaaaca gaagtgaatt tgtctgaatt acatccatat ctacataaca   2880
tgaagaaaag ggatccaccc agtgagccgt ctccactaga ggctgaattc cagagacttc   2940
cttcatatag gagctggagg acacagcaca ttggaaatca agaagaaaat aaaagtaaaa   3000
acaggaattc taatgtcatc ccatatgact ataacagagt gccacttaaa catgagctgg   3060
aaatgagtaa agagagtgag catgattcag atgaatcctc tgatgatgac agtgattcag   3120
aggaaccaag caaatacatc aatgcatctt ttataatgag ctactggaaa cctgaagtga   3180
tgattgctgc tcagggacca ctgaaggaga ccattggtga cttttggcag atgatcttcc   3240
```

```
aaagaaaagt caaagttatt gttatgctga cagaactgaa acatggagac caggaaatct   3300

gtgctcagta ctggggagaa ggaaagcaaa catatggaga tattgaagtt gacctgaaag   3360

acacagacaa atcttcaact tatacccttc gtgtctttga actgagacat tccaagagga   3420

aagactctcg aactgtgtac cagtaccaat atacaaactg gagtgtggag cagcttcctg   3480

cagaacccaa ggaattaatc tctatgattc aggtcgtcaa acaaaaactt ccccagaaga   3540

attcctctga agggaacaag catcacaaga gtacacctct actcattcac tgcagggatg   3600

gatctcagca aacgggaata ttttgtgctt tgttaaatct cttagaaagt gcggaaacag   3660

aagaggtagt ggatattttt caagtggtaa aagctctacg caaagctagg ccaggcatgg   3720

tttccacatt cgagcaatat caattcctat atgacgtcat tgccagcacc taccctgctc   3780

agaatggaca agtaaagaaa aacaaccatc aagaagataa aattgaattt gataatgaag   3840

tggacaaagt aaagcaggat gctaattgtg ttaatccact tggtgcccca gaaaagctcc   3900

ctgaagcaaa ggaacaggct gaaggttctg aacccacgag tggcactgag gggccagaac   3960

attctgtcaa tggtcctgca agtccagctt taaatcaagg ttcataggaa aagacataaa   4020

tgaggaaact ccaaacctcc tgttagctgt tatttctatt tttgtagaag taggaagtga   4080

aaataggtat acagtggatt aattaaatgc agcgaaccaa tatttgtaga agggttatat   4140

tttactactg tggaaaaata tttaagatag ttttgccaga acagtttgta cagacgtatg   4200

cttattttaa aattttatct cttattcagt aaaaaacaac ttctttgtaa tcgttatgtg   4260

tgtatatgta tgtgtgtatg ggtgtgtgtt tgtgtgagag acagagaaag agagagaatt   4320

ctttcaagtg aatctaaaag cttttgcttt tcctttgttt ttatgaagaa aaaatacatt   4380

ttatattaga agtgttaact tagcttgaag gatctgtttt taaaaatcat aaactgtgtg   4440

cagactcaat aaaatcatgt acatttctga aatgacctca agatgtcctc cttgttctac   4500

tcatatatat ctatcttata tacttactat tttacttcta gagatagtac ataaaggtgg   4560

tatgtgtgtg tatgctacta caaaaaagtt gttaactaaa ttaacattgg gaaatcttat   4620

attccatata ttagcattta gtccaatgtc tttttaagct tatttaatta aaaaatttcc   4680

agtgagctta tcatgctgtc tttacatggg gttttcaatt ttgcatgctc gattattccc   4740

tgtacaatat ttaaaattta ttgcttgata cttttgacaa caaattaggt tttgtacaat   4800

tgaacttaaa taaatgtcat taaaataaat aaatgcaata tgtattaata ttcattgtat   4860

aaaaatagaa gaatacaaac atatttgtta aatatttaca tatgaaattt aatatagcta   4920

tttttatgga atttttcatt gatatgaaaa atatgatatt gcatatgcat agttcccatg   4980

ttaaatccca ttcataactt tcattaaagc atttactttg aatttc                 5026
```

<210> SEQ ID NO 59
<211> LENGTH: 625
<212> TYPE: DNA
<213> ORGANISM: human

<400> SEQUENCE: 59

```
aggcgggccg ctcccacttc ggcacgaggg gcacgaggta aatcttttct gcttactgaa     60

aaggaagagt ctgatgatta gttactgatc ctctttgcat ttgtaaagct ttggagatat    120

tgaatcatgt taccatttct gtttttttcc accctgtttt cttccatatt tactgaagct    180

cagaagcagt attgggtctg caactcatcc gatgcaagta tttcatacac ctactgtgat    240

aaaatgcaat acccaatttc aattaatgtt aacccctgta tagaattgaa aggatccaaa    300
```

-continued

```
ggattattgc acattttcta cattccaagg agagatttaa agcaattata tttcaatctc    360

tatataactg tcaacaccat gaatcttcca aagcgcaaag aagttatttg ccgaggatct    420

gatgacgatt actctttttg cagagctctg aagggagaga ctgtgaatac aacaatatca    480

ttctccttca agggaataaa attttctaag ggaaaataca aatgtgttgt tgaagctatt    540

tctgggagcc cagaagaaat gctcttttgc ttggagtttg tcatcctaca ccaacctaat    600

tcaaattaga ataaattgag tattt                                          625


<210> SEQ ID NO 60
<211> LENGTH: 2088
<212> TYPE: DNA
<213> ORGANISM: human

<400> SEQUENCE: 60

gaattcggca cgagcgcgcg gcgaatctca acgctgcgcc gtctgcgggc gcttccgggc     60

caccagtttc tctgctttcc accctggcgc cccccagccc tggctcccca gctgcgctgc    120

cccgggcgtc cacgccctgc gggcttagcg ggttcagtgg gctcaatctg cgcagcgcca    180

cctccatgtt gaccaagcct ctacaggggc ctcccgcgcc ccccgggacc cccacgccgc    240

cgccaggagg caaggatcgg gaagcgttcg aggccgagta tcgactcggc cccctcctgg    300

gtaagggggg ctttggcacc gtcttcgcag gacaccgcct cacagatcga ctccaggtgg    360

ccatcaaagt gattccccgg aatcgtgtgc tgggctggtc cccccttgtca gactcagtca    420

catgcccact cgaagtcgca ctgctatgga aagtgggtgc aggtggtggg caccctggcg    480

tgatccgcct gcttgactgg tttgagacac aggaaggctt catgctggtc ctcgagcggc    540

ctttgcccgc ccaggatctc tttgactata tcacagagaa gggcccactg ggtgaaggcc    600

caagccgctg cttctttggc caagtagtgg cagccatcca gcactgccat tcccgtggag    660

ttgtccatcg tgacatcaag gatgagaaca tcctgataga cctacgccgt ggctgtgcca    720

aactcattga ttttggttct ggtgccctgc ttcatgatga accctacact gactttgatg    780

ggacaagggt gtacagcccc ccagagtgga tctctcgaca ccagtaccat gcactcccgg    840

ccactgtctg gtcactgggc atcctcctct atgacatggt gtgtggggac attccctttg    900

agagggacca ggagattctg gaagctgagc tccacttccc agcccatgtc tccccagact    960

gctgtgccct aatccgccgg tgcctggccc ccaaaccttc ttcccgaccc tcactggaag   1020

agatcctgct ggacccctgg atgcaaacac cagccgagga tgttacccct caacccctcc   1080

aaaggaggcc ctgccccttt ggcctggtcc ttgctaccct aagcctggcc tggcctggcc   1140

tggcccccaa tggtcagaag agccatccca tggccatgtc acagggatag atggacattt   1200

gttgacttgg ttttacaggt cattaccagt cattaaagtc cagtattact aaggtaaggg   1260

attgaggatc aggggttaga agacataaac caagtttgcc cagttccctt cccaatccta   1320

caaaggagcc ttcctcccag aacctgtggt ccctgatttt ggagggggaa cttcttgctt   1380

ctcattttgc taaggaagtt tattttggtg aagttgttcc cattttgagc cccgggactc   1440

ttattttgat gatgtgtcac cccacattgg cacctcctac taccaccaca caaacttagt   1500

tcatatgctt ttacttgggc aagggtgctt tccttccaat accccagtag cttttatttt   1560

agtaaaggga ccctttcccc tagcctaggg tcccatattg ggtcaagctg cttacctgcc   1620

tcagcccagg atttttttatt ttgggggagg taatgccctg ttgttacccc aaggcttctt   1680

tttttttttt tttttttttg ggtgagggga ccctactttg ttatcccaag tgctcttatt   1740

ctggtgagaa gaaccttaat tccataattt gggaaggaat ggaagatgga caccaccgga   1800
```

-continued

```
caccaccaga caataggatg ggatggatgg ttttttgggg gatgggctag gggaaataag   1860

gcttgctgtt tgttttcctg ggcgctcccc tccaattttg cagatttttg caacctcctc   1920

ctgagccggg attgtccaat tactaaaatg taaataatca cgtattgtgg ggaggggagt   1980

tccaagtgtg ccctcctttt ttttcctgcc tggattattt aaaaagccat gtgtggaaac   2040

ccactattta ataaaagtaa tagaatcaga aaaaaaaaaa aaaaaaaa               2088
```

```
<210> SEQ ID NO 61
<211> LENGTH: 2270
<212> TYPE: DNA
<213> ORGANISM: human

<400> SEQUENCE: 61

ctcctccagc ctctcacact ctcctcagct ctctcatctc ctggaaccat ggccagcaca     60

tccaccacca tcaggagcca cagcagcagc cgccggggtt tcagtgccaa ctcagccagg    120

ctccctgggg tcagccgctc tggcttcagc agcgtctccg tgtcccgctc cagggggcagt    180

ggtggcctgg gtggtgcatg tggaggagct ggctttggca gccgcagtct gtatggcctg    240

gggggctcca agaggatctc cattggaggg ggcagctgtg ccatcagtgg cggctatggc    300

agcagagccg gaggcagcta tggctttggt ggcgccggga gtggatttgg tttcggtggt    360

ggagccggca ttggctttgg tctgggtggt ggagccggcc ttgctggtgg ctttgggggc    420

cctggcttcc ctgtgtgccc ccctggaggc atccaagagg tcaccgtcaa ccagagtctc    480

ctgactcccc tcaacctgca aatcgatccc accatccagc gggtgcgggc tgaggagcgt    540

gaacagatca agaccctcaa caacaagttt gcctccttca tcgacaaggt gcggttcctg    600

gagcagcaga acaaggttct ggaaacaaag tggaccctgc tgcaggagca gggcaccaag    660

actgtgaggc agaacctgga gccgttgttc gagcagtaca tcaacaacct caggaggcag    720

ctggacagca ttgtcgggga acggggccgc ctggactcag agctcagagg catgcaggac    780

ctggtggagg acttcaagaa caaatatgag gatgaaatca acaagcgcac agcagcagag    840

aatgaatttg tgactctgaa gaaggatgtg gatgctgcct acatgaacaa ggttgaactg    900

caagccaagg cagacactct cacagacgag atcaacttcc tgagagcctt gtatgatgca    960

gagctgtccc agatgcagac ccacatctca gacacatctg tggtgctgtc catggacaac   1020

aaccgcaacc tggacctgga cagcatcatc gctgaggtca aggcccaata tgaggagatt   1080

gctcagagaa gccgggctga ggctgagtcc tggtaccaga ccaagtacga ggagctgcag   1140

gtcacagcag gcagacatgg ggacgacctg cgcaacacca agcaggagat tgctgagatc   1200

aaccgcatga tccagaggct gagatctgag atcgaccacg tcaagaagca gtgcgccaac   1260

ctgcaggccg ccattgctga tgctgagcag cgtggggaga tggccctcaa ggatgccaag   1320

aacaagctgg aagggctgga ggatgccctg cagaaggcca agcaggacct ggcccggctg   1380

ctgaaggagt accaggagct gatgaatgtc aagctggccc tggacgtgga gatcgccacc   1440

taccgcaagc tgctggaggg tgaggagtgc aggctgaatg gcgaaggcgt tggacaagtc   1500

aacatctctg tggtgcagtc caccgtctcc agtggctatg gcggtgccag tggtgtcggc   1560

agtggcttag gcctgggtgg aggaagcagc tactcctatg gcagtggtct tggcgttgga   1620

ggtggcttca gttccagcag tggcagagcc attgggggtg gcctcagctc tgttggaggc   1680

ggcagttcca ccatcaagta caccaccacc tcctcctcca gcaggaagag ctataagcac   1740

taaagtgcgt ctgctagctc tcggtcccac agtcctcagg cccctctctg gctgcagagc   1800
```

-continued

```
cctctcctca ggttgcctgt cctctcctgg cctccagtct cccctgctgt cccaggtaga   1860

gctggggatg aatgcttagt gccctcactt cttctctctc tctctatacc atctgagcac   1920

ccattgctca ccatcagatc aacctctgat tttacatcat gatgtaatca ccactggagc   1980

ttcactgtta ctaaattatt aatttcttgc ctccagtgtt ctatctctga ggctgagcat   2040

tataagaaaa tgacctctgc tccttttcat tgcagaaaat tgccaggggc ttatttcaga   2100

acaacttcca cttactttcc actggctctc aaactctcta acttataagt gttgtgaacc   2160

cccacccagg cagtatccat gaaagcacaa gtgactagtc ctatgatgta caaagcctgt   2220

atctctgtga tgatttctgt gctcttcact gtttgcaatt gctaaataaa              2270
```

<210> SEQ ID NO 62
<211> LENGTH: 2048
<212> TYPE: DNA
<213> ORGANISM: human

<400> SEQUENCE: 62

```
atgtgaaggc acaagctgct gttatataca acagagtgaa ctgagcatca gtcagaaaaa     60

gtctatgttt gcagaaatac agatccaaga caaagacagg atgggcactg ctggaaaagt    120

tattaaatgc aaagcagctg tgctttggga gcagaagcaa cccttctcca ttgaggaaat    180

agaagttgcc ccaccaaaga ctaaagaagt tcgcattaag attttggcca caggaatctg    240

tcgcacagat gaccatgtga taaaaggaac aatggtgtcc aagtttccag tgattgtggg    300

acatgaggca actgggattg tagagagcat tggagaagga gtgactacag tgaaaccagg    360

tgacaaagtc atccctctct ttctgccaca atgtagagaa tgcaatgctt gtcgcaaccc    420

agatggcaac ctttgcatta ggagcgatat tactggtcgt ggagtactgg ctgatggcac    480

caccagattt acatgcaagg gcaaaccagt acaccacttc atgaacacca gtacatttac    540

cgagtacaca gtggtggatg aatcttctgt tgctaagatt gatgatgcag ctcctcctga    600

gaaagtctgt ttaattggct gtgggttttc cactggatat ggcgctgctg ttaaaactgg    660

caaggtcaaa cctggttcca cttgcgtcgt ctttggcctg ggaggagttg gcctgtcagt    720

catcatgggc tgtaagtcag ctggtgcatc taggatcatt gggattgacc tcaacaaaga    780

caaatttgag aaggccatgg ctgtaggtgc cactgagtgt atcagtccca aggactctac    840

caaacccatc agtgaggtgc tgtcagaaat gacaggcaac aacgtgggat acacctttga    900

agttattggg catcttgaaa ccatgattga tgccctggca tcctgccaca tgaactatgg    960

gaccagcgtg gttgtaggag ttcctccatc agccaagatg ctcacctatg acccgatgtt   1020

gctcttcact ggacgcacat ggaagggatg tgtctttgga ggtttgaaaa gcagagatga   1080

tgtcccaaaa ctagtgactg agttcctggc aaagaaattt gacctggacc agttgataac   1140

tcatgtttta ccatttaaaa aaatcagtga aggatttgag ctgctcaatt caggacaaag   1200

cattcgaacg gtcctgacgt tttgagatcc aaagtggcag gaggtctgtg ttgtcatggt   1260

gaactggagt ttctcttgtg agagttccct catctgaaat catgtatctg tctcacaaat   1320

acaagcataa gtagaagatt tgttgaagac atagaaccct tataaagaat tattaacctt   1380

tataaacatt taaagtcttg tgagcacctg ggaattagta taataacaat gttaatattt   1440

ttgatttaca ttttgtaagg ctataattgt atcttttaag aaaacataca cttggatttc   1500

tatgttgaaa tggagatttt taagagtttt aaccagctgc tgcagatata taactcaaaa   1560

cagatatagc gtataaagat atagtaaatg catctcccag agtaatattc acttaacaca   1620

ttgaaactat tattttttag atttgaatat aaatgtattt tttaaacact tgttatgagt   1680
```

```
taacttggat tacattttga aatcagttca ttccatgatg catattactg gattagatta   1740

agaaagacag aaaagattaa gggacgggca catttttcaa cgattaagaa tcatcattac   1800

ataacttggt gaaactgaaa aagtatatca tatgggtaca caaggctatt tgccagcata   1860

tattaatatt ttagaaaata ttccttttgt aatactgaat ataaacatag agctagagtc   1920

atattatcat acttatcata atgttcaatt tgatacagta gaattgcaag tccctaagtc   1980

cctattcact gtgcttagta gtgactccat ttaataaaaa gtgtttttag tttttaacaa   2040

ctaaaccg                                                            2048
```

```
<210> SEQ ID NO 63
<211> LENGTH: 2048
<212> TYPE: DNA
<213> ORGANISM: human

<400> SEQUENCE: 63
```

```
atgtgaaggc acaagctgct gttatataca acagagtgaa ctgagcatca gtcagaaaaa     60

gtctatgttt gcagaaatac agatccaaga caaagacagg atgggcactg ctggaaaagt    120

tattaaatgc aaagcagctg tgctttggga gcagaagcaa cccttctcca ttgaggaaat    180

agaagttgcc ccaccaaaga ctaaagaagt tcgcattaag attttggcca caggaatctg    240

tcgcacagat gaccatgtga taaaaggaac aatggtgtcc aagtttccag tgattgtggg    300

acatgaggca actgggattg tagagagcat tggagaagga gtgactacag tgaaaccagg    360

tgacaaagtc atccctctct ttctgccaca atgtagagaa tgcaatgctt gtcgcaaccc    420

agatggcaac ctttgcatta ggagcgatat tactggtcgt ggagtactgg ctgatggcac    480

caccagattt acatgcaagg gcaaaccagt acaccacttc atgaacacca gtacatttac    540

cgagtacaca gtggtggatg aatcttctgt tgctaagatt gatgatgcag ctcctcctga    600

gaaagtctgt ttaattggct gtgggttttc cactggatat ggcgctgctg ttaaaactgg    660

caaggtcaaa cctggttcca cttgcgtcgt ctttggcctg ggaggagttg gcctgtcagt    720

catcatgggc tgtaagtcag ctggtgcatc taggatcatt gggattgacc tcaacaaaga    780

caaatttgag aaggccatgg ctgtaggtgc cactgagtgt atcagtccca aggactctac    840

caaacccatc agtgaggtgc tgtcagaaat gacaggcaac aacgtgggat acacctttga    900

agttattggg catcttgaaa ccatgattga tgccctggca tcctgccaca tgaactatgg    960

gaccagcgtg gttgtaggag ttcctccatc agccaagatg ctcacctatg acccgatgtt   1020

gctcttcact ggacgcacat ggaagggatg tgtctttgga ggtttgaaaa gcagagatga   1080

tgtcccaaaa ctagtgactg agttcctggc aaagaaattt gacctggacc agttgataac   1140

tcatgtttta ccatttaaaa aaatcagtga aggatttgag ctgctcaatt caggacaaag   1200

cattcgaacg gtcctgacgt tttgagatcc aaagtggcag gaggtctgtg ttgtcatggt   1260

gaactggagt ttctcttgtg agagttccct catctgaaat catgtatctg tctcacaaat   1320

acaagcataa gtagaagatt tgttgaagac atagaaccct tataaagaat tattaacctt   1380

tataaacatt taaagtcttg tgagcacctg ggaattagta taataacaat gttaatattt   1440

ttgatttaca ttttgtaagg ctataattgt atcttttaag aaaacataca cttggatttc   1500

tatgttgaaa tggagatttt taagagtttt aaccagctgc tgcagatata taactcaaaa   1560

cagatatagc gtataaagat atagtaaatg catctcccag agtaatattc acttaacaca   1620

ttgaaactat tattttttag atttgaatat aaatgtattt tttaaacact tgttatgagt   1680
```

-continued

```
taacttggat tacattttga aatcagttca ttccatgatg catattactg gattagatta   1740

agaaagacag aaaagattaa gggacgggca catttttcaa cgattaagaa tcatcattac   1800

ataacttggt gaaactgaaa aagtatatca tatgggtaca caaggctatt tgccagcata   1860

tattaatatt ttagaaaata ttccttttgt aatactgaat ataaacatag agctagagtc   1920

atattatcat acttatcata atgttcaatt tgatacagta gaattgcaag tccctaagtc   1980

cctattcact gtgcttagta gtgactccat ttaataaaaa gtgtttttag tttttaacaa   2040

ctaaaccg                                                            2048


<210> SEQ ID NO 64
<211> LENGTH: 2816
<212> TYPE: DNA
<213> ORGANISM: human

<400> SEQUENCE: 64

tcgttgatat caaagacagt tgaaggaaat gaattttgaa acttcacggt gtgccaccct     60

acagtactgc cctgaccctt acatccagcg tttcgtagaa acccagctca tttctcttgg    120

aaagaaagtt attaccgatc caccatgtcc cagagcacac agacaaatga attcctcagt    180

ccagaggttt tccagcatat ctgggatttt ctggaacagc ctatatgttc agttcagccc    240

attgacttga actttgtgga tgaaccatca gaagatggtg cgacaaacaa gattgagatt    300

agcatggact gtatccgcat gcaggactcg gacctgagtg accccatgtg gccacagtac    360

acgaacctgg ggctcctgaa cagcatggac cagcagattc agaacggctc ctcgtccacc    420

agtccctata acacagacca cgcgcagaac agcgtcacgg cgccctcgcc ctacgcacag    480

cccagctcca ccttcgatgc tctctctcca tcacccgcca tcccctccaa caccgactac    540

ccaggcccgc acagtttcga cgtgtccttc cagcagtcga gcaccgccaa gtcggccacc    600

tggacgtatt ccactgaact gaagaaactc tactgccaaa ttgcaaagac atgccccatc    660

cagatcaagg tgatgacccc acctcctcag ggagctgtta tccgcgccat gcctgtctac    720

aaaaaagctg agcacgtcac ggaggtggtg aagcggtgcc ccaaccatga gctgagccgt    780

gaattcaacg agggacagat tgcccctcct agtcatttga ttcgagtaga ggggaacagc    840

catgcccagt atgtagaaga tcccatcaca ggaagacaga gtgtgctggt accttatgag    900

ccaccccagg ttggcactga attcacgaca gtcttgtaca atttcatgtg taacagcagt    960

tgtgttggag ggatgaaccg ccgtccaatt ttaatcattg ttactctgga aaccagagat   1020

gggcaagtcc tgggccgacg ctgctttgag gcccggatct gtgcttgccc aggaagagac   1080

aggaaggcgg atgaagatag catcagaaag cagcaagttt cggacagtac aaagaacggt   1140

gatggtacga agcgcccgtt tcgtcagaac acacatggta tccagatgac atccatcaag   1200

aaacgaagat ccccagatga tgaactgtta tacttaccag tgaggggccg tgagacttat   1260

gaaatgctgt tgaagatcaa agagtccctg gaactcatgc agtaccttcc tcagcacaca   1320

attgaaacgt acaggcaaca gcaacagcag cagcaccagc acttacttca gaaacatctc   1380

ctttcagcct gcttcaggaa tgagcttgtg gagccccgga gagaaactcc aaaacaatct   1440

gacgtcttct ttagacattc caagccccca aaccgatcag tgtacccata gagccctatc   1500

tctatatttt aagtgtgtgt gttgtatttc catgtgtata tgtgagtgtg tgtgtgtgta   1560

tgtgtgtgcg tgtgtatcta gccctcataa acaggacttg aagacacttt ggctcagaga   1620

cccaactgct caaaggcaca aagccactag tgagagaatc ttttgaaggg actcaaacct   1680

ttacaagaaa ggatgttttc tgcagatttt gtatccttag accggccatt ggtgggtgag   1740
```

-continued

```
gaaccactgt gtttgtctgt gagctttctg ttgtttcctg ggagggaggg gtcaggtggg   1800
gaaaggggca ttaagatgtt tattggaacc cttttctgtc ttcttctgtt gtttttctaa   1860
aattcacagg gaagcttttg agcaggtctc aaacttaaga tgtcttttta agaaaaggag   1920
aaaaaagttg ttattgtctg tgcataagta agttgtaggt gactgagaga ctcagtcaga   1980
ccctttttaat gctggtcatg taataatatt gcaagtagta agaaacgaag gtgtcaagtg   2040
tactgctggg cagcgaggtg atcattacca aaagtaatca actttgtggg tggagagttc   2100
tttgtgagaa cttgcattat ttgtgtcctc ccctcatgtg taggtagaac atttcttaat   2160
gctgtgtacc tgcctctgcc actgtatgtt ggcatctgtt atgctaaagt ttttcttgta   2220
catgaaaccc tggaagacct actacaaaaa aactgttgtt tggcccccat agcaggtgaa   2280
ctcattttgt gcttttaata gaaagacaaa tccaccccag taatattgcc cttacgtagt   2340
tgtttaccat tattcaaagc tcaaaataga atttgaagcc ctctcacaaa atctgtgatt   2400
aatttgctta attagagctt ctatccctca agcctaccta ccataaaacc agccatatta   2460
ctgatactgt tcagtgcatt tagccaggag acttacgttt tgagtaagtg agatccaagc   2520
agacgtgtta aaatcagcac tcctggactg gaaattaaag attgaaaggg tagactactt   2580
ttcttttttt tactcaaaag tttagagaat ctctgtttct ttccatttta aaaacatatt   2640
ttaagataat agcataaaga ctttaaaaat gttcctcccc tccatcttcc cacacccagt   2700
caccagcact gtattttctg tcaccaagac aatgatttct tgttattgag gctgttgctt   2760
ttgtggatgt gtgattttaa ttttcaataa acttttgcat cttggtttaa aagaaa       2816
```

<210> SEQ ID NO 65
<211> LENGTH: 2816
<212> TYPE: DNA
<213> ORGANISM: human

<400> SEQUENCE: 65

```
tcgttgatat caaagacagt tgaaggaaat gaattttgaa acttcacggt gtgccaccct     60
acagtactgc cctgaccctt acatccagcg tttcgtagaa acccagctca tttctcttgg    120
aaagaaagtt attaccgatc caccatgtcc cagagcacac agacaaatga attcctcagt    180
ccagaggttt tccagcatat ctgggatttt ctggaacagc ctatatgttc agttcagccc    240
attgacttga actttgtgga tgaaccatca gaagatggtg cgacaaacaa gattgagatt    300
agcatggact gtatccgcat gcaggactcg gacctgagtg accccatgtg gccacagtac    360
acgaacctgg ggctcctgaa cagcatggac cagcagattc agaacggctc ctcgtccacc    420
agtccctata acacagacca cgcgcagaac agcgtcacgg cgccctcgcc ctacgcacag    480
cccagctcca ccttcgatgc tctctctcca tcacccgcca tcccctccaa caccgactac    540
ccaggcccgc acagtttcga cgtgtccttc cagcagtcga gcaccgccaa gtcggccacc    600
tggacgtatt ccactgaact gaagaaactc tactgccaaa ttgcaaagac atgccccatc    660
cagatcaagg tgatgacccc acctcctcag ggagctgtta tccgcgccat gcctgtctac    720
aaaaaagctg agcacgtcac ggaggtggtg aagcggtgcc ccaaccatga gctgagccgt    780
gaattcaacg agggacagat tgcccctcct agtcatttga ttcgagtaga ggggaacagc    840
catgcccagt atgtagaaga tcccatcaca ggaagacaga gtgtgctggt accttatgag    900
ccaccccagg ttggcactga attcacgaca gtcttgtaca atttcatgtg taacagcagt    960
tgtgttggag ggatgaaccg ccgtccaatt ttaatcattg ttactctgga aaccagagat   1020
```

-continued

```
gggcaagtcc tgggccgacg ctgctttgag gcccggatct gtgcttgccc aggaagagac   1080

aggaaggcgg atgaagatag catcagaaag cagcaagttt cggacagtac aaagaacggt   1140

gatggtacga agcgcccgtt tcgtcagaac acacatggta tccagatgac atccatcaag   1200

aaacgaagat ccccagatga tgaactgtta tacttaccag tgaggggccg tgagacttat   1260

gaaatgctgt tgaagatcaa agagtccctg gaactcatgc agtaccttcc tcagcacaca   1320

attgaaacgt acaggcaaca gcaacagcag cagcaccagc acttacttca gaaacatctc   1380

ctttcagcct gcttcaggaa tgagcttgtg gagccccgga gagaaactcc aaaacaatct   1440

gacgtcttct ttagacattc caagccccca aaccgatcag tgtacccata gagccctatc   1500

tctatatttt aagtgtgtgt gttgtatttc catgtgtata tgtgagtgtg tgtgtgtgta   1560

tgtgtgtgcg tgtgtatcta gccctcataa acaggacttg aagacacttt ggctcagaga   1620

cccaactgct caaaggcaca aagccactag tgagagaatc ttttgaaggg actcaaacct   1680

ttacaagaaa ggatgttttc tgcagatttt gtatccttag accggccatt ggtgggtgag   1740

gaaccactgt gtttgtctgt gagctttctg ttgtttcctg ggagggaggg gtcaggtggg   1800

gaaaggggca ttaagatgtt tattggaacc cttttctgtc ttcttctgtt gtttttctaa   1860

aattcacagg gaagcttttg agcaggtctc aaacttaaga tgtcttttta agaaaaggag   1920

aaaaaagttg ttattgtctg tgcataagta agttgtaggt gactgagaga ctcagtcaga   1980

ccctttttaat gctggtcatg taataatatt gcaagtagta agaaacgaag gtgtcaagtg   2040

tactgctggg cagcgaggtg atcattacca aaagtaatca actttgtggg tggagagttc   2100

tttgtgagaa cttgcattat ttgtgtcctc ccctcatgtg taggtagaac atttcttaat   2160

gctgtgtacc tgcctctgcc actgtatgtt ggcatctgtt atgctaaagt ttttcttgta   2220

catgaaaccc tggaagacct actacaaaaa aactgttgtt tggcccccat agcaggtgaa   2280

ctcattttgt gcttttaata gaaagacaaa tccaccccag taatattgcc cttacgtagt   2340

tgtttaccat tattcaaagc tcaaaataga atttgaagcc ctctcacaaa atctgtgatt   2400

aatttgctta attagagctt ctatccctca agcctaccta ccataaaacc agccatatta   2460

ctgatactgt tcagtgcatt tagccaggag acttacgttt tgagtaagtg agatccaagc   2520

agacgtgtta aaatcagcac tcctggactg gaaattaaag attgaaaggg tagactactt   2580

ttcttttttt tactcaaaag tttagagaat ctctgtttct ttccatttta aaaacatatt   2640

ttaagataat agcataaaga ctttaaaaat gttcctcccc tccatcttcc cacacccagt   2700

caccagcact gtattttctg tcaccaagac aatgatttct tgttattgag gctgttgctt   2760

ttgtggatgt gtgattttaa ttttcaataa acttttgcat cttggtttaa aagaaa       2816
```

<210> SEQ ID NO 66
<211> LENGTH: 5838
<212> TYPE: DNA
<213> ORGANISM: human

<400> SEQUENCE: 66

```
ccgggcaggt ggctcatgct cgggagcgtg gttgagcggc tggcgcggtt gtcctggagc     60

aggggcgcag gaattctgat gtgaaactaa cagtctgtga gccctggaac ctccgctcag    120

agaagatgaa ggatatcgac ataggaaaag agtatatcat ccccagtcct gggtatagaa    180

gtgtgaggga gagaaccagc acttctggga cgcacagaga ccgtgaagat tccaagttca    240

ggagaactcg accgttggaa tgccaagatg ccttggaaac agcagcccga gccgagggcc    300

tctctcttga tgcctccatg cattctcagc tcagaatcct ggatgaggag catcccaagg    360
```

-continued

```
gaaagtacca tcatggcttg agtgctctga agcccatccg gactacttcc aaacaccagc    420
acccagtgga caatgctggg ctttttttcct gtatgacttt ttcgtggctt tcttctctgg    480
cccgtgtggc ccacaagaag gggggagctct caatggaaga cgtgtggtct ctgtccaagc    540
acgagtcttc tgacgtgaac tgcagaagac tagagagact gtggcaagaa gagctgaatg    600
aagttgggcc agacgctgct tccctgcgaa gggttgtgtg gatcttctgc cgcaccaggc    660
tcatcctgtc catcgtgtgc ctgatgatca cgcagctggc tggcttcagt ggaccagcct    720
tcatggtgaa acacctcttg gagtataccc aggcaacaga gtctaacctg cagtacagct    780
tgttgttagt gctgggcctc ctcctgacgg aaatcgtgcg gtcttggtcg cttgcactga    840
cttgggcatt gaattaccga accggtgtcc gcttgcgggg ggccatccta accatggcat    900
ttaagaagat ccttaagtta aagaacatta aagagaaatc cctgggtgag ctcatcaaca    960
tttgctccaa cgatgggcag agaatgtttg aggcagcagc cgttggcagc ctgctggctg   1020
gaggacccgt tgttgccatc ttaggcatga tttataatgt aattattctg ggaccaacag   1080
gcttcctggg atcagctgtt tttatcctct tttacccagc aatgatgttt gcatcacggc   1140
tcacagcata tttcaggaga aaatgcgtgg ccgccacgga tgaacgtgtc cagaagatga   1200
atgaagttct tacttacatt aaatttatca aaatgtatgc ctgggtcaaa gcattttctc   1260
agagtgttca aaaaatccgc gaggaggagc gtcggatatt ggaaaaagcc gggtacttcc   1320
agggtatcac tgtgggtgtg gctcccattg tggtggtgat tgccagcgtg gtgaccttct   1380
ctgttcatat gaccctgggc ttcgatctga cagcagcaca ggctttcaca gtggtgacag   1440
tcttcaattc catgactttt gctttgaaag taacaccgtt ttcagtaaag tccctctcag   1500
aagcctcagt ggctgttgac agatttaaga gtttgtttct aatggaagag gttcacatga   1560
taaagaacaa accagccagt cctcacatca agatagagat gaaaaatgcc accttggcat   1620
gggactcctc ccactccagt atccagaact cgcccaagct gacccccaaa atgaaaaaag   1680
acaagagggc ttccaggggc aagaaagaga aggtgaggca gctgcagcgc actgagcatc   1740
aggcggtgct ggcagagcag aaaggccacc tcctcctgga cagtgacgag cggcccagtc   1800
ccgaagagga agaaggcaag cacatccacc tgggccacct gcgcttacag aggacactgc   1860
acagcatcga tctggagatc caagagggta aactggttgg aatctgcggc agtgtgggaa   1920
gtggaaaaac ctctctcatt tcagccattt taggccagat gacgcttcta gagggcagca   1980
ttgcaatcag tggaaccttc gcttatgtgg cccagcaggc ctggatcctc aatgctactc   2040
tgagagacaa catcctgttt gggaaggaat atgatgaaga aagatacaac tctgtgctga   2100
acagctgctg cctgaggcct gacctggcca ttcttcccag cagcgacctg acggagattg   2160
gagagcgagg agccaacctg agcggtgggc agcgccagag gatcagcctt gcccgggcct   2220
tgtatagtga caggagcatc tacatcctgg acgacccccct cagtgcctta gatgcccatg   2280
tgggcaacca catcttcaat agtgctatcc ggaaacatct caagtccaag acagttctgt   2340
ttgttaccca ccagttacag tacctggttg actgtgatga agtgatcttc atgaaagagg   2400
gctgtattac ggaaagaggc acccatgagg aactgatgaa tttaaatggt gactatgcta   2460
ccatttttaa taacctgttg ctgggagaga caccgccagt tgagatcaat tcaaaaaagg   2520
aaaccagtgg ttcacagaag aagtcacaag acaagggtcc taaaacagga tcagtaaaga   2580
aggaaaaagc agtaaagcca gaggaagggc agcttgtgca gctggaagag aaagggcagg   2640
gttcagtgcc ctggtcagta tatggtgtct acatccaggc tgctgggggc cccttggcat   2700
```

-continued

```
tcctggttat tatggccctt ttcatgctga atgtaggcag caccgccttc agcacctggt   2760
ggttgagtta ctggatcaag caaggaagcg ggaacaccac tgtgactcga gggaacgaga   2820
cctcggtgag tgacagcatg aaggacaatc ctcatatgca gtactatgcc agcatctacg   2880
ccctctccat ggcagtcatg ctgatcctga aagccattcg aggagttgtc tttgtcaagg   2940
gcacgctgcg agcttcctcc cggctgcatg acgagctttt ccgaaggatc cttcgaagcc   3000
ctatgaagtt ttttgacacg acccccacag ggaggattct caacaggttt tccaaagaca   3060
tggatgaagt tgacgtgcgg ctgccgttcc aggccgagat gttcatccag aacgttatcc   3120
tggtgttctt ctgtgtggga atgatcgcag gagtcttccc gtggttcctt gtggcagtgg   3180
ggccccttgt catcctcttt tcagtcctgc acattgtctc cagggtcctg attcgggagc   3240
tgaagcgtct ggacaatatc acgcagtcac ctttcctctc ccacatcacg tccagcatac   3300
agggccttgc caccatccac gcctacaata aagggcagga gtttctgcac agataccagg   3360
agctgctgga tgacaaccaa gctccttttt ttttgtttac gtgtgcgatg cggtggctgg   3420
ctgtgcggct ggacctcatc agcatcgccc tcatcaccac cacggggctg atgatcgttc   3480
ttatgcacgg gcagattccc ccagcctatg cgggtctcgc catctcttat gctgtccagt   3540
taacggggct gttccagttt acggtcagac tggcatctga gacagaagct cgattcacct   3600
cggtggagag gatcaatcac tacattaaga ctctgtcctt ggaagcacct gccagaatta   3660
agaacaaggc tccctcccct gactggcccc aggagggaga ggtgaccttt gagaacgcag   3720
agatgaggta ccgagaaaac ctccctcttg tcctaaagaa agtatccttc acgatcaaac   3780
ctaaagagaa gattggcatt gtggggcgga caggatcagg gaagtcctcg ctggggatgg   3840
ccctcttccg tctggtggag ttatctggag gctgcatcaa gattgatgga gtgagaatca   3900
gtgatattgg ccttgccgac ctccgaagca aactctctat cattcctcaa gagccggtgc   3960
tgttcagtgg cactgtcaga tcaaatttgg accccttcaa ccagtacact gaagaccaga   4020
tttgggatgc cctggagagg acacacatga aagaatgtat tgctcagcta cctctgaaac   4080
ttgaatctga agtgatggag aatggggata acttctcagt gggggaacgg cagctcttgt   4140
gcatagctag agccctgctc cgccactgta agattctgat tttagatgaa gccacagctg   4200
ccatggacac agagacagac ttattgattc aagagaccat ccgagaagca tttgcagact   4260
gtaccatgct gaccattgcc catcgcctgc acacggttct aggctccgat aggattatgg   4320
tgctggccca gggacaggtg gtggagtttg acaccccatc ggtccttctg tccaacgaca   4380
gttcccgatt ctatgccatg tttgctgctg cagagaacaa ggtcgctgtc aagggctgac   4440
tcctccctgt tgacgaagtc tcttttcttt agagcattgc cattccctgc ctggggcggg   4500
cccctcatcg cgtcctccta ccgaaacctt gcctttctcg attttatctt tcgcacagca   4560
gttccggatt ggcttgtgtg tttcactttt agggagagtc atattttgat tattgtattt   4620
attccatatt catgtaaaca aaatttagtt tttgttctta attgcactct aaaaggttca   4680
gggaaccgtt attataattg tatcagaggc ctataatgaa gctttatacg tgtagctata   4740
tctatatata attctgtaca tagcctatat ttacagtgaa aatgtaagct gtttatttta   4800
tattaaaata agcactgtgc taataacagt gcatattcct ttctatcatt tttgtacagt   4860
ttgctgtact agagatctgg ttttgctatt agactgtagg aagagtagca tttcattctt   4920
ctctagctgg tggtttcacg gtgccaggtt ttctgggtgt ccaaaggaag acgtgtggca   4980
atagtgggcc ctccgacagc cccctctgcc gcctccccac agccgctcca ggggtggctg   5040
gagacgggtg ggcggctgga gaccatgcag agcgccgtga gttctcaggg ctcctgcctt   5100
```

```
ctgtcctggt gtcacttact gtttctgtca ggagagcagc ggggcgaagc ccaggcccct   5160
tttcactccc tccatcaaga atggggatca cagagacatt cctccgagcc ggggagtttc   5220
tttcctgcct tcttcttttt gctgttgttt ctaaacaaga atcagtctat ccacagagag   5280
tcccactgcc tcaggttcct atggctggcc actgcacaga gctctccagc tccaagacct   5340
gttggttcca agccctggag ccaactgctg ctttttgagg tggcactttt tcatttgcct   5400
attcccacac ctccacagtt cagtggcagg gctcaggatt tcgtgggtct gttttccttt   5460
ctcaccgcag tcgtcgcaca gtctctctct ctctctcccc tcaaagtctg caactttaag   5520
cagctcttgc taatcagtgt ctcacactgg cgtagaagtt tttgtactgt aaagagacct   5580
acctcaggtt gctggttgct gtgtggtttg gtgtgttccc gcaaaccccc tttgtgctgt   5640
ggggctggta gctcaggtgg gcgtggtcac tgctgtcatc agttgaatgg tcagcgttgc   5700
atgtcgtgac caactagaca ttctgtcgcc ttagcatgtt tgctgaacac cttgtggaag   5760
caaaaatctg aaaatgtgaa taaaattatt ttggattttg taaaaaaaaa aaaaaaaaaa   5820
aaaaaaaaaa aaaaaaaa                                                 5838
```

<210> SEQ ID NO 67
<211> LENGTH: 6841
<212> TYPE: DNA
<213> ORGANISM: human

<400> SEQUENCE: 67

```
gccggagggc gcccgagggg ccccgggccg cggcgctcag ggcccgggcg gccggcggcg     60
gccccggggc tggggggagt ccagcccgga tattgagtgc agccattgag aaaagccaaa    120
ctcttgtgtg tgcgcgtctc gatagccccc aagatggccg ccaatgtggg atcgatgttt    180
caatattgga agcgatttga tctacggcga ctccagaagg agcttaattc cgtcgcttct    240
gagctgtctg cacggcagga ggagagtgaa cattctcata aacatttaat tgaactccgc    300
cgggaattta agaaaaatgt acctgaggaa atcagagaga tggtggctcc tgtattaaaa    360
agcttccaag ccgaggtggt ggcccttagt aagagaagtc aggaggcgga ggctgctttt    420
ctgagtgttt acaagcaatt aattgaagca ccagaccccg tgcctgtgtt tgaggcggca    480
cgcagcctag acgacagact gcagcccccc agctttgacc ccagtgggca gccccggcga    540
gacctccaca cttcgtggaa gaggaacccc gagctcctca gccccaaaga gcagagagag    600
gggacgtcgc ctgccgggcc cacgctgacc gagggaagcc gcctcccagg cattcccggg    660
aaagccctcc tgacagaaac cttgctgcag agaaatgagg cggaaaaaca aaagggcctt    720
caagaagtac agatcacttt ggcggccaga ctgggggagg cagaggagaa aatcaaagtc    780
ctacattcag cgctaaaggc tacgcaggca gagctgctag agctgcggcg gaagtacgac    840
gaggaggcag catccaaggc agatgaagtc ggcctgatca tgaccaacct ggagaaagct    900
aatcagcgag ctgaggctgc ccagcgggag gtggaaagtc tccgggaaca gctggcctct    960
gtcaacagct ccatccgcct ggcttgctgc tctccccagg ggcccagtgg ggataaggtg   1020
aacttcactc tgtgctcggg ccctcggctg gaggccgcgc tggcctccaa ggacagggag   1080
atcctgcggc tgctgaagga cgtgcagcac ctccagagct cactgcagga gctggaggag   1140
gcatccgcca accagatcgc cgacctggag cggcagctca cggccaagtc cgaggccata   1200
gaaaagctgg aagagaagct ccaggcccag tctgactatg aggaaattaa aacggagctg   1260
agcatcctga aagccatgaa gctggcctcc agcacctgca gcctccccca gggcatggcc   1320
```

-continued

```
aagcctgaag actcactgct tattgcaaag gaggccttct tccccacgca gaaattcctt   1380
ctggagaagc ccagcctcct ggccagccct gaggaagacc catcagagga cgattccatc   1440
aaggattcac tgggcacgga gcagtcctac ccctcccctc agcagctccc acctccacca   1500
gggccagaag accccctgtc tcccagcccc gggcagcccc tgctgggccc cagcttgggg   1560
cctgacggca ctcggacttt ctcgctgtcc cccttcccca gcctggcatc aggggagaga   1620
ctgatgatgc ccccagccgc cttcaaggga gaggcgggcg gcctgctggt gttcccccca   1680
gccttctatg gcgccaagcc ccccacagcc cctgccaccc cggcccctgg ccctgagcca   1740
ctgggcggtc ctgagcccgc ggatggtggt gggggcggag cggcggggcc cggggcagag   1800
gaggagcagc tggacacggc agagatcgcc ttccaggtga aggagcagct gctgaaacac   1860
aacatcgggc agcgggtgtt tgggcattac gtgctggggc tgtcgcaggg ctcggtcagc   1920
gagatcctag cccggcccaa gccctggcgc aagctcacgg tgaagggcaa ggagcccttc   1980
atcaagatga agcagttcct gtcggatgag cagaatgtac tggcgctcag gaccatccaa   2040
gtgcggcagc gaggcagcat caccccgaga atccgcacgc ctgagacagg ctcagacgac   2100
gccatcaaga gcattctaga gcaggccaag aaggagatcg agtcgcagaa gggcggcgag   2160
cccaagacct cggtggcccc gctgagcatc gccaacggca cgacccccgc cagcacctcg   2220
gaggacgcca tcaagagcat cctggagcag gcacgccgtg agatgcaggc gcaacagcag   2280
gcgctgctgg agatggaggt ggcgcccagg ggccgctcgg tgccccccctc gcccccggag   2340
cggccatcac tggccaccgc gagccagaac ggggccccgg ccttggtgaa gcaggaggag   2400
ggcagcgggg gccccgcgca ggcgccgctc ccggtcctgt cccccgccgc cttcgtgcag   2460
agcatcatcc gcaaggtcaa gtccgagatc ggcgacgccg gctacttcga ccaccactgg   2520
gcctccgacc gcggcctgct cagccgcccc tacgcctccg tgtcgccctc gctgtcctcc   2580
tcctcctcct ctggctactc tggccagccc aacggccgcg cctggccccg cggggacgag   2640
gcccctgtgc cccccgagga cgaggcggcg gcaggggcgg aggacgaacc ccccaggacg   2700
ggcgagctca aggctgaggg cgcgacggcc gaggcgggcg cgcggctgcc ctactacccg   2760
gcctacgtgc cgcgcaccct gaagcccacc gtgccgccgc tgacccccga gcagtacgag   2820
ctgtacatgt accgtgaggt agacacgctg gagctcaccc gccaggtcaa ggagaagctg   2880
gccaagaacg gcatctgcca gaggatcttc ggggagaagg tgctgggcct gtcacagggc   2940
agcgtgagcg acatgctgtc ccggccgaag ccatggagca agctgacgca gaaggggcgg   3000
gagcccttca tccgcatgca gctgtggctc tctgaccagc tcggccaggc agtgggccag   3060
cagcctggtg cctcccaggc cagtcccaca gaaccaaggt cctcaccatc cccacccccc   3120
agccccacag agcctgagaa gagctcccag gagccgttga gcctgtccct ggagagcagc   3180
aaggagaacc agcagccaga gggccgctcc agctcctcgt tgagcgggaa gatgtactca   3240
ggcagccagg ccccaggggg catccaggag atcgtggcca tgtcccccga gctggacacg   3300
tactccatca ccaagagggt gaaggaggtc ctcacagaca acaatctagg gcagcggctg   3360
tttggggaaa gcatcctggg tctgacacag ggctccgtgt ctgacctgct gtcccggccc   3420
aaaccctggc acaagctgag cctgaagggg cgggagcctt ttgtccgcat gcagctgtgg   3480
ctcaatgacc cccataacgt ggagaagctg agggatatga agaagctgga gaagaaagcc   3540
tacctgaaac gtcgctatgg cctcatcagc accggctcag acagtgagtc cccggccacc   3600
cgctcagagt gccccagccc ctgcctgcag ccccaggacc tgagcctcct gcagatcaag   3660
aagccccggg tggtgctggc acccgaggag aaggaggcac tgcggaaggc ctatcagctg   3720
```

-continued

```
gaaccctacc cctcgcagca gaccatcgag ctcctctcct tccagctcaa cctcaagacc   3780
aacaccgtca tcaactggtt ccacaactac aggtcccgga tgcgccggga gatgttggtg   3840
gaggggaccc aggatgagcc agaccttgat ccaagcgggg gtcctggaat cctaccgcca   3900
ggccactccc acccagaccc caccccgcag agccctgact ctgagactga ggaccagaag   3960
ccaaccgtga aggaactgga gcttcaggag ggccctgagg agaacagcac acccctgacc   4020
acccaggaca aggcccaagt gaggatcaag caggaacaga tggaggagga tgctgaggaa   4080
gaggcaggca gccagcccca ggactcaggg gagctggaca aggccaagg tccccccaaa    4140
gaggagcatc ccgaccctcc gggtaatgat ggactcccaa aagtggctcc cgggcccctc   4200
cttccaggtg gatccacccc agactgtccc tcacttcatc cccaacagga gagtgaggcc   4260
ggggagcgac ttcacccgga ccctttaagt tttaagtcag cctcagagtc ctcacgctgc   4320
agcctggagg tgtcactgaa ctcgccctcg gccgcctcct caccaggcct catgatgtct   4380
gtgtcacctg tcccctcctc ctcagctccc atctccccat ccccacctgg cgccccccct   4440
gccaaagtgc cgagtgccag ccccactgct gacatggctg gagccttgca ccccagtgcc   4500
aaggtgaacc ccaacttgca gcggcggcat gagaagatgg ccaatctgaa caacatcatt   4560
taccgactag agcgggctgc caatcgggag gaggccctgg agtgggagtt ctgaaggcag   4620
ggtgaggggg caagggacat accctggtaa ctaccttcct tctcgcactt actctcctca   4680
acaggatggg gtaagggagg gaggaactca accatcaaaa tgtggacagc aatgttatgc   4740
cgtttacgtt ttttgttgta atcctagttc tatgaagctg tgtgagcagg tgggtcaaat   4800
gccattgcct ccacttttct gcaccccccct gctcctcttc accctgaccc ctctgcagga  4860
ggcagaagca aaatggcacc acatattcac ctgaaaactc caaactcttt tagaaaaata   4920
aataaatatt tatagacctc ttttagatat tttaataaag gatcctttgg aatttatccc   4980
agctgatgct gttttgatat tacagagagt tataaaatca ggatgctgtc acaactgttg   5040
cgaagtatac actgaagttg tgtcgttttt gccactagat gagattaaaa gaagacaatt   5100
attcaaagcc atcacaaaac actataagac tgaccaaaat ttagataacc tttgaaccac   5160
gatttttttc cacatctgtc tgtgagacac agcgcaatgc tactgccctt ccagaaactg   5220
tgctaaaaag agaaagtcca aaagactcta aacaaaaacc tcgacgccgt tgaggatgtg   5280
tttcattctg gtggtctgtt ttgcaagctt gataacagaa tgtccgtgcc attgtaaatg   5340
ttgtagagat gtgggccgtg gcccaaccgt cctatatgag atgtagcatg gtacagaaca   5400
aactgcttac acaggtctca ctagttagaa acctgtgggc catggaggtc agacatccat   5460
cttgtccatc tataggcaag aagtgtttcc agatcctttg gaaaggtggg catggggcag   5520
gtgcttggag agtggcgttt gagccagagc gaccccattt cccgtgtgaa ccataggcac   5580
aacccaggaa gtttccccac ttgtaggagt gtgggtattc cagagcaaga ctgtggccac   5640
catcttcccc tcttggtgtt ttccgaaagt gacagtgttg gtcatcccat gaccactgaa   5700
gcttagtaac cagcgccaaa aagtagattc atcaaactag agaccccagc tccccttctc   5760
gccatcttct ttctcaagtt gaccgtggtg ctgtttctgg aaggcatctg caactccaag   5820
tccatgcaga actctggaag gccaagttca tcgcagcatg ttcaccatat cccagcctcc   5880
aaatctatcc tcctaccttc caacgcatga cctgttgggg agcagagact taacccccaa   5940
ctcagaggaa cccttcctcc agcgtctttg gcatggtttc tagggtgaga gttcccaatt   5ok000
tggatagaac ggccaccata ttggttactg aatctctctc ccttgttttt attacgtttc   6060
```

-continued

```
cttttcaaa ctgtccatgg gaaggctgaa ttgagtgact ccccagaatg aagatgagaa   6120

ggtgaatata atcaatgcca atgtaatgcc agcgggtgag atggccgatg gaggtttcaa   6180

agatgtagct agcattttga aaccatatgg gcaaaacccg gcaaccagaa ggggacagat   6240

aaggaccgtt ccagaaatcc caactctcac acccagccca ggctgcagtc tccacaccaa   6300

acagtcaaca aaacacaaac cctgaaggaa aaccttttcc atacacccag gctatgcatt   6360

gaagagtttt ccactgtata catttttatc cagatgaagg tatttttata ttttgacaat   6420

aggaaacagt gaccattttc agagtaatca aatctggaac aaatgaaaca tcttttagcc   6480

accaccaccc tgttgcaatt aagacaaccg tgggggaaca caccactttt tactgttgaa   6540

accaacacaa cgttgaaatc caggcttata cgcagactcc gattcctaga gaactaaatt   6600

tggctttagt gtgacgggat ttgattaagc acttagtata gtcttttgaa cacggaaatc   6660

ctgttgtact taaagctagc ggacccgtga acaactttgt caggttcacg tcctataacg   6720

gttaaaaaac acacacacac atacacaaac cgtttctatg agagattgat gaactttgtt   6780

taaaatttta aaaaaaggaa cacgttctgt aaacgagtcg ctaaatacag aattgtataa   6840

t                                                                   6841
```

<210> SEQ ID NO 68
<211> LENGTH: 1181
<212> TYPE: DNA
<213> ORGANISM: human

<400> SEQUENCE: 68

```
ggcacgaggc ccgggccccc caaagtcccg gccgggccga gggtcggcgg ccgccggcgg     60

gccgggcccg cgcacagcgc ccgcatgtac aacatgatgg agacggagct gaagccgccg    120

ggcccgcagc aaacttcggg gggcggcggc ggcaactcca ccgcggcggc ggccggcggc    180

aaccagaaaa acagcccgga ccgcgtcaag cggcccatga atgccttcat ggtgtggtcc    240

cgcgggcagc ggcgcaagat ggcccaggag aaccccaaga tgcacaactc ggagatcagc    300

aagcgcctgg gcgccgagtg gaaacttttg tcggagacgg agaagcggcc gttcatcgac    360

gaggctaagc ggctgcgagc gctgcacatg aaggagcacc cggattataa ataccggccc    420

cggcggaaaa ccaagacgct catgaagaag gataagtaca cgctgcccgg cgggctgctg    480

gcccccggcg gcaatagcat ggcgagcggg gtcggggtgg gcgccggcct gggcgcgggc    540

gtgaaccagc gcatggacag ttacgcgcac atgaacggct ggagcaacgg cagctacagc    600

atgatgcagg accagctggg ctacccgcag cacccgggcc tcaatgcgca cggcgcagcg    660

cagatgcagc ccatgcaccg ctacgacgtg agcgccctgc agtacaactc catgaccagc    720

tcgcagacct acatgaacgg ctcgcccacc tacagcatgt cctactcgca gcagggcacc    780

cctggcatgg ctcttggctc catgggttcg gtggtcaagt ccgaggccag ctccagcccc    840

cctgtggtta cctcttcctc ccactccagg gcgccctgcc aggccgggga cctccgggac    900

atgatcagca tgtatctccc cggcgccgag gtgccggaac ccgccgcccc cagcagactt    960

cacatgtccc agcactacca gagcggcccg gtgcccggca cggccattaa cggcacactg   1020

cccctctcac acatgtgagg gccggacagc gaactggagg ggggagaaat tttcaaagaa   1080

aaacgaggga aatgggaggg gtgcaaaaga ggagagtaag aaacagcatg gagaaaaccc   1140

ggtacgctca aaaaaaaaaa aaaaaaaaaa aaaaaaaaaa a                       1181
```

<210> SEQ ID NO 69
<211> LENGTH: 4755

-continued

<212> TYPE: DNA
<213> ORGANISM: human

<400> SEQUENCE: 69

```
gctgctctcg ttcgcttggc tcagctcagc tcagctcagc gcagctccgc ggccgccaag     60
ccgaggcggg cacggtctcc gagtcgcgga cgccagctcc gagctccctc tctccgccgc    120
gcctccgcca ggtcgcgcct tcgtcgggac cacttcgggc aggagtcgcg tggcgaaggc    180
ctgcggccgc ggcacaaagt tgggggccgc gaagatgagg ctgtccccgg cgcccctgaa    240
gctgagccgg actccggcac tgctggccct ggcgctgccc ctggccgcgg cgctggcctt    300
ctccgacgag accctggaca aagtgcccaa gtcagagggc tactgcagcc gtatcctgcg    360
cgcccagggc acgcggcgcg agggctacac cgagttcagc ctccgcgtgg agggcgaccc    420
cgacttctac aagccgggaa ccagctaccg cgtaacactt tcagctgctc ctccctccta    480
cttcagagga ttcacattaa ttgccctcag agagaacaga gagggtgata aggaagaaga    540
ccatgctggg accttccaga tcatagacga agaagaaact cagtttatga gcaattgccc    600
tgttgcagtc actgaaagca ctccacggag gaggacccgg atccaggtgt tttggatagc    660
accaccagcg ggaacaggct gcgtgattct gaaggccagc atcgtacaaa aacgcattat    720
ttattttcaa gatgagggct ctctgaccaa gaaactttgt gaacaagatt ccacatttga    780
tggggtgact gacaaaccca tcttagactg ctgtgcctgc ggaactgcca agtacagact    840
cacattttat gggaattggt ccgagaagac acacccaaag gattaccctc gtcgggccaa    900
ccactggtct gcgatcatcg gaggatccca ctccaagaat tatgtactgt gggaatatgg    960
aggatatgcc agcgaaggcg tcaaacaagt tgcagaattg ggctcacccg tgaaaatgga   1020
ggaagaaatt cgacaacaga gtgatgaggt cctcaccgtc atcaaagcca aagcccagtg   1080
gccagcctgg cagcctctca acgtgagagc agcaccttca gctgaatttt ccgtggacag   1140
aacgcgccat ttaatgtcct tcctgaccat gatgggccct agtcccgact ggaacgtagg   1200
cttatctgca gaagatctgt gcaccaagga atgtggctgg gtccagaagg tggtgcaaga   1260
cctgattccc tgggacgctg gcaccgacag cggggtgacc tatgagtcac ccaacaaacc   1320
caccattccc caggagaaaa tccggcccct gaccagcctg gaccatcctc agagtccttt   1380
ctatgaccca gagggtgggt ccatcactca agtagccaga gttgtcatcg agagaatcgc   1440
acggaagggt gaacaatgca atattgtacc tgacaatgtc gatgatattg tagctgacct   1500
ggctccagaa gagaaagatg aagatgacac ccctgaaacc tgcatctact ccaactggtc   1560
cccatggtcc gcctgcagct cctccacctg tgacaaaggc aagaggatgc gacagcgcat   1620
gctgaaagca cagctggacc tcagcgtccc ctgccctgac acccaggact tccagccctg   1680
catgggccct ggctgcagtg acgaagacgg ccccacctgc accatgtccg agtggatcac   1740
ctggtcgccc tgcagcatct cctgcggcat gggcatgagg tcccgggaga ggtatgtgaa   1800
gcagttcccg gaggacggct ccgtgtgcac gctgcccact gaggaaacgg agaagtgcac   1860
ggtcaacgag gagtgctctc ccagcagctg cctgatgacc gagtggggcg agtgggacga   1920
gtacagcgcc acctgcggca tgggcatgaa gaagcggcac cgcatgatca agatgaaccc   1980
cgcagatggc tccatgtgca aagccgagac atcacaggca gagaagcgca tgatgccaga   2040
gtgccacacc atcccatgct tgctgtcccc atggtccgag tggagtgact gcagcgtgac   2100
ctgcgggaag ggcatgcgaa cccgacagcg gatgctcaag tctctggcag aacttggaga   2160
ctgcaatgag gatctggagc aggtggagaa gtgcatgctc cctgaatgcc ccattgactg   2220
```

-continued

```
tgagctcacc gagtggtccc agtggtcgga atgtaacaag tcatgtggga aaggccacgt   2280
gattcgaacc cggatgatcc aaatggagcc tcagtttgga ggtgcaccct gcccagagac   2340
tgtgcagcga aaaaagtgcc gcatccgaaa atgccttcga aatccatcca tccaaaagct   2400
acgctggagg gaggcccgag agagccggcg gagtgagcag ctgaaggaag agtctgaagg   2460
ggagcagttc ccaggttgta ggatgcgccc atggacggcc tggtcagaat gcaccaaact   2520
gtgcggaggt ggaattcagg aacgttacat gactgtaaag aagagattca aaagctccca   2580
gtttaccagc tgcaaagaca agaaggagat cagagcatgc aatgttcatc cttgttagca   2640
agggtacgag ttccccaggg ctgcactcta gattccagag tcaccaatgg ctggattatt   2700
tgcttgttta agacaattta aattgtgtac gctagttttc atttttgcag tgtggttcgc   2760
ccagtagtct tgtggatgcc agagacatcc tttctgaata cttcttgatg ggtacaggct   2820
gagtggggcg ccctcacctc cagccagcct cttcctgcag aggagtagtg tcagccacct   2880
tgtactaagc tgaaacatgt ccctctggag cttccacctg gccagggagg acggagactt   2940
tgacctactc cacatggaga ggcaaccatg tctggaagtg actatgcctg agtcccaggg   3000
tgcggcaggt aggaaacatt cacagatgaa gacagcagat tccccacatt ctcatctttg   3060
gcctgttcaa tgaaaccatt gtttgcccat ctcttcttag tggaacttta ggtctctttt   3120
caagtctcct cagtcatcaa tagttcctgg ggaaaaacag agctggtaga cttgaagagg   3180
agcattgatg ttgggtggct tttgttcttt cactgagaaa ttcggaatac atttgtctca   3240
cccctgatat tggttcctga tgcccccca acaaaaataa ataaataaat tatggctgct   3300
ttatttaaat ataaggtagc tagtttttac acctgagata aataataagc ttagagtgta   3360
tttttccctt gcttttgggg gttcagagga gtatgtacaa ttcttctggg aagccagcct   3420
tctgaacttt ttggtactaa atccttattg gaaccaagac aaaggaagca aaattggtct   3480
ctttagagac caatttgcct aaattttaaa atcttcctac acacatctag acgttcaagt   3540
ttgcaaatca gtttttagca agaaaacatt tttgctatac aaacattttg ctaagtctgc   3600
ccaaagcccc cccaatgcat tccttcaaca aaatacaatc tctgtacttt aaagttattt   3660
tagtcatgaa attttatatg cagagagaaa aagttaccga gacagaaaac aaatctaagg   3720
gaaaggaata ttatgggatt aagctgagca agcaattctg gtggaaagtc aaacctgtca   3780
gtgctccaca ccagggctgt ggtcctccca gacatgcata ggaatggcca caggtttaca   3840
ctgccttccc agcaattata agcacaccag attcagggag actgaccacc aagggatagt   3900
gtaaaaggac attttctcag ttgggtccat cagcagtttt tcttcctgca tttattgttg   3960
aaaactattg tttcatttct tcttttatag gccttattac tgcttaatcc aaatgtgtac   4020
cattggtgag acacatacaa tgctctgaat acactacgaa tttgtattaa acacatcaga   4080
atatttccaa atacaacata gtatagtcct gaatatgtac ttttaacaca agagagacta   4140
ttcaataaaa actcactggg tctttcatgt ctttaagcta agtaagtgtt cagaaggttc   4200
ttttttatat tgtcctccac ctccatcatt ttcaataaaa gatagggctt ttgctccctt   4260
gttcttggag ggaccattat tacatctctg aactaccttt gtatccaaca tgttttaaat   4320
ccttaaatga attgctttct cccaaaaaaa gcacagtata aagaaacaca agatttaatt   4380
atttttctac ttggggggaa aaaagtcctc atgtagaagc acccactttt gcaatgttgt   4440
tctaagctat ctatctaact ctcagcccat gataaagttc cttaagctgg tgattcctaa   4500
tcaaggacaa gccaccctag tgtctcatgt ttgtatttgg tcccagttgg gtacatttta   4560
aaatcctgat tttggagact taaaaccagg ttaatggcta agaatgggta acatgactct   4620
```

```
tgttggattg ttattttttg tttgcaatgg ggaatttata agaagcatca agtctctttc   4680

ttaccaaagt cttgttaggt ggtttatagt tcttttggct aacaaatcat tttggaaata   4740

aagatttttt actac                                                    4755


<210> SEQ ID NO 70
<211> LENGTH: 443
<212> TYPE: DNA
<213> ORGANISM: human

<400> SEQUENCE: 70

tttttttttt tttttccatt aacccaacac aagtttattt actaagtcaa gtcaaactga     60

ggagtatttg tttctttggt agttggtaga caaagaatac atatacatat tctatttccc    120

attaagcatt cgatcatgtt acaaaacaat ggcctagaga actatcattg aagatttacc    180

aaatctgcct gaagcaaaat gtgataaact gcagaaatgg tggagaatga cactggaagt    240

cataaagttg attctcaaac acgggtttga actgcatagg accgcttata tgcatatttt    300

gataaatata ttgaaaattt ttttggaaat ttgcaacaat ttaaaaaact tgcagatgca    360

ccatgtagct tagaaatact gaaaaactaa gaaaaaggtg tgtcatgaat tcatataata    420

tatgtagaca ctagtctatt tta                                            443


<210> SEQ ID NO 71
<211> LENGTH: 2432
<212> TYPE: DNA
<213> ORGANISM: human

<400> SEQUENCE: 71

ggcgagtggc gagtggcgag tgtcaggggg gcggccggcg ggggcggggc ggccggagga     60

ggcgttggca gcgggctcgg acccacgcgg cgccgcggcc cgcctggcct gcagcgctcc    120

cacccccggc ggcggcacga tgccctttga cttcaggagg tttgacatct acaggaaggt    180

gcccaaggac cttacgcagc caacgtacac cggggccatt atctccatct gctgctgcct    240

cttcatcctc ttcctcttcc tctcggagct caccggattt ataacgacag aagttgtgaa    300

cgagctctat gtcgatgacc cagacaagga cagcggtggc aagatcgacg tcagtctgaa    360

catcagttta cccaatctgc actgcgagtt ggttgggctt gacattcagg atgagatggg    420

caggcacgaa gtgggccaca tcgacaactc catgaagatc ccgctgaaca atggggcagg    480

ctgccgcttc gaggggcagt tcagcatcaa caaggtcccc ggcaacttcc acgtgtccac    540

acacagtgcc acagcccagc cacagaaccc agacatgacg catgtcatcc acaagctctc    600

ctttggggac acgctacagg tccagaacat ccacggagct ttcaatgctc tcgggggagc    660

agacagactc acctccaacc ccctggcctc ccacgactac atcctgaaga ttgtgcccac    720

ggtttatgag gacaagagtg gcaagcagcg gtactcctac cagtacacgg tggccaacaa    780

ggaatacgtc gcctacagcc acacgggccg catcatccct gcaatctggt tccgctacga    840

cctcagcccc atcacggtca agtacacaga gagacggcag ccgctgtaca gattcatcac    900

cacgatctgt gccatcattg gcgggacctt caccgtcgcc ggcatcctgg actcatgcat    960

cttcacagcc tctgaggcct ggaagaagat ccagctgggc aagatgcatt gacgccacac   1020

ccagcctaat ggccgaggac cctgggcatc gccagccttg cctccagtgc cctgtctcct   1080

ttggccctca atctggtccc aaatctggct gtgtcccaaa gggtgtgtgg gaagtggggg   1140

gaaagtagag gatggctcga tgttttgcag ctacctcttt tccccgtgtt tctttttaga   1200
```

-continued

```
caaattacac tgcctgaagt tgcagttccc ctttccctgg ggagccccaa gaacagagtc   1260

aggcaagggg tggggagtcc agggatcttg gggacccctc ctaggagagc tgcagtctct   1320

tccctcaggg gaacatccca gaatgcatat cgatcagctc tcagccaggc ttcgacaatc   1380

tcgcagcccc cactaggtgg acacattaat gatttggttt ctcccctggg cagccaacct   1440

gccccagagg caccagacct gggctttcag ctttgggacc aggctgccca aaggtactcc   1500

tttatacacc cggcaccttc cacgaaagat ggtacttccc aagcaagccc ctatgatttg   1560

tcactataga tggaaccctg acttctgccc catcccttcc tgcccaacct agaacccagg   1620

cctcaagtct ttaccccacc cctttcttgt tcttccaaga agcagatgcc cagttgctca   1680

gcagcagcgg tagagacttg aatctgccca ccagtcacaa ggcgggtcac agattcctct   1740

tcctctcttc tcctcgttcc tctgaaccct ccaccaatgt gcctcagcct gtgtgctgtg   1800

tggcaacagc attctggttc ccactgccaa gatctcccac cactctgctg ggatctgcag   1860

tggcagggag tgggggttgt gtaaagggga agtcatcttt tgagatccag atagacatgg   1920

tttgtgcact tacgtccaga tgggaagcat ccttcctgca accctaaaat aatcatgcag   1980

cctctcagac ggacgccatc ggtcccaagg ccttaggtgg aggaagcaaa gcaggccagg   2040

cctgtcctgt ccgtggacct ctaccttctg gactccctac gggtgcagag cacttgggtt   2100

tctctacagc catcgtggcc cacttgacac tgtgctcctc catcagctgg tcacatgcca   2160

acacgttccc agcccctgag gcagctccag ggtgccccac ctgctcctga ggtgggtccc   2220

taccctgctg ctcctcttca tcctttccct tttgtcctga aagggaggag caatggtcca   2280

ggcattaatt ccacccaggg aattttagct atgccctcat gtcccaggga gagagccaca   2340

cgcctgtttt ccatttatag caagattgtt tgcatacttt tgtaatgaag gggagtgtcc   2400

agtggaagga tttttaaaat tatcttatgg at                                 2432
```

<210> SEQ ID NO 72
<211> LENGTH: 2782
<212> TYPE: DNA
<213> ORGANISM: human

<400> SEQUENCE: 72

```
gcggccgcgg cggggcggcg cgggaaccgg gccccggggg gagtcggccg ggctgctgct     60

gctgctgctc caggtgctgc cgcccggggc tacggcaggg ccgggacgcc ggggcacgcg    120

gggcgctggc ggcggcggcg tctgctggcc cggcgcggcc ccagcctttc cccgggacgc    180

gcggctgctg ctgctcctgc cgccgctgcc gccactgtcg ccgccgccgc cgagctccgc    240

gcccgcagcc tccgcctccc ggatggacgc tctgccccgc agcgggctga acctgaagga    300

ggagccgctg ctgcccgccg gcctgggctc agtgcgctcc tggatgcagg gcgcgggcat    360

cctggacgcc agcaccgcgg cgcagagtgg cgtgggtctg gcacgagcac attttgagaa    420

gcagcctccc tccaacctca ggaaatccaa cttcttccac ttcgtgctgg ccatgtacga    480

ccggcagggg cagcccgtgg aggtggagcg cacagccttc atcgacttcg tggaaaagga    540

ccgagagccc ggggcggaaa agactaacaa tgggatccat taccgcctcc ggctggtgta    600

taacaatgga ctgcggacag agcaagacct ctacgtgcgt ctcatcgact ccatgtccaa    660

acaggccatc atctatgagg ggcaggacaa gaaccccgaa atgtgccgag tgctgctcac    720

ccatgagatc atgtgcagcc ggtgctgtga ccggaagagc tgtggcaacc ggaatgagac    780

gccctcagac cccgtcatca ttgacaggtt cttcctcaag ttcttcctca aatgcaacca    840

gaactgcctg aagaatgcgg ggaatcccag agacatgcgc cgcttccagg tggtggtgtc    900
```

-continued

```
cacgacggtg agcgtggacg gacacgtgct ggccgtgtcc gacaacatgt ttgtgcacaa     960
caactccaag catggccgca gggcgcgccg cctggacccc tccgaagctg ccaccccctg    1020
catcaaggcc atcagccccg gggagggctg gaccacgggc ggcgccaccg tcattgtcat    1080
cggcgacaac ttcttcgacg ggttgcaggt cgtgttcgga aacgtgctcg tgtggagcga    1140
gctcatcacg ccccacgcca tccgggtgca gacgcccccg cggcacatcc ccggggtggt    1200
ggaggtgacc ctctcctaca agtccaagca gttttgcaag ggatgccccg gccgctttgt    1260
ctacacagct ctgaacgagc ccaccattga ctacggattc cagaggctac agaaagtcat    1320
tcccagacac ccccggagacc ccgagaggct gcccaaggaa gtgctgctga agcgggcggc    1380
cgacttggca gaagccctgt acggagtgcc cggcagtaac caggagctgc tcctgaagcg    1440
cgcggcggac gtggccgagg ctctgtacag cacccccccgc gcacccgggc cgctcgcacc    1500
cctggccccg agccacccac actccgccgt cgtgggcatc aacgccttca gcagcccgct    1560
ggccatcgcc gtcggggacg ccaccccggg gcccgagccg ggctacgcgc gcagctgcag    1620
cagcgcgtcc ccccgcgggt tcgcgcccag ccccggctcg cagcagagcg gctacggcgg    1680
cggcctcgga gctggcctgg gcggctacgg cgcgccgggc gtggccggcc tcggcgtgcc    1740
tgggtccccc agcttcctca atggctccac cgccacctcg cccttcgcca aggagcgcct    1800
tcgcccccgt gctgcgcccc ccaagctccc caccccaggc ctgccccaga gcccacggag    1860
aggggcttcc agaccagtct tttgaggatt ctgacaagtt ccactctcca gcccgggggc    1920
ttcagggcct ggcatactcc taattacggt ctgcagctgt tcccatggag cccggactgg    1980
aggtccctct gggattcaca gccacacccc ggatggtggc acagacagat gcagggccag    2040
ggccatgggc ggacctcaac ccgtgagctg aacggggaga ggccttcacc ccatgctcaa    2100
gcctccccgc tagcagcccc acaggcttct ctcgcctccc tgtcttgggg tagtcagaag    2160
ccccagcact gtgcagatgc tcttggcagg acagcatcgc agggaggtgc tgggattctg    2220
ggcctcactg tctgggtctt ggttcctctg aaagagatgg atcttgtgca gaccagggtt    2280
gttgagtgag gggagcgtgg gatggggacc gtgggaaaga ggacagctca gggagaagtg    2340
acctggaaag gtcctgtttg catctgaccc atctcaactg gcccagcatc ccaacttctc    2400
tgcagcgaaa gggtggcgcc ccgcagcctc gggaggcctg cccaggctcc cgtggagctt    2460
ccaacagctg cttggccccg cagctgcccc cacttccttt gagacctgca ctctcatgct    2520
tgccgcatca tgcctccctg tgggggcttt gggcatggag gaggcagaag agggggtgcc    2580
aggcctcctg tatttggggt cttcccccag tggatgtctc atggactctg gccccacaca    2640
ctcacaatga ctctggctgg ccccacgcag cgggcccagc cgccccccag gtggcctcac    2700
attctgctct gctaagtttg gagaaaacag aacaataaac cagatgcagg tggtgcccgc    2760
ccggcctctc acctgcctcc tt                                             2782
```

<210> SEQ ID NO 73
<211> LENGTH: 1722
<212> TYPE: DNA
<213> ORGANISM: human

<400> SEQUENCE: 73

```
ggggaaaaga gctaggaaag agctgcaaag cagtgtgggc tttttccctt tttttgctcc      60
ttttcattac ccctcctccg ttttcaccct tctccggact tcgcgtagaa cctgcgaatt     120
tcgaagagga ggtggcaaag tgggagaaaa gaggtgttag ggtttggggt ttttttgttt     180
```

-continued

```
ttgtttttgt tttttaattt cttgatttca acattttctc ccaccctctc ggctgcagcc    240

aacgcctctt acctgttctg cggcgccgcg caccgctggc agctgagggt tagaaagcgg    300

ggtgtatttt agattttaag caaaaatttt aaagataaat ccatttttct ctcccacccc    360

caacgccatc tccactgcat ccgatctcat tatttcggtg gttgcttggg ggtgaacaat    420

tttgtggctt tttttcccct ataattctga cccgctcagg cttgagggtt tctccggcct    480

ccgctcactg cgtgcacctg gcgctgccct gcttcccccca acctgttgca aggctttaat    540

tcttgcaact gggacctgct cgcaggcacc ccagccctcc acctctctct acatttttgc    600

aagtgtctgg gggagggcac ctgctctacc tgccagaaat tttaaaacaa aaacaaaaac    660

aaaaaaatct ccgggggccc tcttggcccc tttatccctg cactctcgct ctcctgcccc    720

accccgaggt aaagggggcg actaagagaa gatggtgttg ctcaccgcgg tcctcctgct    780

gctggccgcc tatgcggggc cggcccagag cctgggctcc ttcgtgcact gcgagccctg    840

cgacgagaaa gccctctcca tgtgcccccc cagccccctg ggctgcgagc tggtcaagga    900

gccgggctgc ggctgctgca tgacctgcgc cctggccgag gggcagtcgt gcggcgtcta    960

caccgagcgc tgcgcccagg ggctgcgctg cctcccccgg caggacgagg agaagccgct   1020

gcacgccctg ctgcacggcc gcggggtttg cctcaacgaa aagagctacc gcgagcaagt   1080

caagatcgag agagactccc gtgagcacga ggagcccacc acctctgaga tggccgagga   1140

gacctactcc cccaagatct tccggcccaa acacacccgc atctccgagc tgaaggctga   1200

agcagtgaag aaggaccgca gaaagaagct gacccagtcc aagtttgtcg gggggagccga   1260

gaacactgcc cacccccgga tcatctctgc acctgagatg agacaggagt ctgagcaggg   1320

cccctgccgc agacacatgg aggcttccct gcaggagctc aaagccagcc cacgcatggt   1380

gccccgtgct gtgtacctgc ccaattgtga ccgcaaagga ttctacaaga gaaagcagtg   1440

caaaccttcc cgtggccgca agcgtggcat ctgctggtgc gtggacaagt acgggatgaa   1500

gctgccaggc atggagtacg ttgacgggga ctttcagtgc cacaccttcg acagcagcaa   1560

cgttgagtga tgcgtccccc cccaaccttt ccctcacccc ctcccacccc cagccccgac   1620

tccagccagc gcctccctcc accccaggac gccactcatt tcatctcatt taagggaaaa   1680

atatatatct atctatttga ggaaaaaaaa aaaaaaaaaa aa                      1722
```

<210> SEQ ID NO 74
<211> LENGTH: 2626
<212> TYPE: DNA
<213> ORGANISM: human

<400> SEQUENCE: 74

```
gggtacggct gcgagaagac gacagaaggg gatgtcacct gctttatttc tggctttggc     60

ctgtggtctg tgataccccat cctgcttgat gttctgcaga atggcacttg actgctgggc    120

atgcatgaag ttaagggcaa gaaacagtat gccatgtgtt ctgtaccatc atgtgtctct    180

tcttgcttct gggcccttct actggtgaac tttcatcaag atctgcgcca tgccgtgtca    240

ctatcaagcc attaagtttt gtctgggttg ctgtcagccc cagttggctt cctggtcaac    300

aaggacctca agaactgcct gtggaccgag gccccctacc agtgcatgag acacacacct    360

accctcccca gctttccagg aaccctactg gctgccagac tgatgggcgg gctggtatgt    420

gtggacatgt gttcactgtc attatgctgt ggctccaggt gagggtgagg actgggccta    480

tatagaatcc agataccatt gtcaacttcc cttattcccg tctaagatgt gagcagagtg    540

ccatagtagg ggttctggga agaggtattt ctgatttgtg ggcctctgct tgcttgactt    600
```

```
caggtcactt atacttctta ttttgcttgc ctgccttcat ccctcatttc ctccctctca     660

ttcttctttc ctccctccct ttcctggtag cctcctttcc tccccttctg ccttcccctt     720

ccttctttcc ttattctttt ttattttgtt taaatagtac cacagagaaa acaactgaaa     780

aaccacattt ttctacatac agctggggag gtagctgaga acttggcact gcgcacacat     840

actaggttga aagagagttg aggaaaccag aaggccaagt ggatctgctg gcaaaccctg     900

aacctgtctc ctgcgcttgc tctacagttc tgaagttgaa aatcgttttc atgcctagca     960

tctgcttgag ttataaaccc caaggcagcc atgtcataga ctagtgttta ctcttgtttt    1020

gactttgttt taatgcttcc taagacccaa gtgcctcctg ctgtttcctc ctttgtggta    1080

gcctctggcc atctggacct caatccccag ctttcccact ttcagcagtc ctttgctctc    1140

tttgcttcta cctcaaatag ccccaggagt gggctttagt ctccaatatg gagcatctca    1200

agcttctcct gggggatggg gattgggatg ggcggaatct gttttggatc tccgggttat    1260

ttccagtggg tgtaaaagca gagctgggcc tttccctctc ttatccctga gggtgggtaa    1320

gaaggactgt atctacacct gttcttccct accttctctt ttgttaggga ggcctcattc    1380

taagttcctc aagagagtcc ttggcttaaa gctgtagcaa gggtgtgcta ggtgggggat    1440

ttggagcaaa accgtcgagt aggcatgata ctggtatgga gtgggcctgc aaaatcagac    1500

agaaatggct tgagaagccg cagggggagc atgcctgtct ctcagtgata gagtatggga    1560

gggacctccc tagcttggaa aatgagaatt gaaggggtta tgaacaaata ggatgcctag    1620

ttgaggatgt tcccaaagtt ttgtccaatc ttatcattag tagattttat aagccacaga    1680

gacaaaccag aaacggaata atgttacttt ggatgcttta tttttttgtt ctaggtgtgg    1740

ctttgtacat gcagaagaat gctatatgct gcacattttg cctttaaagt cttacgactt    1800

tccccatttt agtctaatgg gaagatacag atgtgcaagt ctgctttttt gtttttttgtt    1860

attatttttt tttttgctct gtgttatgga cattttcaga catgcacaga agtggagagg    1920

atggtccttg gaccccatgt gtccatcacc tagctgcatc acttatcagc tatggtcaac    1980

ctggtttcat ctgtatctct ctcttttcac ctgtattgtt tattgaaaat ccaagacact    2040

atgccaatgc aaccgtgact actttgggag attggtagtc tcttttgatg gtgatagtga    2100

tggggtgcac tatcataatc acatcaggtc tgctttttgc ttttaatgtt aactaatgaa    2160

gttccagaga tgggccttag aaatgtgttt taagaattaa caaggagtct caaaaagaaa    2220

tgagagggat gcttcctttc ccttgcatct acaaaacaag agagagactg ttctgttgta    2280

aaactctttc aaaaattctg atatggtaag gtacttgaga cccttcacca gaatgtcaat    2340

ctttttttct gtgtaacatg gaaacttgtg tgaccattag cattgttatc agcttgtact    2400

ggtctcataa ctctggtttt ggaagaataa tttggaaatt gttgctgtgt tctgtgaaaa    2460

taacctcccc aaaataatta gtaactggtt gttctacttg gtaatttgac accctgttaa    2520

taacgcaatt atttctgtgt tcttaaacag tataaatagt tgtaagtttg catgcatgat    2580

ggaaaaataa aaacctgtat ctctgtcaaa aaaaaaaaaa aaaaaa                   2626
```

```
<210> SEQ ID NO 75
<211> LENGTH: 3337
<212> TYPE: DNA
<213> ORGANISM: human

<400> SEQUENCE: 75

gtcgagcctc tagcccgccc gggtttcctt cgcagtcgcg caccgacgct caaacgcgcg      60
```

-continued

```
ctccaacccg cagcctcctc ctgcctcacc gcccgaagat ggcggctctc aaactcctct    120

cctccgggct tcggctctgc gcctctgccc gcggatctgg ggcaacctgg tacaagggat    180

gtgtttgttc cttttccacc agtgctcatc gccataccaa gttttataca gatccagtag    240

aagctgtaaa agacatccct gatggtgcca cggttttggt tggtggtttt gggctatgtg    300

gaattccaga gaatcttata gatgctttac tgaaaactgg agtaaaagga ctaactgcag    360

tcagcaacaa tgcaggggtt gacaattttg gtttggggct tttgcttcgg tcgaagcaga    420

taaaacgcat ggtctcttca tatgtgggag aaaatgcaga atttgaacga cagtacttat    480

ctggtgaatt agaagtggag ctgacaccac agggcacact tgcagagagg atccgtgcag    540

gcggggctgg agttcctgca ttttacaccc caacagggta tgggaccctg gtacaagaag    600

gaggatcgcc catcaaatac aacaaagatg gcagtgttgc cattgccagt aagccaagag    660

aggtgaggga gttcaatggt cagcacttta ttttggagga agcaattaca ggggattttg    720

ctttggtgaa agcctggaag gcggaccgag caggaaacgt gattttcagg aaaagtgcaa    780

ggaatttcaa cttgccaatg tgcaaagctg cagaaaccac agtggtagag gttgaagaaa    840

ttgtggatat tggagcattt gctccagaag acatccatat tcctcagatt tatgtacatc    900

gccttataaa gggagaaaaa tatgagaaaa gaattgagcg tttatcaatc cggaaagagg    960

gagatgggga agccaaatct gctaaacctg gagatgacgt aagggaacga atcatcaaga   1020

gggccgctct tgagtttgag gatggcatgt atgctaattt gggcatagga atccctctcc   1080

tggccagcaa ttttatcagc ccaaatataa ctgttcatct tcaaagtgaa aatggagttc   1140

tgggtttggg tccatatcca cgacaacatg aagctgatgc agatctcatc aatgcaggca   1200

aggaaacagt tactattctt ccaggagcct ctttttctc cagcgatgaa tcatttgcaa   1260

tgattagagg tggacacgtc gatctgacaa tgctaggagc gatgcaggtt tccaaatatg   1320

gtgacctggc taactggatg atacctggga agatggtgaa aggaatggga ggtgctatgg   1380

atttagtgtc cagtgcgaaa accaaagtgg tggtcaccat ggagcattct gcaaagggaa   1440

atgcacataa aatcatggag aaatgtacat taccattgac tggaaagcaa tgtgtcaacc   1500

gcattattac tgaaaaggct gtgtttgatg tggacaagaa gaaagggttg actctgattg   1560

agctctggga aggcctgaca gtggatgacg tacaaaagag tactgggtgt gattttgcag   1620

tttcaccaaa actcatgcca atgcagcaga tcgcaaattg aaatatggat atttgtacca   1680

ggctgcgtgt ttttcatttt aaacacacaa gatttaattg aaaggacatc aataatcata   1740

attgtgtatt taacaggtgg ttttttatta gttttcttgt gtttcagact ttatgcagcc   1800

atataaactg ttctctaggc atgctgtgac attttaataa aaagcaaaag gagcatttat   1860

aattatctca tttgttaagg ctgagaaggt tgtttttata ataggtaatt atattgaatg   1920

cattttcact gaatatggta tgtatgctaa attatatgaa cctttcccca agaagggccc   1980

tagaaattga tgtggctttc ctcttaaata ttaattatta gtcctgaaag aaagataaca   2040

tatgtgattt ttgtggttag gagagttgct gtcatgattg ttttttcttc agcctcctct   2100

gacttttctt ttggggcttc agattttatg attacatctt gtccccctag aacatccccc   2160

ttcctcccat actgctttta aacagatgcc caagaaggca agcaggaatg cctcttgtgg   2220

gggagggcag ggagaaataa ctagttcaaa ccaactatct atctatgctt tgcaaagact   2280

aaggcgtatt ataggaagag ggctagaaac ctaactgatt cttctcagtt ttctcatttt   2340

aaaacagccc agtattcctt tgtatcctca agggtccttg agaatacttc tgttattgaa   2400

accctgtggg ctacttgtac tgtacctcct ctcaagccaa gaagggctgt gggataattt   2460
```

```
accatgaatc cttagtagca atgacagcag agttaaaaaa taaaaggtgt tttactttca   2520

ggctcttgtt ttggttcaga ggagatttta aatattgaat gacacttcta cagaacaacg   2580

gtttttcttc tgccaaggct acttccttta acgaagtgcc tttaattcag ccttatccaa   2640

ctagggaaaa taatgttgga caagtctagg atttgaagag tcagtgaact tttagtgtca   2700

gggaataaac atggtgggta gattaggttt gaaaaaaact tccttagagg tatttattct   2760

caatacctga caggggccca tgggaatgac ttcagaagca tcccggataa tagatgggta   2820

aaaagtctag gcaccctgaa gaacaggtga gacagctggc ctctggacag aggtaggcat   2880

agtacagtac gatatatcat tcctctggtc ctaaatatac aaacttattc atgtttttag   2940

gtgatgatgg tcattgaaac tcacttcttt tcaggtgtag ctacaattgt gtaatgtaca   3000

atattagaga aaggacaggc tttttatgag taacacacac catatataaa acagcctttc   3060

tggctgacca catggttaaa tgcatacctt cccagtactg gggggaaaat gacccttctt   3120

agaatgtgca agttccatag agtaatatat tgatatgatt ttgaaaagaa ttgttgatag   3180

ttacatcttc aaacttatca ttccagtatg catctttaag ataatgtgat tctaagtaga   3240

tgactttata ttcttgatta aagagtgcta tacatgttaa gaaatgcatt aaggaataca   3300

ataaatattc taaactgatg aaaaaaaaaa aaaaaaa                            3337


<210> SEQ ID NO 76
<211> LENGTH: 2460
<212> TYPE: DNA
<213> ORGANISM: human

<400> SEQUENCE: 76

aaagtcaaac cccgacaccg cggcgggccg gtgagctcac tagctgaccc ggcaggtcag     60

gatctggctt agcggcgccg cgagctccag tgcgcgcacc cgtggccgcc tcccagccct    120

ctttgccgga cgagctctgg gccgccacaa gactaaggaa tggccacccc gcccaagaga    180

agctgcccgt ctttctcagc cagctctgag gggacccgca tcaagaaaat ctccatcgaa    240

gggaacatcg ctgcagggaa gtcaacattt gtgaatatcc ttaaacaatt gtgtgaagat    300

tgggaagtgg ttcctgaacc tgttgccaga tggtgcaatg ttcaaagtac tcaagatgaa    360

tttgaggaac ttacaatgtc tcagaaaaat ggtgggaatg ttcttcagat gatgtatgag    420

aaacctgaac gatggtcttt taccttccaa acatatgcct gtctcagtcg aataagagct    480

cagcttgcct ctctgaatgg caagctcaaa gatgcagaga aacctgtatt attttttgaa    540

cgatctgtgt atagtgacag gtatattttt gcatctaatt tgtatgaatc tgaatgcatg    600

aatgagacag agtggacaat ttatcaagac tggcatgact ggatgaataa ccaatttggc    660

caaagccttg aattggatgg aatcatttat cttcaagcca ctccagagac atgcttacat    720

agaatatatt tacggggaag aaatgaagag caaggcattc ctcttgaata tttagagaag    780

cttcattata aacatgaaag ctggctcctg cataggacac tgaaaaccaa cttcgattat    840

cttcaagagg tgcctatctt aacactggat gttaatgaag actttaaaga caaatatgaa    900

agtctggttg aaaaggtcaa agagtttttg agtactttgt gatcttgctg aagactacag    960

gcagccaaat ggttccagat acttcagctt tgtgtatctt cgtaacttca tattaatata   1020

agtttcttta gaaaacccaa gtttttaatc gtttttgttt taaggaaaaa agatttttaa   1080

aatgaatctt atgcaaaact tttgatcag tttcttttct tttgtttttt ttttaaaaaa   1140

gacatttaaa gacaaagaca ttatttctca tagcaggaaa tgtagaggta gatggttcca   1200
```

-continued

```
gtatcagcat agtgactaaa ctacattata aaagatccag cttccttctg tcattcccct   1260
cttttgtctt cctcagcagg ttggcttttt tccctggtgc ctctcacttc gttggtgacc   1320
agtttcttaa actgaaagct ttaatgttac atagtaaatg gtagtgtgtc ctgtgtaaat   1380
tagtgtacct attaaaagtt gcaaagtgga attaaaggaa tccctagaat aaggattctg   1440
aagttttatt ttaaattatt atcttcttaa cagtttagtc ccacctctta cttcctgcct   1500
cagtctgctt tctctactgt ctggattaat taggcagcct gctataaagt taaagtcaca   1560
catttctatt ttgcaaacac tgtgattact ctttgctttg tagtttgctt tgctttgtag   1620
ggttctgctt ttaagttttt ctctttttca gacaaattac tgataaaaat gatattgctc   1680
tatatgtaat atatcctgaa agcattattt tttgttgaat aggaaataaa attaatgaag   1740
acagaggcta gaaagcatcc attaattaat gagacacact taactactta tctctaaacc   1800
atctatgtga atatttgtaa aaataatgaa tggactcatc ttagttctgt atataaatat   1860
attttctttc tagtttgttt agttaaggtg tgcagtgttt ttcctgtgta ttaaaccttt   1920
ccattttacg ttttagaaaa ttttatgtat tttaaaataa ggggaagagt cattttcacc   1980
tttaaactac tatttttctt tccaagtcat ttttgttttt ggtttcttat tcaaagatga   2040
taatttagtg gattaaccag tccagacgca ctgatctttg caaaggagac ttaatttcaa   2100
atctgtaatt accatacata aactgtctca ttatacgtat gcattttttt agtttgtttt   2160
tgtttggtat aaattaattt gttaattaaa tatttcttaa gtataaacct tatgaactac   2220
agtggagcta cactcattga aatgtaattt cagttctaaa aagatgtaat aatcatttta   2280
gaattaaaat ttattctact tttaaataaa ttatgaatat taaaggtgaa aattgtataa   2340
attactttga ttccatttta agtggagaca tatttcagtg atttttagta acctttaaaa   2400
atgtataatg acttttaaaa tttgtagaat tgaaaagacg ctaataaaaa tttattattt   2460
```

<210> SEQ ID NO 77
<211> LENGTH: 7680
<212> TYPE: DNA
<213> ORGANISM: human

<400> SEQUENCE: 77

```
gcggacactc ctctcggctc ctccccggca gcggcggcgg ctcggagcgg gctccggggc     60
tcgggtgcag cggccagcgg gcctggcggc gaggattacc cggggaagtg gttgtctcct    120
ggctggagcc gcgagacggg cgctcagggc gcggggccgg cggcggcgaa cgagaggacg    180
gactctggcg gccgggtcgt tggccggggg agcgcgggca ccgggcgagc aggccgcgtc    240
gcgctcacca tggtcagcta ctgggacacc ggggtcctgc tgtgcgcgct gctcagctgt    300
ctgcttctca caggatctag ttcaggttca aaattaaaag atcctgaact gagtttaaaa    360
ggcacccagc acatcatgca agcaggccag acactgcatc tccaatgcag gggggaagca    420
gcccataaat ggtctttgcc tgaaatggtg agtaaggaaa gcgaaaggct gagcataact    480
aaatctgcct gtggaagaaa tggcaaacaa ttctgcagta ctttaacctt gaacacagct    540
caagcaaacc acactggctt ctacagctgc aaatatctag ctgtacctac ttcaaagaag    600
aaggaaacag aatctgcaat ctatatattt attagtgata caggtagacc tttcgtagag    660
atgtacagtg aaatccccga aattatacac atgactgaag gaagggagct cgtcattccc    720
tgccgggtta cgtcacctaa catcactgtt actttaaaaa agtttccact tgacactttg    780
atccctgatg gaaaacgcat aatctgggac agtagaaagg gcttcatcat atcaaatgca    840
acgtacaaag aaatagggct tctgacctgt gaagcaacag tcaatgggca tttgtataag    900
```

```
acaaactatc tcacacatcg acaaaccaat acaatcatag atgtccaaat aagcacacca    960
cgcccagtca aattacttag aggccatact cttgtcctca attgtactgc taccactccc   1020
ttgaacacga gagttcaaat gacctggagt taccctgatg aaaaaaataa gagagcttcc   1080
gtaaggcgac gaattgacca aagcaattcc catgccaaca tattctacag tgttcttact   1140
attgacaaaa tgcagaacaa agacaaagga ctttatactt gtcgtgtaag gagtggacca   1200
tcattcaaat ctgttaacac ctcagtgcat atatatgata aagcattcat cactgtgaaa   1260
catcgaaaac agcaggtgct tgaaaccgta gctggcaagc ggtcttaccg gctctctatg   1320
aaagtgaagg catttccctc gccggaagtt gtatggttaa aagatgggtt acctgcgact   1380
gagaaatctg ctcgctattt gactcgtggc tactcgttaa ttatcaagga cgtaactgaa   1440
gaggatgcag ggaattatac aatcttgctg agcataaaac agtcaaatgt gtttaaaaac   1500
ctcactgcca ctctaattgt caatgtgaaa ccccagattt acgaaaaggc cgtgtcatcg   1560
tttccagacc cggctctcta cccactgggc agcagacaaa tcctgacttg taccgcatat   1620
ggtatccctc aacctacaat caagtggttc tggcacccct gtaaccataa tcattccgaa   1680
gcaaggtgtg acttttgttc caataatgaa gagtccttta tcctggatgc tgacagcaac   1740
atgggaaaca gaattgagag catcactcag cgcatggcaa taatagaagg aaagaataag   1800
atggctagca ccttggttgt ggctgactct agaatttctg gaatctacat ttgcatagct   1860
tccaataaag ttgggactgt gggaagaaac ataagctttt atatcacaga tgtgccaaat   1920
gggtttcatg ttaacttgga aaaaatgccg acggaaggag aggacctgaa actgtcttgc   1980
acagttaaca agttcttata cagagacgtt acttggattt tactgcggac agttaataac   2040
agaacaatgc actacagtat tagcaagcaa aaaatggcca tcactaagga gcactccatc   2100
actcttaatc ttaccatcat gaatgtttcc ctgcaagatt caggcaccta tgcctgcaga   2160
gccaggaatg tatacacagg ggaagaaatc ctccagaaga aagaaattac aatcagagat   2220
caggaagcac catacctcct gcgaaacctc agtgatcaca cagtggccat cagcagttcc   2280
accactttag actgtcatgc taatggtgtc cccgagcctc agatcacttg gtttaaaaac   2340
aaccacaaaa tacaacaaga gcctggaatt attttaggac caggaagcag cacgctgttt   2400
attgaaagag tcacagaaga ggatgaaggt gtctatcact gcaaagccac caaccagaag   2460
ggctctgtgg aaagttcagc atacctcact gttcaaggaa cctcggacaa gtctaatctg   2520
gagctgatca ctctaacatg cacctgtgtg gctgcgactc tcttctggct cctattaacc   2580
ctccttatcc gaaaaatgaa aaggtcttct tctgaaataa agactgacta cctatcaatt   2640
ataatggacc cagatgaagt tcctttggat gagcagtgtg agcggctccc ttatgatgcc   2700
agcaagtggg agtttgcccg ggagagactt aaactgggca aatcacttgg aagaggggct   2760
tttggaaaag tggttcaagc atcagcattt ggcattaaga aatcacctac gtgccggact   2820
gtggctgtga aaatgctgaa agagggggcc acggccagcg agtacaaagc tctgatgact   2880
gagctaaaaa tcttgaccca cattggccac catctgaacg tggttaacct gctgggagcc   2940
tgcaccaagc aaggagggcc tctgatggtg attgttgaat actgcaaata tggaaatctc   3000
tccaactacc tcaagagcaa acgtgactta ttttttctca acaaggatgc agcactacac   3060
atggagccta agaaagaaaa aatggagcca ggcctggaac aaggcaagaa accaagacta   3120
gatagcgtca ccagcagcga aagctttgcg agctccggct ttcaggaaga taaaagtctg   3180
agtgatgttg aggaagagga ggattctgac ggtttctaca aggagcccat cactatggaa   3240
```

-continued

```
gatctgattt cttacagttt tcaagtggcc agaggcatgg agttcctgtc ttccagaaag   3300
tgcattcatc gggacctggc agcgagaaac attcttttat ctgagaacaa cgtggtgaag   3360
atttgtgatt ttggccttgc ccgggatatt tataagaacc ccgattatgt gagaaaagga   3420
gatactcgac ttcctctgaa atggatggct cccgaatcta tctttgacaa aatctacagc   3480
accaagagcg acgtgtggtc ttacggagta ttgctgtggg aaatcttctc cttaggtggg   3540
tctccatacc caggagtaca aatggatgag gacttttgca gtcgcctgag ggaaggcatg   3600
aggatgagag ctcctgagta ctctactcct gaaatctatc agatcatgct ggactgctgg   3660
cacagagacc caaaagaaag gccaagattt gcagaacttg tggaaaaact aggtgatttg   3720
cttcaagcaa atgtacaaca ggatggtaaa gactacatcc caatcaatgc catactgaca   3780
ggaaatagtg ggtttacata ctcaactcct gccttctctg aggacttctt caaggaaagt   3840
atttcagctc cgaagtttaa ttcaggaagc tctgatgatg tcagatatgt aaatgctttc   3900
aagttcatga gcctggaaag aatcaaaacc tttgaagaac ttttaccgaa tgccacctcc   3960
atgtttgatg actaccaggg cgacagcagc actctgttgg cctctcccat gctgaagcgc   4020
ttcacctgga ctgacagcaa acccaaggcc tcgctcaaga ttgacttgag agtaaccagt   4080
aaaagtaagg agtcggggct gtctgatgtc agcaggccca gtttctgcca ttccagctgt   4140
gggcacgtca gcgaaggcaa gcgcaggttc acctacgacc acgctgagct ggaaaggaaa   4200
atcgcgtgct gctccccgcc cccagactac aactcggtgg tcctgtactc caccccaccc   4260
atctagagtt tgacacgaag ccttatttct agaagcacat gtgtatttat acccccagga   4320
aactagcttt tgccagtatt atgcatatat aagtttacac ctttatcttt ccatgggagc   4380
cagctgcttt ttgtgatttt tttaatagtg cttttttttt ttgactaaca agaatgtaac   4440
tccagataga gaaatagtga caagtgaaga acactactgc taaatcctca tgttactcag   4500
tgttagagaa atccttccta aacccaatga cttccctgct ccaacccccg ccacctcagg   4560
gcacgcagga ccagtttgat tgaggagctg cactgatcac ccaatgcatc acgtacccca   4620
ctgggccagc cctgcagccc aaaacccagg gcaacaagcc cgttagcccc aggggatcac   4680
tggctggcct gagcaacatc tcgggagtcc tctagcaggc ctaagacatg tgaggaggaa   4740
aaggaaaaaa agcaaaaagc aagggagaaa agagaaaccg ggagaaggca tgagaaagaa   4800
tttgagacgc accatgtggg cacggagggg gacggggctc agcaatgcca tttcagtggc   4860
ttcccagctc tgacccttct acatttgagg gcccagccag gagcagatgg acagcgatga   4920
ggggacattt tctggattct gggaggcaag aaaaggacaa atatcttttt tggaactaaa   4980
gcaaatttta gacctttacc tatggaagtg gttctatgtc cattctcatt cgtggcatgt   5040
tttgatttgt agcactgagg gtggcactca actctgagcc catacttttg gctcctctag   5100
taagatgcac tgaaaactta gccagagtta ggttgtctcc aggccatgat ggccttacac   5160
tgaaaatgtc acattctatt ttgggtatta atatatagtc cagacactta actcaatttc   5220
ttggtattat tctgttttgc acagttagtt gtgaaagaaa gctgagaaga atgaaaatgc   5280
agtcctgagg agagttttct ccatatcaaa acgagggctg atggaggaaa aaggtcaata   5340
aggtcaaggg aagaccccgt ctctatacca accaaaccaa ttcaccaaca cagttgggac   5400
ccaaaacaca ggaagtcagt cacgtttcct tttcatttaa tggggattcc actatctcac   5460
actaatctga aaggatgtgg aagagcatta gctggcgcat attaagcact ttaagctcct   5520
tgagtaaaaa ggtggtatgt aatttatgca aggtatttct ccagttggga ctcaggatat   5580
tagttaatga gccatcacta gaagaaaagc ccattttcaa ctgctttgaa acttgcctgg   5640
```

-continued

```
ggtctgagca tgatgggaat agggagacag ggtaggaaag ggcgcctact cttcagggtc   5700

taaagatcaa gtgggccttg gatcgctaag ctggctctgt ttgatgctat ttatgcaagt   5760

tagggtctat gtatttagga tgcgcctact cttcagggtc taaagatcaa gtgggccttg   5820

gatcgctaag ctggctctgt ttgatgctat ttatgcaagt tagggtctat gtatttagga   5880

tgtctgcacc ttctgcagcc agtcagaagc tggagaggca acagtggatt gctgcttctt   5940

ggggagaaga gtatgcttcc ttttatccat gtaatttaac tgtagaacct gagctctaag   6000

taaccgaaga atgtatgcct ctgttcttat gtgccacatc cttgtttaaa ggctctctgt   6060

atgaagagat gggaccgtca tcagcacatt ccctagtgag cctactggct cctggcagcg   6120

gcttttgtgg aagactcact agccagaaga gaggagtggg acagtcctct ccaccaagat   6180

ctaaatccaa acaaaagcag gctagagcca gaagagagga caaatctttg ttgttcctct   6240

tctttacaca tacgcaaacc acctgtgaca gctggcaatt ttataaatca ggtaactgga   6300

aggaggttaa actcagaaaa aagaagacct cagtcaattc tctacttttt tttttttttt   6360

tccaaatcag ataatagccc agcaaatagt gataacaaat aaaaccttag ctgttcatgt   6420

cttgatttca ataattaatt cttaatcatt aagagaccat aataaatact ccttttcaag   6480

agaaaagcaa aaccattaga attgttactc agctccttca aactcaggtt tgtagcatac   6540

atgagtccat ccatcagtca aagaatggtt ccatctggag tcttaatgta gaaagaaaaa   6600

tggagacttg taataatgag ctagttacaa agtgcttgtt cattaaaata gcactgaaaa   6660

ttgaaacatg aattaactga taatattcca atcatttgcc atttatgaca aaaatggttg   6720

gcactaacaa agaacgagca cttcctttca gagtttctga gataatgtac gtggaacagt   6780

ctgggtggaa tggggctgaa accatgtgca agtctgtgtc ttgtcagtcc aagaagtgac   6840

accgagatgt taattttagg gacccgtgcc ttgtttccta gcccacaaga atgcaaacat   6900

caaacagata ctcgctagcc tcatttaaat tgattaaagg aggagtgcat ctttggccga   6960

cagtggtgta actgtgtgtg tgtgtgtgtg tgtgtgtgtg tgtgtgtgtg tgtgggtgtg   7020

ggtgtatgtg tgttttgtgc ataactattt aaggaaactg gaattttaaa gttactttta   7080

tacaaaccaa gaatatatgc tacagatata agacagacat ggtttggtcc tatatttcta   7140

gtcatgatga atgtattttg tataccatct tcatataata tacttaaaaa tatttcttaa   7200

ttgggatttg taatcgtacc aacttaattg ataaacttgg caactgcttt tatgttctgt   7260

ctccttccat aaatttttca aaatactaat tcaacaaaga aaaagctctt tttttcccta   7320

aaataaactc aaatttatcc ttgtttagag cagagaaaaa ttaagaaaaa ctttgaaatg   7380

gtctcaaaaa attgctaaat attttcaatg gaaaactaaa tgttagttta gctgattgta   7440

tggggttttc gaacctttca ctttttgttt gttttaccta tttcacaact gtgtaaattg   7500

ccaataattc ctgtccatga aaatgcaaat tatccagtgt agatatattt gaccatcacc   7560

ctatggatat tggctagttt tgcctttatt aagcaaattc atttcagcct gaatgtctgc   7620

ctatatattc tctgctcttt gtattctcct ttgaacccgt taaaacatcc tgtggcactc   7680
```

<210> SEQ ID NO 78
<211> LENGTH: 3160
<212> TYPE: DNA
<213> ORGANISM: human

<400> SEQUENCE: 78

```
attctcgccg cgcccgggcg gacgatccag cgaacagccc cgcttctaac ccgagatgct     60
```

-continued

```
gctgccggcg cccgcgctcc gccgcgccct gctgtcccgc ccctggaccg gggccggcct    120
gcggtggaag cacacctcct ccctgaaggt ggccaacgag cccgtcttag ccttcacgca    180
gggcagccct gagcgagatg ccctgcaaaa ggccttgaag gacctgaagg gccggatgga    240
agccatccca tgcgtggtgg gggatgagga ggtgtggacg tcggacgtgc agtaccaagt    300
gtcgcctttt aaccatggac ataaggtggc caagttctgt tatgcagaca agagcctgct    360
caacaaagcc attgaggctg ccctggctgc ccggaaagag tgggacctga agcctattgc    420
agaccgggcc cagatcttcc tgaaggcggc agacatgctg agtgggccgc gcagggctga    480
gatcctcgcc aagaccatgg tgggacaggg taagaccgtg atccaagcgg agattgacgc    540
tgcagcggaa ctcatcgact tcttccggtt caatgccaag tatgcggtgg agctggaggg    600
gcagcagccc atcagcgtgc ccccgagcac caacagcacg gtgtaccggg gtctggaggg    660
cttcgtggcg gccatctcgc cctttaactt cactgcaatc ggcggcaacc tggcgggggc    720
accggccctg atgggcaacg tggtcctatg gaagcccagt gacactgcca tgctggccag    780
ctatgctgtc taccgcatcc ttcgggaggc tggcctgccc cccaacatca tccagtttgt    840
gccagctgat gggcccctat ttggggacac tgtcaccagc tcagagcacc tctgtggcat    900
caacttcaca ggcagtgtgc ccaccttcaa acacctgtgg aagcaggtgg cccagaacct    960
ggaccggttc cacaccttcc cacgcctggc tggagagtgc ggcggaaaga acttccactt   1020
cgtgcaccgc tcggccgacg tggagagcgt ggtgagcggg accctccgct cagccttcga   1080
gtacggtggc cagaagtgtt ccgcctgctc gcgtctctac gtgccgcact cgctgtggcc   1140
gcagatcaaa gggcggctgc tggaggagca cagtcggatc aaagtgggcg accctgcaga   1200
ggattttggg accttcttct ctgcagtgat tgatgccaag tcctttgccc gtatcaagaa   1260
gtggctggag cacgcgcgct cctcgcccag cctcaccatc ctggctgggg gcaagtgtga   1320
tgactccgtg ggctactttg tggagccctg catcgtggag agcaaggacc ctcaggagcc   1380
catcatgaag gaggagatct tcgggcctgt actgtctgtg tacgtctacc cggacgacaa   1440
gtacaaggag acgctgcagc tggttgacag caccaccagc tatggcctca cgggggcagt   1500
gttctcccag gataaggacg tcgtgcagga ggccacaaag gtgctgagga atgctgccgg   1560
caacttctac atcaacgaca agtccactgg ctcgatagtg ggccagcagc cctttggggg   1620
ggcccgagcc tctggaacca atgacaagcc agggggccca cactacatcc tgcgctggac   1680
gtcgccgcag gtcatcaagg agacacataa gccccctggg gactggagct acgcgtacat   1740
gcagtgagcc cctctcgggc tccaccgtcc agctgtctgt ccgtccaggt ggccgacctc   1800
actgcacaga ccccactcca gcccctccac cccttcttca tgcacagctg cctttctata   1860
atccgggctt gactcccttc ttaccactgt attctggcct ctcccatgcc tcaggctctg   1920
gtttgagatc gtgctgggga ggaacatggc cactacccct tatcccatcg gccatgtggg   1980
aggtatgacc ctggtgcctg gcaggttctc cctctgccct ccactgggcc cagtggctca   2040
gggacctggg gaaaggagat ggagcagctc ttgggatcct ttggggaaaa ggaggccatt   2100
ctgggcccct tggcaaacct caccactcac agaggctcct ggccttgatc cctgcccctc   2160
caggtgtcca gggtaaagtg taactcagac tgacctgtgg ggcacagggg gcaccagctg   2220
gccttgccct ctctggtctg ggctgtctac cttcctcact gtatctttgc ccagacccac   2280
ctgggccagt aggcccctgt ccccagccac acaccttaga tgctggcatg ccttactcca   2340
ggtgcctgtg tttggccgag gcctgtgtga ttcccggtct gcaccacatg gcggggttgg   2400
ggggccgctg gaggccacct gccaaggcgt gggatgggat ggtcctgccg gtttaggccg   2460
```

-continued

```
tgattctgga aaaccttgga tgggccttcg tcctatgtca gccttccctt tgatcctcag   2520
gccctacctg tagagacctc cactcctaga gccagtctca gggtctggga tttccctgca   2580
ggagctcagc caccactgtg ccatggtgac acaggccaag gcagacattg gccctccctt   2640
ctcccagccc ccagaggcct ggccttgggt tcgtcagcat gggccgagga cgttgcctgt   2700
agaatcctcc tctgcctggg agtggctctg tgtggaccag tccctcactg gcccattctt   2760
tttttgacgc agccaatctg tgaccacgat tcctcccaca gatgcctcct gcttggattc   2820
tgagtggtca gagatctgta aagcatgact ttcaaggatg gttcttaggg gactgtgaaa   2880
gtgttgggtc ttcctccagg atgcctgcat gggaccccac ccggagctgg tgtggccatt   2940
ccccaagtgc cactggccca tggatggggg tgggtgctgg tgccagctgg gctgggtgtg   3000
ggttctgtgt ccttccagga tatgtgtcat ttcccatgag gggccggggc aggtggctgg   3060
gtgggggcac aggctggagt attcttagtt ctactggttc tacactgtga ggtggcaatg   3120
ggatttgctc agatgccacc caataaaatg cctgttactt                         3160
```

<210> SEQ ID NO 79
<211> LENGTH: 1546
<212> TYPE: DNA
<213> ORGANISM: human

<400> SEQUENCE: 79

```
cacggccgga gagacgcgga ggaggagaca tgagccggcg ggcgcccaga cggagcggcc     60
gtgacgcttt cgcgctgcag ccgcgcgccc cgaccccgga gcgctgaccc ctggccccac    120
gcagctccgc gcccgggccg gagagcgcaa ctcggcttcc agacccgccg cgcatgctgt    180
ccccggactg agccgggcag ccagcctccc acggacgccc ggacggccgg ccggccagca    240
gtgagcgagc ttccccgcac cggccaggcg cctcctgcac agcggctgcc gccccgcagc    300
ccctgcgcca gcccggaggg cgcagcgctc gggaggagcc gcgcggggcg ctgatgccgc    360
agggcgcgcc gcggagcgcc ccggagcagc agagtctgca gcagcagcag ccggcgagga    420
gggagcagca gcagcggcgg cggcggcggc ggcggcggcg gaggcgcccg gtcccggccg    480
cgcggagcgg acatgtgcag gctgggctag gagccgccgc ctccctcccg cccagcgatg    540
tattcagcgc cctccgcctg cacttgcctg tgtttacact tcctgctgct gtgcttccag    600
gtacaggtgc tggttgccga ggagaacgtg gacttccgca tccacgtgga gaaccagacg    660
cgggctcggg acgatgtgag ccgtaagcag ctgcggctgt accagctcta cagccggacc    720
agtgggaaac acatccaggt cctgggccgc aggatcagtg cccgcggcga ggatggggac    780
aagtatgccc agctcctagt ggagacagac accttcggta gtcaagtccg gatcaagggc    840
aaggagacgg aattctacct gtgcatgaac cgcaaaggca agctcgtggg gaagcccgat    900
ggcaccagca aggagtgtgt gttcatcgag aaggttctgg agaacaacta cacggccctg    960
atgtcggcta agtactccgg ctggtacgtg ggcttcacca agaaggggcg gccgcggaag   1020
ggccccaaga cccgggagaa ccagcaggac gtgcatttca tgaagcgcta ccccaagggg   1080
cagccggagc ttcagaagcc cttcaagtac acgacggtga ccaagaggtc ccgtcggatc   1140
cggcccacac accctgccta ggccaccccg ccgcggcccc tcaggtcgcc ctggccacac   1200
tcacactccc agaaaactgc atcagaggaa tatttttaca tgaaaaataa ggaagaagct   1260
ctatttttgt acattgtgtt taaaagaaga caaaaactga accaaaactc ttgggggggag   1320
gggtgataag gattttattg ttgacttgaa acccccgatg acaaaagact cacgcaaagg   1380
```

```
gactgtagtc aacccacagg tgcttgtctc tctctaggaa cagacaactc taaactcgtc   1440

cccagaggag gacttgaatg aggaaaccaa cactttgaga aaccaaagtc ctttttccca   1500

aaggttctga aaggaaaaaa aaaaaaaaac aaaaaaaaaa aaaaaa                  1546


<210> SEQ ID NO 80
<211> LENGTH: 2819
<212> TYPE: DNA
<213> ORGANISM: human

<400> SEQUENCE: 80

ctgggcccag ctcccccgag aggtggtcgg atcctctggg ctgctcggtc gatgcctgtg     60

ccactgacgt ccaggcatga ggtggttcct gccctggacg ctggcagcag tgacagcagc    120

agccgccagc accgtcctgg ccacggccct ctctccagcc cctacgacca tggactttac    180

cccagctcca ctggaggaca cctcctcacg cccccaattc tgcaagtggc catgtgagtg    240

cccgccatcc ccaccccgct gcccgctggg ggtcagcctc atcacagatg gctgtgagtg    300

ctgtaagatg tgcgctcagc agcttgggga caactgcacg gaggctgcca tctgtgaccc    360

ccaccggggc ctctactgtg actacagcgg ggaccgcccg aggtacgcaa taggagtgtg    420

tgcacaggtg gtcggtgtgg gctgcgtcct ggatggggtg cgctacaaca acggccagtc    480

cttccagcct aactgcaagt acaactgcac gtgcatcgac ggcgcggtgg gctgcacacc    540

actgtgcctc cgagtgcgcc ccccgcgtct ctggtgcccc cacccgcggc gcgtgagcat    600

acctggccac tgctgtgagc agtgggtatg tgaggacgac gccaagaggc cacgcaagac    660

cgcaccccgt gacacaggag ccttcgatgc tgtgggtgag gtggaggcat ggcacaggaa    720

ctgcatagcc tacacaagcc cctggagccc ttgctccacc agctgcggcc tgggggtctc    780

cactcggatc tccaatgtta acgcccagtg ctggcctgag caagagagcc gcctctgcaa    840

cttgcggcca tgcgatgtgg acatccatac actcattaag gcagggaaga agtgtctggc    900

tgtgtaccag ccagaggcat ccatgaactt cacacttgcg ggctgcatca gcacacgctc    960

ctatcaaccc aagtactgtg gagtttgcat ggacaatagg tgctgcatcc cctacaagtc   1020

taagactatc gacgtgtcct tccagtgtcc tgatgggctt ggcttctccc gccaggtcct   1080

atggattaat gcctgcttct gtaacctgag ctgtaggaat cccaatgaca tctttgctga   1140

cttggaatcc taccctgact tctcagaaat tgccaactag gcaggcacaa atcttgggtc   1200

ttggggacta acccaatgcc tgtgaagcag tcagccctta tggccaataa cttttcacca   1260

atgagcctta gttaccctga tctggaccct tggcctccat ttctgtctct aaccattcaa   1320

atgacgcctg atggtgctgc tcaggcccat gctatgagtt ttctccttga tatcattcag   1380

catctactct aaagaaaaat gcctgtctct agctgttctg gactacaccc aagcctgatc   1440

cagcctttcc aagtcactag aagtcctgct ggatcttgcc taaatcccaa gaaatggaat   1500

caggtagact tttaatatca ctaatttctt ctttagatgc caaaccacaa gactctttgg   1560

gtccattcag atgaatagat ggaatttgga acaatagaat aatctattat ttggagcctg   1620

ccaagaggta ctgtaatggg taattctgac gtcagcgcac caaaactatc ctgattccaa   1680

atatgtatgc acctcaaggt catcaaacat ttgccaagtg agttgaatag ttgcttaatt   1740

ttgattttta atggaaagtt gtatccatta acctgggcat tgttgaggtt aagtttctct   1800

tcacccctac actgtgaagg gtacagatta ggtttgtccc agtcagaaat aaaatttgat   1860

aaacattcct gttgatggga aaagcccca gttaatactc cagagacagg gaaaggtcag   1920

cccgtttcag aaggaccaat tgactctcac actgaatcag ctgctgactg gcagggcttt   1980
```

-continued

```
gggcagttgg ccaggctctt ccttgaatct tctcccttgt cctgcttggg gttcatagga   2040

attggtaagg cctctggact ggcctgtctg gcccctgaga gtggtgccct ggaacactcc   2100

tctactctta cagagccttg agagacccag ctgcagacca tgccagaccc actgaaatga   2160

ccaagacagg ttcaggtagg ggtgtgggtc aaaccaagaa gtgggtgccc ttggtagcag   2220

cctggggtga cctctagagc tggaggctgt gggactccag gggcccccgt gttcaggaca   2280

catctattgc agagactcat ttcacagcct ttcgttctgc tgaccaaatg gccagttttc   2340

tggtaggaag atggaggttt accggttgtt tagaaacaga aatagactta ataaaggttt   2400

aaagctgaag aggttgaagc taaaaggaaa aggttgttgt taatgaatat caggctatta   2460

tttattgtat taggaaaata taatatttac tgttagaatt cttttattta gggccttttc   2520

tgtgccagac attgctctca gtgctttgca tgtattagct cactgaatct tcacgacaat   2580

gttgagaagt tcccattatt atttctgttc ttacaaatgt gaaacggaag ctcatagagg   2640

tgagaaaact caaccagagt cacccagttg gtgactggga aagttaggat tcagatcgaa   2700

attggactgt ctttataacc catattttcc ccctgttttt agagcttcca aatgtgtcag   2760

aataggaaaa cattgcaata aatggcttga tttttttaaaa aaaaaaaaaa aaaaaaaaa   2819
```

<210> SEQ ID NO 81
<211> LENGTH: 2584
<212> TYPE: DNA
<213> ORGANISM: human

<400> SEQUENCE: 81

```
tggcggcggc ggcggcggtt gtcccggctg tgccggttgg tgtggcccgt cagcccgcgt     60

accacagcgc ccgggccgcg tcgagcccag tacagccaag ccgctgcggc cgggtccggc    120

gcgggcggcg cgcgcagacg gagggcggcg gccgcggcca gggcggcccg tgggaccgcg    180

ggcccccggc gcagcgctgc ccggctcccg gccctgccgg cctcctccct tggcgccgcg    240

gccatggcgg ccagcgcgaa gcggaagcag gaggagaagc acctgaagat gctgcgggac    300

atgaccggcc tcccgcgcaa ccgaaagtgc ttcgactgcg accagcgcgg ccccacctac    360

gttaacatga cggtcggctc cttcgtgtgt acctcctgct ccggcagcct gcgaggatta    420

aatccaccac acagggtgaa atctatctcc atgacaacat tcacacaaca ggaaattgaa    480

ttcttacaaa aacatggaaa tgaagtctgt aaacagattt ggctaggatt atttgatgat    540

agatcttcag caattccaga cttcagggat ccacaaaaag tgaaagagtt tctacaagaa    600

aagtatgaaa agaaaagatg gtatgtcccg ccagaacaag ccaaagtcgt ggcatcagtt    660

catgcatcta tttcagggtc ctctgccagt agcacaagca gcacacctga ggtcaaacca    720

ctgaaatctc ttttagggga ttctgcacca acactgcact taaataaggg cacacctagt    780

cagtccccag ttgtaggtcg ttctcaaggg cagcagcagg agaagaagca atttgacctt    840

ttaagtgatc tcggctcaga catctttgct gctccagctc ctcagtcaac agctacagcc    900

aattttgcta actttgcaca tttcaacagt catgcagctc agaattctgc aaatgcagat    960

tttgcaaact ttgatgcatt tggacagtct agtggttcga gtaattttgg aggtttcccc   1020

acagcaagtc actctccttt tcagccccaa actacaggtg gaagtgctgc atcagtaaat   1080

gctaattttg ctcattttga taacttcccc aaatcctcca gtgctgattt tggaaccttc   1140

aatacttccc agagtcatca aacagcatca gctgttagta aagtttcaac gaacaaagct   1200

ggtttacaga ctgcagacaa atatgcagca cttgctaatt tagacaatat cttcagtgcc   1260
```

-continued

```
gggcaaggtg gtgatcaggg aagtggcttt gggaccacag gtaaagctcc tgttggttct   1320

gtggtttcag ttcccagtca gtcaagtgca tcttcagaca agtatgcagc tctggcagaa   1380

ctagacagcg ttttcagttc tgcagccacc tccagtaatg cgtatacttc cacaagtaat   1440

gctagcagca atgtttttgg aacagtgcca gtggttgctt ctgcacagac acagcctgct   1500

tcatcaagtg tgcctgctcc atttggacgt acgccttcca caaatccatt tgttgctgct   1560

gctggtcctt ctgtggcatc ttctacaaac ccatttcaga ccaatgccag aggagcaaca   1620

gcggcaacct ttggcactgc atccatgagc atgcccacgg gattcggcac tcctgctccc   1680

tacagtcttc ccaccagctt tagtggcagc tttcagcagc ctgcctttcc agcccaagca   1740

gctttccctc aacagacagc tttttctcaa cagcccaatg gtgcaggttt tgcagcattt   1800

ggacaaacaa agccagtagt aaccccttt ggtcaagttg cagctgctgg agtatctagt   1860

aatcctttta tgactggtgc accaacagga caatttccaa caggaagctc atcaaccaat   1920

cctttcttat agccttatat agacaattta ctggaacgaa cttttatgtg gtcacattac   1980

atctctccac ctcttgcact gttgtcttgt ttcactgatc ttagctttaa acacaagaga   2040

agtctttaaa aagcctgcat tgtgtattaa acaccaggta atatgtgcaa aaccgagggc   2100

tccagtaaca ccttctaacc tgtgaattgg cagaaaaggg tagcggtatc atgtatatta   2160

aaattggcta atattaagtt attgcagata ccacattcat tatgctgcag tactgtacat   2220

atttttctta gaaattagct atttgtgcat atcagtattt gtaactttaa cacattgtta   2280

tgtgagaaat gttactgggg aaatagatca gccactttta aggtgctgtc atatatcttg   2340

gaatgaatga cctaaaatca ttttaaccat tgctactgga aagtaacaga gtcaaaattg   2400

gaaggtttta ttcattcttg aatttttcct ttctaaagag ctcttctatt tatacatgcc   2460

taaattcttt taaaatgtag agggatacct gtctgcataa taaagctgat catgttttgc   2520

tacagtttgc aggtgaaaaa aaataaatat tataaaataa aaaaaaaaaa aaagaaaaaa   2580

aaaa                                                                2584
```

<210> SEQ ID NO 82
<211> LENGTH: 2115
<212> TYPE: DNA
<213> ORGANISM: human

<400> SEQUENCE: 82

```
gaaatgaacc tctcttattg atttttattg gcctagagcc aggagtactg cattcagttg     60

actttcaggg taaaaagaaa acagtcctgg ttgttgtcat cataaacata tggaccagtg    120

tgatggtgaa atgagatgag gctccgcaat ggaactgtag ccactgcttt agcatttatc    180

acttccttcc ttactttgtc ttggtatact acatggcaaa atgggaaaga aaaactgatt    240

gcttatcaac gagaattcct tgctttgaaa gaacgtcttc gaatagctga acacagaatc    300

tcacagcgct cttctgaatt aaatacgatt gtgcaacagt tcaagcgtgt aggagcagaa    360

acaaatggaa gtaaggatgc gttgaataag ttttcagata ataccctaaa gctgttaaag    420

gagttaacaa gcaaaaaatc tcttcaagtg ccaagtattt attatcattt gcctcattta    480

ttgaaaaatg aaggaagtct tcaacctgct gtacagattg gcaacggaag aacaggagtt    540

tcaatagtca tgggcattcc cacagtgaag agagaagtta aatcttacct catagaaact    600

cttcattccc ttattgataa cctgtatcct gaagagaagt tggactgtgt tatagtagtc    660

ttcataggag agacagatat tgattatgta catggtgttg tagccaacct ggagaaagaa    720

ttttctaaag aaatcagttc tggcttggtg gaagtcatat caccccctga aagctattat    780
```

```
cctgacttga caaacctaaa ggagacattt ggagactcca aagaaagagt aagatggaga     840

acaaagcaaa acctagatta ctgttttcta atgatgtatg ctcaagaaaa gggcatatat     900

tacattcagc ttgaagatga tattattgtc aaacaaaatt attttaatac cataaaaaat     960

tttgcacttc aactttcttc tgaggaatgg atgattctag agttttccca gctgggcttc    1020

attggtaaaa tgtttcaagc gccggatctt actctgattg tagaattcat attcatgttt    1080

tacaaggaga aacccattga ttggctcctg gaccatattc tctgggtgaa agtctgcaac    1140

cctgaaaaag atgcaaaaca ttgtgataga cagaaagcaa atctgcgaat tcgcttcaga    1200

ccttcccttt tccaacatgt tggtctgcac tcatcactat caggaaaaat ccaaaaactc    1260

acggataaag attatatgaa accattactt cttaaaatcc atgtaaaccc acctgcggag    1320

gtatctactt ccttgaaggt ctaccaaggg catacgctgg agaaaactta catgggagag    1380

gatttcttct gggctatcac accgatagct ggagactaca tcttgtttaa atttgataaa    1440

ccagtcaatg tagaaagtta tttgttccat agcggcaacc aagaacatcc tggagatatt    1500

ctgctaaaca caactgtgga agttttgcct tttaagagtg aaggtttgga aataagcaaa    1560

gaaaccaaag acaaacgatt agaagatggc tatttcagaa taggaaaatt tgagaatggt    1620

gttgcagaag gaatggtgga tccaagtctc aatcccattt cagcctttcg actttcagtt    1680

attcagaatt ctgctgtttg ggccattctt aatgagattc atattaaaaa agccaccaac    1740

tgatcatctg agaaaccaac acattttttc ctgtgaattt gttaattaaa gatagttaag    1800

catgtatctt tttttattt ctacttgaac actacctctt gtgaagtcta ctgtagataa    1860

gacgattgtc atttccactt ggaaagtgaa tctcccataa taattgtatt tgtttgaaac    1920

taagctgtcc tcagatttta acttgactca aacatttttc aattatgaca gcctgttaat    1980

atgacttgta ctattttggt attatactaa tacataagag ttgtacatat tgttacattc    2040

tttaaatttg agaaaaacta atgttacata cattttatga agggggtact tttgaggttc    2100

acttatttta ctatt                                                     2115
```

<210> SEQ ID NO 83
<211> LENGTH: 1635
<212> TYPE: DNA
<213> ORGANISM: human

<400> SEQUENCE: 83

```
gggggtggcg gggacgcgag tggcggccgc ggggccccgg acaagggtcc gcagagctgc      60

agccttcgag ggccagccct ctccgagtcc ggggctgggt cccaccagtg acaaggcggc     120

agccccgcgc acaccaaaga gaaagcggct gtggcggcag cggcagcccc agccatgctg     180

tgttatgtga cgaggccgga cgcggtgctg atggaggtgg aggtggaggc gaaagccaac     240

ggcgaggact gcctcaacca ggtgtgcagg cgactgggaa tcatagaagt tgactatttt     300

ggactgcaat ttacgggtag caaaggtgaa agtttatggc taaacctgag aaaccggatc     360

tcccagcaga tggatgggct agccccttac aggcttaaac ttagagtcaa gttcttcgtg     420

gagcctcatc tcatcttaca ggagcagact aggcatatct tttcttgca catcaaggag     480

gccctcttgg caggccacct cttgtgttcc ccagagcagg cagtggaact cagtgccctc     540

ctggcccaga ccaagtttgg agactacaac cagaacactg ccaagtataa ctatgaggag     600

ctctgtgcca aggagctctc ctctgccacc ttgaacagca ttgttgcaaa acataaggag     660

ttggagggga ccagccaggc ttcagctgaa taccaagttt tgcagattgt gtcggcaatg     720
```

-continued

```
gaaaactatg gcatagaatg gcattctgtg cgggatagcg aagggcagag actgctcatt     780
ggggttggac ctgaaggaat ctcaatttgt aaagatgact ttagcccaat taataggata     840
gcttatcctg tggtgcagat ggccacccag tcaggaaaga atgtatattt gacggtcacc     900
aaggaatctg ggaacagcat cgtgctcttg tttaaaatga tcagcaccag ggcggccagc     960
gggctctacc gagcgataac agagacgcac gcattctaca ggtgtgacac agtgaccagc    1020
gccgtgatga tgcagtatag ccgtgacttg aagggccact tggcatctct gtttctgaat    1080
gaaaacatta accttggcaa gaaatatgtc tttgatatta aaagaacatc aaaggaggtg    1140
tatgaccatg ccaggagggc tctgtacaat gctggcgttg tggacctcgt ttcaagaagc    1200
aaccagagcc cttcacactc gcctctgaag tcctcagaaa gcagcatgaa ctgcagcagc    1260
tgcgagggcc tcagctgcca gcagacccgg gtgctgcagg agaagctacg caagctgaag    1320
gaagccatgc tgtgcatggt gtgctgcgag gaggagatca actccacctt ctgtccctgt    1380
ggccacactg tgtgctgtga gagctgcgcc gcccagctac agtcatgtcc cgtctgcagg    1440
tcgcgtgtgg agcatgtcca gcacgtctat ctgccaacgc acaccagtct tctcaatctg    1500
actgtaatct aatctgttgt gcttttgttg gacttggcat gtttccatga actgcactat    1560
tataaactat taaaatgata gatgttggag aaagtaatta ttccaacacc catctgccca    1620
tgcgatgtta aaaaa                                                     1635
```

<210> SEQ ID NO 84
<211> LENGTH: 2118
<212> TYPE: DNA
<213> ORGANISM: human

<400> SEQUENCE: 84

```
ctgtgaagat ggcgctctcc agggtgtgct gggctcggtc ggctgtgtgg ggctcggcag      60
tcacccctgg acattttgtc acccggaggc tgcaacttgg tcgctctggc ctggcttggg     120
gggcccctcg gtcttcaaag cttcaccttt ctccaaaggc agatgtgaag aacttgatgt     180
cttatgtggt aaccaagaca aaagcgatta atgggaaata ccatcgtttc ttgggtcgtc     240
atttcccccg cttctatatc ctgtacacaa tcttcatgaa aggattgcag atgttatggg     300
ctgatgccaa aaaggctaga agaataaaga caaatatgtg gaagcacaat ataaagtttc     360
atcaacttcc ataccgggag atggagcatt tgagacagtt ccgccaagac gtcaccaagt     420
gtcttttcct aggtattatt tccattccac cttttgccaa ctacctggtc ttcttgctaa     480
tgtacctgtt tcccaggcaa ctactgatca ggcatttctg gaccccaaaa caacaaactg     540
atttcttaga tatctatcat gctttccgga agcagtccca cccagaaatt attagttatt     600
tagaaaaggt catccctctc atttctgatg caggactccg gtggcgtctg acagatctgt     660
gcaccaagat acagcgtggt acccacccag caatacatga tatcttggct ctgagagagt     720
gtttctctaa ccatcctctg ggcatgaacc aactccaggc tttgcacgtg aaagccttga     780
gccgggccat gcttctcaca tcttacctgc ctcctccctt gttgagacat cgtttgaaga     840
ctcatacaac tgtgattcac caactggaca aggctttggc aaagctgggg attggccagc     900
tgactgctca ggaagtaaaa tcggcttgtt atctccgtgg cctgaattct acgcatattg     960
gtgaagatag gtgtcgaact tggctgggag aatggctgca gatttcctgc agcctgaaag    1020
aagctgagct gtctctcttg ctgcacaacg tggtcctgct ctccaccaac taccttggga    1080
caaggcgctg aatgaaccat ggagcggatg gcattgtcct gcagtcgtat agtatagcag    1140
tgcaggaaca aacagcactt gccagcaaag tctgtgtgta ctgttaagtg tgtgggaggc    1200
```

```
agagagagga gcaggggcca tgggcttcac agcatggcac acctgtggga actgcagaca   1260

ttcctctcac agctagaact gaaacaaacc ctcttgctag gggtggtccg tgtgaggtgt   1320

catcctgtcc ccctcataat tactaatagc tggaactggc agcagcctct actgggcttt   1380

tactgtgatg tgttcagttc atgtcctagg aagtcagctt ttgccccagg tgggaatcct   1440

tatttggctt aggactgatc cacttccatg ttacttacat ctgtgggttt ttgttgttgc   1500

tgttagaaaa tttttggctg gtgaaaacag cactcctttg gctggagcac ttgtgtccat   1560

gcatgtactt gggtgtttcc ctccatcctt tctgatatga ccaaaaatca agttgttttg   1620

ttttttgtca ccttcactgg catgggctaa ccacttcttt ttcaaaccct ctgaacacct   1680

ttttctgatg ggtaacttgc aggaatattc tattggaaaa gataacagga agtacaagtg   1740

cttcttgacc ccttcctcaa tgtttctagc cttcactctc cattgtcttt tctgggctgt   1800

attacagccc tctgtggatc ttcaactctg ctgcctccac tgtgatgcag cagtccaact   1860

gtaactgaca gtggctgcct tctctgggcc atggatcaca cctgtaaggt actaattact   1920

gcccagcctg gggagatcag gagaggtctg catagttagt aagttgggtt tagcttttgt   1980

gtgtgcatca gtgacttaga gttctgtaat aacttattgt aaatgcatga agcactgttt   2040

ttaaacccaa gtaaagactg cttgaaacct gttgatggaa aaaaaaaaaa aaaaaaaaaa   2100

aaaaaaaaaa aaaaaaaa                                                 2118
```

```
<210> SEQ ID NO 85
<211> LENGTH: 4221
<212> TYPE: DNA
<213> ORGANISM: human

<400> SEQUENCE: 85

cgataacgat ttgtgttgtg agaggcgcaa gctgcgattt ctgctgaact tggaggcatt     60

tctacgactt ttctctcagc tgaggctttt cctccgaccc tgatgctctt caattcggtg    120

ctccgccagc cccagcttgg cgtcctgaga aatggatggt cttcacaata ccctcttcaa    180

tcccttctga ctggttatca gtgcagtggt aatgatgaac acacttctta tggagaaaca    240

ggagtcccag ttcctccttt tggatgtacc ttctcttctg ctcccaatat ggaacatgta    300

ctagcagttg ccaatgaaga aggctttgtt cgattgtata acacagaatc acaaagtttc    360

agaaagaagt gcttcaaaga atggatggct cactggaatg ccgtctttga cctggcctgg    420

gttcctggtg aacttaaact tgttacagca gcaggtgatc aaacagccaa attttgggac    480

gtaaaagctg gtgagctgat tggaacatgc aaaggtcatc aatgcagcct caagtcagtt    540

gccttttcta agtttgagaa agctgtattc tgtacgggtg gaagagatgg caacattatg    600

gtctgggata ccaggtgcaa caaaaaagat gggttttata ggcaagtgaa tcaaatcagt    660

ggagctcaca atacctcaga caagcaaacc ccttcaaaac ccaagaagaa acagaattca    720

aaaggacttg ctccttctgt ggatttccag caaagtgtta ctgtggtcct ctttcaagac    780

gagaatacct tagtctcagc aggagctgtg gatgggataa tcaaagtatg ggatttacgt    840

aagaattata ctgcttatcg acaagaaccc atagcatcca agtctttcct gtacccaggt    900

agcagcactc gaaaacttgg atattcaagt ctgattttgg attccactgg ctctacttta    960

tttgctaatt gcacagacga taacatctac atgtttaata tgactgggtt gaagacttct   1020

ccagtggcta ttttcaatgg acaccagaac tctacctttt atgtaaaatc cagccttagt   1080

ccagatgacc agtttttagt cagtggctca agtgatgaag ctgcctacat atggaaggtc   1140
```

-continued

```
tccacaccct ggcaacctcc tactgtgctc ctgggtcatt ctcaagaggt cacgtctgtg   1200
tgctggtgtc catctgactt cacaaagatt gctacctgtt ctgatgacaa tacactaaaa   1260
atctggcgct tgaatagagg cttagaggag aaaccaggag gtgataaact ttccacggtg   1320
ggttgggcct ctcagaagaa aaaagagtca agacctggcc tagtaacagt aacgagtagc   1380
cagagtactc ctgccaaagc ccccagggta aagtgcaatc catccaattc ttccccgtca   1440
tccgcagctt gtgccccaag ctgtgctgga gacctccctc ttccttcaaa tactcctacg   1500
ttctctatta aaacctctcc tgccaaggcc cggtctccca tcaacagaag aggctctgtc   1560
tcctccgtct ctcccaagcc accttcatct ttcaagatgt cgattagaaa ctgggtgacc   1620
cgaacacctt cctcatcacc acccatcact ccacctgctt cggagaccaa gatcatgtct   1680
ccgagaaaag cccttattcc tgtgagccag aagtcatccc aagcagaggc ttgctctgag   1740
tctagaaata gagtaaagag gaggctagac tcaagctgtc tggagagtgt gaaacaaaag   1800
tgtgtgaaga gttgtaactg tgtgactgag cttgatggcc aagttgaaaa tcttcatttg   1860
gatctgtgct gccttgctgg taaccaggaa gaccttagta aggactctct aggtcctacc   1920
aaatcaagca aaattgaagg agctggtacc agtatctcag agcctccgtc tcctatcagt   1980
ccgtatgctt cagaaagctg tggaacgcta cctcttcctt tgagaccttg tggagaaggg   2040
tctgaaatgg taggcaaaga gaatagttcc ccagagaata aaaactggtt gttggccatg   2100
gcagccaaac ggaaggctga gaatccatct ccacgaagtc cgtcatccca gacacccaat   2160
tccaggagac agagcggaaa gacattgcca agcccggtca ccatcacgcc cagctccatg   2220
aggaaaatct gcacatactt ccatagaaag tcccaggagg acttctgtgg tcctgaacac   2280
tcaacagaat tatagattct aatctgagtg agttactgag ctttggtcca ctaaaacaag   2340
ctgagctttg gtccactaaa acaagatgaa aaatacaaga gtgactctat aactctggtc   2400
tttaagaaag ctgccttttc atttttagac aaaatctttt caacgctgaa atgtacctaa   2460
tctggttcta ctaccataat gtatatgcag cttcccgagg atgaatgctg tgtttaaatt   2520
tcataaagta aatttgtcac tctagcattt tgaatgaata gtcttcactt tttaaattat   2580
tcatcttctc tataataatg acatcccagt tcatggaggc aaaaaacaag tttcttgtta   2640
tcctgaaact ttctatgctc agtggaaagt atctgccagc cacagcatga ggcctgtgaa   2700
ggctgactga gaaatcctct gctgaagacc cctggttctg ttctgcctcc aacatgtata   2760
attttatttg aaatacataa tcttttcact atgcttttgt ggggtttttt ttaagtatgt   2820
gtaaaaatgt gatgctcaga taagtacatt tatatcagtt cagtgttaaa atgcagtctc   2880
ttgagttaaa gtcatcttta ttttaaatgc agtgataaat gtcaactctt cggagaaact   2940
aggagaacaa caacagaaag ctgtgtttgt cttttttctc tcaaatatat ctcccgtatg   3000
agatttcagg tccccatgtt ttcaccaagc aatctgctat gtcagccaac ccaacatcac   3060
tttctacagg aggttatgat ttttgccatt tactagagga agatgtttta tgaaatcaat   3120
ttggggtttg aattcaggtg cagtcatcag ttctttaggg gctgcaatgt tttaaaaaaa   3180
ataagtcatc agattttaag aaaaaagtga tgatttctta ttgatatttt tgtaacagaa   3240
tatagctctt aactgaaaat ccagaaccag aaacataaat cttgagtttc ttttcatgta   3300
cataaaaagc aatagccttt tagtatagat agccctgagc caaaaagtaa tagaattttc   3360
tctagatatt taatacagag agtgtataga ctgactctaa gttaataatg tgcaaaatat   3420
cttaaacatc cctcccctta ttcaacaatt atgtatcagt gatcttgaac cattgtttta   3480
tatttttcac ctttgtaacc tcatggaaag aggctttaca tactttctat gtactattta   3540
```

```
cttagaaggg agccccttc cagtcatgaa acttcatttg ttttatccat atccctgagg   3600

actgtgtaga ctttatgtca gttctgtgta gactttatgt cagtttttgt cattatttga   3660

aaatctattc tgacaacttt ttaattcctt tgatcttata agttaaagct gtaacaactg   3720

aaattgcatg gatcaagtaa gcatagtttt atccagggag aaaaataaaa ggaagccata   3780

gaattgctct ggtcaaaacc aagcacacca tagccttaac tgaatattta ggaaatctgc   3840

ctaatctgct tatatttggt gtttgttttt tgactgttgg gctttgggaa gatgttattt   3900

atgaccaata tctgccagta acgctgttta tctcacttgc tttgaaagcc aatgggggaa   3960

aaaaatccat gaaaaaaaaa agattgataa agtagatgat tttgtttgta tccctaccca   4020

tctcctggca gccctactga gtgaaattgg gatacatttg gctgtcagaa attataccga   4080

gtctactggg tataacatgt ctcacttgga aagctagtac ttttaaatgg gtgccaaagg   4140

tcaactgtaa tgagataatt atccctgcct gtgtccatgt cagactttga gctgatcctg   4200

aataataaag ccttttacct t                                              4221
```

```
<210> SEQ ID NO 86
<211> LENGTH: 867
<212> TYPE: DNA
<213> ORGANISM: human

<400> SEQUENCE: 86

cgtttcagcg tggcggcgct ggtgctggcg ttggccctgg aggacggccc cgagtgatgg     60

ctggcgcctg cctcccgggt gtctcccggg tacagatgga gtcgtcccgc ggccgccggc    120

ggcaaggtcg gcagctgcga ggccaagaga gaccccagga cacacacagc tgcctcccgg    180

tgcgagaaga agaccccggc ttgagagtga gatggcgttt aatgattgct tcagtttgaa    240

ctaccctggc aacccctgcc caggggactt gatcgaagtg ttccgtcctg gctatcagca    300

ctgggccctg tacttgggtg atggttacgt tatcaacata gcacctgtag atggcattcc    360

tgcgtccttt acaagcgcca agtctgtatt cagcagtaag gccctggtga aaatgcagct    420

cttgaaggat gttgtgggaa atgacacata cagaataaac aataaatacg atgaaacgta    480

ccccctctc cctgtggaag aaatcataaa gcggtcagag tttgtaattg gacaggaggt    540

ggcctataac ttacttgtca acaactgtga acattttgtg acattgcttc gctatggaga    600

aggagtttca gagcaggcca accgagcgat aagtaccgtt gagtttgtga cagctgctgt    660

tggtgtcttc tcattcctgg gcttgtttcc aaaaggacaa agagcaaaat actattaaca    720

atttaccaaa gagatattga tattgaagga atttgggagg aggaaaagaa acctggggtg    780

aatacttatt ttcagtgcat cattactgtt ccagattcct atgatggatg gcagactctt    840

taataaattg cttactgata ttatctt                                        867
```

```
<210> SEQ ID NO 87
<211> LENGTH: 561
<212> TYPE: DNA
<213> ORGANISM: human
<220> FEATURE:
<221> NAME/KEY: misc_feature
<222> LOCATION: (534)..(534)
<223> OTHER INFORMATION: any kind of base

<400> SEQUENCE: 87

tttttttttc aaattttatt ttttgtactt ttattgaaaa ggtacattta aaaaaataca     60

cagacatttt accatttaca ggttgcagat atagatgctc taaaagagtc cactctattt    120
```

-continued

```
tgttgttcta tgataactct tgcccctgat atcacaaaca ttccagtctt gttgatatcg    180

gcttaaaaag gggggcatgg gagcatgacc tgcaatatat tcagcgaaca gaaagacaaa    240

ttgttcaatt ataaattttt ttatcttctg tacattattg cattagggag ccacaaaatt    300

atgtagcatc attacaaatg aaaacaggtt aaaaatgaag aagatactta tatagaaata    360

catggattca ttgtcttctt gcagaatgca caagaggtgc aaaaatgtgc aatttaggaa    420

gctctttttc tgtttgtata cgtttgctta gcaacacaaa ccagtgagga agctacaaaa    480

taagttaaac aaaaatagca aacaggtagt aattatagct atgttatatg gctntctatt    540

tcatttaaat atctccaaat a                                              561
```

<210> SEQ ID NO 88
<211> LENGTH: 471
<212> TYPE: DNA
<213> ORGANISM: human

<400> SEQUENCE: 88

```
tttcatgaat aattttattt ttattttggt catgactttt taaaattaat ggaaagtctc     60

agtctgctca aatgataaac caaaaaatgg ggtcatgaag caaattcagt ctttgcattt    120

cttcaacaac caactcacat ttctctgctc cttgactcag aggctggaca tgtgctaaca    180

gctttttgc ttctgtatat ccttaatagg atggcagaat cccggtgtta aaagaatctt    240

aaagtcagcc gtgtcaccat gggacctcga ttagcaaaca gatgtagaca ttccttccaa    300

attcagtcaa agaaaaaact ctaataccag cagccatgtt cagggtgtgc acgacatgct    360

gagcgcttgg gatacatccc cttgtttaat tctcacagaa actttgtgag acaagtacta    420

taatccctgt ttaacagatg ggcaaactga ggtttggaaa aacactcatt t             471
```

<210> SEQ ID NO 89
<211> LENGTH: 727
<212> TYPE: DNA
<213> ORGANISM: human

<400> SEQUENCE: 89

```
taaaatatta ccttttattt tctcaggcac acaagtgatt tggataccaa ttatcaagac     60

attttactga tttcccttta gaatgatcta ttttaaatct tcagccacct tagaaaaagt    120

ttgcagcaat cactttgcaa ttcataagta tcaggttaga atttagttgt ggaataagtt    180

aacagtttat gttcaatatg tgaggttatt tgaactcctg agttttaaat atcctgtgga    240

acagtgattc ctctcccttc taatggcttt tcagattaaa gcaatgactt taaaaagatt    300

acatcctaaa tacttgatta caacagaaat cgaccaatct aaaaatcaga tagtgttata    360

ctgaacatca ttctgatata atgagtagcc tctggctgaa acaaaattcc accaccaagg    420

ccatcaacca ggttagtact gtttttcctg ggtctatgt aaactctcct tttctctgca    480

aatgctgctt ggctgtgaac agcatggatt tacctgcacc aatgtggcac acacctagca    540

actttctcaa gcattctaaa gatatcccca gagctacaat attgacatat gcacagcact    600

ttctctagac agtccaatca gcgtgcacat cacacacaca gaatgctggg atatgctata    660

ctgcacactt agtacacagg tggaatagag tacaatgact aaagctcaca gaaaatgttt    720

tagtctt                                                              727
```

<210> SEQ ID NO 90
<211> LENGTH: 460
<212> TYPE: DNA
<213> ORGANISM: human

<400> SEQUENCE: 90
tttttgatat aaagggcttt tattttcttt acagttttct gtattttcca aatttctaca 60
taaacataca cataaaagtc ataaaaatgt ccctcaaaat gacactccct ccaatgcagg 120
gagtgaggag gtgtgtgctg ggacgccaca gggtggctgc tgcagctaat ccctgtgcag 180
gtgcagccac tgctacactc cagcgtctga ggcccctctg cactggcagt gttagaatgg 240
ctgtctgaga gccaaggctg ttcacccgag cagagagtca tggagctggt acaggcagga 300
gccaaggtaa gcactaggct ggtgtgtgcc ctccaggggg caccctcctt gaagcaggcc 360
ctccaaggta ctcgcccccct gaggcagccg ataacagccg gaagccttcc cctgggggga 420
cctggccatt tgtggagcag ggaaaggctc cactgccagt 460

<210> SEQ ID NO 91
<211> LENGTH: 392
<212> TYPE: DNA
<213> ORGANISM: human

<400> SEQUENCE: 91
tttttttttt tttttttgag ttgctgaaaa gtttactttt gagttttaaa ctgtactttg 60
aaaactatat tgtgaactgt gttgacatga ggaaaggctg ggctccctga aaacatccag 120
ttccacagca gggcgggccc aagcccagcc aatccccagg caatgcaggg cagggatccc 180
acctggtata agtacgggca gagggcagag ccaggctgta tcgaggggcg gcgctgggac 240
cctcctcgcc cagaattcct actcatcccc agcacagaag tgctctgtag ggccagctga 300
ggacaccccg gttcactgag ggtggcccac agtaagtcgc cgtctggcag taagttagct 360
ctgcaggtgt ggaccccaag accacacacg gc 392

<210> SEQ ID NO 92
<211> LENGTH: 496
<212> TYPE: DNA
<213> ORGANISM: human

<400> SEQUENCE: 92
ttttttgtat ttttctcaat ataatgttgc aagatgtcat tatattctca ttacccataa 60
cttcccatcc aaatcttaat ggcacatttg atattttttc aaatggcttt gagatataat 120
tcacatacca cacaattcat gtatctaaag tatacagttc tgtagttctg tggttgttgg 180
ttacatccac cagactgagg gctccctgag ggttggtgcc tcagctttcc cttcacttac 240
tcattcacca aacattcagc gcctactgag tactggggtt atgatggcca acaggagaga 300
cagtctctgc ctactgtttg gtgggggtgg agtacttagt aaccgtcgtc attattgagt 360
gcttacctgt gctgggcaca gtgctgctac tgggtgactg tgtccccagg gctgtcccag 420
gctgggggtc tggaggagta gttatcagtt gaactgagtt aatccacagt ggaaggtaac 480
ccactccctg ccctag 496

<210> SEQ ID NO 93
<211> LENGTH: 472
<212> TYPE: DNA
<213> ORGANISM: human

<400> SEQUENCE: 93
ttaacacaaa agcttttact tggaaactgg caaatactgg actagaatac tgacatgctc 60
acgctctggc gggagctcgg atgcagaagc tattgcacaa agcccctctg attgccttgc 120

-continued

```
tcctctttgg catgtatcag cagagcccca agggccaatt gcccacaggt ggggactgtt    180
ctccatcaag gtatggggac ccctacttcc ttgttttgtt aaaaagtgca ggtaggcgaa    240
gaaagcccag gcagttgacc cagtctttga aacagctgac tccccagagc tggggccagg    300
ggagcctggt cttgaggggt aagggctgca gggccaggct gatggcctgt gtcatggcat    360
tggccatctc ctctccagct tctcctcagc catcgcccgt ccgtcatggt ggtgtcggct    420
gcacctggac cttcctgcct ctccgctcag ggcagcagca gtgagtgcag ca            472
```

<210> SEQ ID NO 94
<211> LENGTH: 585
<212> TYPE: DNA
<213> ORGANISM: human

<400> SEQUENCE: 94

```
tttttatatt atagtaaatt tatttggtat aattacatat taacattatt tacaatgcta     60
atttttttat ttataaagta tctttatatg gacaaaaaga tacaaactgt tatcatttta    120
agtacaaagt atttctagaa atacattata agccattaaa aaaaaaaacg atatttcaag    180
attggttctt acatgctatg accaactcat atgaaagagc aagttgctcc cccttcattc    240
cttcccccaa ctccaaaggg aaaggaattt gatatttagg ctttaaaaaa tttcctacta    300
cctttatctt ttaaaaaacc ctactcaaaa caactatctc ttataaggga aaatatcata    360
gataagattt tcctttagaa aatgacatta aaagtggcat gagccctaga atgatatgtg    420
tattagaggc acttaaaaaa aatcagaagg gatccatagg aaggaattta attcagcaaa    480
tactgagtgt ccactgcatg caaggtaccc tgccagaaat ctcaaatgag taagttgtcc    540
ttagggatag aaggtgctaa gcatcatgca aaagatatga actga                    585
```

<210> SEQ ID NO 95
<211> LENGTH: 400
<212> TYPE: DNA
<213> ORGANISM: human

<400> SEQUENCE: 95

```
ttattgtttt ttaaaaatac aattttgaaa tttattgttg aaaatggaca catggaacaa     60
accaaacctt gttttatcat gtaattttca gaaaatatgt gatccataaa gattaaaaga    120
aagttgtatt aagtctggca gctttagtat taacttgaaa taaaatatgg caagctttcc    180
acgtcctcct ttatttccac aatccatatg tacgagctag attccagtca gaacttccac    240
aaatacttca ctctttggta gcagcggtta taaattacgc ctttgctaat ttgcgttgtt    300
cccaaccagg agaaacatta ccacaaaaaa agtcagtttc atcctgcagt gttcccgcag    360
caaccatatt aaagctgaag aataaagctc ctttgtagta                          400
```

<210> SEQ ID NO 96
<211> LENGTH: 461
<212> TYPE: DNA
<213> ORGANISM: human

<400> SEQUENCE: 96

```
ttatgccatg aattcctttt tactgaaata ccgtaggact cactaccaca ataagtactt     60
aagctgaaag agtttctaat gggagccaag taaattcagc tctccactgt gcaaagcatc    120
ttgtcatttc tataataaaa gtctttccat gttcagtcca ctttggctct ggaacctgga    180
tgagtcatgc ttggggccca gggtgcctgt gaggatgctg catgagaatt tcagctgtgg    240
tggcagtggc tgggagtccc actgactcag gggaggccca ggcgagatga gctggaactt    300
```

ttaggggaga gctggcactt agggacatca ttgattgtgc ttttcttagc ctagttctgt 360
cctgcaattt atttttctta tcatgtgact gtcggctgaa gtctggggtt atttggtttc 420
tttttcttct tccttgctgg acagtctcca tggggtcacg g 461

<210> SEQ ID NO 97
<211> LENGTH: 542
<212> TYPE: DNA
<213> ORGANISM: human

<400> SEQUENCE: 97
taaatccagt aaagcatagt actagattca tcatacttgt acaatacaac gggcgacatg 60
aaaatggcaa aggctctcct ttttgtgaac aatttaatac aactggtggt ccaataactc 120
tacaatcagc cttgtagagg tcattaaaga cagaatcctg aaagtccgtg actacaaata 180
cattttcaaa ttccggagaa tccaaacctt caaattcttc cactgactcc atctttacaa 240
agcccacttt aatgtccttt aaggctttta taagttcttc ttgttttcca gcttcttgaa 300
ccaatatcac tcttgtttca atctgaggca tctcttcttc tacatatgaa gtagatccaa 360
taagtaagtt ttccttggaa atctcagtaa ctttagaatc aaaaatggaa gagtctgcca 420
agctagtcct cccagtagtg gatgttaata cactattttc agccatgatt tgtattcttc 480
taaatcagca ctctcaaaaa agccctagga gttccacctc ttcaaacgcc gactcctctc 540
ac 542

<210> SEQ ID NO 98
<211> LENGTH: 1017
<212> TYPE: DNA
<213> ORGANISM: human

<400> SEQUENCE: 98
atgggcacct ggcttctggc ctgcacctgc gtctgcacct gtgtctgctc gggagtctct 60
gtctcagggg atggacgagg gccaagggct ggaacctcca cctgcctcac caacaacatt 120
ctcaggattg attgccactg gtctgcccca gagctgggtc agggctccag ccccgggctc 180
cccttcatca gccccgtggt gctgacacat gcccttttca gcaaccaggc tgctggtggc 240
acacagaagt gcatctggca gggcagtgag tgcactgtag tgttgccgcc caaggcagca 300
ctcctgccat ctgacaattt catcatcact ttctaccact gcatgtccgg gagggatcag 360
agcacgtcag ctcgccactg catcctgacc tggagcctca gtcctgcctt ggagtcaatg 420
accacacttc tcagctatga gctggacttc aagaggcagg aagaggcctg ggagcgggcc 480
cagcacaggg atcacattgt cggggtgacc tggctcatac ttgaagcctt tgagctggac 540
cctggcttta tccttgaggc caggctgcgt gtccagacgg ccatgctggg ggatgacggg 600
gcacaggagg agcgagggga gccagcccat gggaagagtg aggcccagga gtgtggttca 660
cacaaggtcc ttcagcaggt gacacaaacc tccaaggccc atcacaaggt ccttcagcag 720
atgacacaaa cctccaaggc tcatcacaaa ccttccactt tggcccaggg cactaaaggg 780
cgcacttttg ccagccctgg gcccttcctg cccacggacc ctctgatccc accctggggg 840
tggccaggca acacctttgt tgctgtgtcc atctttctcc tgctgactgg cccgacctac 900
ctcctgttca agctgtcgcc cagactcctc actttgggca aaggacaaga agcaactcgg 960
atgggggccc acagggctgg tgtgctgctg agccaggact gtgctggcac ccgatga 1017

<210> SEQ ID NO 99

<211> LENGTH: 1099
<212> TYPE: DNA
<213> ORGANISM: human

<400> SEQUENCE: 99

```
agccccaagc ttaccacctg cacccggaga gctgtgtcac catgtgggtc ccggttgtct     60

tcctcaccct gtccgtgacg tggattggtg agaggggcca tggttggggg gatgcaggag    120

agggagccag ccctgactgt caagctgagg ctctttcccc cccaacccag caccccagcc    180

cagacaggga gctgggctct tttctgtctc tcccagcccc actccaagcc catacccccca    240

gcccctccat attgcaacag tcctcactcc cacaccaggt ccccgctccc tcccacttac    300

cccagaactt tctccccatt gcccagccag ctccctgctc ccagctgctt tactaaaggg    360

gaagttcctg ggcatctccg tgtttctctt tgtggggctc aaaacctcca aggacctctc    420

tcaatgccat tggttccttg gaccgtatca ctggtccacc tcctgagccc ctcaatccta    480

tcacagtcta ctgacttttc ccattcagct gtgagtgccc aaccctatcc cagagacctt    540

gatgcttggc ctcccaatct tgccctagga tacccagatg ccaaccagac acctccttct    600

tcctagccag gctatctggc ctgagacaac aaatgggtcc ctcagtctgg caatgggact    660

ctgagaactc ctcattccct gactcttagc cccagactct tcattcagtg gcccacattt    720

tccttaggaa aaacatgagc atccccagcc acaactgcca gctctctgat tccccaaatc    780

tgcatccttt tcaaaaccta aaaacaaaaa gaaaaacaaa taaaacaaaa ccaactcaga    840

ccagaactgt tttctcaacc tgggacttcc taaactttcc aaaaccttcc tcttccagca    900

actgaacctc gccataaggc acttatccct ggttcctagc accccttatc ccctcagaat    960

ccacaacttg taccaagttt cccttctccc agtccaagac cccaaatcac cacaaaggac   1020

ccaatcccca gactcaagat atggtctggg cgctgtcttg tgtctcctac cctgatccct   1080

gggttcaact ctgctccca                                                1099
```

<210> SEQ ID NO 100
<211> LENGTH: 1095
<212> TYPE: DNA
<213> ORGANISM: human

<400> SEQUENCE: 100

```
ccaagcttac cacctgcacc cggagagctg tgtcaccatg tgggtcccgg ttgtcttcct     60

caccctgtcc gtgacgtgga ttggtgagag gggccatggt tgggggggatg caggagaggg    120

agccagccct gactgtcaag ctgaggctct ttccccccca acccagcacc ccagcccaga    180

cagggagctg ggctcttttc tgtctctccc agccccactt caagcccata cccccagccc    240

ctccatattg caacagtcct cactcccaca ccaggtcccc gctccctccc acttacccca    300

gaactttctc cccattgccc agccagctcc ctgctcccag ctgctttact aaaggggaag    360

ttcctgggca tctccgtgtt tctctttgtg gggctcaaaa cctccaagga cctctctcaa    420

tgccattggt tccttggacc gtatcactgg tccatctcct gagcccctca atcctatcac    480

agtctactga cttttcccat tcagctgtga gtgtccaacc ctatcccaga gaccttgatg    540

cttggcctcc caatcttgcc ctaggatacc cagatgccaa ccagacacct ccttcttcct    600

agccaggcta tctggcctga gacaacaaat gggtccctca gtctggcaat gggactctga    660

gaactcctca ttccctgact cttagcccca gactcttcat tcagtggccc acattttcct    720

taggaaaaac atgagcatcc ccagccacaa ctgccagctc tctgagtccc caaatctgca    780

tccttttcaa aacctaaaaa caaaaagaaa aacaaataaa acaaaaccaa ctcagaccag    840
```

-continued

```
aactgttttc tcaacctggg acttcctaaa ctttccaaaa ccttcctctt ccagcaactg    900

aacctcgcca taaggcactt atccctggtt cctagcaccc cttatcccct cagaatccac    960

aacttgtacc aagtttccct tctcccagtc caagacccca aatcaccaca aaggacccaa   1020

tccccagact caagatatgg tctgggcgct gtcttgtgtc tcctaccctg atccctgggt   1080

tcaactctgc tccca                                                    1095
```